(12) United States Patent
Blackburn et al.

(10) Patent No.: US 9,382,197 B2
(45) Date of Patent: Jul. 5, 2016

(54) SUBSTITUTED HYDROXAMIC ACIDS AND USES THEREOF

(71) Applicant: Millennium Pharmaceuticals, Inc., Cambridge, MA (US)

(72) Inventors: Christopher Blackburn, Natick, MA (US); Kenneth M. Gigstad, Westford, MA (US); Sean J. Harrison, Belmont, MA (US); He Xu, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/054,970

(22) Filed: Oct. 16, 2013

(65) Prior Publication Data

US 2014/0275093 A1 Sep. 18, 2014

Related U.S. Application Data

(63) Continuation of application No. 13/034,974, filed on Feb. 25, 2011, now abandoned.

(60) Provisional application No. 61/339,138, filed on Feb. 26, 2010, provisional application No. 61/426,314, filed on Dec. 22, 2010.

(51) Int. Cl.

| | | |
|---|---|---|
| *C07C 259/08* | (2006.01) |
| *A61K 31/166* | (2006.01) |
| *A61K 31/341* | (2006.01) |
| *A61K 31/343* | (2006.01) |
| *A61K 31/381* | (2006.01) |
| *A61K 31/404* | (2006.01) |
| *A61K 31/407* | (2006.01) |
| *A61K 31/437* | (2006.01) |
| *A61K 31/4965* | (2006.01) |
| *A61K 31/498* | (2006.01) |
| *A61K 31/502* | (2006.01) |
| *C07D 491/048* | (2006.01) |
| *A61K 31/505* | (2006.01) |
| *C07C 259/10* | (2006.01) |
| *C07C 275/26* | (2006.01) |
| *C07C 275/28* | (2006.01) |
| *C07C 275/34* | (2006.01) |
| *C07C 311/06* | (2006.01) |
| *C07C 311/19* | (2006.01) |

(Continued)

(52) U.S. Cl.
CPC .............. *C07C 259/08* (2013.01); *A61K 31/166* (2013.01); *A61K 31/341* (2013.01); *A61K 31/343* (2013.01); *A61K 31/381* (2013.01); *A61K 31/404* (2013.01); *A61K 31/407* (2013.01); *A61K 31/437* (2013.01); *A61K 31/498* (2013.01); *A61K 31/4965* (2013.01); *A61K 31/502* (2013.01); *A61K 31/505* (2013.01); *C07C 259/10* (2013.01); *C07C 275/26* (2013.01); *C07C 275/28* (2013.01); *C07C 275/34* (2013.01); *C07C 311/06* (2013.01); *C07C 311/19* (2013.01); *C07D 207/34* (2013.01); *C07D 209/42* (2013.01); *C07D 211/62* (2013.01); *C07D 231/14* (2013.01); *C07D 233/84* (2013.01); *C07D 237/28* (2013.01); *C07D 239/28* (2013.01); *C07D 241/44* (2013.01); *C07D 277/56* (2013.01); *C07D 277/64* (2013.01); *C07D 285/14* (2013.01); *C07D 307/84* (2013.01); *C07D 307/85* (2013.01); *C07D 311/14* (2013.01); *C07D 333/68* (2013.01); *C07D 333/70* (2013.01); *C07D 417/04* (2013.01); *C07D 491/04* (2013.01); *C07D 491/048* (2013.01); *C07C 2101/04* (2013.01); *C07C 2101/06* (2013.01)

(58) Field of Classification Search
CPC ..... A61K 31/19; A61K 31/185; A61K 31/16; C07D 277/46; C07D 215/40; C07D 417/12; C07D 215/36; C07D 215/38; C07D 401/06; C07D 213/80; C07D 213/82; C07D 215/42; C07D 217/02; C07D 217/06; C07D 217/08; C07D 277/82; C07D 295/08
See application file for complete search history.

(56) References Cited

FOREIGN PATENT DOCUMENTS

WO     WO 03070691 A1 *  8/2003

OTHER PUBLICATIONS

New et al. (Molecular Oncology, Dec. 2012, vol. 6, pp. 637-656).*

(Continued)

*Primary Examiner* — Sean Basquill
*Assistant Examiner* — Mark V Stevens
(74) *Attorney, Agent, or Firm* — Millennium Pharmaceuticals, Inc.

(57) ABSTRACT

This invention provides compounds of formula (I):

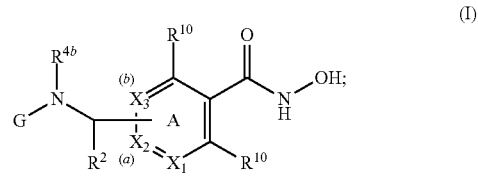

wherein ring A, $X_1$, $X_2$, $X_3$, $R^2$, $R^{4b}$, $R^{10}$, and G have values as described in the specification, useful as inhibitors of HDAC6. The invention also provides pharmaceutical compositions comprising the compounds of the invention, and methods of using the compositions in the treatment of proliferative, inflammatory, infectious, neurological or cardiovascular diseases or disorders.

24 Claims, No Drawings

(51) Int. Cl.

| | | |
|---|---|---|
| *C07D 207/34* | (2006.01) | |
| *C07D 209/42* | (2006.01) | |
| *C07D 211/62* | (2006.01) | |
| *C07D 231/14* | (2006.01) | |
| *C07D 233/84* | (2006.01) | |
| *C07D 237/28* | (2006.01) | |
| *C07D 239/28* | (2006.01) | |
| *C07D 277/56* | (2006.01) | |
| *C07D 277/64* | (2006.01) | |
| *C07D 307/84* | (2006.01) | |
| *C07D 311/14* | (2006.01) | |
| *C07D 333/68* | (2006.01) | |
| *C07D 417/04* | (2006.01) | |
| *C07D 491/04* | (2006.01) | |
| *C07D 241/44* | (2006.01) | |
| *C07D 285/14* | (2006.01) | |
| *C07D 307/85* | (2006.01) | |
| *C07D 333/70* | (2006.01) | |

(56) References Cited

OTHER PUBLICATIONS

Sigma-Aldrich (Hydroxamic acid inhibitors, 2015, Sigma Aldrich website).*
Maeda et al (Biol. Pharm. Bull., 2005, vol. 28, pp. 849-853).*
English translation of WO 03070691 A1, Microsoft translator, May 23, 2015.*
Patani et al (Chem Rev, 1996, pp. 3147-3176).*
Price, Steve et al., "Histone Deacetylase Inhibitors: An Analysis of Recent Patenting Activity," *Expert Opinion on Therapeutic Patents*, vol. 17, No. 7 (2007) pp. 745-765.

\* cited by examiner

SUBSTITUTED HYDROXAMIC ACIDS AND USES THEREOF

PRIORITY CLAIM

The present application is a continuation of U.S. patent application Ser. No. 13/034,974, filed Feb. 25, 2011, which claims the benefit under 35 U.S.C. §119(e) of U.S. Provisional Patent Application Ser. No. 61/339,138, filed Feb. 26, 2010, and U.S. Provisional Patent Application Ser. No. 61/426,314, filed Dec. 22, 2010. The entire contents of each of the above-referenced patent applications are incorporated herein by this reference.

FIELD OF THE INVENTION

The invention relates to compounds and methods for the selective inhibition of HDAC6. The present invention relates to compounds useful as HDAC6 inhibitors. The invention also provides pharmaceutical compositions comprising the compounds of the invention and methods of using the compositions in the treatment of various diseases.

BACKGROUND OF THE INVENTION

Histone deacetylase 6 (HDAC6) is a member of a family of amidohydrolases commonly referred as histone or lysine deacetylases (HDACs or KDACs) as they catalyze the removal of acetyl groups from the s-amino group of lysine residues from proteins. The family includes 18 enzymes which can be divided in 3 main classes based on their sequence homology to yeast enzymes Rpd3 (Class I), Hda1 (Class II) and Sir2 (Class III). A fourth class was defined with the finding of a distinct mammalian enzyme—HDAC11 (reviewed in Yang, et al., *Nature Rev. Mol. Cell. Biol.* 2008, 9:206-218 and in Saunders and Verdin, *Oncogene* 2007, 26(37):5489-5504). Biochemically, Class I (HDAC1, 2, 3, 8) and Class II (HDAC4, 5, 6, 7, 9, 10) and Class IV (HDAC11) are $Zn^{2+}$-dependent enzymes, while Class III (SIRT1-7) are dependent on nicotinamide adenine dinucleotide ($NAD^+$) for activity. Unlike all other HDACs, HDAC6 resides primarily in the cytosol. It has 2 functional catalytic domains and a carboxy-terminal $Zn^{2+}$-finger ubiquitin binding domain that binds ubiquitinated misfolded proteins (Kawaguchi et al., *Cell* 2003, 115(6):727-738), ubiquitin (Boyaullt et al., *EMBO J.* 2006, 25(14): 3357-3366), as well as ubiquitin-like FAT10 modifier (Kalveram et al., *J. Cell Sci.* 2008, 121(24):4079-4088). Known substrates of HDAC6 include cytoskeletal proteins α-tubulin and cortactin; β-catenin which forms part of adherens junctions and anchors the actin cytoskeleton; the chaperone Hsp90; and the redox regulatory proteins peroxiredoxin (Prx) I and Prx II (reviewed in Boyault et al., *Oncogene* 2007, 26(37):5468-5476; Matthias et al., *Cell Cycle* 2008, 7(1):7-10; Li et al., *J Biol. Chem.* 2008, 283(19):12686-12690; Parmigiani et al., *Proc. Natl. Acad. Sci. USA* 2009, 105(28):9633-9638). Thus, HDAC6 mediates a wide range of cellular functions including microtubule-dependent trafficking and signaling, membrane remodeling and chemotactic motility, involvement in control of cellular adhesion, ubiquitin level sensing, regulation of chaperone levels and activity, and responses to oxidative stress. All of these functions may be important in tumorigenesis, tumor growth and survival as well as metastasis (Simms-Waldrip et al., *Mol. Genet. Metabolism* 2008, 94(3):283-286; Rodriguez-Gonzalez et al., *Cancer Res.* 2008, 68(8):2557-2560; Kapoor, *Int. J. Cancer* 2009, 124:509; Lee et al., *Cancer Res.* 2008, 68(18):7561-7569). Recent studies have shown HDAC6 to be important in autophagy, an alternative pathway for protein degradation that compensates for deficiencies in the activity of the ubiquitin proteasome system or expression of proteins prone to form aggregates and can be activated following treatment with a proteasome inhibitor (Kawaguchi et al., *Cell* 2003, 115(6):727-738; Iwata et al., *J. Biol. Chem.* 2005, 280(48): 40282-40292; Ding et al., *Am. J. Pathol.* 2007, 171:513-524, Pandey et al., *Nature* 2007, 447(7146):860-864). Although the molecular mechanistic details are not completely understood, HDAC6 binds ubiquitinated or ubiquitin-like conjugated misfolded proteins which would otherwise induce proteotoxic stress and then serves as an adaptor protein to traffic the ubiquitinated cargo to the microtubule organizing center using the microtubule network via its known association with dynein motor protein. The resulting perinuclear aggregates, known as aggresomes, are then degraded by fusion with lysosomes in an HDAC6- and cortactin-dependent process which induces remodeling of the actin cytoskeleton proximal to aggresomes (Lee et al., *EMBO J.* 2010, 29:969-980). In addition, HDAC6 regulates a variety of biological processes dependent on its association with the microtubular network including cellular adhesion (Tran et al., *J. Cell Sci.* 2007, 120(8):1469-1479) and migration (Zhang et al., *Mol. Cell.* 2007, 27(2):197-213; reviewed in Valenzuela-Fernandez et al., *Trends Cell. Biol.* 2008, 18(6):291-297), epithelial to mesenchymal transition (Shan et al., *J. Biol. Chem.* 2008, 283 (30):21065-21073), resistance to anoikis (Lee et al., *Cancer Res.* 2008, 68(18):7561-7569), epithelial growth factor-mediated Wnt signaling via β-catenin deacetylation (Li et al., *J. Biol. Chem.* 2008, 283(19):12686-12690) and epithelial growth factor receptor stabilization by endocytic trafficking (Lissanu Deribe et al., *Sci. Signal.* 2009, 2(102): ra84; Gao et al., *J. Biol. Chem.* 2010, 285:11219-11226); all events that promote oncogenesis and metastasis (Lee et al., *Cancer Res.* 2008, 68(18):7561-7569). HDAC6 activity is known to be upregulated by Aurora A kinase in cilia formation (Pugacheva et al., *Cell* 2007, 129(7):1351-1363) and indirectly by farnesyl transferase with which HDAC6 forms a complex with microtubules (Zhou et al., *J. Biol. Chem.* 2009, 284(15): 9648-9655). Also, HDAC6 is negatively regulated by tau protein (Perez et al., *J. Neurochem.* 2009, 109(6): 1756-1766).

Diseases in which selective HDAC6 inhibition could have a potential benefit include cancer (reviewed in Simms-Waldrip et al., *Mol. Genet. Metabolism* 2008, 94(3):283-286 and Rodriguez-Gonzalez et al., *Cancer Res.* 2008, 68(8):2557-2560), specifically: multiple myeloma (Hideshima et al., *Proc. Natl. Acad. Sci. USA* 2005, 102(24):8567-8572); lung cancer (Kamemura et al., *Biochem. Biophys. Res. Commun.* 2008, 374(1):84-89); ovarian cancer (Bazzaro et al., *Clin. Cancer Res.* 2008, 14(22):7340-7347); breast cancer (Lee et al., *Cancer Res.* 2008, 68(18):7561-7569); prostate cancer (Mellado et al., *Clin. Trans. Onco.* 2009, 11(1):5-10); pancreatic cancer (Nawrocki et al., *Cancer Res.* 2006, 66(7): 3773-3781); renal cancer (Cha et al., *Clin. Cancer Res.* 2009, 15(3):840-850); and leukemias such as acute myeloid leukemia (AML) (Fiskus et al., *Blood* 2008, 112(7):2896-2905) and acute lymphoblastic leukemia (ALL) (Rodriguez-Gonzalez et al., *Blood* 2008, 112(11): Abstract 1923).

Inhibition of HDAC6 may also have a role in cardiovascular disease, i.e. cardiovascular stress, including pressure overload, chronic ischemia, and infarction-reperfusion injury (Tannous et al., *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Huntington's disease (reviewed in Kazantsev et al., *Nat. Rev. Drug Disc.* 2008, 7(10):854-868; see also Dompierre et al., *J. Neurosci.* 2007, 27(13):3571-3583; Kozikowski et al., *J. Med. Chem.* 2007, 50:3054-3061) or central nervous system trauma caused by tissue injury, oxidative-stress induced neuronal or axomal degeneration (Rivieccio et al., *Proc. Natl. Acad. Sci. USA* 2009, 106(46):19599-195604); and inflammation, including reduction of pro-inflammatory cytokine IL-1β (Carta et al., *Blood* 2006, 108(5):1618-1626), increased expression of the FOXP3 transcription factor, which induces immunosuppressive function of regulatory T-cells resulting in benefits in chronic diseases such as rheumatoid arthritis, psoriasis, multiple sclerosis, lupus and organ transplant rejection (reviewed in Wang et al., *Nat. Rev. Drug Disc.* 2009, 8(12):969-981).

Given the complex function of HDAC6, selective inhibitors could have potential utility when used alone or in combination with other chemotherapeutics such as microtubule destabilizing agents (Zhou et al., *J. Biol. Chem.* 2009, 284 (15): 9648-9655); Hsp90 inhibitors (Rao et al., *Blood* 2008, 112(5)1886-1893); inhibitors of Hsp90 client proteins, including receptor tyrosine kinases such as Her-2 or VEGFR (Bhalla et al., *J. Clin. Oncol.* 2006, 24(18S): Abstract 1923; Park et al., *Biochem. Biophys. Res. Commun.* 2008, 368(2): 318-322), and signaling kinases such as Bcr-Abl, Akt, mutant FLT-3, c-Raf, and MEK (Bhalla et al., *J. Clin. Oncol.* 2006, 24(18S): Abstract 1923; Kamemura et al., *Biochem. Biophys. Res. Commun.* 2008, 374(1):84-89); inhibitors of cell cycle kinases Aurora A and Aurora B (Pugacheva et al., *Cell* 2007, 129(7):1351-1363; Park et al., *J. Mol. Med.* 2008, 86(1):117-128; Cha et al., *Clin. Cancer Res.* 2009, 15(3):840-850); EGFR inhibitors (Lissanu Deribe et al., *Sci. Signal.* 2009, 2(102): ra84; Gao et al., *J. Biol. Chem.* 2010, 285:11219-11226) and proteasome inhibitors (Hideshima et al., *Proc. Natl. Acad. Sci. USA* 2005, 102(24):8567-8572) or other inhibitors of the ubiquitin proteasome system such as ubiquitin and ubiqutin-like activating (E1), conjugation (E2), ligase enzymes (E3, E4) and deubiquitinase enzymes (DUBs) as well as modulators of autophagy and protein homeostasis pathways. In addition, HDAC6 inhibitors could be combined with radiation therapy (Kim et al., *Radiother. Oncol.* 2009, 92(1):125-132.

Clearly, it would be beneficial to provide novel HDAC6 inhibitors that possess good therapeutic properties, especially for the treatment of proliferative diseases or disorders.

DETAILED DESCRIPTION OF THE INVENTION

1. General Description of Compounds of the Invention

The present invention provides compounds that are effective inhibitors of HDAC6. These compounds are useful for inhibiting HDAC6 activity in vitro and in vivo, and are especially useful for the treatment of various cell proliferative diseases or disorders. The compounds of the invention are represented by formula (I):

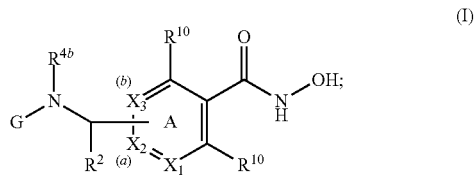

or a pharmaceutically acceptable salt thereof; wherein:
ring A is an aromatic 6-membered ring connected through one of positions (a) or (b);
$X_1$ is $CR^1$ or N;
(i) when ring A is connected through position (a), $X_2$ is C; and $X_3$ is $CR^1$ or N; or
(ii) when ring A is connected through position (b), $X_3$ is C; and $X_2$ is $CR^1$ or N;
each occurrence of $R^1$ is independently hydrogen, halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —NHC$_{1-3}$ alkyl, —N($C_{1-3}$alkyl)$_2$, —C(O)NHC$_{1-3}$ alkyl, —NHC(O)NHC$_{1-3}$ alkyl, or —NHS(O)$_2$C$_{1-3}$ alkyl;
each occurrence of $R^{10}$ is independently hydrogen, halogen, hydroxy, —O—$C_{1-3}$ alkyl, or —O—$C_{1-3}$-fluoroalkyl;
$R^2$ is $C_{1-6}$ aliphatic, $C_{1-6}$ fluoroaliphatic, or unsubstituted or substituted 6-10-membered aryl;
$R_{4b}$ is hydrogen, or $C_{1-4}$ aliphatic;
G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$;
$L_1$ is an unsubstituted or substituted $C_{1-3}$ alkylene chain;
$L_2$ is an unsubstituted or substituted $C_{2-3}$ alkylene chain;
$V_1$ is —C(O)—, —C(S)—, —C(O)—$CR^A$=$CR^A$—, —C(O)—N($R^{4a}$)—, —C(O)—O—, or —S(O)$_2$—;
$V_2$ is —N($R^{4a}$)—, —N($R^{4a}$)—C(O)—, —SO$_2$—N ($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—;
$R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each occurrence of $R^A$ is independently hydrogen, fluoro, or unsubstituted or substituted $C_{1-4}$ aliphatic; and
each occurrence of $R^{4a}$ is independently hydrogen, or unsubstituted or substituted $C_{1-4}$ aliphatic.

2. Compounds and Definitions

Compounds of this invention include those described generally for formula (I) above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms.

Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide.

When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR+ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_n-$, wherein n' is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents, can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-OR^+$, $-SR^\circ$, $-S(O)R^\circ$, $-SO_2R^\circ$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^\circ$, $-NR^+CO_2R^+$, $-NR^+SO_2R^\circ$, $-NR^+SO_2N(R^+)_2$, $-O-C(O)R^+$, $-O-CO_2R^+$, $-OC(O)N(R^+)_2$, $-C(O)R^+$, $-C(S)R^\circ$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^\circ)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^\circ$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: $=O$, $=S$, $=C(R^*)_2$, $=N-N(R^*)_2$, $=N-OR^*$, $=N-NHC(O)R^*$, $=N-NHCO_2R^\circ$, $=N-NHSO_2R^\circ$ or $=N-R^*$ where $R^\circ$ is defined above, and each $R^*$ is independently selected from hydrogen or an optionally substituted $C_{1-6}$ aliphatic group.

In addition to the substituents defined above and herein, optional substituents on the nitrogen of a non-aromatic heterocyclic ring also include and are generally selected from $-R^+$, $-N(R^+)_2$, $-C(O)R^+$, $-C(O)OR^+$, $-C(O)C(O)R^+$, $-C(O)CH_2C(O)R^+$, $-S(O)_2R^+$, $-S(O)_2N(R^+)_2$, $-C(S)N(R^+)_2$, $-C(=NH)-N(R^+)_2$, or $-N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R⁺ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R⁺ (or any other variable similarly defined in the specification and claims herein), are taken together with their intervening atom(s) include, but are not limited to the following: a) two independent occurrences of R⁺ (or any other variable similarly defined in the specification or claims herein) that are bound to the same atom and are taken together with that atom to form a ring, for example, N(R⁺)₂, where both occurrences of R⁺ are taken together with the nitrogen atom to form a piperidin-1-yl, piperazin-1-yl, or morpholin-4-yl group; and b) two independent occurrences of R⁺ (or any other variable similarly defined in the specification or claims herein) that are bound to different atoms and are taken together with both of those atoms to form a ring, for example where a phenyl group is substituted with two occurrences of OR⁺

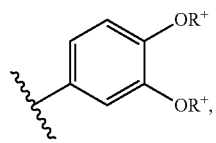

these two occurrences of R⁺ are taken together with the oxygen atoms to which they are bound to form a fused 6-membered oxygen containing ring:

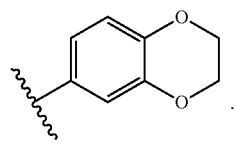 [SMILES: *c1ccc2c(c1)OCCO2]

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention. Such compounds are useful, for example, as analytical tools or probes in biological assays.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

It is to be understood that, when a disclosed compound has at least one chiral center, the present invention encompasses one enantiomer of the compound, substantially free from the corresponding optical isomer, a racemic mixture of both optical isomers of the compound, and mixtures enriched in one enantiomer relative to its corresponding optical isomer. When a mixture is enriched in one enantiomer relative to its optical isomer, the mixture contains, for example, an enantiomeric excess of at least 50%, 75%, 90%, 95%, 99%, or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer substantially free of other diastereomers, an enantiomeric pair of diastereomers substantially free of other stereoisomers, mixtures of diastereomers, mixtures of enantiomeric pairs of diastereomers, mixtures of diastereomers in which one diastereomer is enriched relative to the other diastereomer(s), and mixtures of enantiomeric pairs of diastereomers in which one enantiomeric pair of diastereomers is enriched relative to the other stereoisomers. When a mixture is enriched in one diastereomer or enantiomeric pair of diastereomers pairs relative to the other stereoisomers, the mixture is enriched with the depicted or referenced diastereomer or enantiomeric pair of diastereomers relative to other stereoisomers for the compound, for example, by a molar excess of at least 50%, 75%, 90%, 95%, 99%, or 99.5%.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer=(R*R+S*S): (R*S+S*R).

One of ordinary skill in the art will recognize that additional stereoisomers are possible when the molecule has more than two chiral centers. For purposes of the present invention, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diastereomeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (HPLC) methods.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In some embodiments, the compound of formula (I) is represented by:

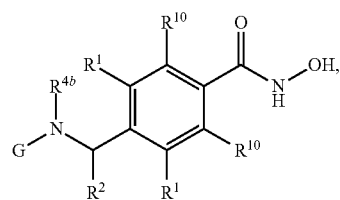

(I-i)

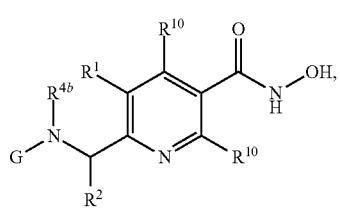

(I-ii)

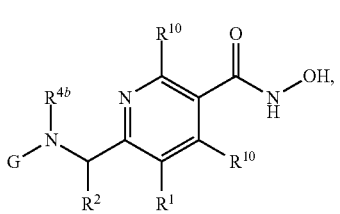

(I-iii)

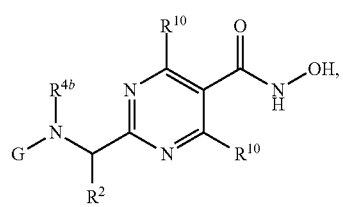

(I-iv)

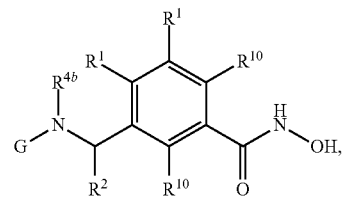

(I-v)

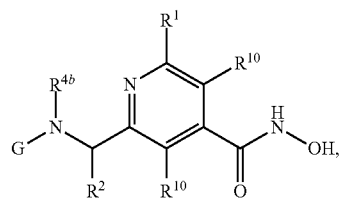

(I-vi)

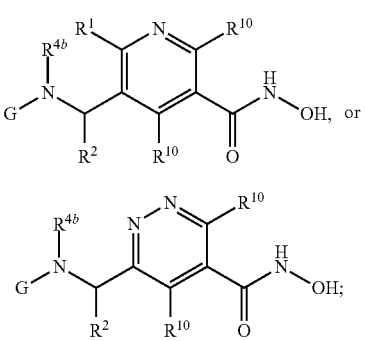

(I-vii)

(I-viii)

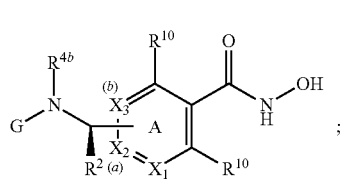

wherein $R^{10}$, $R^{10}$, $R^2$, $R^{4b}$, and G have the values described herein. In certain embodiments, the compound of formula (I) is represented by formulas (I-i) or (I-v), wherein $R^1$, $R^{10}$, $R^2$, $R^b$, and G have the values described herein.

In some embodiments, the compound of formula (I) is represented by formula (II-a):

(II-a)

wherein:
ring A is an aromatic 6-membered ring connected through one of positions (a) or (b);
$X_1$ is $CR^1$ or N;
(i) when ring A is connected through position (a), $X_2$ is C; and $X_3$ is $CR^1$ or N; or
(ii) when ring A is connected through position (b), $X_3$ is C; and $X_2$ is $CR^1$ or N;
and $R^1$, $R^{10}$, $R^2$, $R^{4b}$, and G have the values described herein.

In some embodiments, the compound of formula (II-a) is represented by:

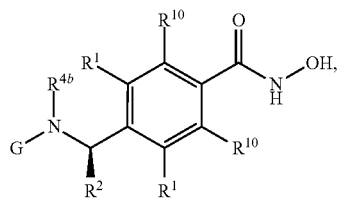
(II-a-i)

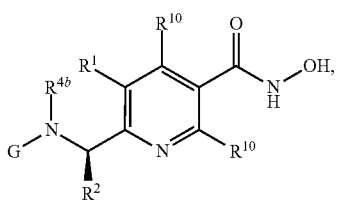
(II-a-ii)

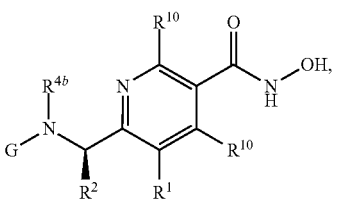
(II-a-iii)

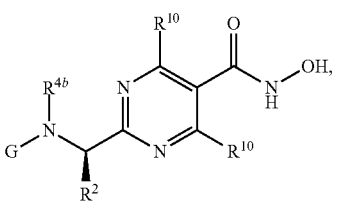
(II-a-iv)

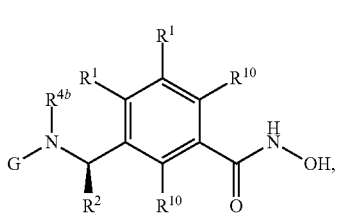
(II-a-v)

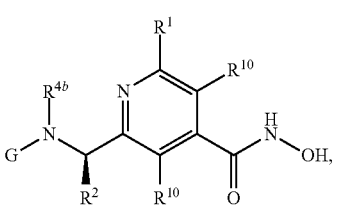
(II-a-vi)

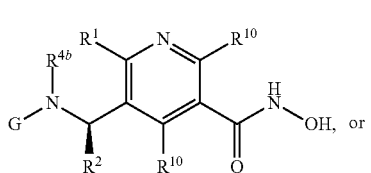
(II-a-vii)

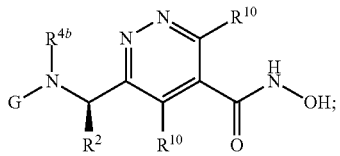
(II-a-viii)

wherein $R^1$, $R^{10}$, $R^2$, $R^{4b}$, and G have the values described herein. In certain embodiments, the compound of formula (II-a) is represented by formulas or (II-a-v), wherein $R^1$, $R^{10}$, $R^2$, $R^{4b}$, and G have the values described herein.

In some embodiments, the compound of formula (I) is represented by formula (II-b):

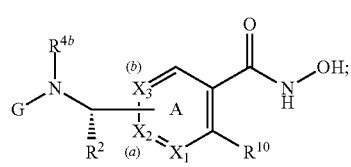
(II-b)

wherein:

ring A is an aromatic 6-membered ring connected through one of positions (a) or (b);

wherein:

$X_1$ is $CR^1$ or N;

(i) when ring A is connected through position (a), $X_2$ is C; and $X_3$ is $CR^1$ or N; or (ii) when ring A is connected through position (b), $X_3$ is C; and $X_2$ is $CR^1$ or N; and $R^1$, $R^{10}$, $R^2$, $R^{4b}$, and G have the values described herein.

In some embodiments, the compound of formula (II-b) is represented by:

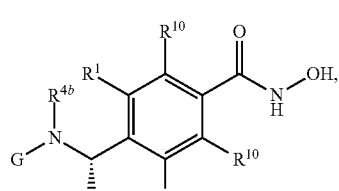
(II-b-i)

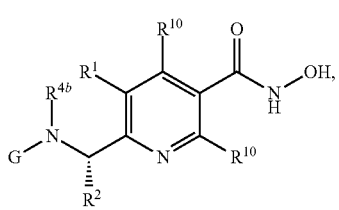
(II-b-ii)

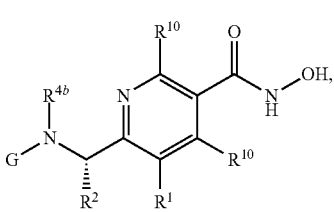
(II-b-iii)

-continued

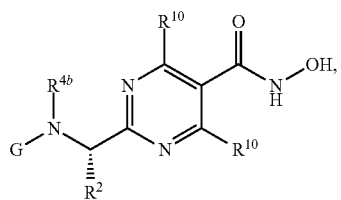
(II-b-iv)

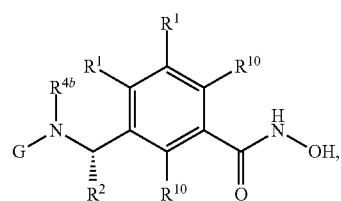
(II-b-v)

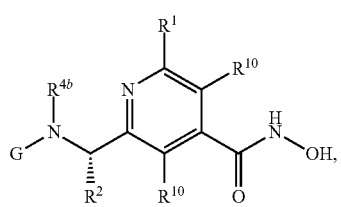
(II-b-vi)

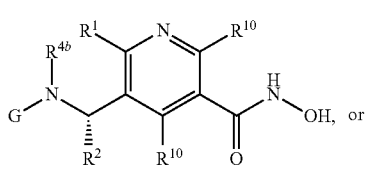
(II-b-vii)

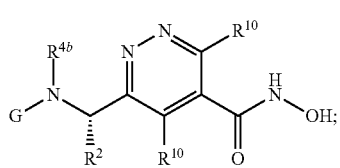
(II-b-viii)

wherein $R^1$, $R^{10}$, $R^2$, $R^{4b}$, and G have the values described herein. In certain embodiments, the compound of formula (II) is represented by formulas (II-b-i) or (II-b-v), wherein $R^1$, $R^{10}$, $R^2$, $R^{4b}$, and G have the values described herein.

In some embodiments, the compound of formula (I) is represented by:

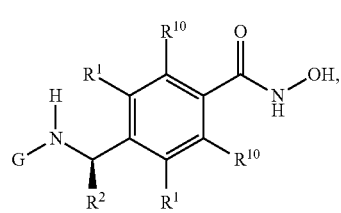
(III-a-i)

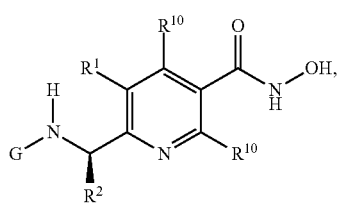
(III-a-ii)

-continued

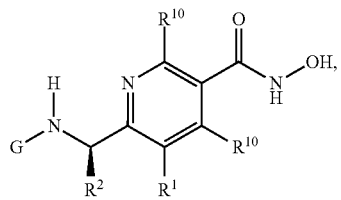
(III-a-iii)

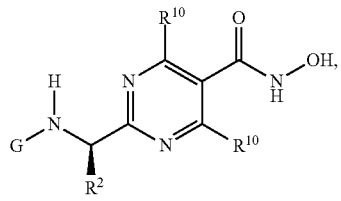
(III-a-iv)

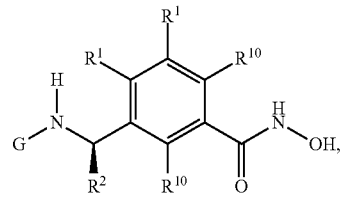
(III-a-v)

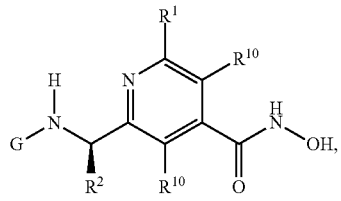
(III-a-vi)

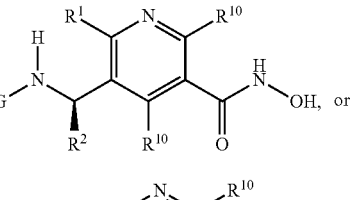
(III-a-vii)

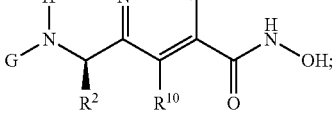
(III-a-viii)

wherein $R^1$, $R^{10}$, $R^2$, and G have the values described herein. In certain embodiments, the compound of formula (I) is represented by formulas (III-a-i) or (III-a-v), wherein $R^1$, $R^{10}$, $R^2$, and G have the values described herein.

The values described below for each variable are with respect to any of formulas (I), (II), (III), (IV), (V), (VI), or their sub-formulas as described herein.

Each occurrence of the variable $R^1$ is independently hydrogen, halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —NHC$_{1-3}$ alkyl, —N($C_{1-3}$ alkyl)$_2$, —C(O)NHC$_{1-3}$ alkyl, —NHC(O)NHC$_{1-3}$ alkyl, or —NHS(O)$_2$C$_{1-3}$ alkyl. In some embodiments, each occurrence of $R^1$ is independently hydrogen, chloro, fluoro, $C_{1-4}$ alkyl, —O—$C_{1-3}$ alkyl, trifluoromethyl, hydroxy, or cyano. In certain embodiments, each occurrence of $R^1$ is independently hydrogen, chloro, fluoro, hydroxy, methoxy, ethoxy, n-propoxy, isopropoxy, cyano, trifluoromethyl, methyl, ethyl, isopropyl, n-propyl, or tert-butyl. In certain embodiments, each occurrence of $R^1$ is independently hydrogen, chloro, fluoro, hydroxy, trifluoromethyl, or methyl. In certain embodiments, $R^1$ is hydrogen.

Each occurrence of the variable $R^{10}$ is independently hydrogen, halogen, hydroxy, alkyl, or —O—$C_{1-3}$ fluoroalkyl. In some embodiments, $R^{10}$ is hydrogen, chloro, fluoro, hydroxy, methoxy, or ethoxy. In some embodiments, $R^{10}$ is hydrogen.

The variable $R^2$ is $C_{1-6}$ aliphatic, $C_{1-6}$ fluoroaliphatic, or unsubstituted or substituted 6-10-membered aryl. In some embodiments, $R^2$ is methyl, ethyl, isopropyl, n-propyl, n-butyl, isobutyl, sec-butyl, tert-butyl, pentyl, hexyl, cyclopropyl, cyclobutyl, cyclopentyl, cyclohexyl, trifluoromethyl, or phenyl. In certain embodiments, $R^2$ is methyl, ethyl, isopropyl, n-propyl, trifluoromethyl, tert-butyl, cyclopropyl, or phenyl. In certain embodiments, $R^2$ is methyl, ethyl, isopropyl, or n-propyl.

The variable $R^{4b}$ is hydrogen, or $C_{1-4}$ aliphatic. In some embodiments, $R^{4b}$ is hydrogen.

The variable G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$, wherein $L_1$, $L_2$, $V_1$, $V_2$, and $R^3$ have the values described herein. In some embodiments, G is —$V_1$—$R^3$, or —$V_1$-$L_1$-$R^3$, wherein $L_1$, $V_1$, and $R^3$ have the values described herein. In certain embodiments, G is —$V_1$—$R^3$, wherein $V_1$, and $R^3$ have the values described herein.

The variable $L_1$ is an unsubstituted or substituted $C_{1-3}$ alkylene chain. In some embodiments, $L_1$ is —$CH_2$—, —$CH_2CH_2$—, or —$CH_2CH_2CH_2$—. In certain embodiments, $L_1$ is —$CH_2$—.

The variable $L_2$ is an unsubstituted or substituted $C_{2-3}$ alkylene chain. In some embodiments, $L_2$ is —$CH_2CH_2$— or —$CH_2CH_2CH_2$—.

The variable $V_1$ is —C(O)—, —C(S)—, —C(O)—$CR^A$=$CR^A$—, —C(O)—N($R^{4a}$)—, —C(O)—O—, or —S(O)$_2$—, wherein $R^A$ and $R^{4a}$ have the values described herein. In some embodiments, $V_1$ is —C(O)—, —C(O)—N($R^{4a}$)—, or —S(O)$_2$—, wherein $R^{4a}$ has the values described herein. In certain embodiments, $V_1$ is —C(O)—, —C(O)—NH—, or —S(O)$_2$—. In other certain embodiments, $V_1$ is —C(O)—.

Each occurrence of the variable $R^A$ is independently hydrogen, halo, or an optionally substituted $C_{1-4}$ aliphatic group. In some embodiments, each occurrence of $R^A$ is independently hydrogen, fluoro or methyl. In certain embodiments, each occurrence of $R^A$ is hydrogen.

Each occurrence of the variable $R^{4a}$ is independently hydrogen, or unsubstituted or substituted $C_{1-4}$ aliphatic. In certain embodiments, $R^{4a}$ is hydrogen.

The variable $V_2$ is —N($R^{4a}$)—, —N($R^{4a}$)—C(O)—, —SO$_2$—N($R^{4a}$)—, —N$R^{4a}$—SO$_2$—, —O—, —S—, —S(O)—, —N($R^{4a}$)—C(O)—N$R^{4a}$—, —N($R^{4a}$)—C(O)—O—, —O—C(O)—N$R^{4a}$—, or —N($R^{4a}$)—SO$_2$—N($R^{4a}$)—, wherein $R^{4a}$ has the values described herein. In some embodiments, $V_2$ is —N($R^{4a}$)—, —N$R^{4a}$—C(O)—, —SO$_2$—N($R^{4a}$)—, —N($R^{4a}$)—SO$_2$—, —O—, or —S—, wherein $R^{4a}$ has the values described herein. In certain embodiments, $V_2$ is —N($R^{4a}$)—, —O—, or —S—, wherein $R^{4a}$ has the values described herein. In certain embodiments, $V_2$ is —NH—, or —O—.

The variable $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:
  each substitutable carbon chain atom in $R^3$ is unsubstituted or substituted with 1-2 occurrences of —$R^{5dd}$;
  each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;
  each substitutable unsaturated ring carbon atom in $R^3$ is unsubstituted or is substituted with —$R^{5a}$; and
  each substitutable ring nitrogen atom in $R^3$ is unsubstituted or substituted with —$R^{9b}$;
  wherein $R^{5dd}$, $R^4$, $R^5$, $R^6$, $R^{5a}$, and $R^{9b}$ have the values described herein.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:
  each substitutable carbon chain atom in $R^3$ is unsubstituted or substituted with 1-2 occurrences of —$R^{5dd}$;
  each substitutable saturated ring carbon atom in $R^3$ is unsubstituted or substituted with =O, =S, =C($R^5$)$_2$, =N—$R^5$ or —$R^{5a}$;
  each substitutable unsaturated ring carbon atom in $R^3$ is unsubstituted or is substituted with —$R^{5a}$; and
  each substitutable ring nitrogen atom in $R^3$ is unsubstituted or substituted with —$R^{9b}$;
  wherein $R^{5dd}$, $R^5$, $R^{5a}$, and $R^{9b}$ have the values described herein.

In certain embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:
  each substitutable carbon chain atom in $R^3$ is unsubstituted or substituted with 1-2 occurrences of —$R^{5dd}$;
  each substitutable saturated ring carbon atom in $R^3$ is unsubstituted or substituted with —$R^{5a}$;
  each substitutable unsaturated ring carbon atom in $R^3$ is unsubstituted or is substituted with —$R^{5a}$;
  the total number of $R^{5a}$ substituents is p; and
  each substitutable ring nitrogen atom in $R^3$ is unsubstituted or substituted with —$R^{9b}$;
  wherein $R^{5dd}$, $R^{5a}$, $R^{9b}$, and p have the values described herein.

In some embodiments, $R^3$ is unsubstituted or substituted $C_{1-6}$ aliphatic. In certain embodiments, each substitutable carbon chain atom in $R^3$ is unsubstituted or substituted with 1-2 occurrences of —$R^{5dd}$, wherein $R^{5dd}$ has the values described herein. In certain embodiments, $R^3$ is methyl, ethyl, n-propyl, isopropyl, tert-butyl; n-butyl, iso-butyl, pentyl, hexyl, butenyl, propenyl, pentenyl, or hexenyl, wherein each of the forementioned groups is unsubstituted or substituted.

In certain embodiments, $R^3$ is methyl, ethyl, n-propyl, isopropyl, tert-butyl, n-butyl, iso-butyl, pentyl, hexyl, butenyl, propenyl, pentenyl, or hexenyl, wherein each substitutable carbon chain atom in $R^3$ is unsubstituted or substituted with 1-2 occurrences of —$R^{5dd}$, wherein $R^{5dd}$ has the values described herein.

In some embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:
  each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;
  each substitutable unsaturated ring carbon atom in $R^3$ is unsubstituted or is substituted with —$R^{5a}$; and
  each substitutable ring nitrogen atom in $R^3$ is unsubstituted or substituted with —$R^{9b}$;
  wherein $R^4$, $R^5$, $R^6$, $R^{5a}$, and $R^{9b}$ have the values described herein.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:
  each substitutable saturated ring carbon atom in $R^3$ is unsubstituted or substituted with =O, =S, =C($R^5$)$_2$, =N—$R^5$ or —$R^{5a}$;
  each substitutable unsaturated ring carbon atom in $R^3$ is unsubstituted or is substituted with —$R^{5a}$; and
  each substitutable ring nitrogen atom in $R^3$ is unsubstituted or substituted with —$R^{9b}$;
  wherein $R^5$, $R^{5a}$, and $R^{9b}$ have the values described herein.

In certain embodiments, $R^3$ is unsubstituted or substituted unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:
  each substitutable saturated ring carbon atom in $R^3$ is unsubstituted or substituted with —$R^{5a}$;
  each substitutable unsaturated ring carbon atom in $R^3$ is unsubstituted or is substituted with —$R^{5a}$;
  the total number of $R^{5a}$ substituents is p; and
  each substitutable ring nitrogen atom in $R^3$ is unsubstituted or substituted with —$R^{9b}$;
  wherein $R^{5a}$, $R^{9b}$, and p have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:
  each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;
  each substitutable unsaturated ring carbon atom in $R^3$ is unsubstituted or is substituted with —$R^{5a}$; and each substitutable ring nitrogen atom in $R^3$ is unsubstituted or substituted with —$R^{9b}$;
  wherein $R^4$, $R^5$, $R^6$, $R^{5a}$, and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:
  each substitutable saturated ring carbon atom in $R^3$ is unsubstituted or substituted with =O, =S, =C($R^5$)$_2$, =N—$R^5$, or —$R^{5a}$;
  each substitutable unsaturated ring carbon atom in $R^3$ is unsubstituted or is substituted with —$R^{5a}$; and
  each substitutable ring nitrogen atom in $R^3$ is unsubstituted or substituted with —$R^{9b}$;
  wherein $R^5$, $R^{5a}$, and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiamorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with —$R^{5a}$;

each substitutable unsaturated ring carbon atom in $R^3$ is unsubstituted or is substituted with —$R^{5a}$;

the total number of $R^{5a}$ substituents is p; and each substitutable ring nitrogen atom in $R^3$ is unsubstituted or substituted with —$R^{9b}$;

wherein $R^{5a}$, $R^{9b}$, and p have the values described herein.

In some embodiments, each occurrence of $R^{5dd}$ is independently halogen, hydroxy, alkyl), cyano, —$N(R^4)_2$, —$C(O)(C_{1-3}$ alkyl), —$CO_2H$, —$CO_2(C_{1-3}$ alkyl), —$C(O)NH_2$, or —$C(O)NH(C_{1-3}$ alkyl). In certain embodiments, each occurrence of $R^{5dd}$ is independently fluoro, hydroxy, methoxy, ethoxy, or —$C(O)NHCH_3$.

Each $R^4$ is independently hydrogen, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur.

Each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^6$ is independently unsubstituted or substituted $C_{1-6}$ aliphatic, or unsubstituted or substituted 6-10-membered aryl.

Each $R^7$ is independently unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^{9b}$ is independently —$C(O)R^5$, —$C(O)N(R^4)_2$, —$CO_2R^6$, —$SO_2R^6$, —$SO_2N(R^4)_2$, unsubstituted $C_{1-4}$ aliphatic, or $C_{1-4}$ aliphatic substituted with 1-2 independent occurrences of $R^7$ or $R^8$, wherein $R^7$ and $R^8$ have the values described herein.

Each $R^8$ is independently halogen, —OH, —O($C_{1-3}$ alkyl), —CN, —$N(R^4)_2$, —$C(O)(C_{1-3}$ alkyl), —$CO_2H$, —$CO_2(C_{1-3}$ alkyl), —$C(O)NH_2$, or —$C(O)NH(C_{1-3}$ alkyl), wherein $R^4$ has the values described herein.

Each $R^{5a}$ is independently halogen, —$NO_2$, —CN, —$C(R^5)=C(R^5)_2$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —$OC(O)N(R^4)_2$, —$C(O)$—$C(O)R^5$, —$C(O)R^5$, —$C(O)N(R^4)_2$, —$C(=NR^4)$—$N(R^4)_2$, —$C(=NR^4)$—$OR^5$, —$N(R^4)$—$N(R^4)_2$, —$N(R^4)C(=NR^4)$—$N(R^4)_2$, —$N(R^4)SO_2R^6$, —$N(R^4)SO_2N(R^4)_2$, —$P(O)(R^5)_2$, —$P(O)(OR^5)_2$, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{ya}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur, wherein $R^5$, $R^6$, and $R^4$ have the values described herein.

In some embodiments, each $R^{5a}$ is independently halogen, —CN, —OH, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{2-3}$ alkyl, —NHC(O)NHC$_{1-3}$ alkyl, —NHS(O)$_2C_{1-3}$ alkyl, 3-10-membered cycloaliphatic substituted with 0-2 occurrences of —$R^{7a}$, 4-10-membered heterocyclyl having 1-5 heteroatoms independently selected from nitrogen, oxygen, and sulfur substituted with 0-2 occurrences of —$R^{7a}$, 6-10-membered aryl substituted with 0-2 occurrences of —$R^{7a}$, or 5-10-membered heteroaryl having 1-5 heteroatoms independently selected from nitrogen, oxygen, and sulfur substituted with 0-2 occurrences of —$R_{7a}$ wherein $R^{7a}$ has the values described herein.

In certain embodiments, each $R^{5a}$ is independently chloro, fluoro, hydroxy, methoxy, ethoxy, n-propoxy, isopropoxy, cyano, trifluoromethyl, methyl, ethyl, isopropyl, n-propyl, tert-butyl or phenyl.

Each occurrence of the variable $R^{7a}$ is independently halogen, $C_{1-3}$ alkyl, $C_{1-3}$ fluoroalkyl, $C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, or —NHS(O)$_2C_{1-3}$ alkyl.

The variable p is 1-2. In some embodiments, p is 1.

In some embodiments, G is:

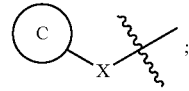

wherein X and Ring C have the values described herein.

In certain embodiments, G is:

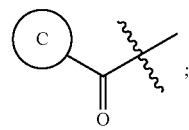

wherein Ring C has the values described herein.

The variable X is —C(O)— or -$L_{2a}$-$R^{3aa}$—$V_{2a}$—, wherein $L_{2a}$, $R^{3aa}$, and $V_{2a}$ have the values described herein. In some embodiments, X is —C(O)—. In some embodiments, X is -$L_{2a}$-$R^{3aa}$—$V_{2a}$—, wherein $L_{2a}$, $R^{3aa}$, and $V_{2a}$ have the values described herein. In some embodiments, X is —C(O)—, X-a 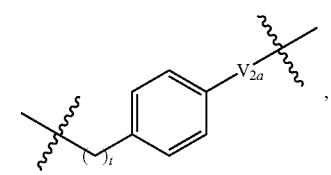
X-b 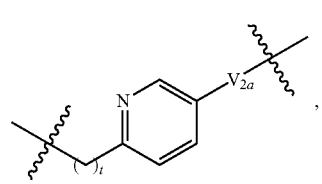
X-c 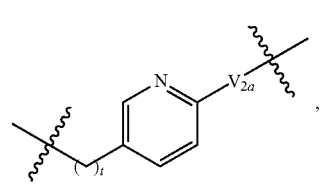
X-d 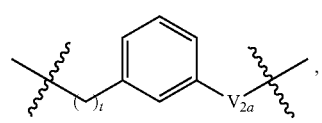
X-e 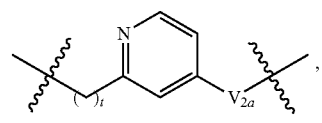
X-f 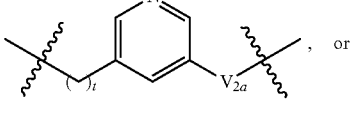, or
X-g 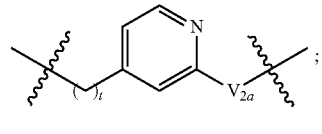;
wherein $V_{2a}$ and t have the values described herein. In certain embodiments, X is —C(O)—,
X-i 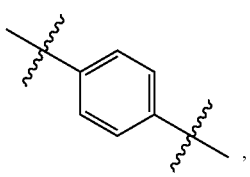
X-ii 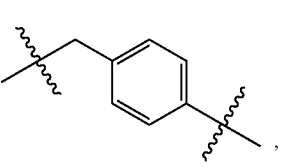
X-iii 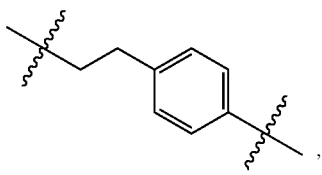
X-iv 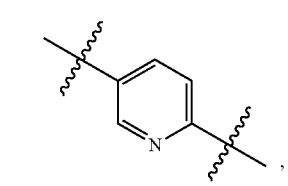
X-v 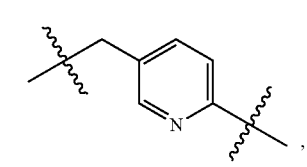
X-vi 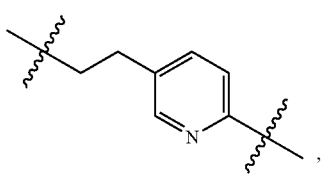
X-vii 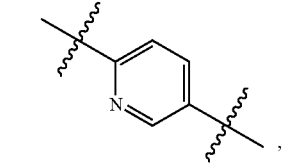
X-viii 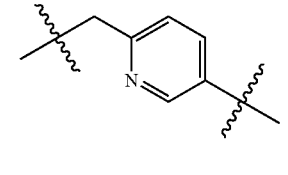
X-ix 
X-x 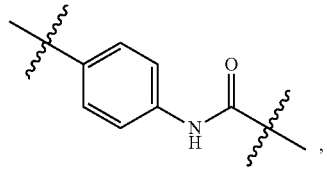
X-xi 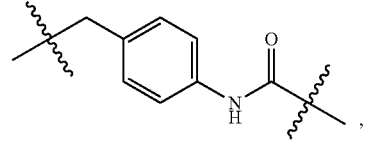

X-xii 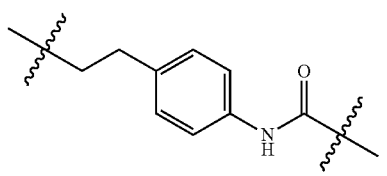,

X-xiii 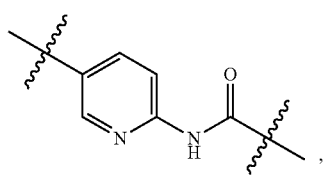,

X-xiv 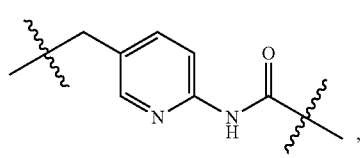,

X-xv ,

X-xvi 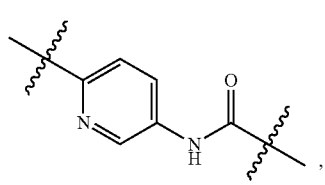,

X-xvii 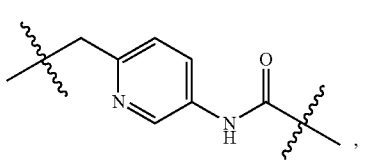,

X-xviii 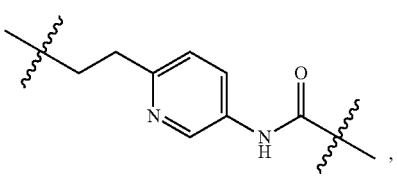,

X-xix 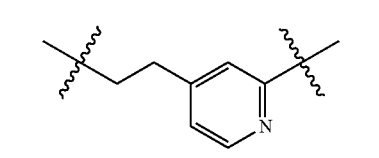,

X-xx 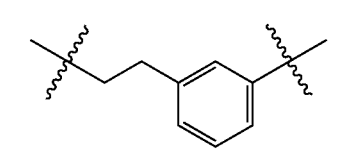,

X-xxi 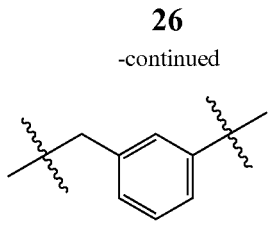,

X-xxii 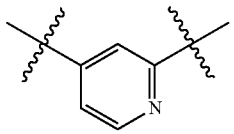,

X-xxiii 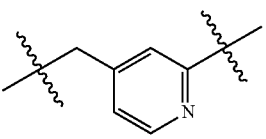,

X-xxiv 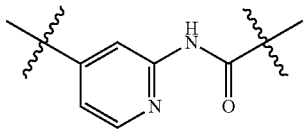, or

X-xxv 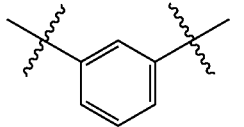.

In certain embodiments, X is —C(O)—, X-ii, X-xi, X-xii, X-xxii, X-xxiv, or X-xxv.

Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-4 occurrences of $R^{5b}$; wherein $R^{9bb}$, X, and $R^{5b}$ have the values described herein. In some embodiments, Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-2 occurrences of $R^{5b}$; wherein $R^{9bb}$, X, and $R^{5b}$ have the values described herein.

In certain embodiments, Ring C is:

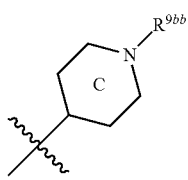

wherein Ring C is unsubstituted or substituted with 1 occurrence of $R^{5b}$, wherein $R^{9bb}$ and $R^{5b}$ have the values described herein. In certain embodiments, Ring C is:

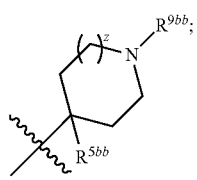

wherein $R^{9bb}$, z and $R^{5bb}$ have the values described herein.

The variable $V_{2a}$ is a bond, —NH—C(O)—, —NH—S(O)$_2$—, or —NH—C(O)—NH—. In some embodiments, $V_{2a}$ is a bond or —NH—C(O)—. In certain embodiments, $V_{2a}$ is a bond. In certain embodiments, $V_{2a}$ is —NH—C(O)—.

The variable t is 0-2. In some embodiments, t is 0-1. In certain embodiments, t is 0. In certain embodiments, t is 1. In certain embodiments, t is 2.

The variable $L_{2a}$ is a bond or unsubstituted or substituted $C_{1-3}$ alkylene chain. In some embodiments, $L_{2a}$ is a bond, —CH$_2$—, —CH$_2$CH$_2$—, or —CH$_2$CH$_2$CH$_2$—. In certain embodiments, $L_{2a}$ is a bond. In certain embodiments, $L_{2a}$ is —CH$_2$—. In certain embodiments, $L_{ea}$ is —CH$_2$CH$_2$—.

The variable $R^{3aa}$ is a 6-membered aromatic ring containing 0-2 nitrogen atoms which is unsubstituted or substituted with 1-2 independent occurrences of $R^{4c}$, wherein $R^{4c}$ has the values described herein. In some embodiments, $R^{3aa}$ is phenyl or pyridyl, each of which is unsubstituted or substituted with 1-2 independent occurrences of $R^{4c}$, wherein $R^{4c}$ has the values described herein. In some embodiments, $R^{3aa}$ is:

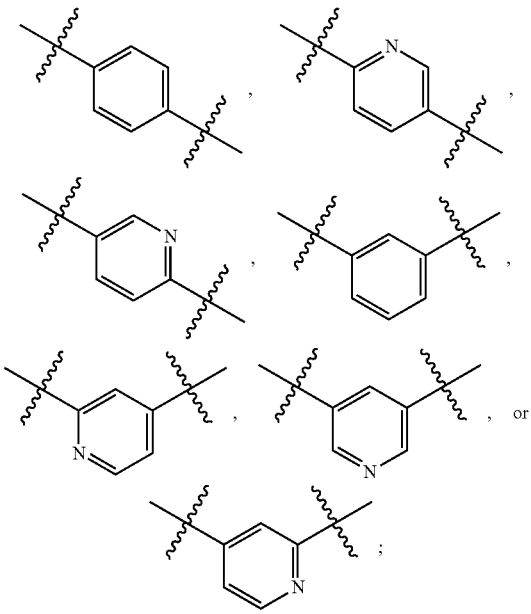

wherein each ring is unsubstituted or substituted with 1-2 independent occurrences of $R^{4c}$.

The variable $R^{4c}$ is chloro, fluoro, cyano, hydroxy, methoxy, ethoxy, trifluoromethoxy, trifluoromethyl, methyl, or ethyl. In some embodiments, e is chloro, fluoro, methyl or ethyl.

The variable z is 0-1. In some embodiments, z is 0. In some embodiments, z is 1.

Each occurrence of the variable $R^{5b}$ is independently chloro, fluoro, hydroxy, methyl, ethyl, methoxy, ethoxy, trifluoromethyl, trifluoromethoxy, —C(O)NH$_2$, or —CO$_2$H. In some embodiments, each occurrence of the variable $R^{5b}$ is independently chloro, fluoro, hydroxy, methyl, or ethyl. In certain embodiments, each occurrence of the variable $R^{5b}$ is methyl.

The variable $R^{5bb}$ is hydrogen or methyl. In some embodiments, $R^{5bb}$ is hydrogen. In some embodiments, $R^{5bb}$ is methyl.

The variable $R^{9bb}$ is hydrogen, unsubstituted C(O)—O—C$_{1-6}$ aliphatic, unsubstituted C(O)—C$_{1-6}$ aliphatic, unsubstituted C(O)—C$_{3-10}$ cycloaliphatic, or unsubstituted C$_{1-6}$ aliphatic. In some embodiments, $R^{9bb}$ is hydrogen, methyl, ethyl, isopropyl, or tert-butoxycarbonyl. In some embodiments, $R^{9bb}$ is methyl, ethyl, or isopropyl. In certain embodiments, $R^{9bb}$ is hydrogen.

In certain embodiments, the compound of formula (I) is represented by:

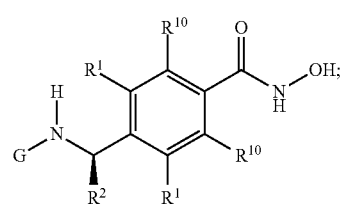

(III-a-i)

wherein:

each occurrence of $R^1$ is independently hydrogen, chloro, fluoro, hydroxy, trifluoromethyl, or methyl;

$R^{10}$ is hydrogen;

G is —V$_1$—R$^3$; and

V$_1$ is —C(O)—, —C(O)—N(R$^{4a}$)— or —S(O)$_2$—;

wherein $R^2$, $R^3$, and $R^{4c}$ have the values described herein.

In certain embodiments, the compound of formula (I) is represented by:

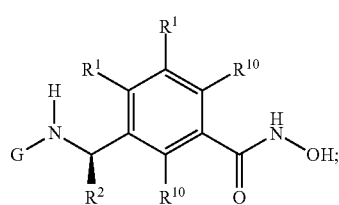

(III-a-v)

wherein:

each occurrence of $R^1$ is independently hydrogen, chloro, fluoro, hydroxy, trifluoromethyl, or methyl;

$R^{10}$ is hydrogen;

G is —V$_1$—R$^3$; and

V$_1$ is —C(O)—, —C(O)—N(R$^{4a}$)— or —S(O)$_2$—;

wherein $R^2$, $R^3$, and $R^{4a}$ have the values described herein.

In certain embodiments, the compound of formula (I) is represented by:

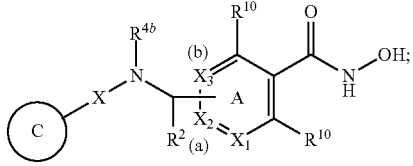

(IV)

wherein:
ring A is an aromatic 6-membered ring connected through one of positions (a) or (b);
$X_1$ is $CR^1$ or N;
(i) when ring A is connected through position (a), $X_2$ is C; and $X_3$ is $CR^1$ or N; or
(ii) when ring A is connected through position (b), $X_3$ is C; and $X_2$ is $CR^1$ or N;
$R^{4b}$ is hydrogen, or $C_{1-4}$ aliphatic;
$R^2$ is methyl, ethyl, isopropyl, n-propyl, trifluoromethyl, tert-butyl, cyclopropyl, or phenyl;
$R^1$ is hydrogen, chloro, fluoro, hydroxy, methoxy, ethoxy, n-propoxy, isopropoxy, cyano, trifluoromethyl, methyl, ethyl, isopropyl, n-propyl, or tert-butyl;
$R^{10}$ is hydrogen; and
wherein Ring C and X have the values described herein.
In such embodiments:
$R^2$ is methyl, ethyl, isopropyl, or n-propyl;
$R^1$ is hydrogen; and
$R^{4b}$ is hydrogen.

In certain embodiments, the compound of formula (I) is represented by:

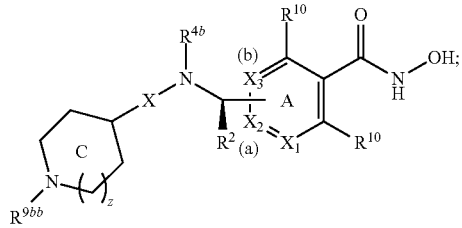

(V)

wherein:
ring A is an aromatic 6-membered ring connected through one of positions (a) or (b);
$X_1$ is $CR^1$ or N;
(i) when ring A is connected through position (a), $X_2$ is C; and $X_3$ is $CR^1$ or N; or
(ii) when ring A is connected through position (b), $X_3$ is C; and $X_2$ is $CR^1$ or N;
$R^{4b}$ is hydrogen;
$R^2$ is methyl, ethyl, isopropyl, n-propyl, trifluoromethyl, tert-butyl, cyclopropyl, or phenyl;
each occurrence of $R^1$ is independently hydrogen, chloro, fluoro, hydroxy, trifluoromethyl, or methyl;
$R^{10}$ is hydrogen;
$R^{9bb}$ is hydrogen, methyl, ethyl, isopropyl, or tert-butoxycarbonyl;
X is —C(O)—, X-a, X-b, X-c, X-d, X-e, X-f, or X-g;
Ring C is unsubstituted or substituted with one occurrence of $R^{5b}$; and z, $R^{5b}$, t, and $V_{2a}$ have the values described herein.
In such embodiments:
$R^2$ is methyl, ethyl, isopropyl, or n-propyl;
$R^1$ is hydrogen; and
$R^{5b}$ is methyl.

In certain embodiments, the compound of formula (I) is represented by:

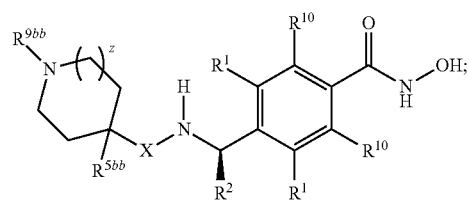

(VI-a-i)

wherein:
each occurrence of $R^1$ is independently hydrogen, chloro, fluoro, hydroxy, trifluoromethyl, or methyl;
$R^2$ is methyl, ethyl, isopropyl, n-propyl, trifluoromethyl, tert-butyl, cyclopropyl, or phenyl;
$R^1$ is hydrogen;
$R^{9bb}$ is hydrogen, methyl, ethyl, isopropyl, or tert-butoxycarbonyl;
X is —C(O)—, X-ii, X-xi, X-xii, X-xxii, X-xxiv, or X-xxv;
$R^{5bb}$ is hydrogen or methyl; and
z has the values described herein.
In certain such embodiments,
$R^1$ is hydrogen;
$R^2$ is methyl, ethyl, isopropyl, or n-propyl;
$R^{5bb}$ is methyl; and
z is 1.

In certain embodiments, the compound of formula (I) is represented by:

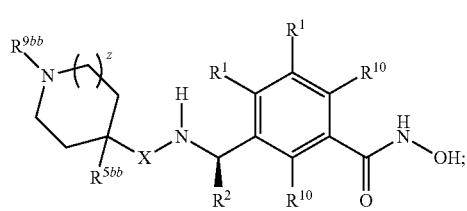

(VI-a-v)

wherein:
each occurrence of $R^1$ is independently hydrogen, chloro, fluoro, hydroxy, trifluoromethyl, or methyl;
$R^2$ is methyl, ethyl, isopropyl, n-propyl, trifluoromethyl, tert-butyl, cyclopropyl, or phenyl;
$R^{10}$ is hydrogen;
$R^{9bb}$ is hydrogen, methyl, ethyl, isopropyl, or tert-butoxycarbonyl;
X is —C(O)—, X-ii, X-xi, X-xii, X-xxii, X-xxiv, or X-xxv;
$R^{5bb}$ is hydrogen or methyl; and
z has the values described herein.
In certain such embodiments,
$R^1$ is hydrogen;
$R^2$ is methyl, ethyl, isopropyl, or n-propyl;
$R^{5bb}$ is methyl; and
z is 1.

In certain embodiments, the compound of formula (I) is represented by:

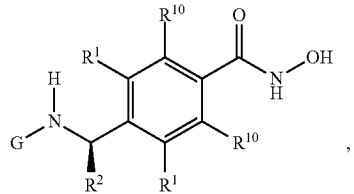 (III-a-i)

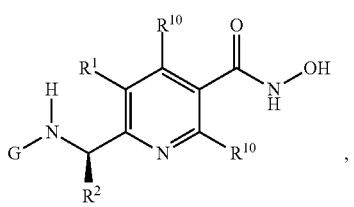 (III-a-ii)

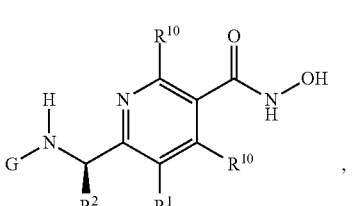 (III-a-iii)

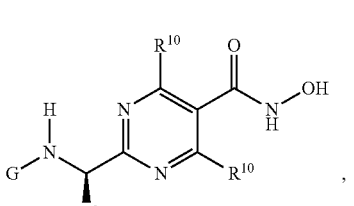 (III-a-iv)

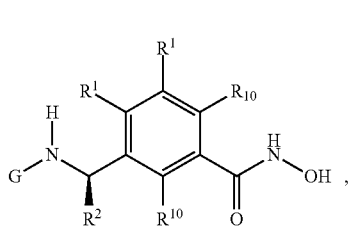 (III-a-v)

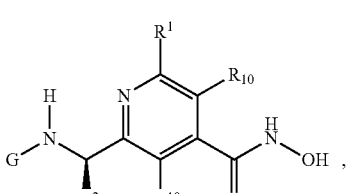 (III-a-vi)

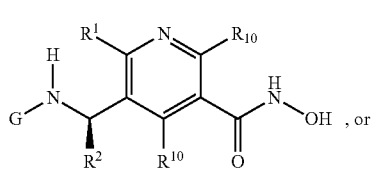 (III-a-vii)

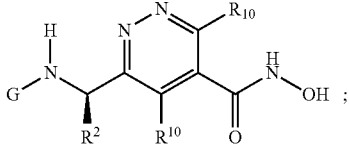 (III-a-viii)

wherein:
each occurrence of $R^1$ is independently hydrogen, chloro, fluoro, hydroxy, trifluoromethyl, or methyl;
$R^{10}$ is hydrogen;
G is $-V_1-R^3$;
$V_1$ is $-C(O)-$, $-C(O)-NH-$ or $-S(O)_2-$;
$R^2$ is methyl, ethyl, isopropyl, or n-propyl; and
wherein $R^3$ has the values described herein.

In certain such embodiments, the compound of formula (I) is represented by formula (III-a-i). In certain such embodiments, the compound of formula (I) is represented by formula (III-a-ii). In certain such embodiments, the compound of formula (I) is represented by formula (III-a-iii). In certain such embodiments, the compound of formula (I) is represented by formula (III-a-iv). In certain such embodiments, the compound of formula (I) is represented by formula (III-a-v). In certain such embodiments, the compound of formula (I) is represented by formula (III-a-vi). In certain such embodiments, the compound of formula (I) is represented by formula (III-a-vii). In certain such embodiments, the compound of formula (I) is represented by formula (III-a-viii).

In certain such embodiments, the compound of formula (I) is represented by formula (III-a-i), wherein $R^1$ is hydrogen. In certain such embodiments, the compound of formula (I) is represented by formula (III-a-ii), wherein $R^1$ is hydrogen. In certain such embodiments, the compound of formula (I) is represented by formula (III-a-iii), wherein $R^1$ is hydrogen. In certain such embodiments, the compound of formula (I) is represented by formula (III-a-iv), wherein $R^1$ is hydrogen. In certain such embodiments, the compound of formula (I) is represented by formula (III-a-v), wherein $R^1$ is hydrogen. In certain such embodiments, the compound of formula (I) is represented by formula (III-a-vi) wherein $R^1$ is hydrogen. In certain such embodiments, the compound of formula (I) is represented by formula (III-a-vii) wherein $R^1$ is hydrogen. In certain such embodiments, the compound of formula (I) is represented by formula (III-a-viii), wherein $R^1$ is hydrogen.

Representative examples of compounds of formula (I) are shown in Table 1.

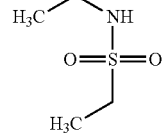 I-1

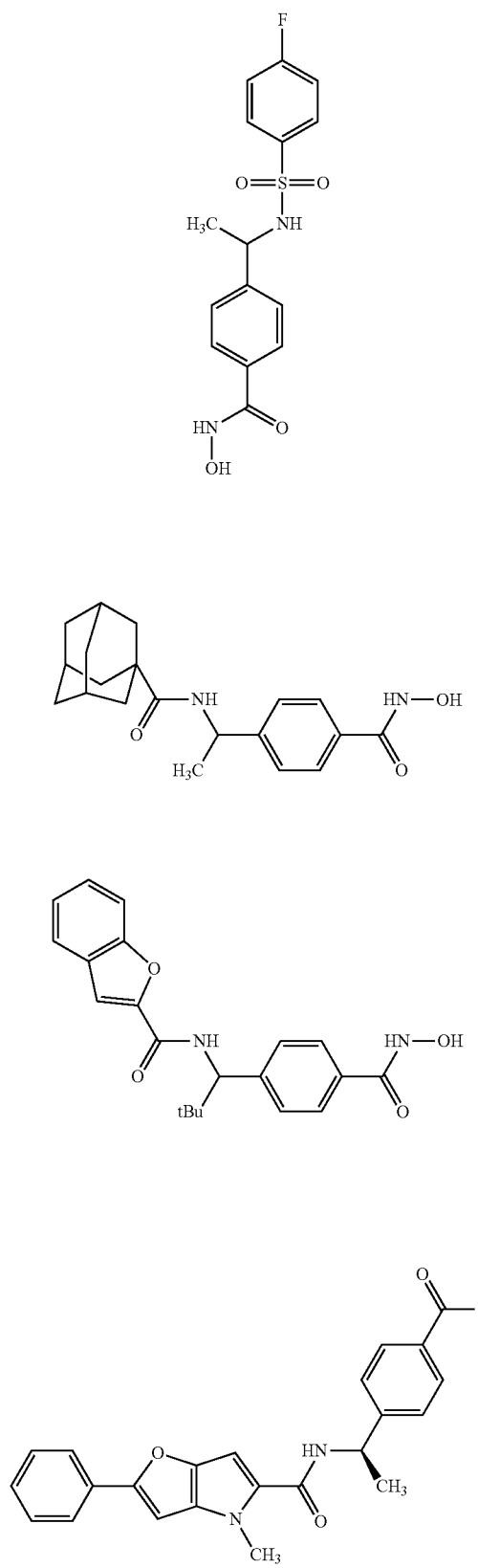
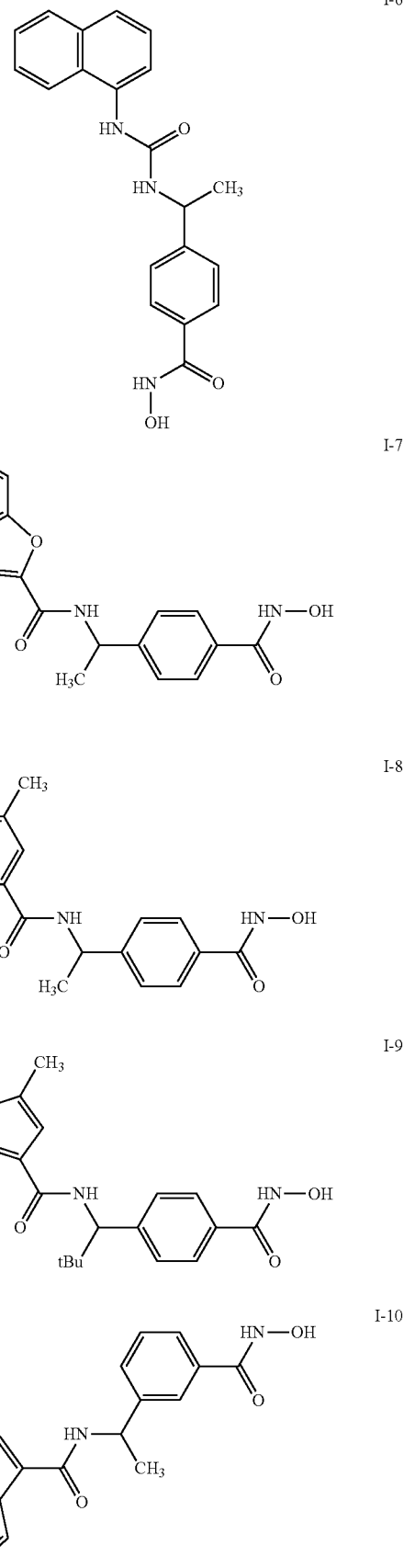

I-11
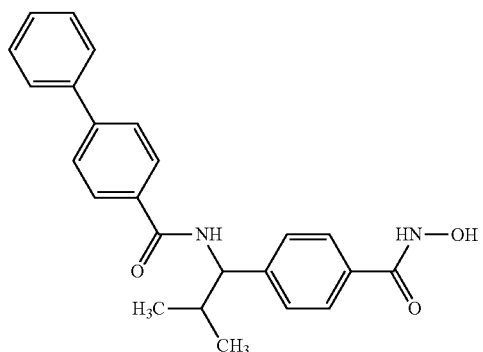
I-12
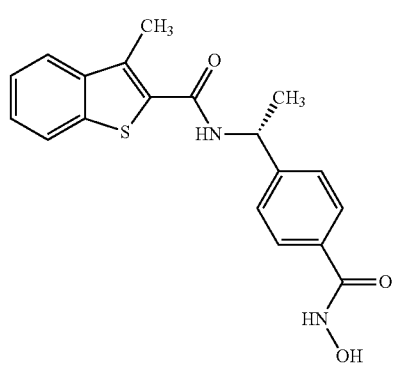
I-13
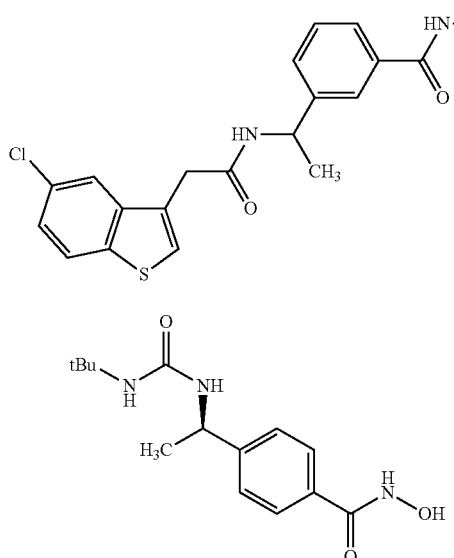
I-14
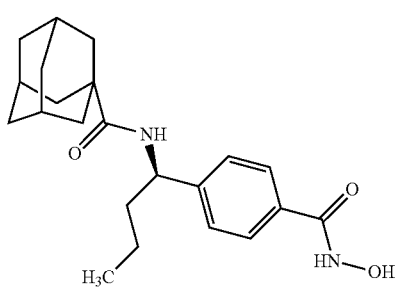
I-15
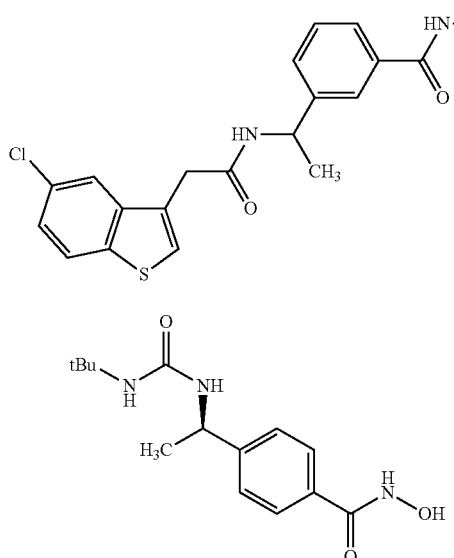
I-16
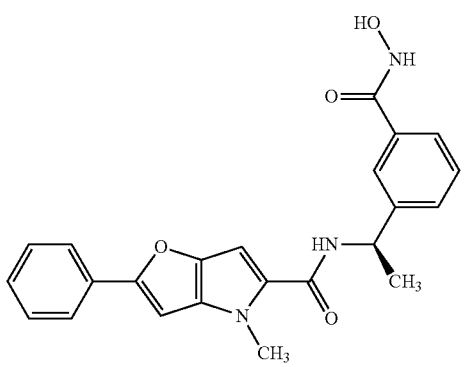
I-17
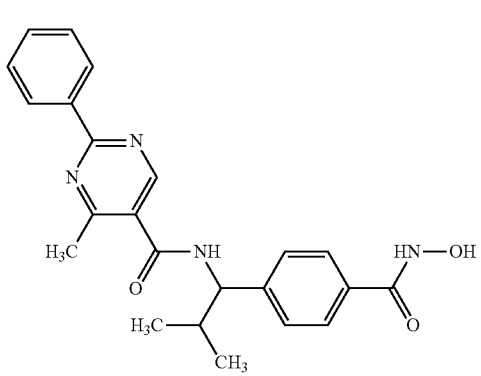
I-18
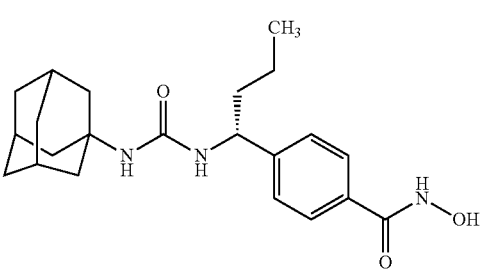
I-19
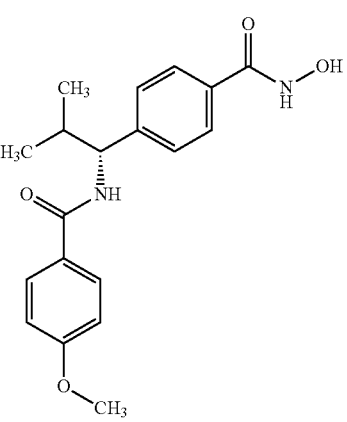

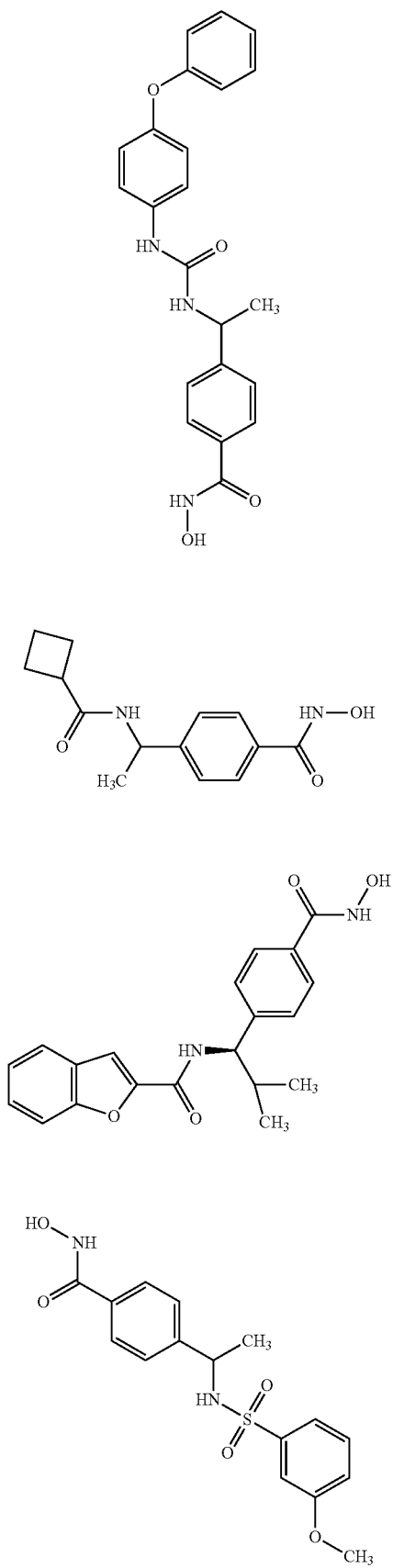
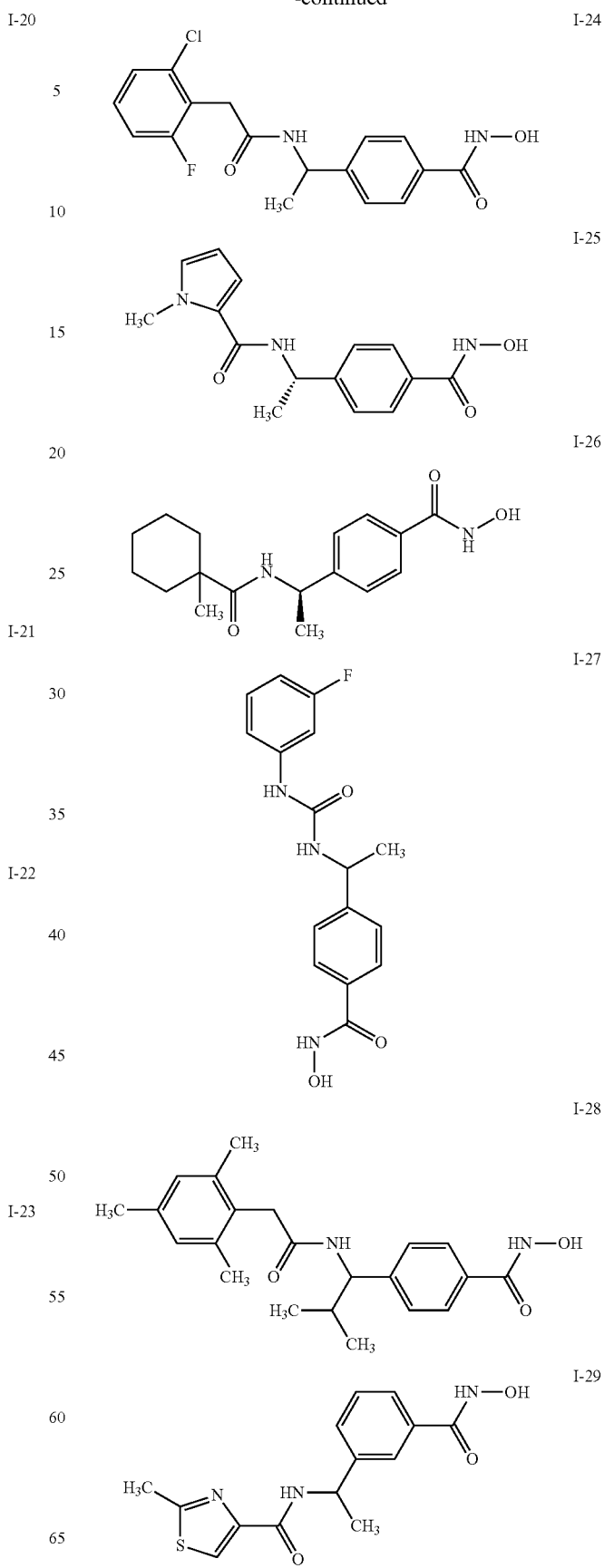

I-30 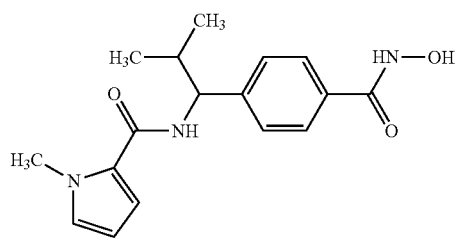
I-31 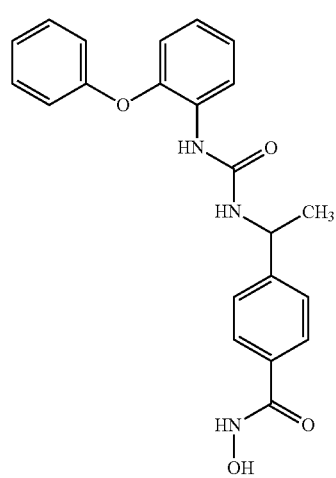
I-32 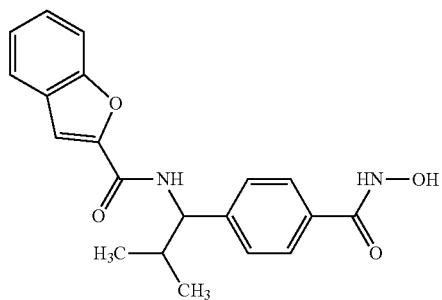
I-33 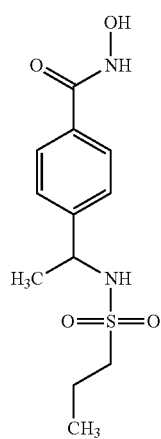
I-34 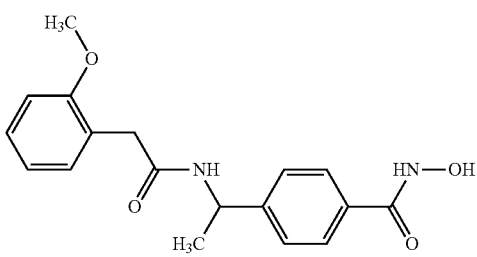
I-35 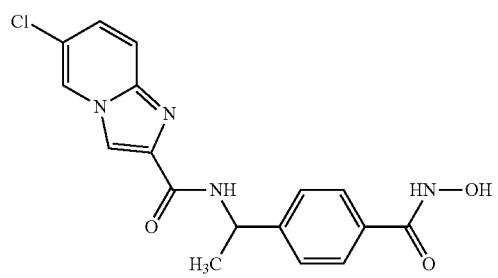
I-36 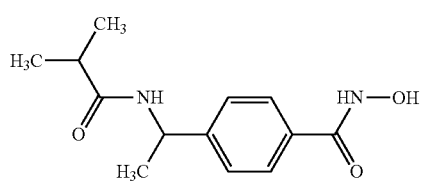
I-37 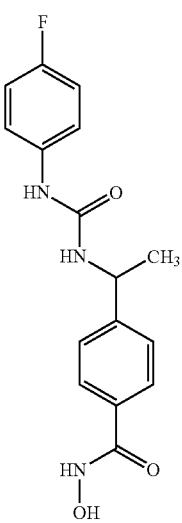
I-38 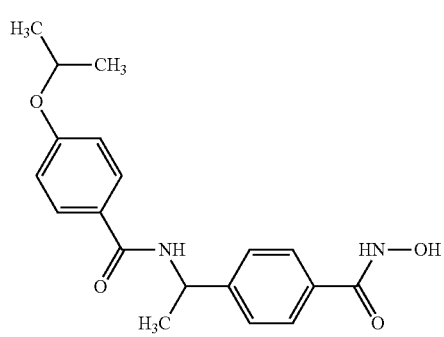

I-39 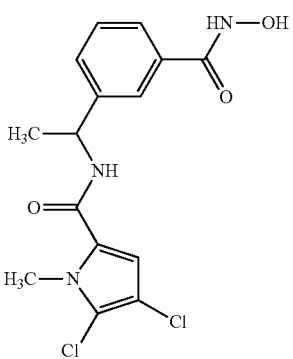
I-40 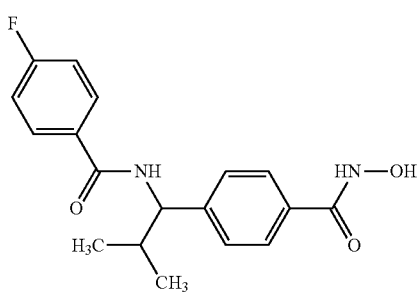
I-41 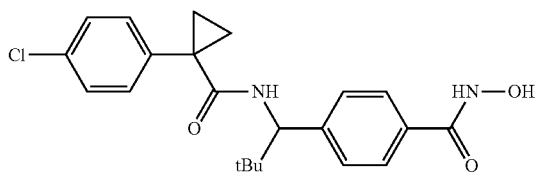
I-42 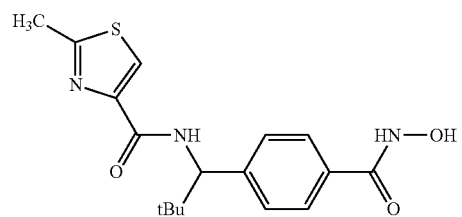
I-43 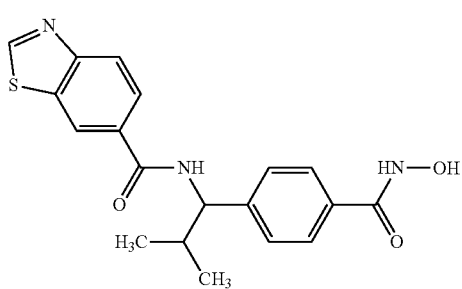
I-44 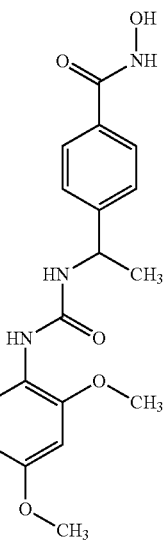
I-45 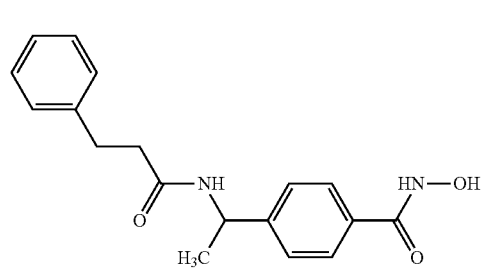
I-46 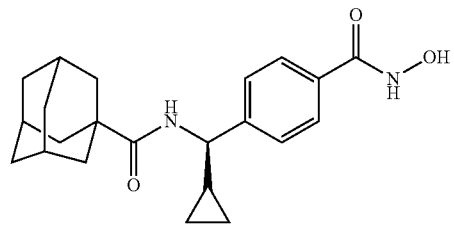
I-47 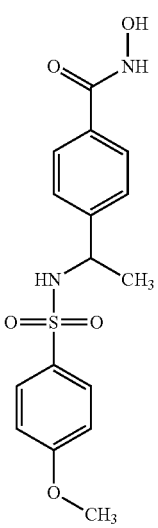

I-48
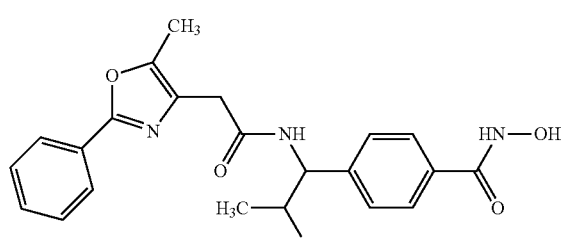
I-49
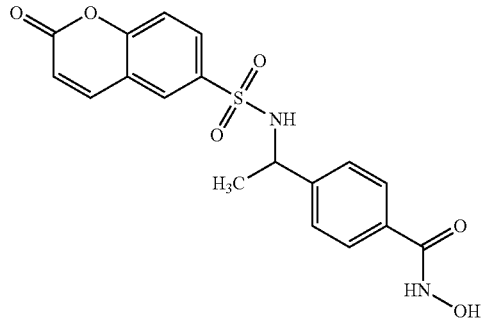
I-50
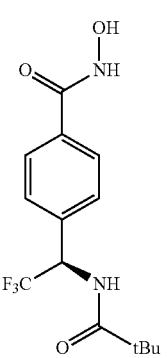
I-51
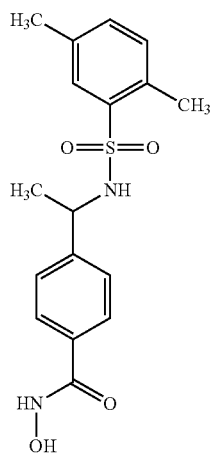
I-52
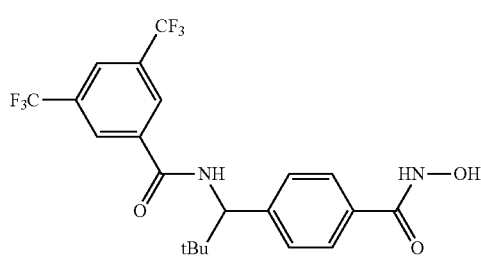
I-53
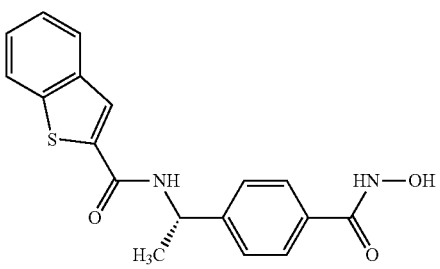
I-54
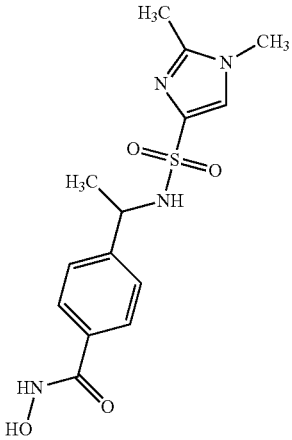
I-55
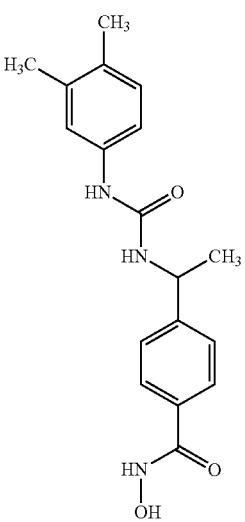
I-56
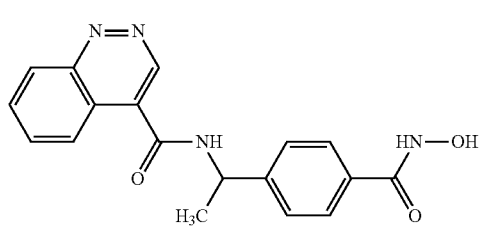

-continued
I-57
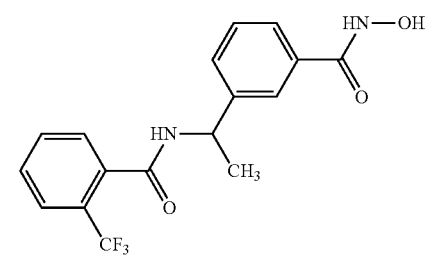
I-58
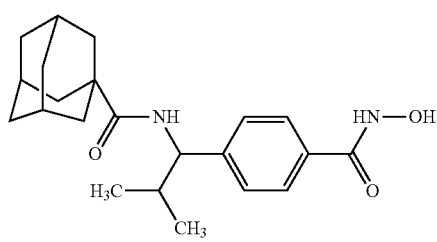
I-59
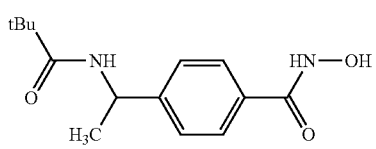
I-60
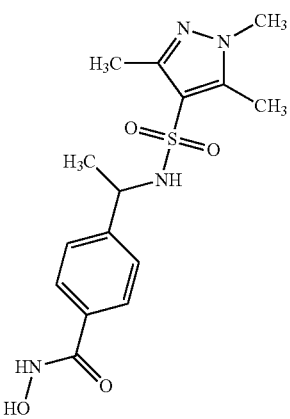
I-61
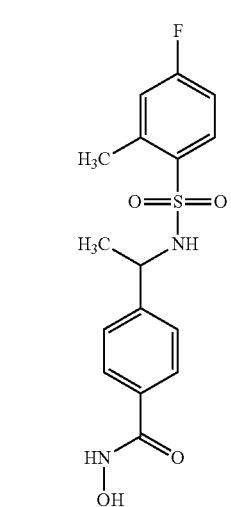
-continued
I-62
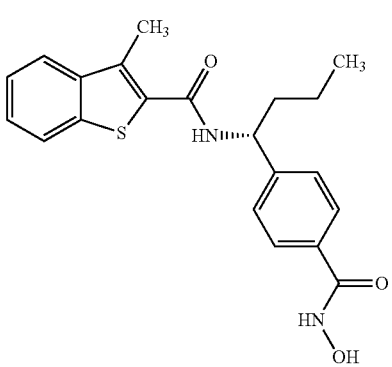
I-63
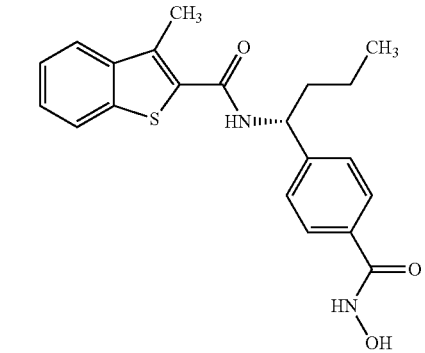
I-64
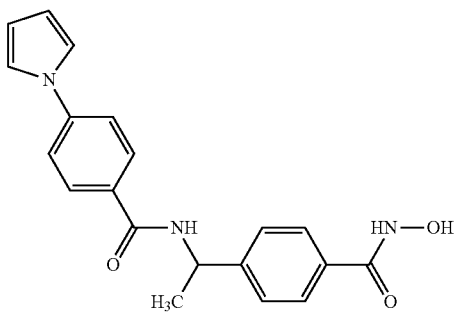
I-65
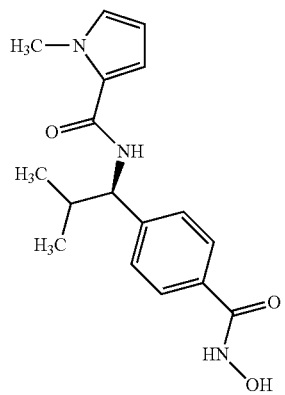

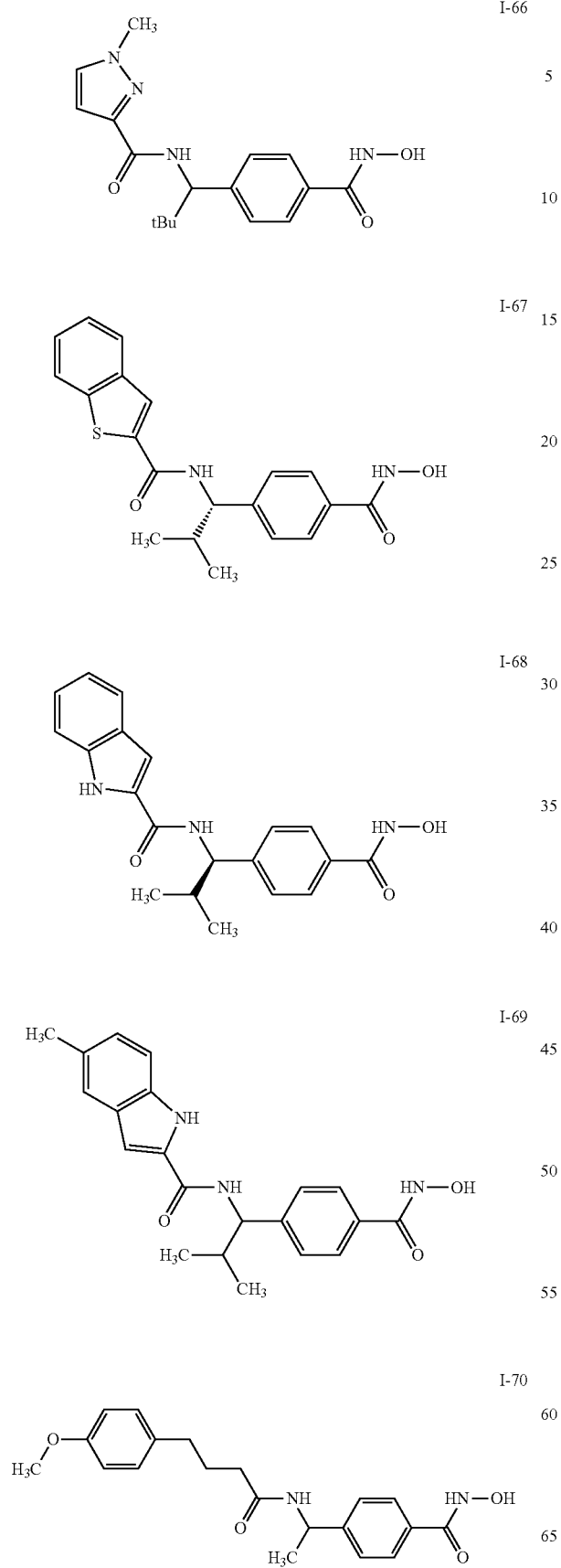

I-75
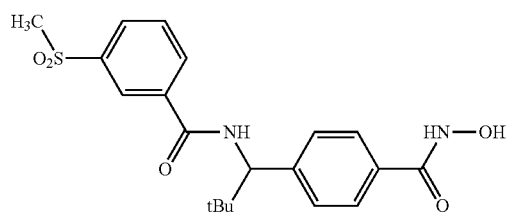
I-76
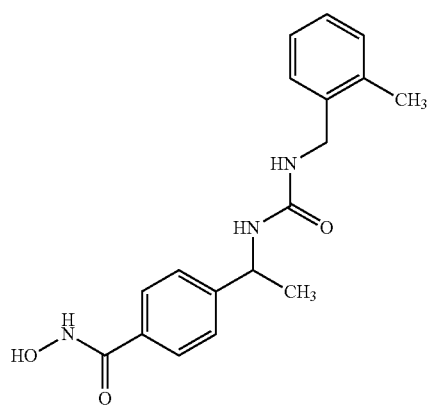
I-77
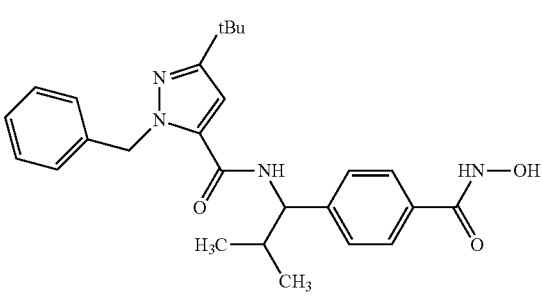
I-78
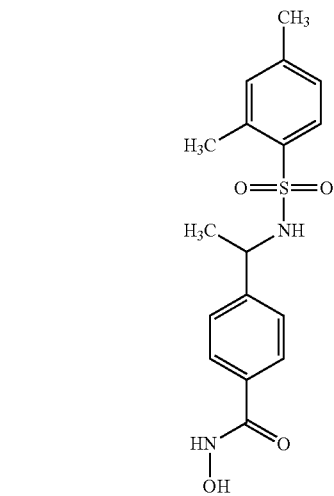
I-79
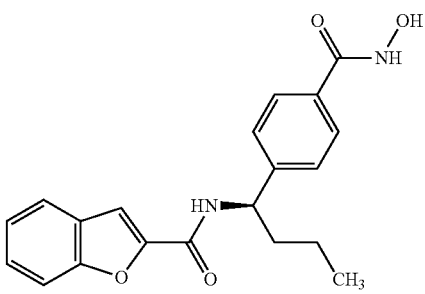
I-80
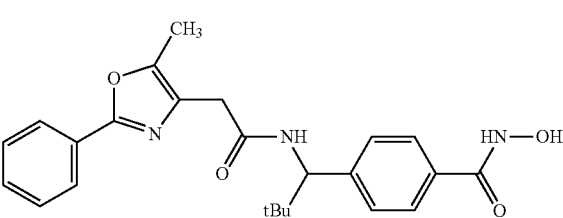
I-81
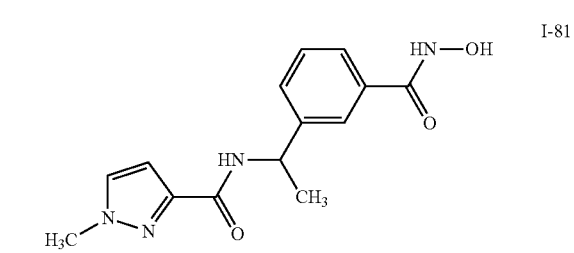
I-82
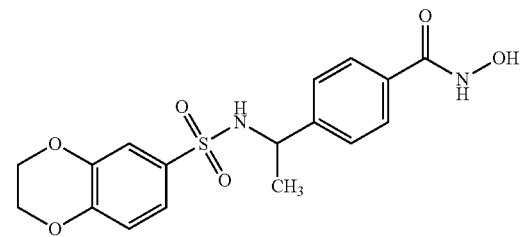
I-83
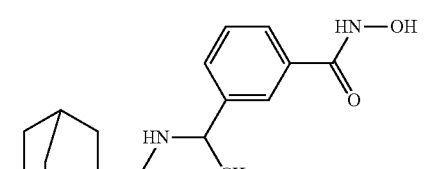
I-84
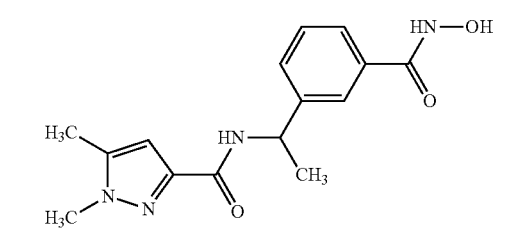

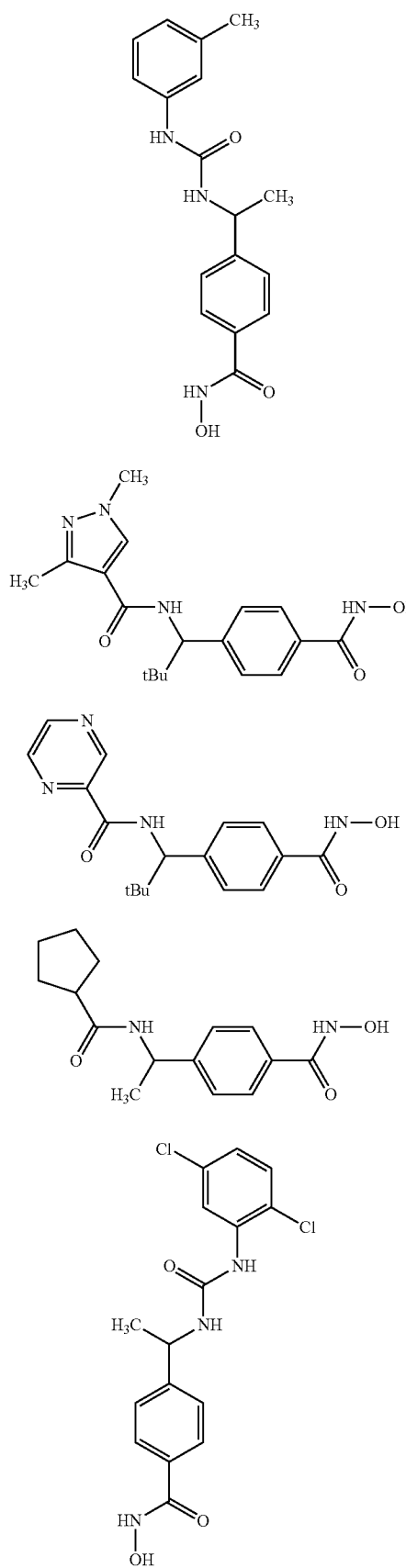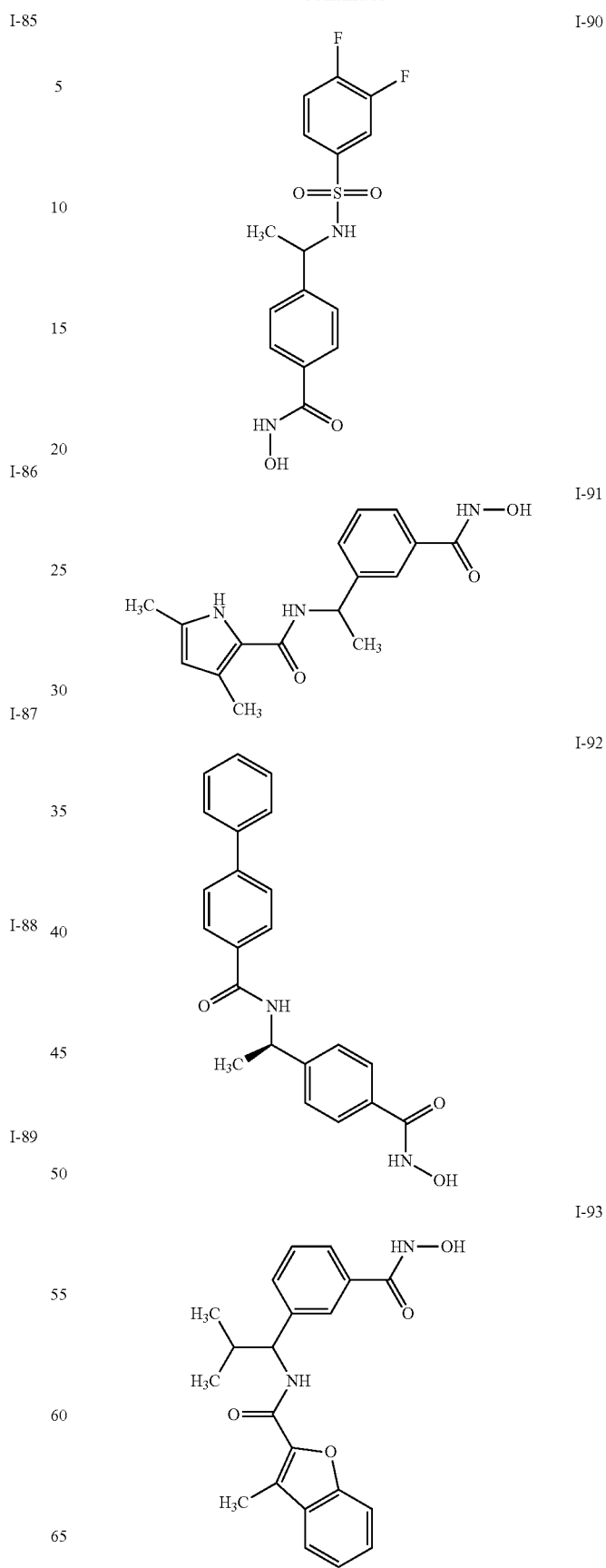

I-94
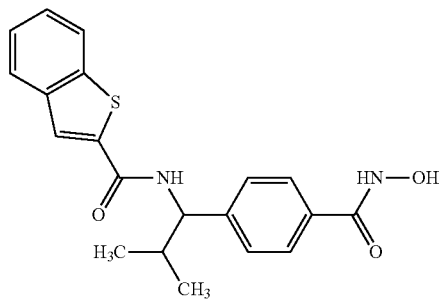
I-95
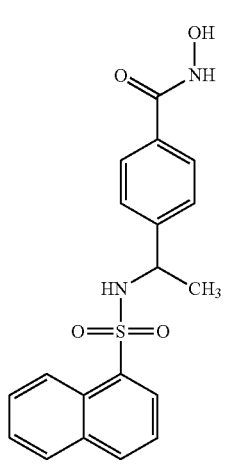
I-96
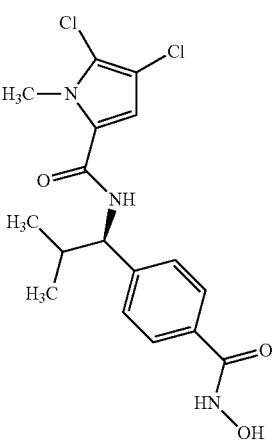
I-97
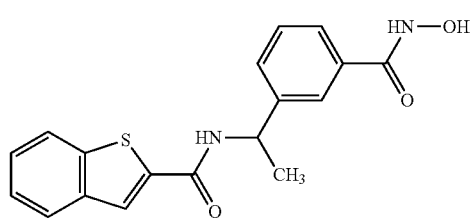
I-98
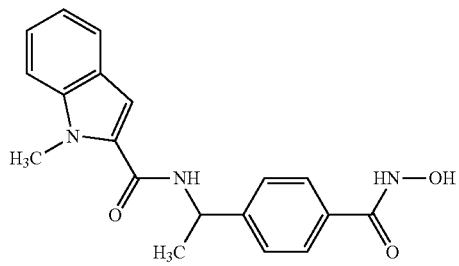
I-99
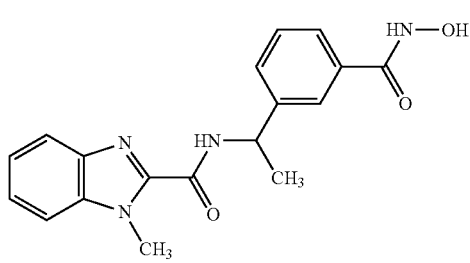
I-100
I-101
I-102
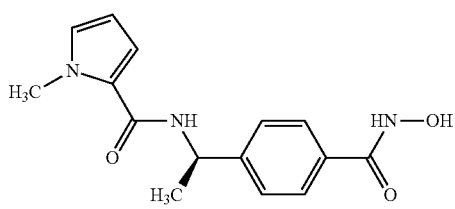

I-103 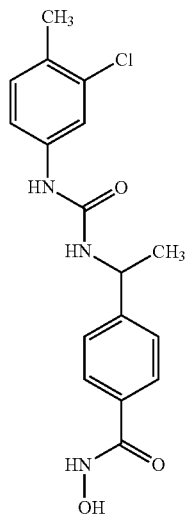
I-104 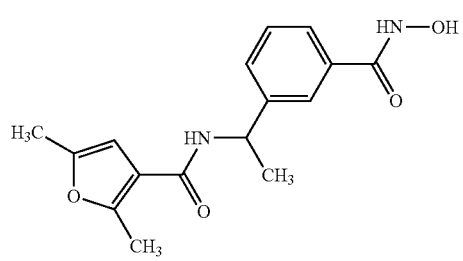
I-105 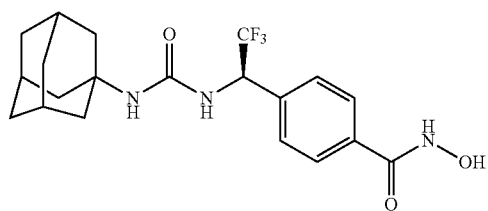
I-106 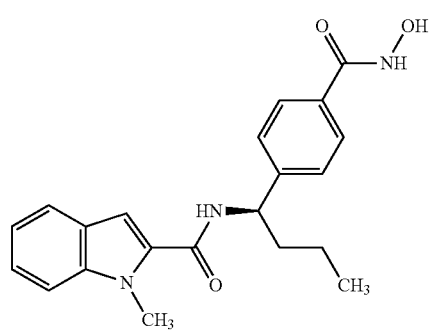
I-107 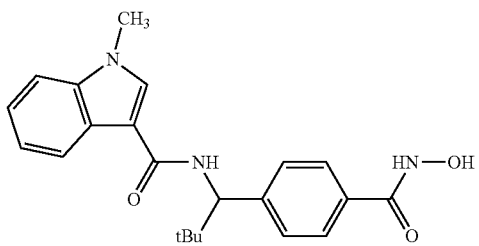
I-108 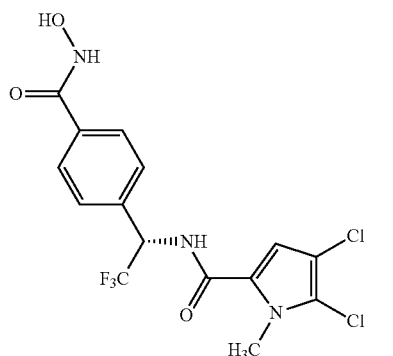
I-109 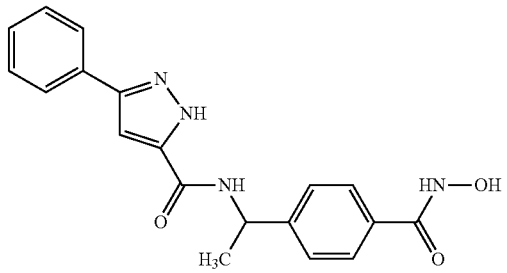
I-110 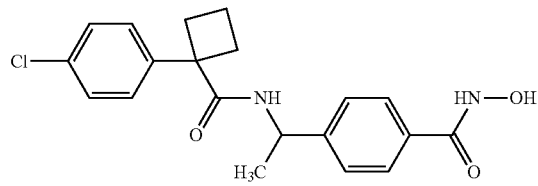
I-111 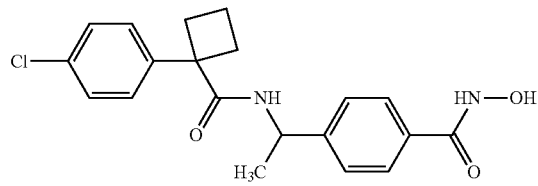
I-112 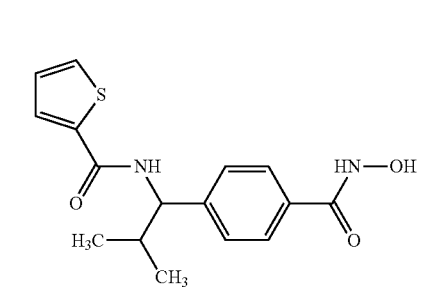

I-113
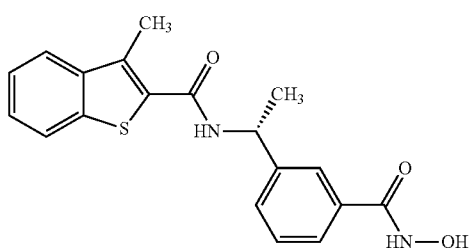
I-114
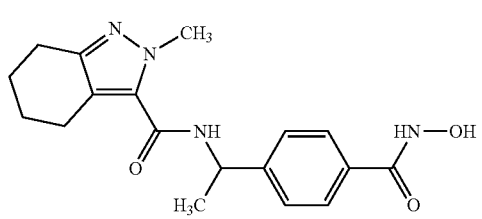
I-115
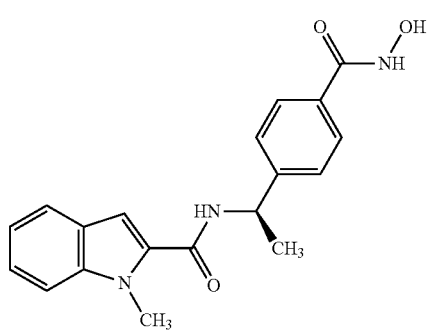
I-116
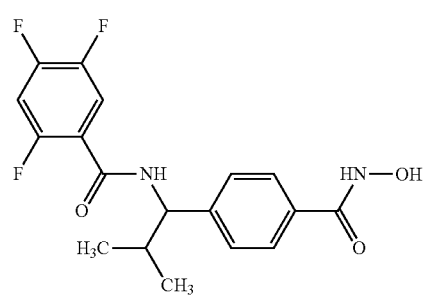
I-117
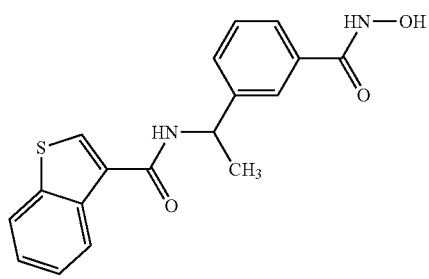
I-118
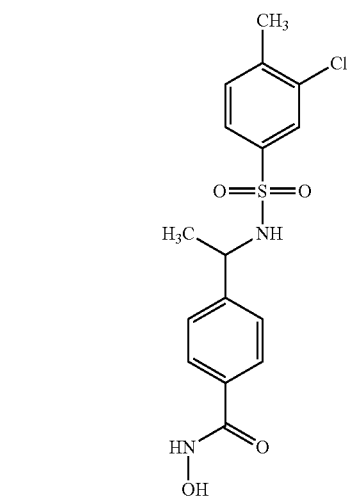
I-119
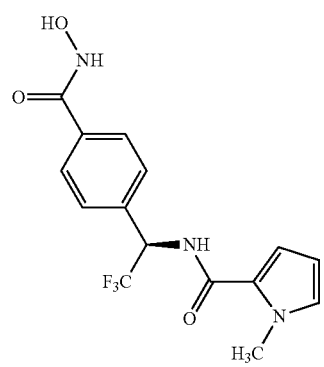
I-120
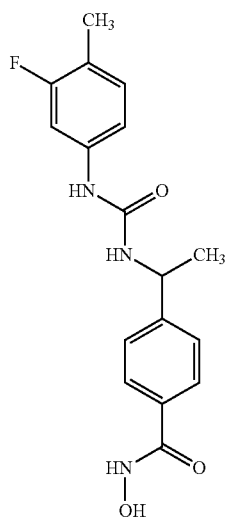
I-121
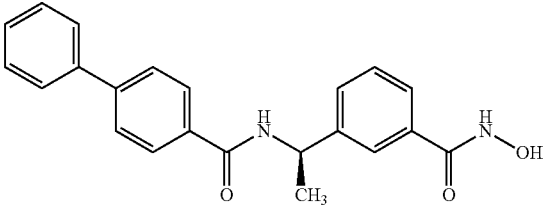

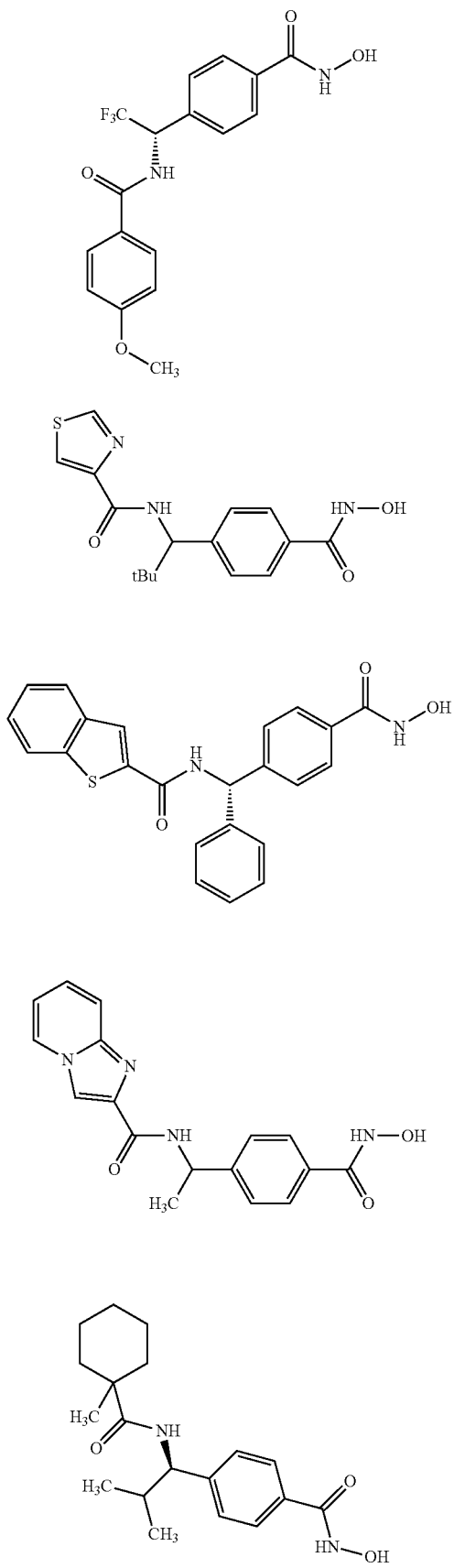
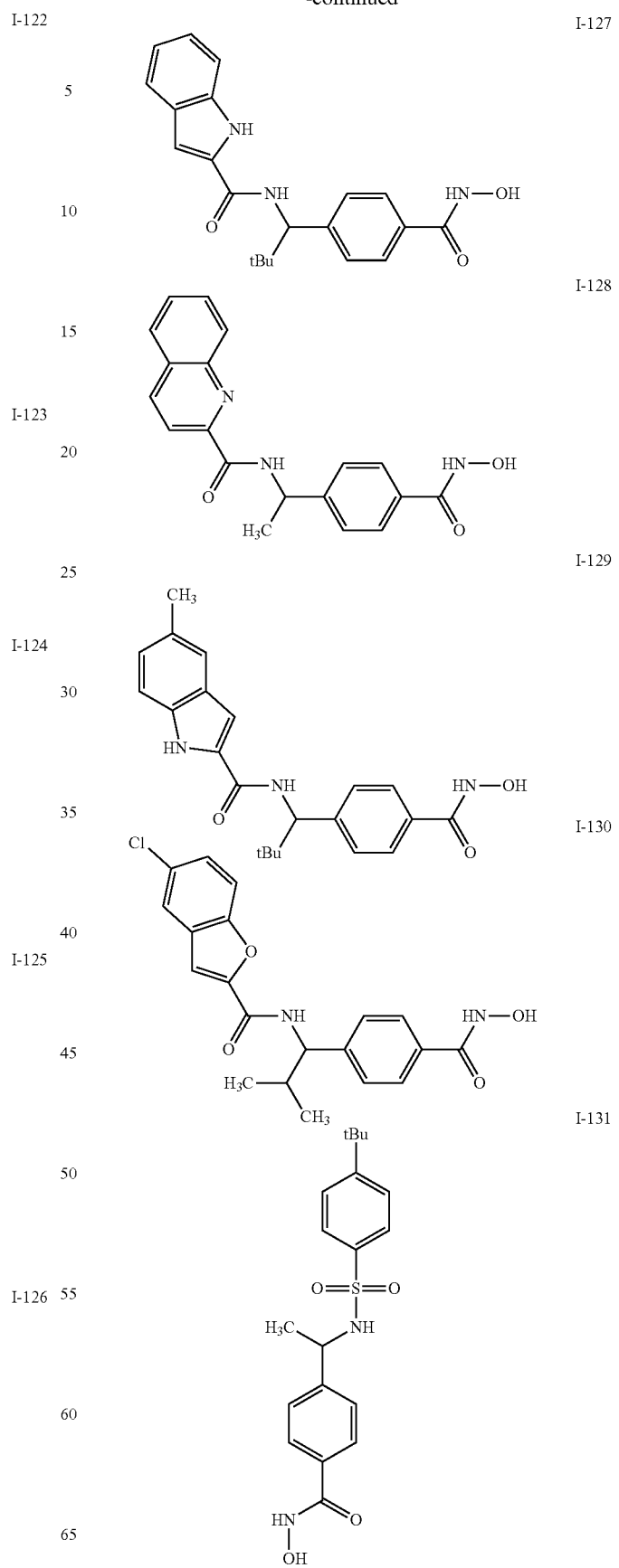

I-132
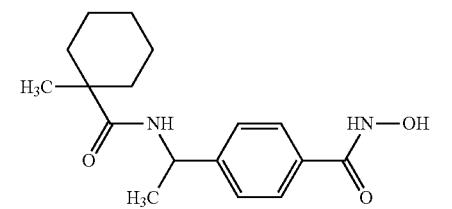
I-133
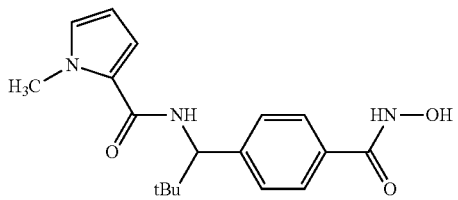
I-134
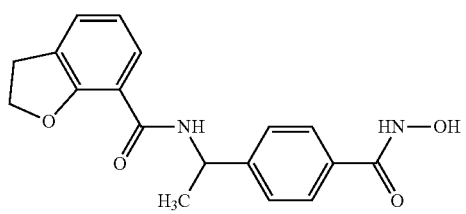
I-135
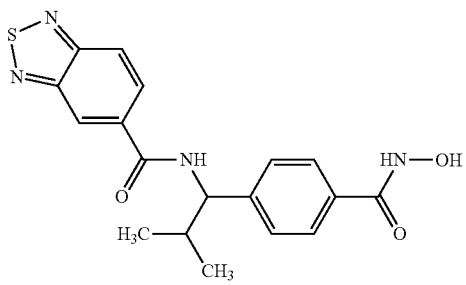
I-136
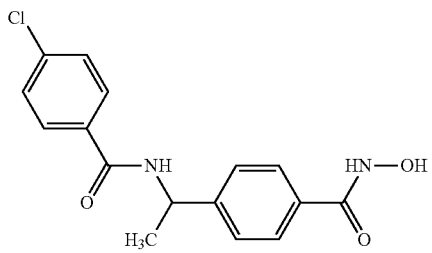
I-137
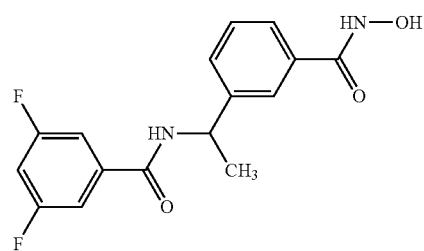
I-138
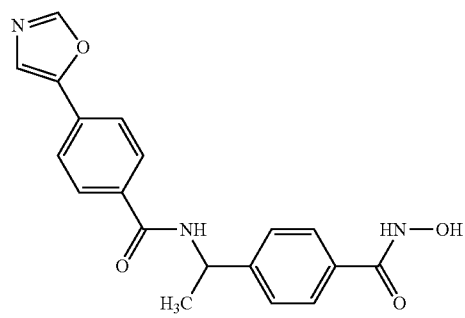
I-139
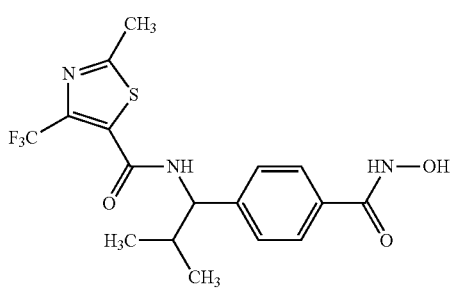
I-140
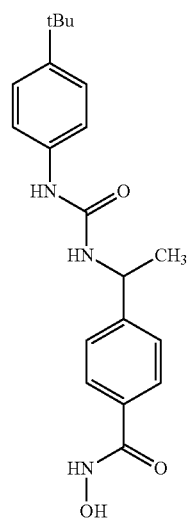
I-141
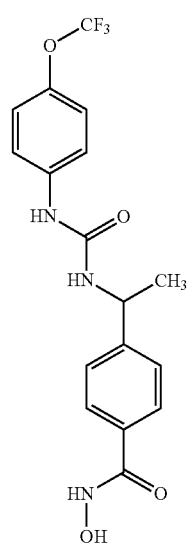

I-142 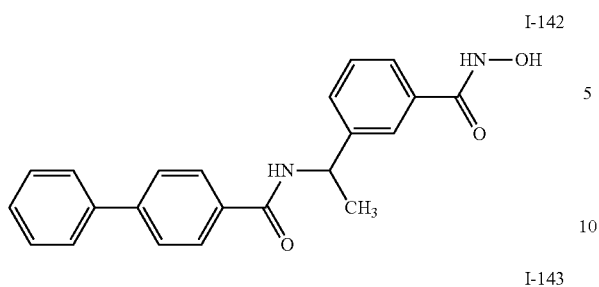
I-147 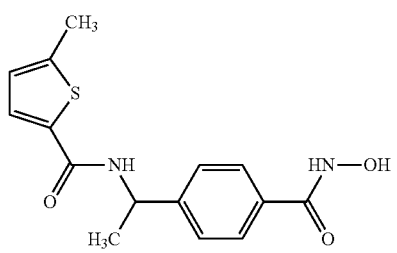
I-143 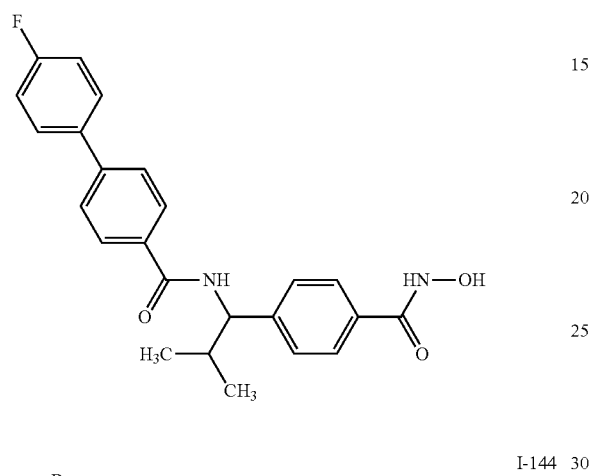
I-148 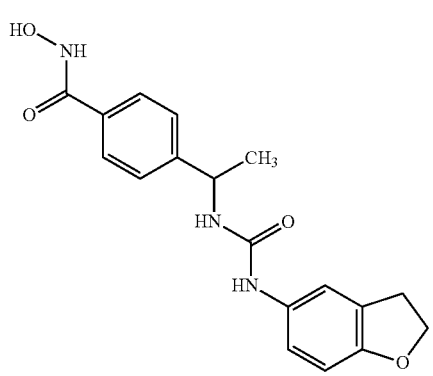
I-144 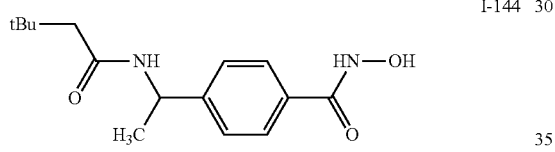
I-149 
I-145 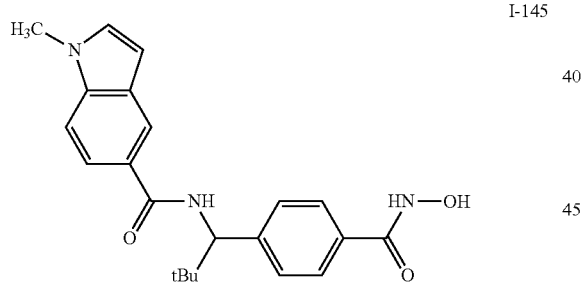
I-149 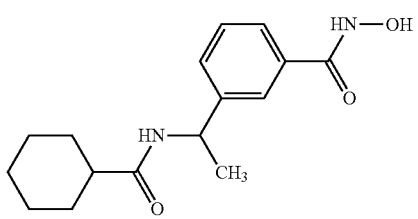
I-146 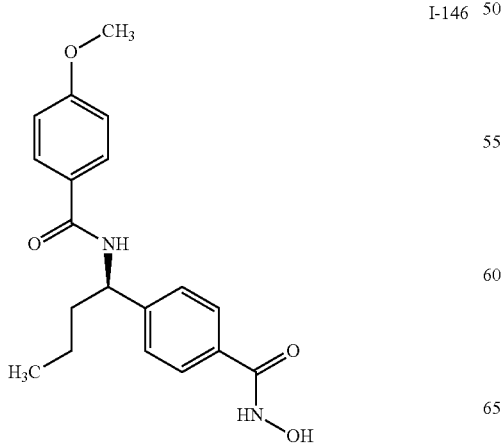
I-150 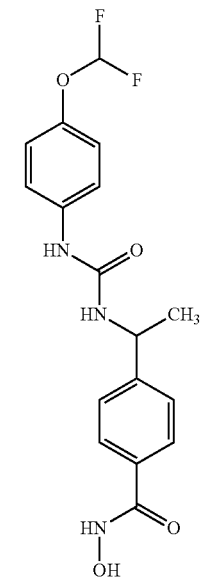

I-151
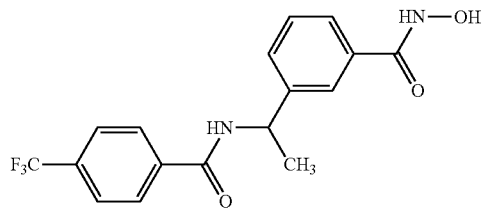
I-155
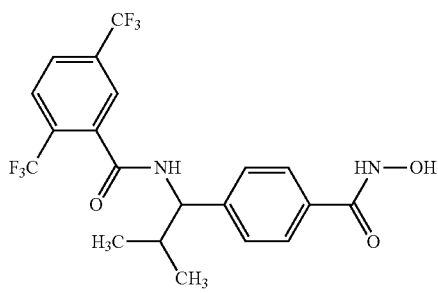
I-152
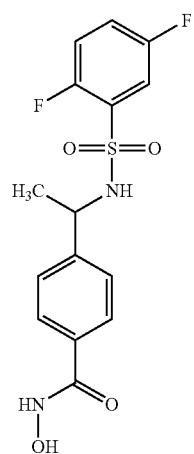
I-156
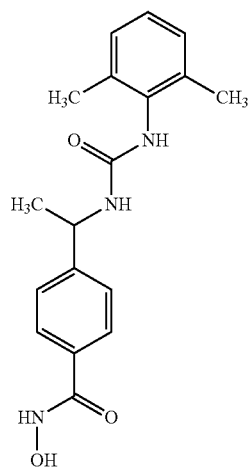
I-153
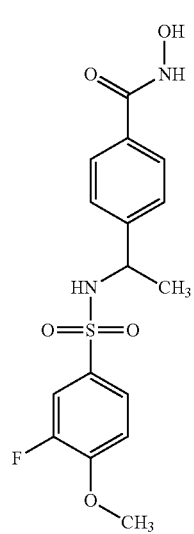
I-157
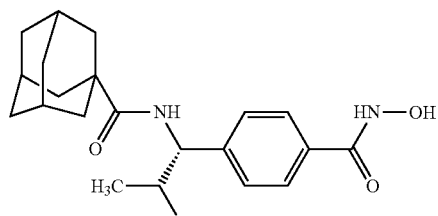
I-158
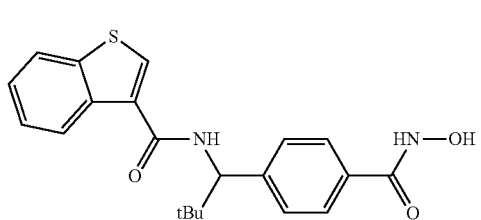
I-154
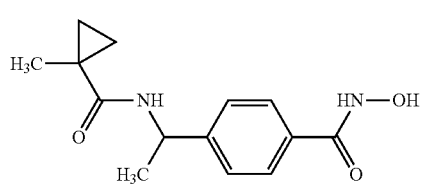
I-159
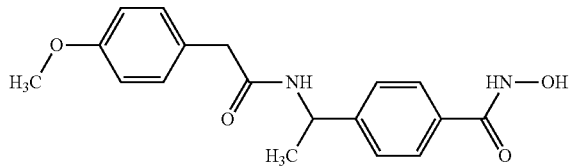

I-160 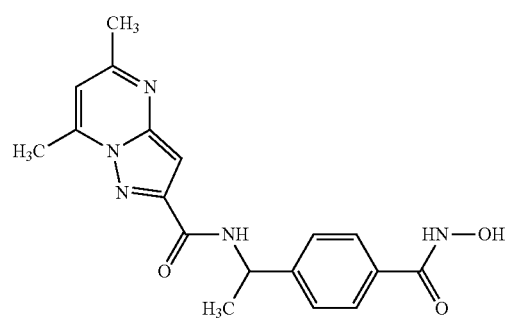
I-161 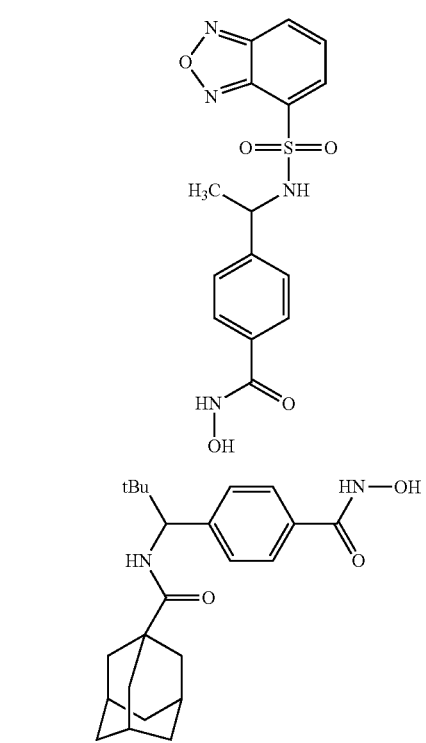
I-162 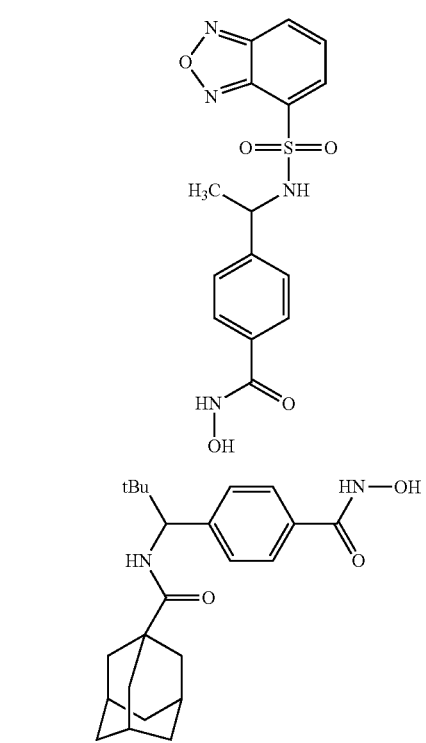
I-163 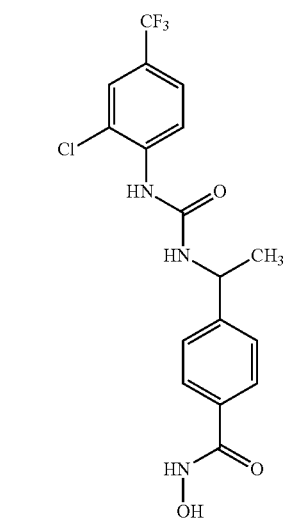
I-164 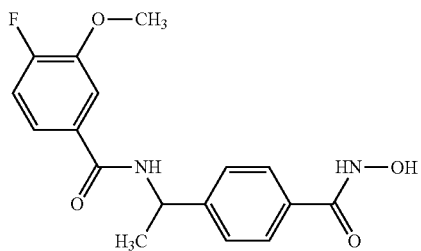
I-165 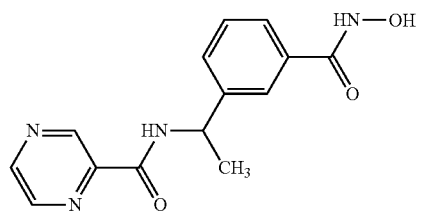
I-166 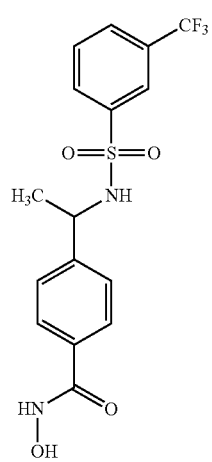
I-167 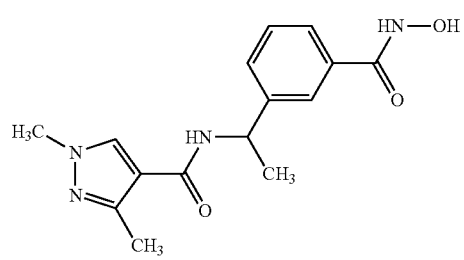
I-168 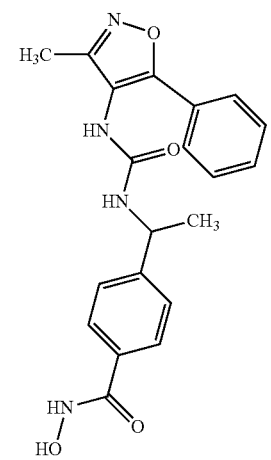

I-169
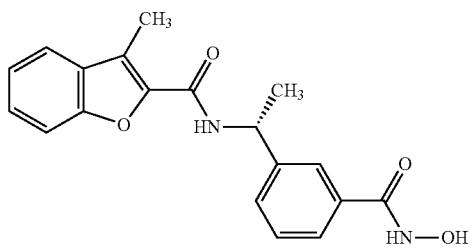
I-170
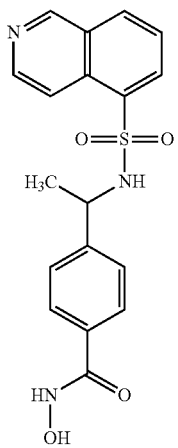
I-171
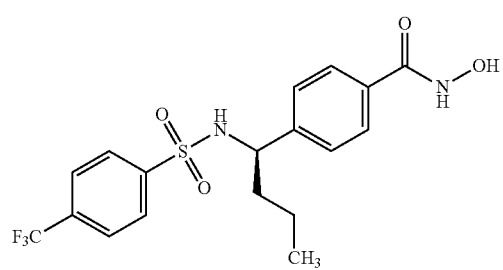
I-172
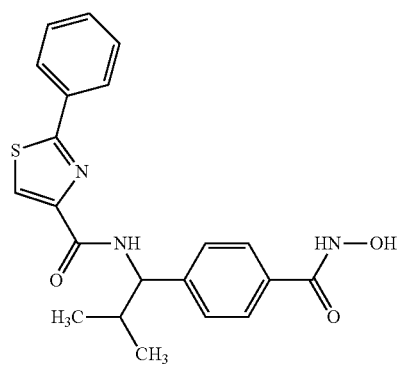
I-173
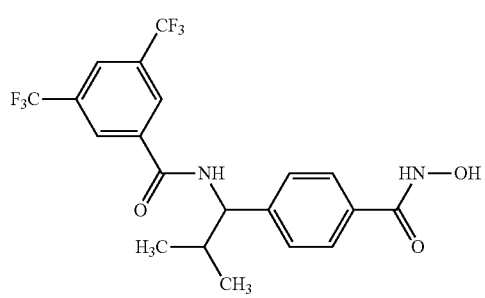
I-174
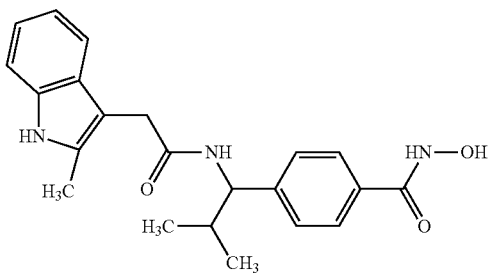
I-175
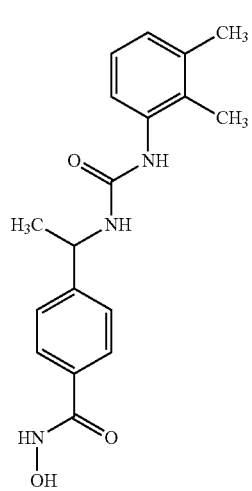
I-176
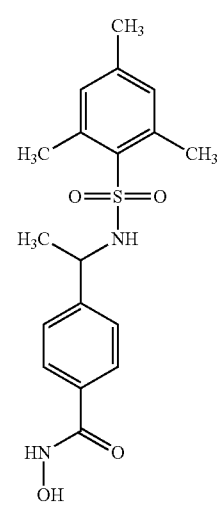
I-177
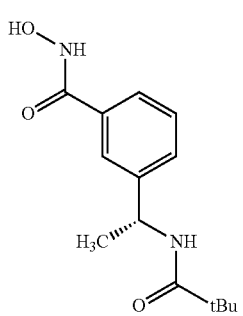

-continued
I-178
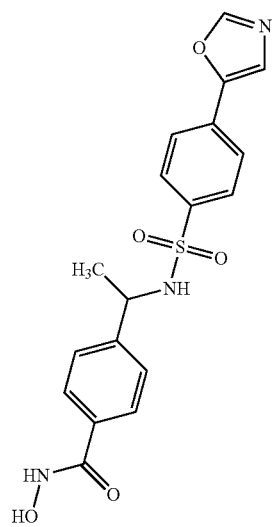
I-179
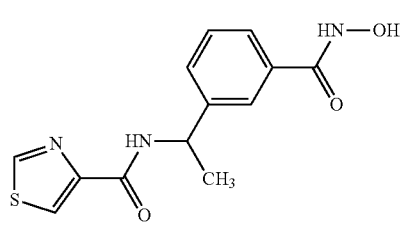
I-180
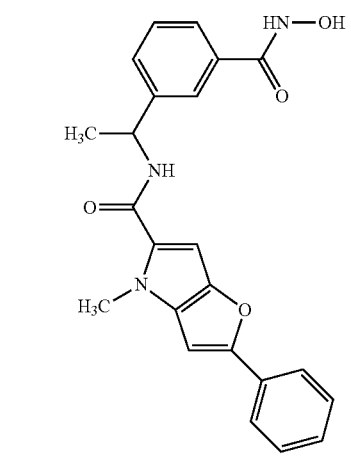
I-181
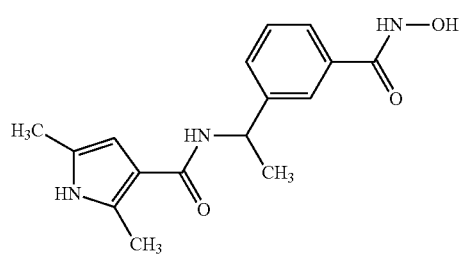
-continued
I-182
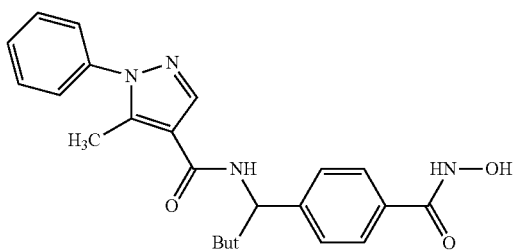
I-183
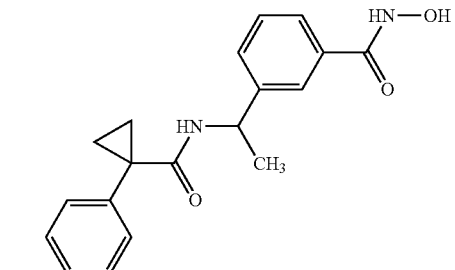
I-184
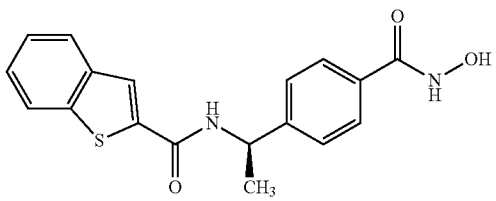
I-185
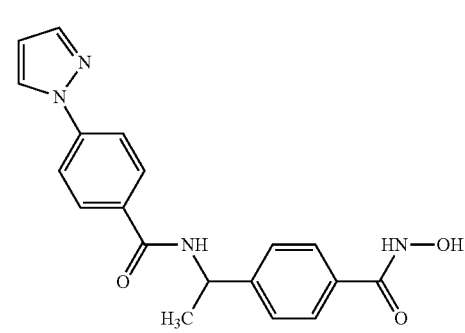
I-186
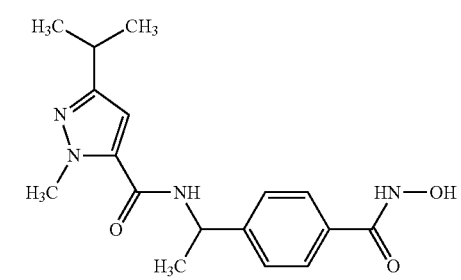

I-187
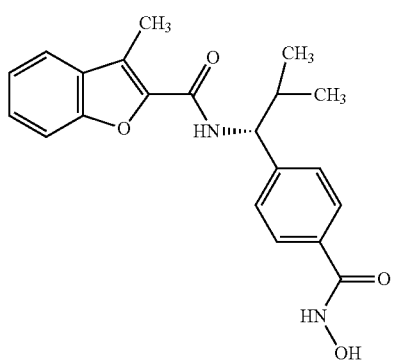
I-191
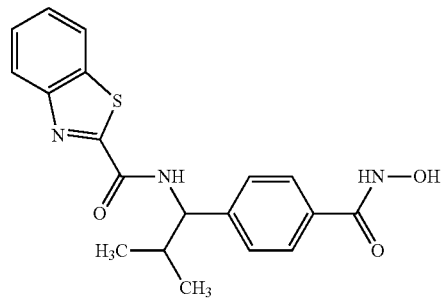
I-188
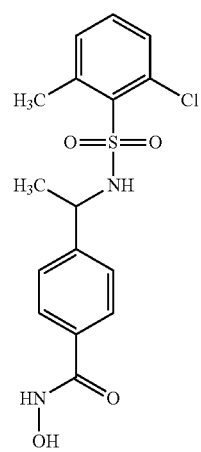
I-192
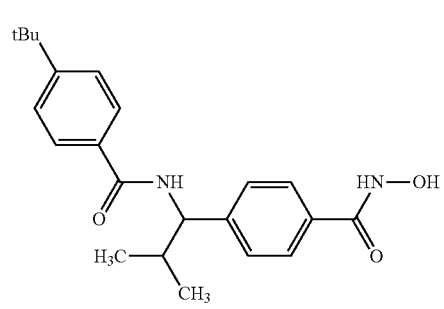
I-193
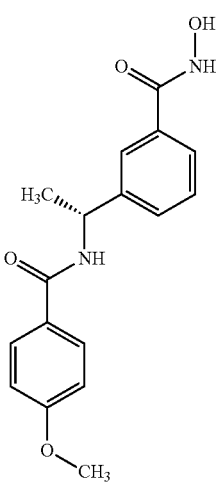
I-189
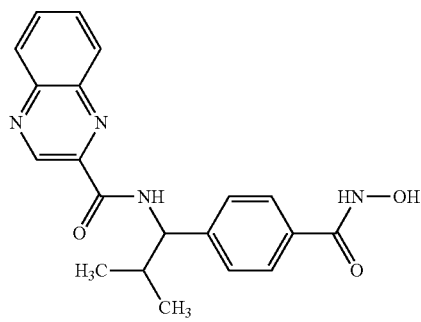
I-190
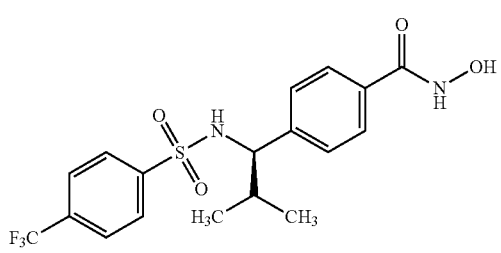
I-194
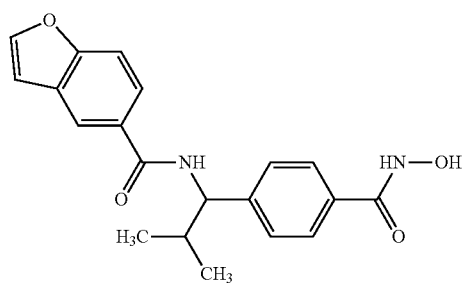

I-195 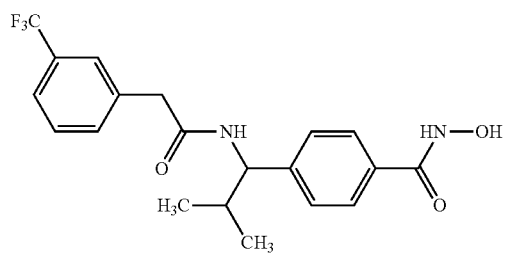
I-196 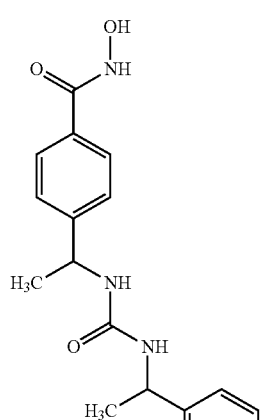
I-197 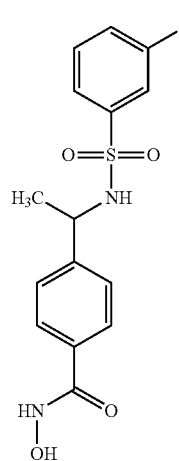
I-198 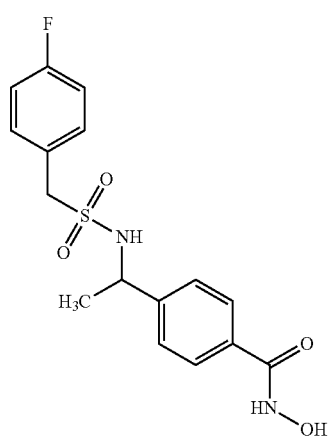
I-199 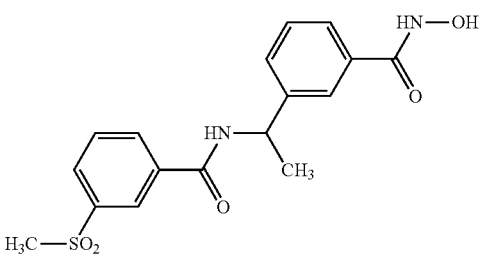
I-200 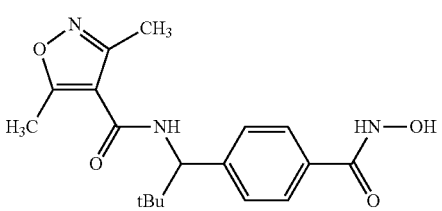
I-201 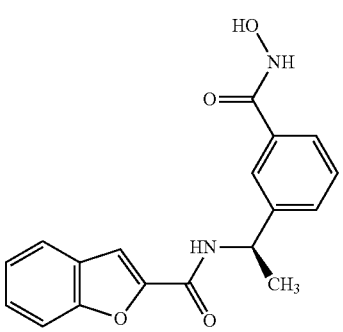
I-202 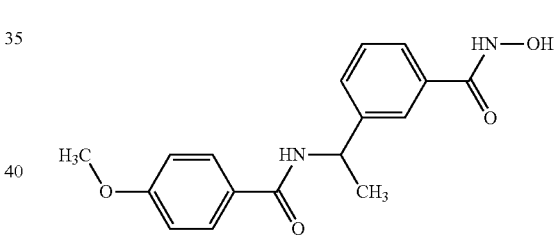
I-203 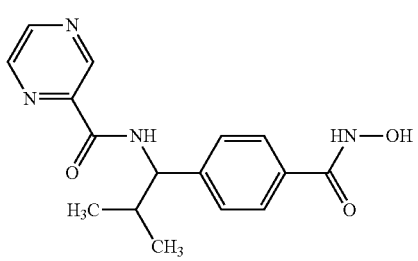
I-204 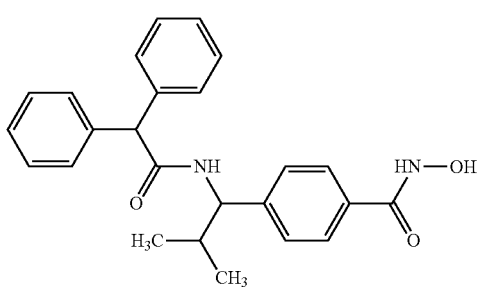

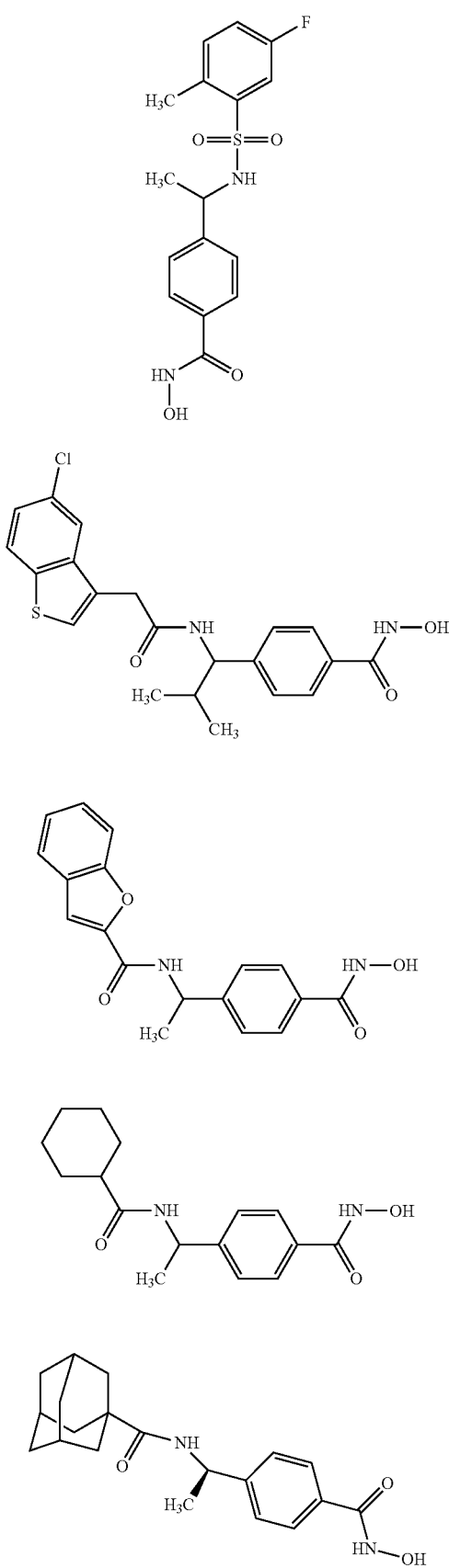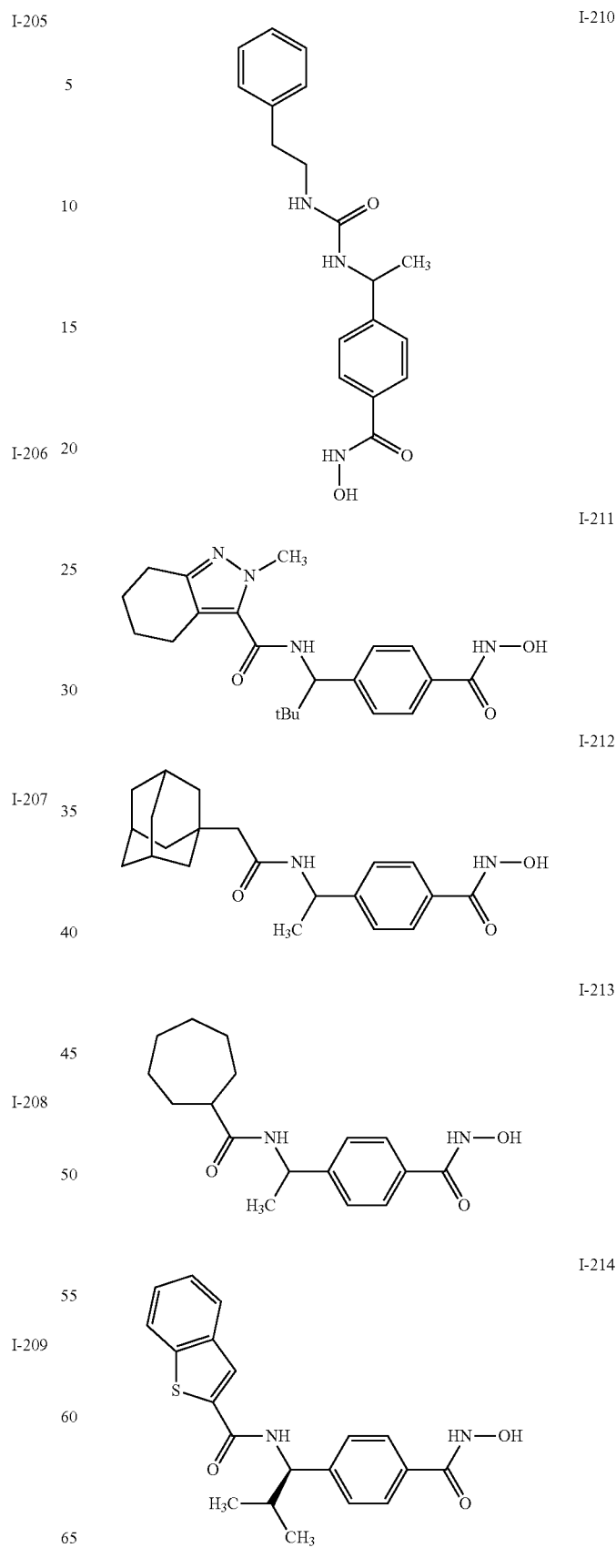

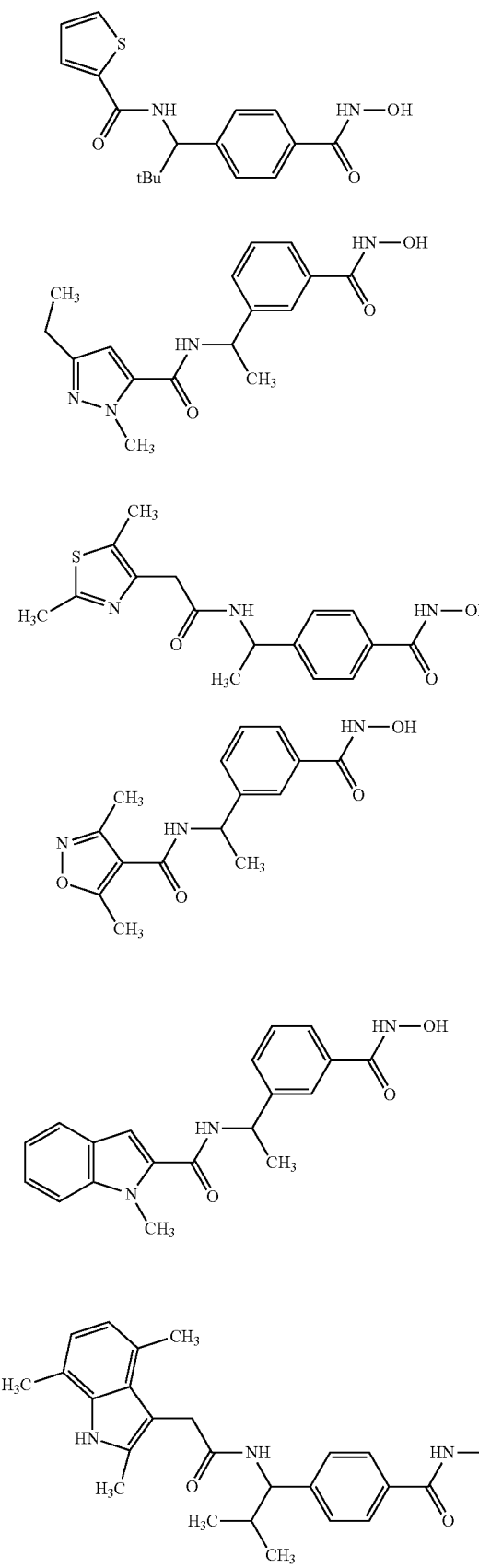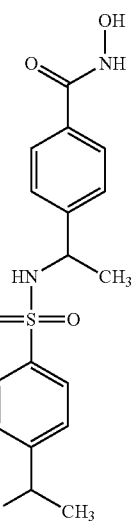

81
-continued
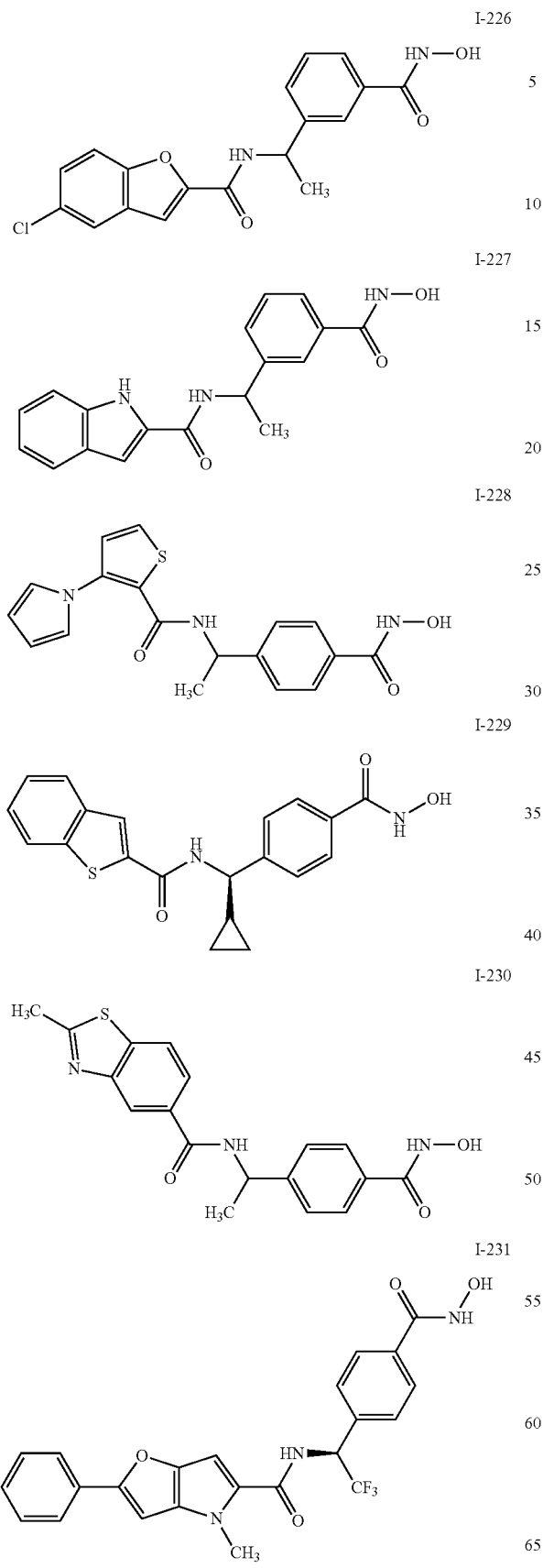
I-226
I-227
I-228
I-229
I-230
I-231
82
-continued
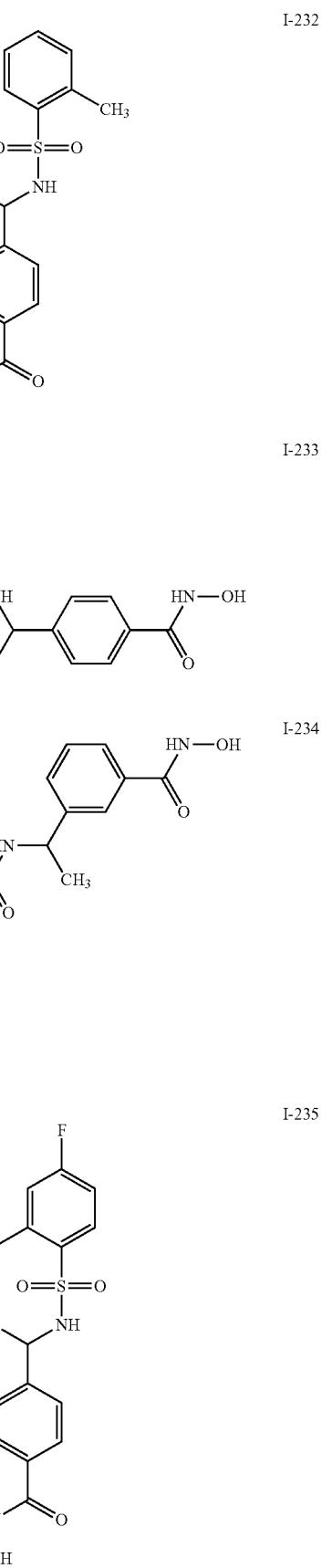
I-232
I-233
I-234
I-235

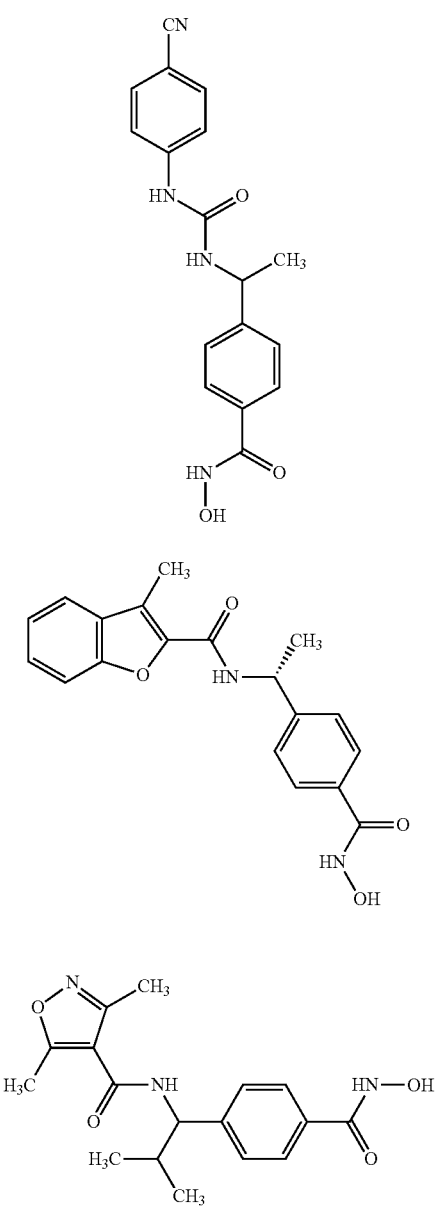
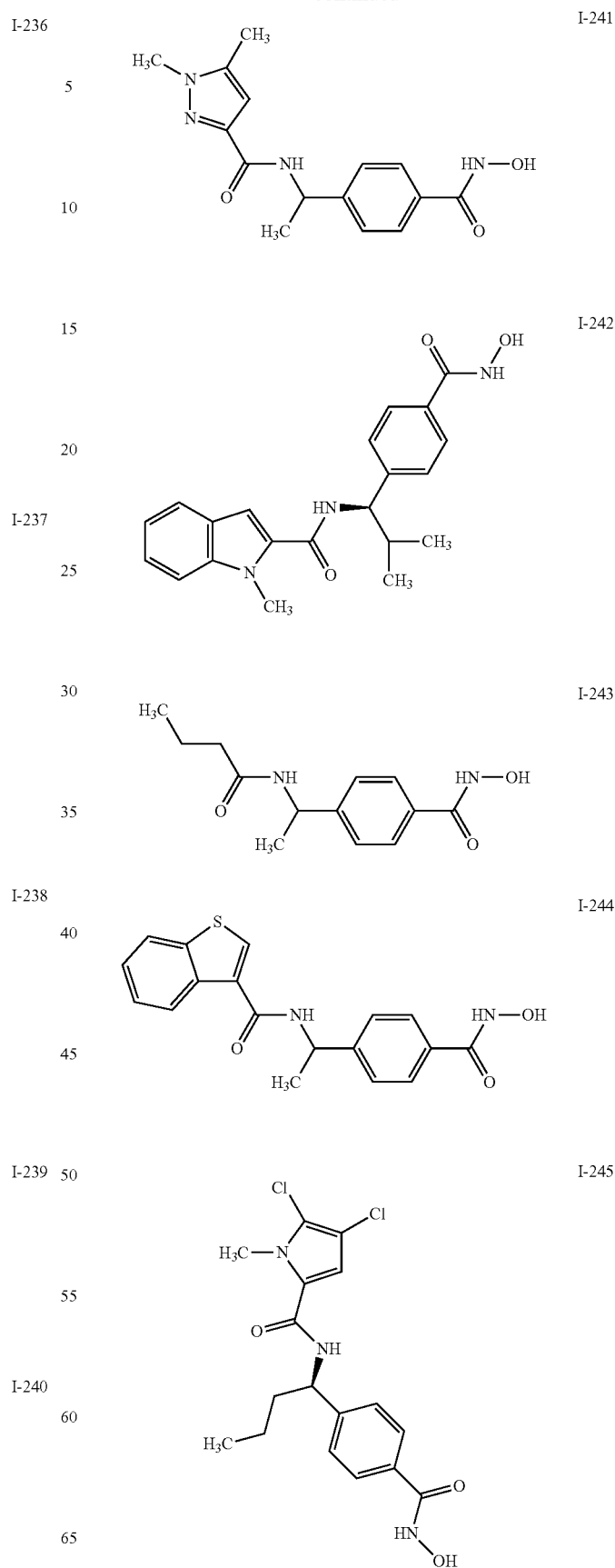

I-246
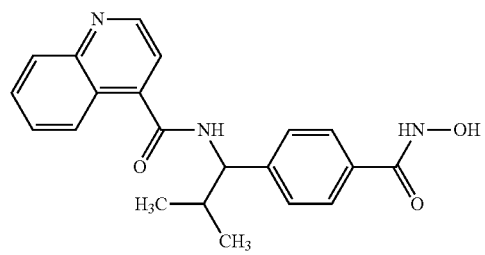
I-247
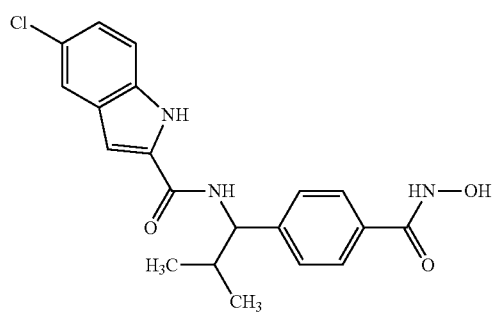
I-248
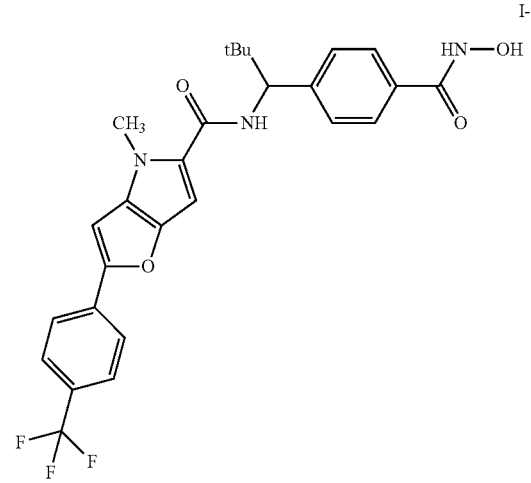
I-249
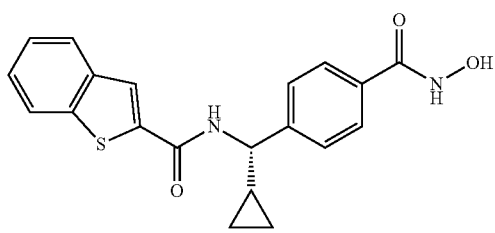
I-250
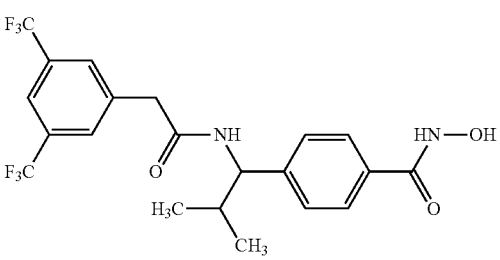
I-251
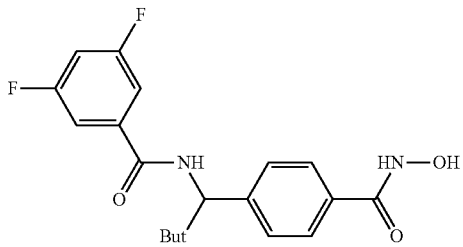
I-252
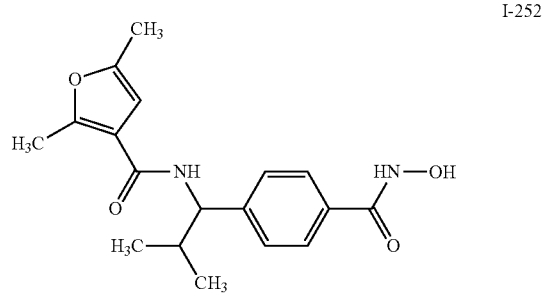
I-253
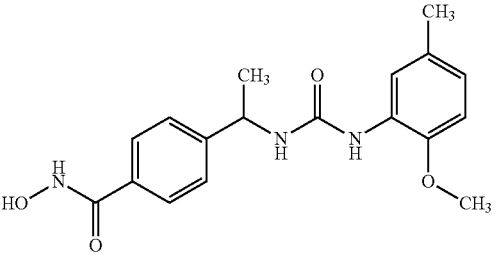
I-254
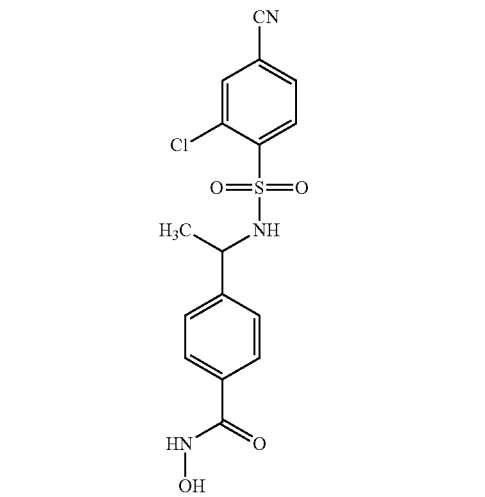
I-255
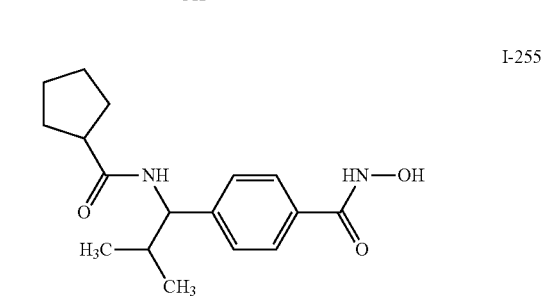

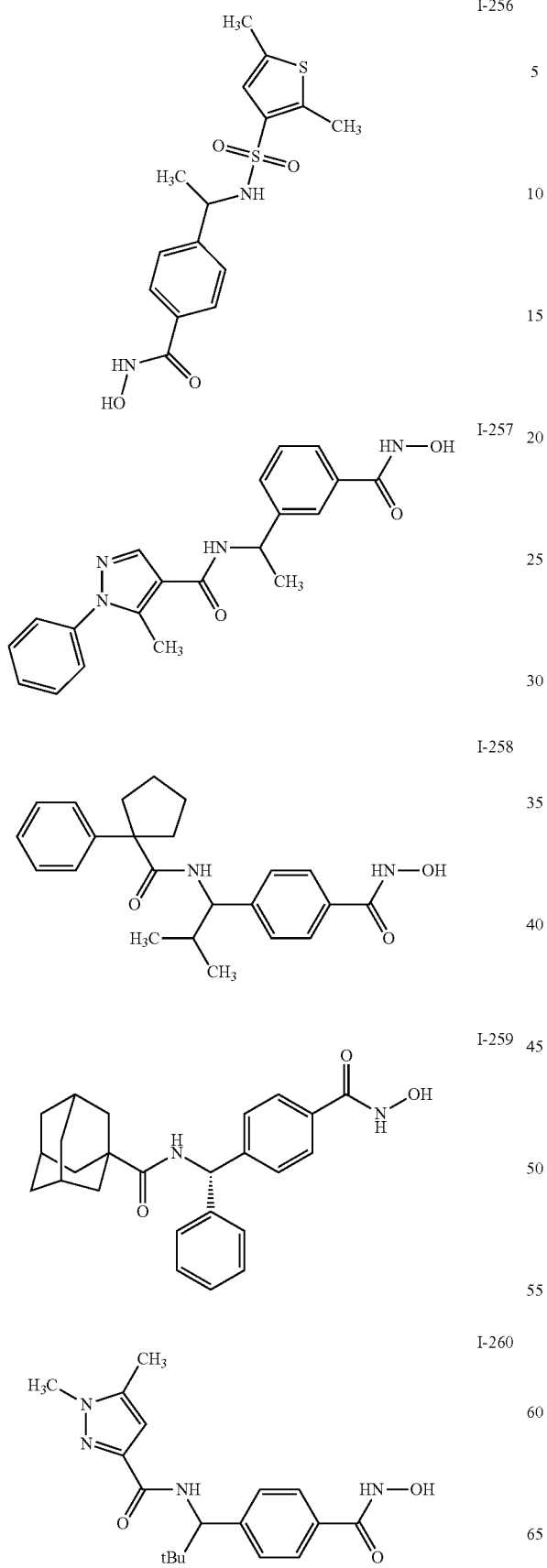
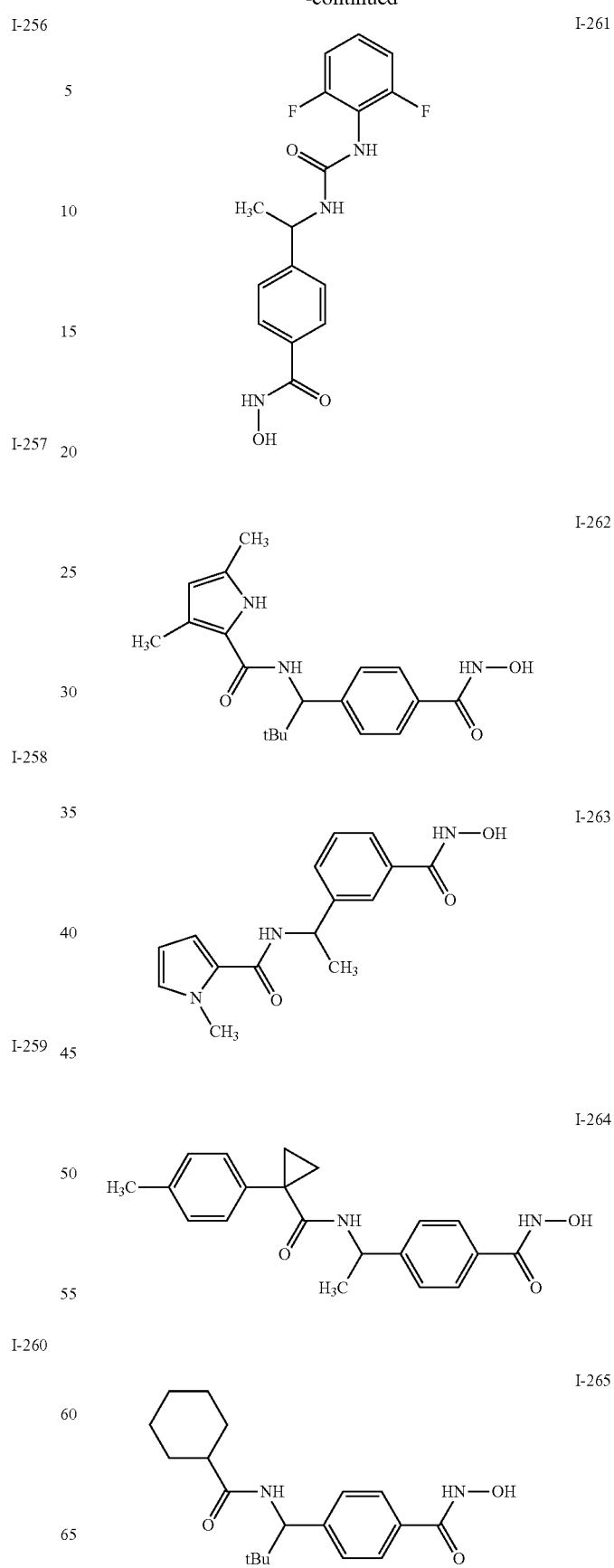

I-266 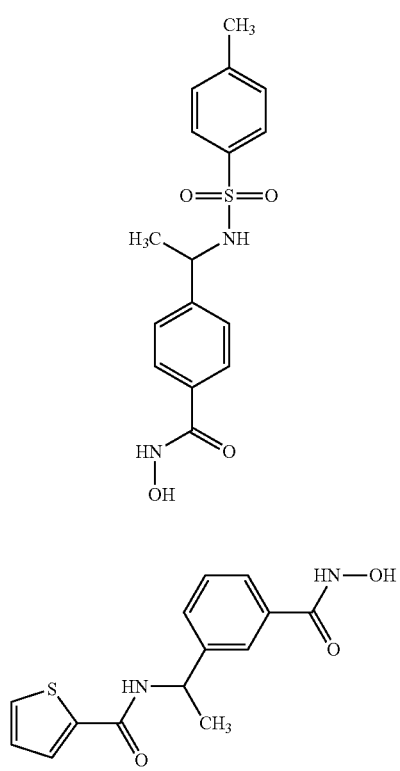
I-267 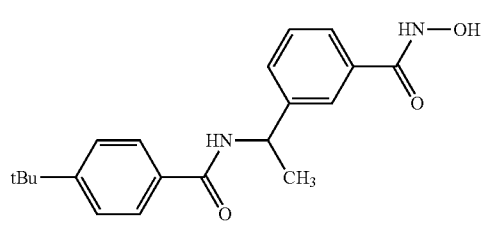
I-268 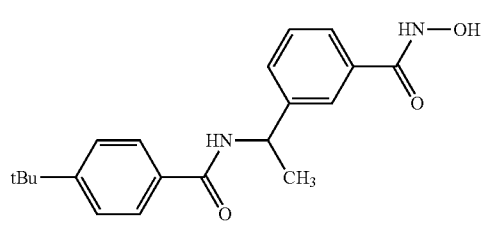
I-269 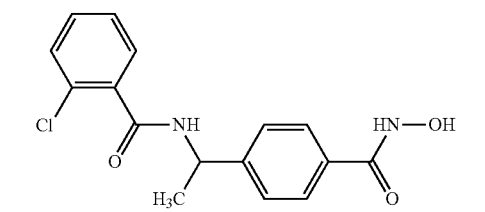
I-270 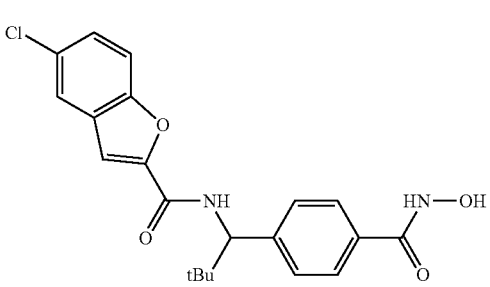
I-271 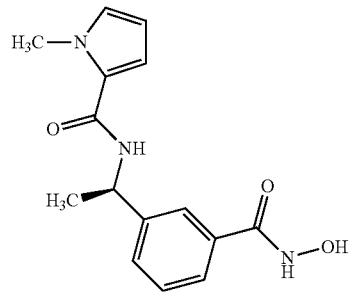
I-272 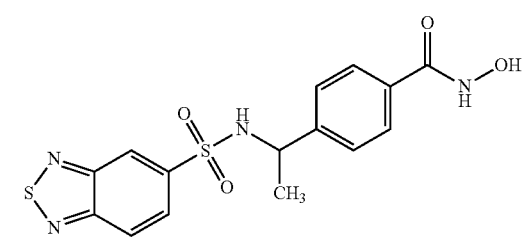
I-273 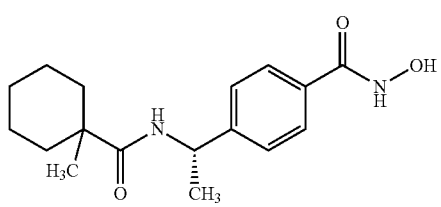
I-274 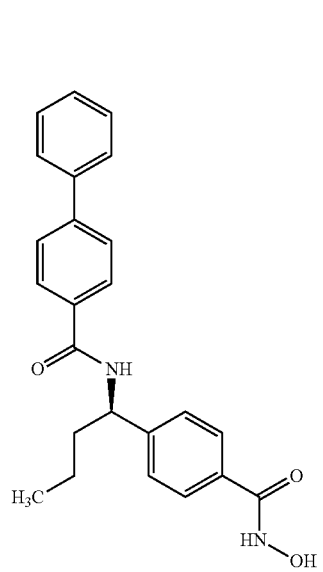

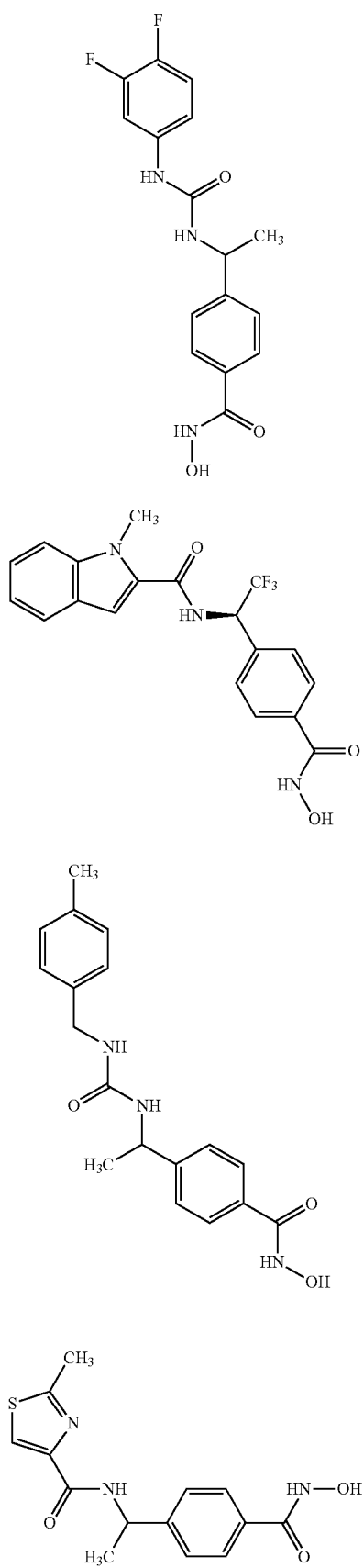
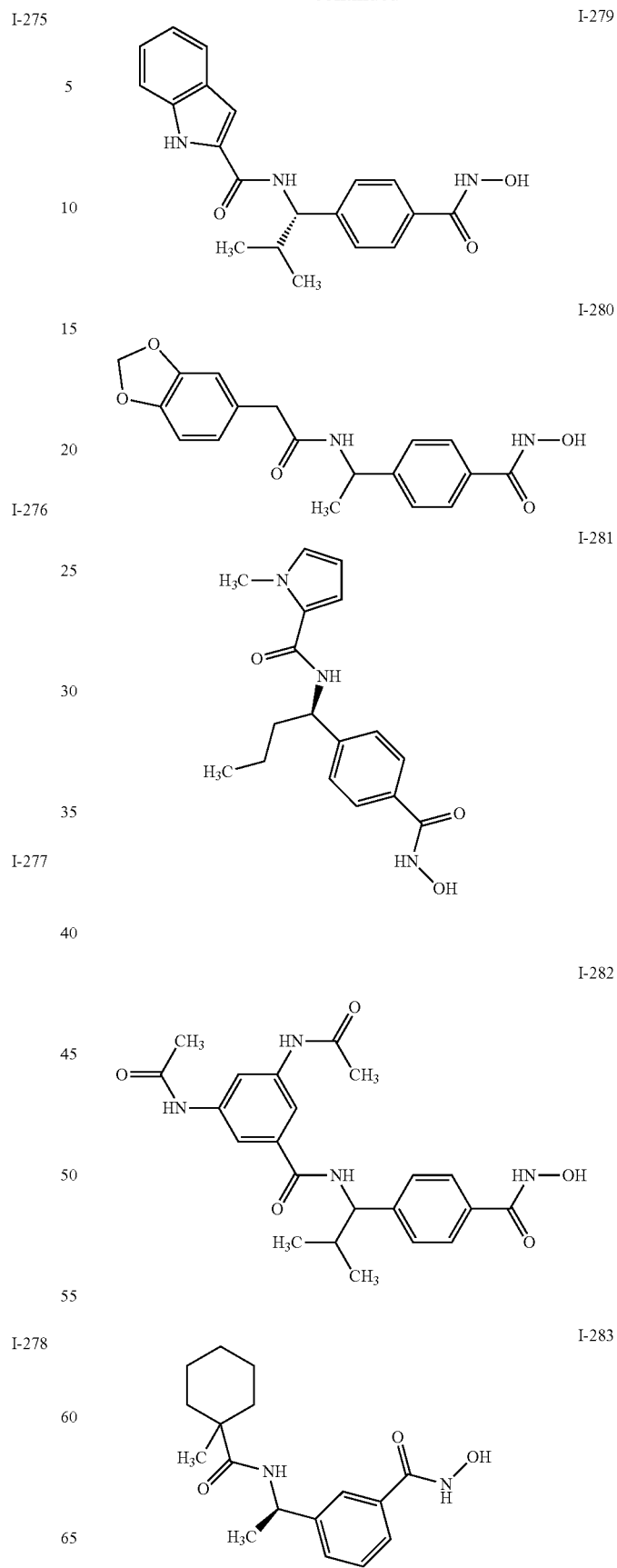

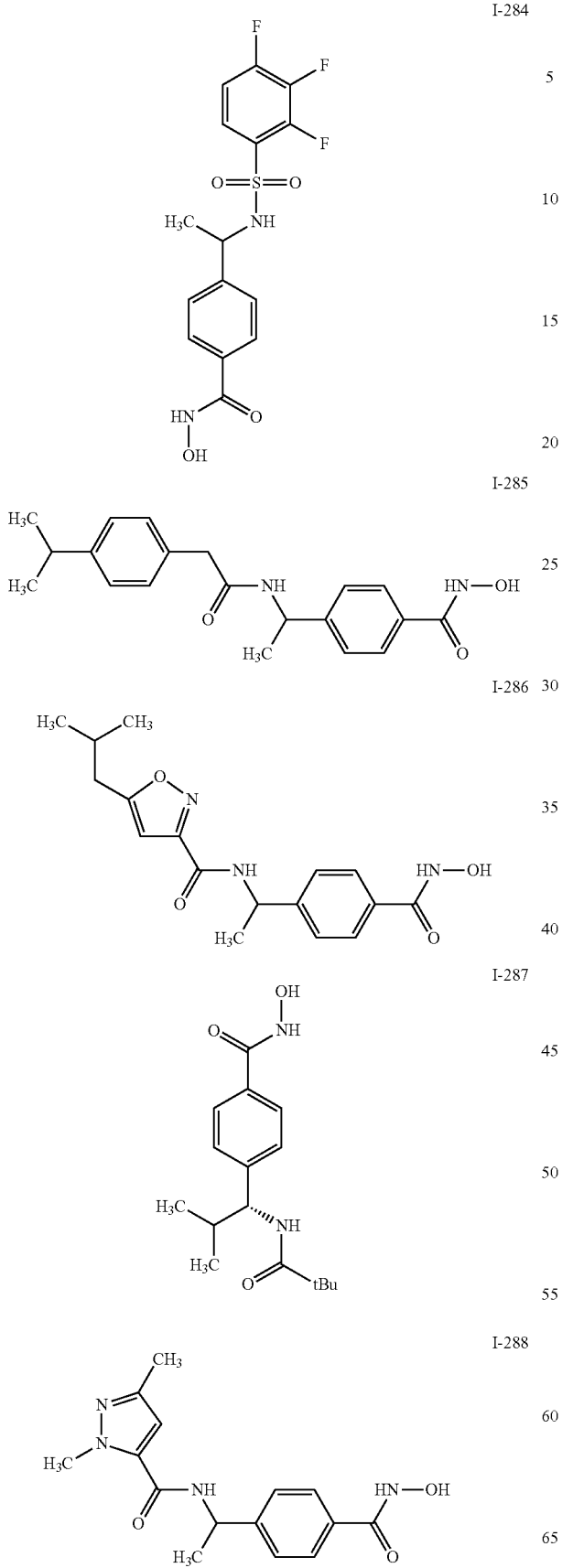

I-294
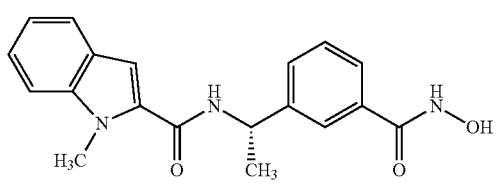
I-295
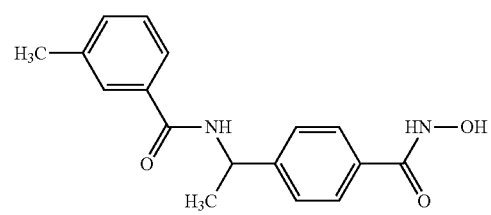
I-296
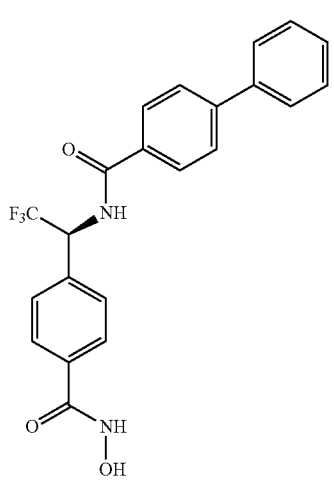
I-297
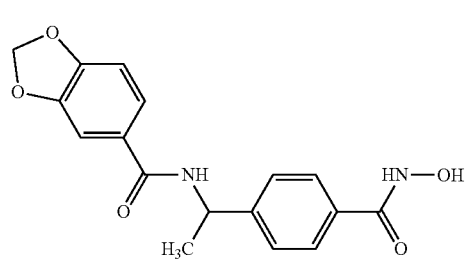
I-298
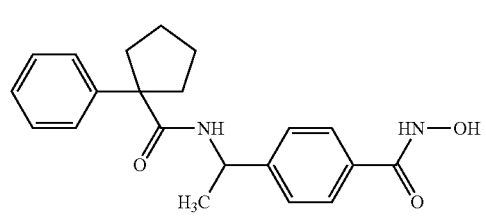
I-299
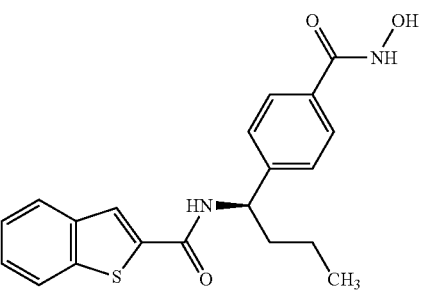
I-300
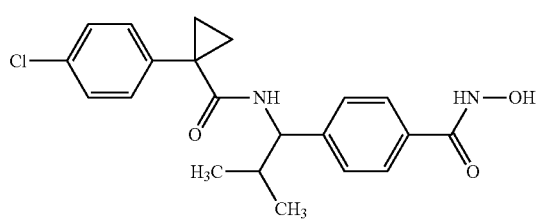
I-301
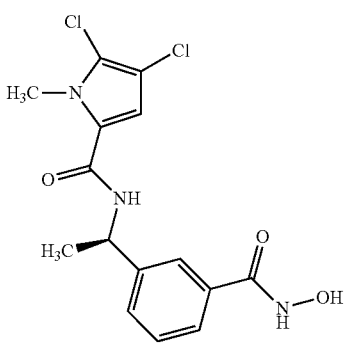
I-302
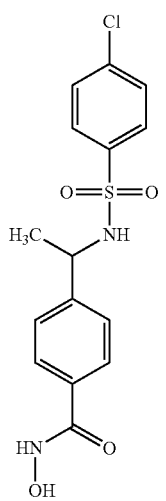
I-303
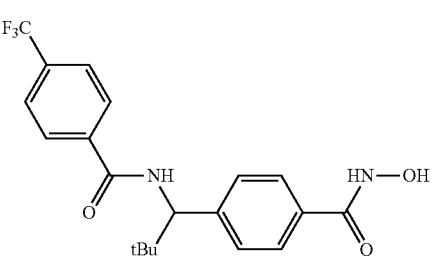

I-304
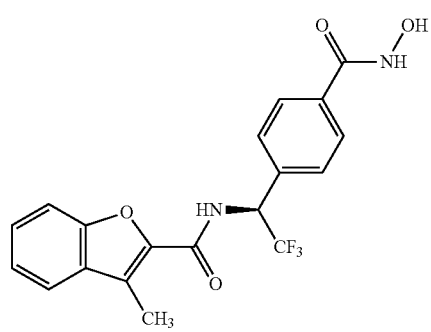
I-305
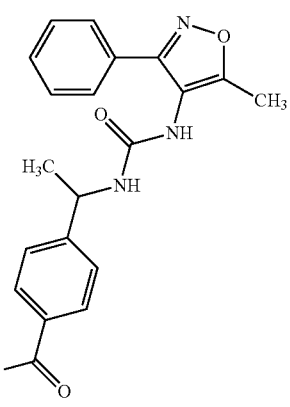
I-306
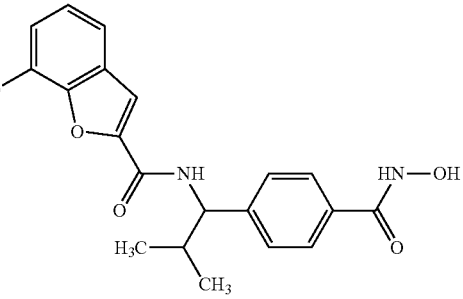
I-307
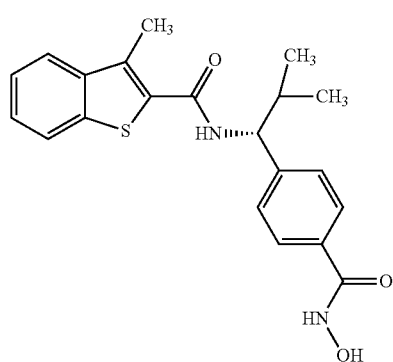
I-308
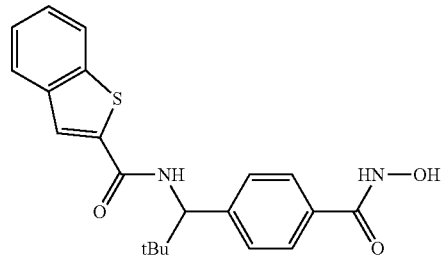
I-309
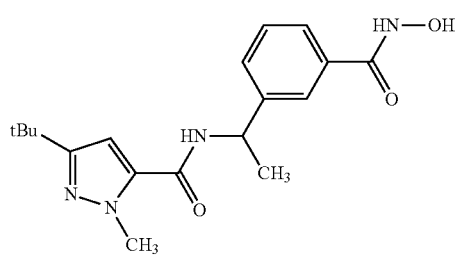
I-310
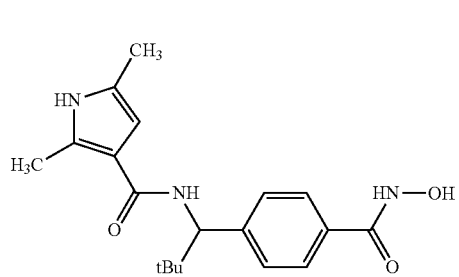
I-311
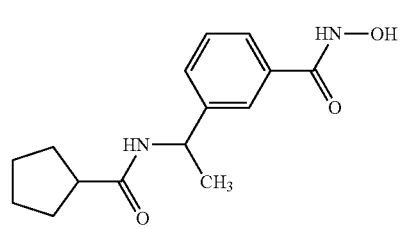
I-312
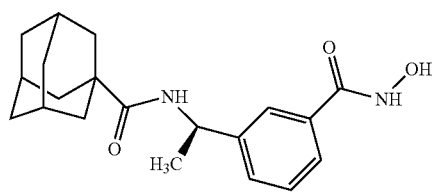
I-313
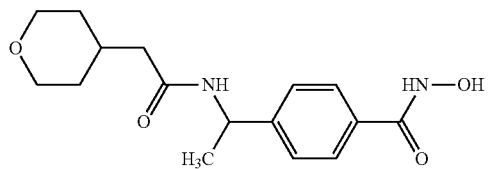

I-314
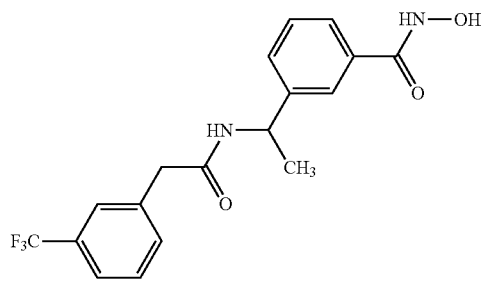
I-315
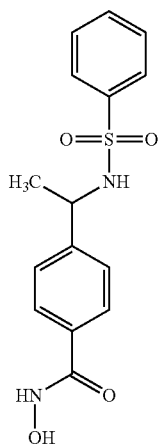
I-316
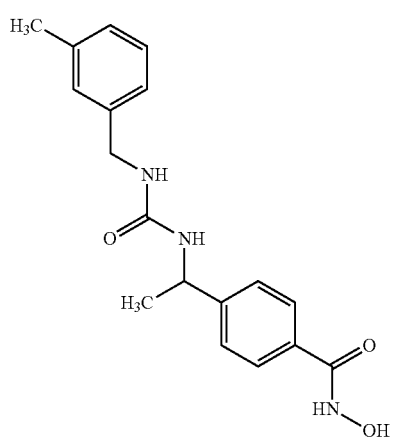
I-317
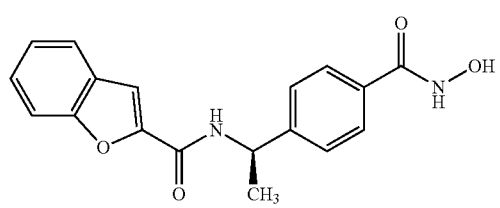
I-318
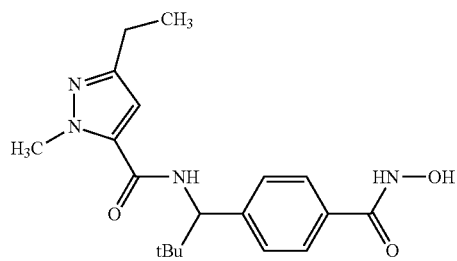
I-319
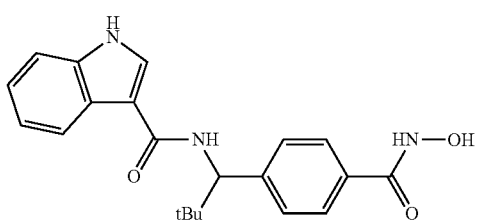
I-320
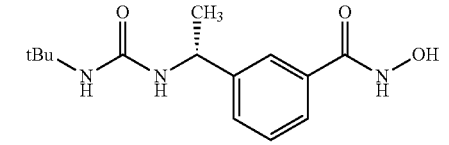
I-321
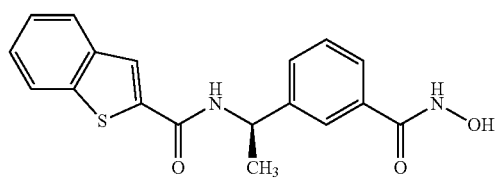
I-322
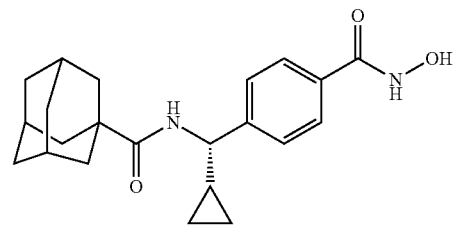
I-323
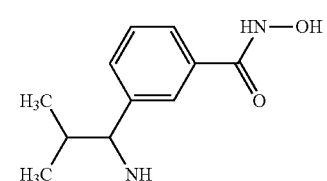
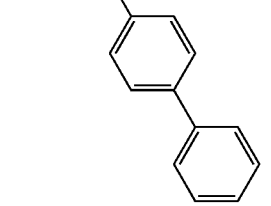

-continued
I-324
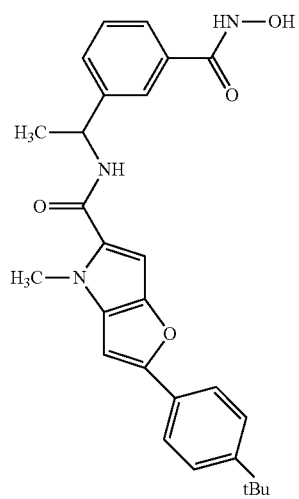
I-325
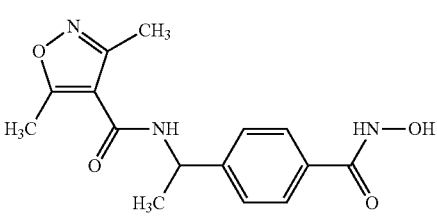
I-326
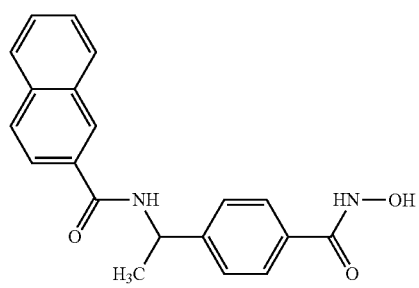
I-327
-continued
I-328
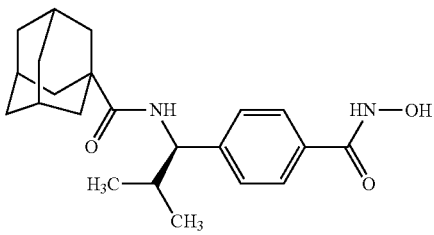
I-329
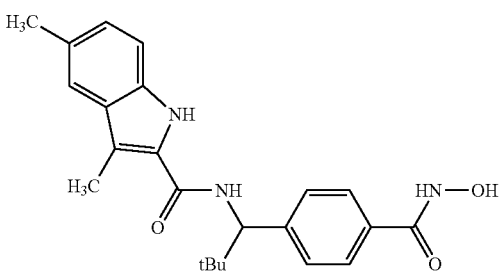
I-330
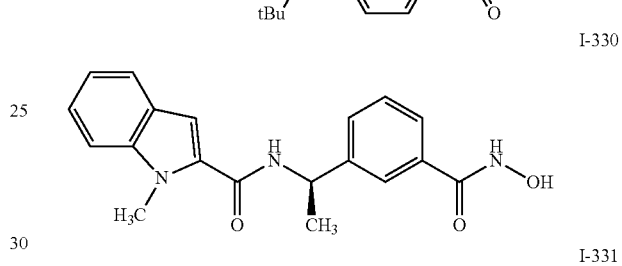
I-331
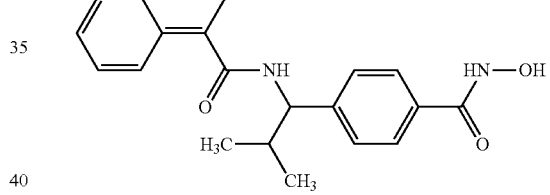
I-332
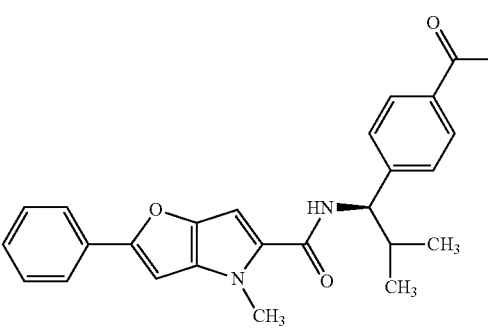
I-333

I-334 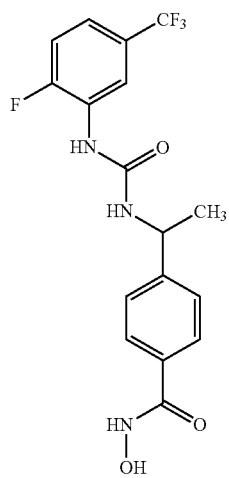
I-335 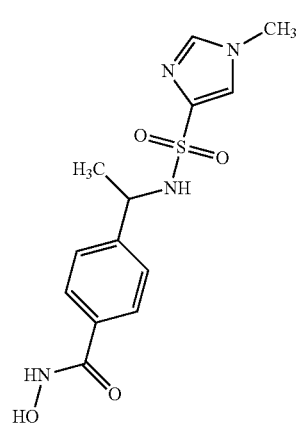
I-336 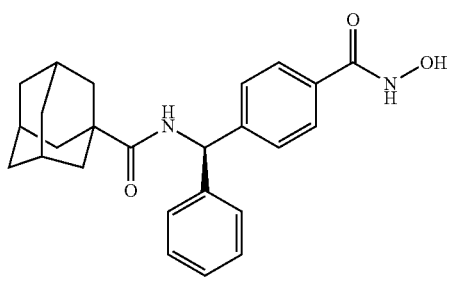
I-337 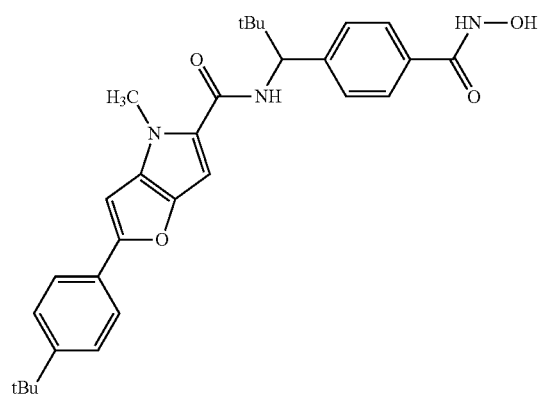
I-338 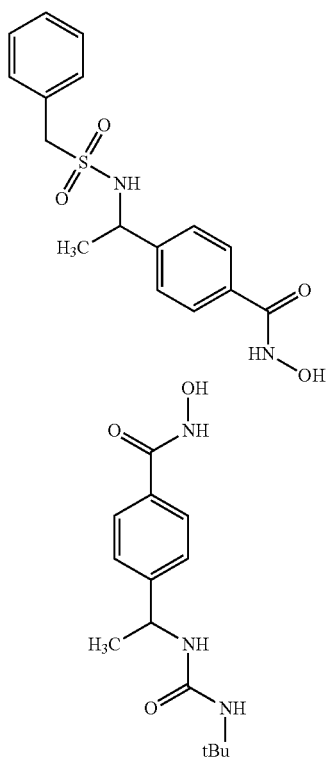
I-339
I-340 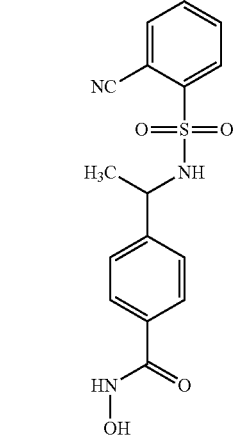
I-341 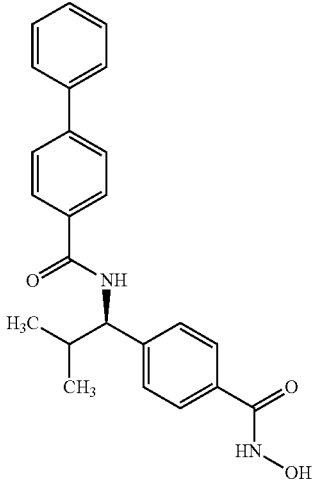

I-342
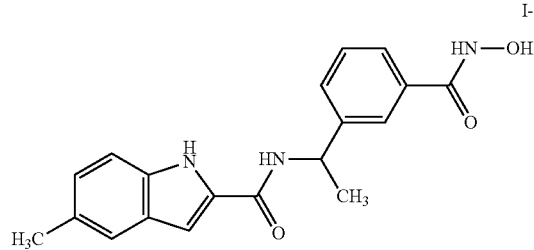
I-343
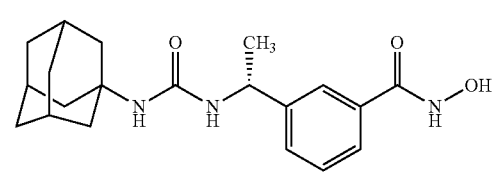
I-344
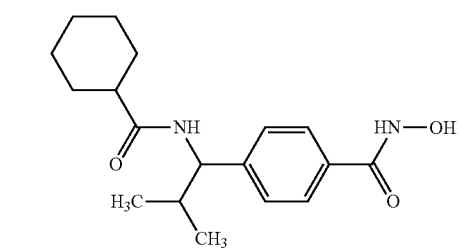
I-345
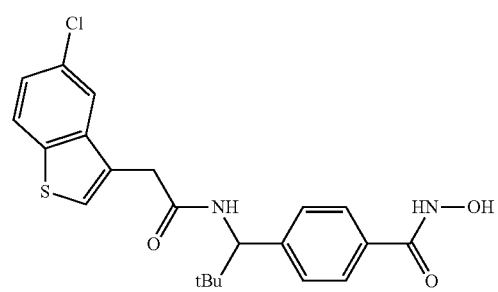
I-346
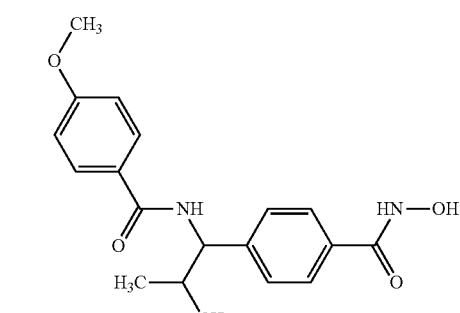
I-347
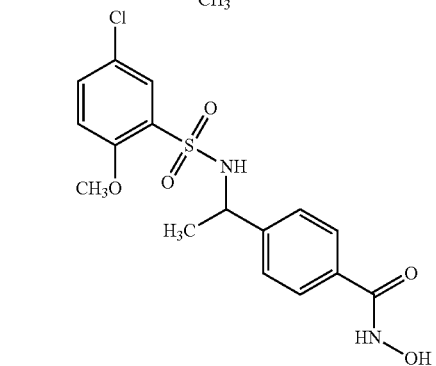
I-348
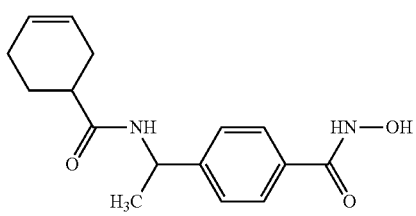
I-349
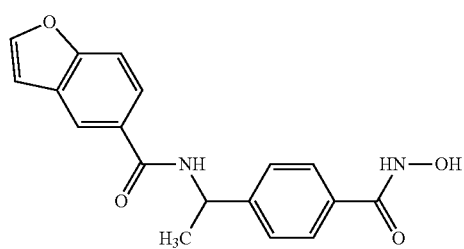
I-350
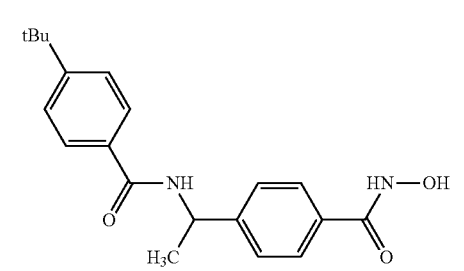
I-351
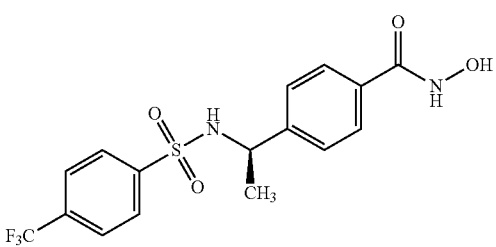
I-352
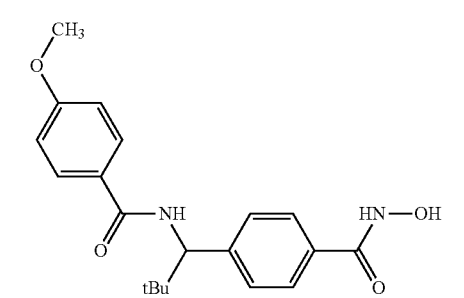
I-353
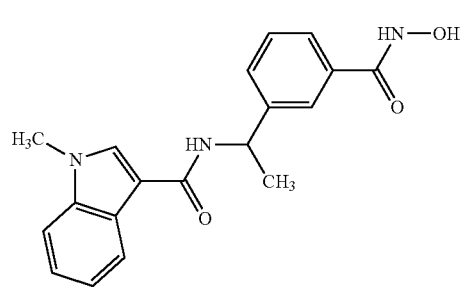

I-354
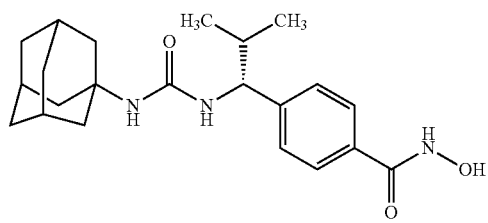
I-355
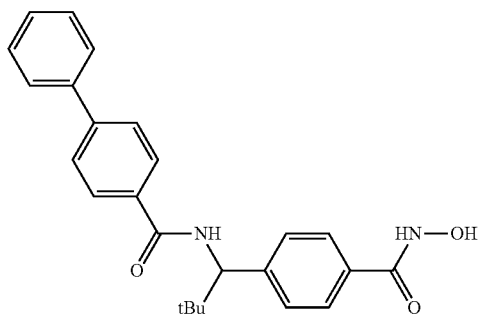
I-356
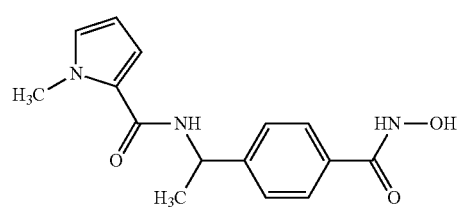
I-357
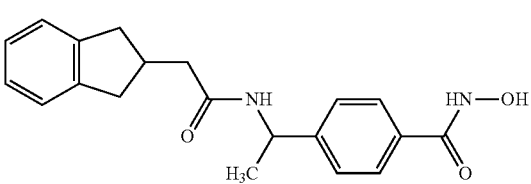
I-358
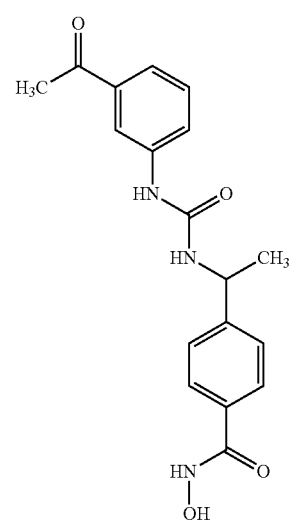
I-359
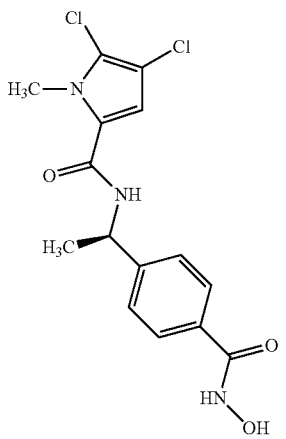
I-360
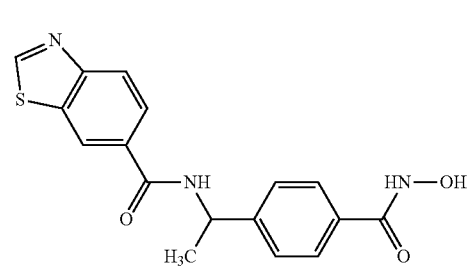
I-361
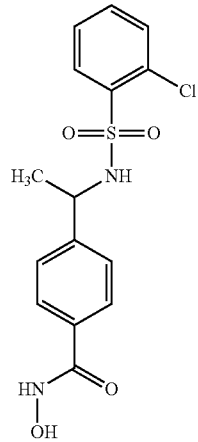
I-362
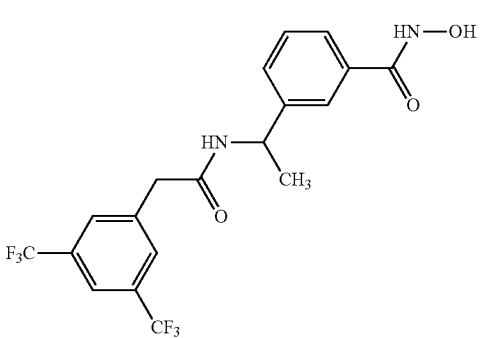

I-363
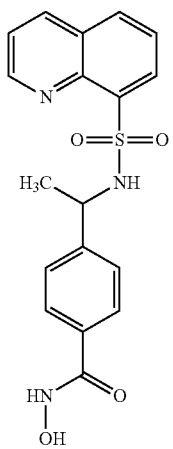
I-364
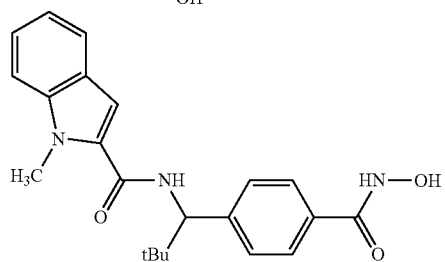
I-365
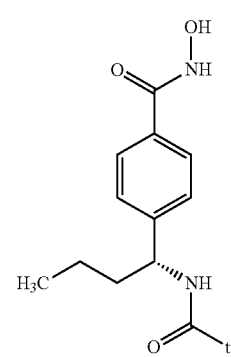
I-366
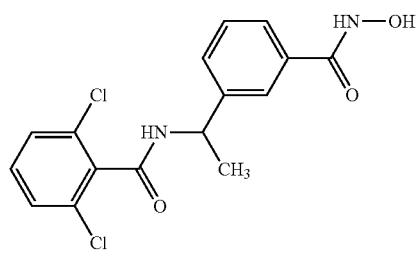
I-367
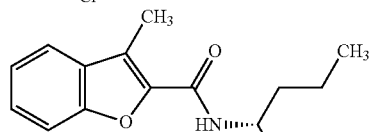
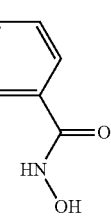
I-368
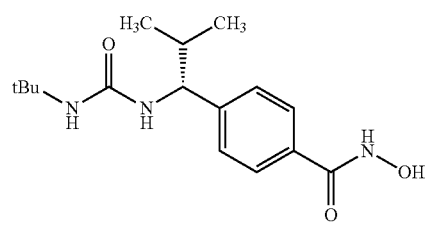
I-369
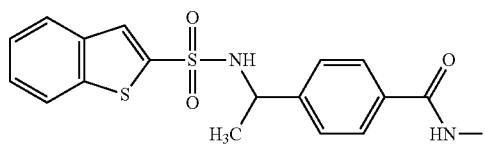
I-370
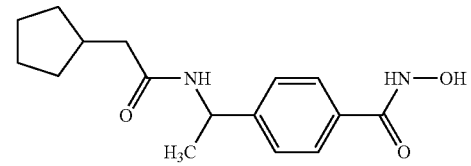
I-371
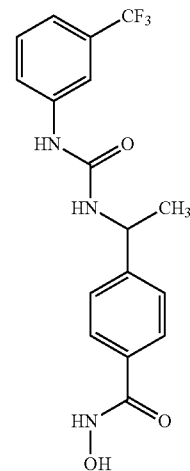
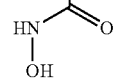
I-372
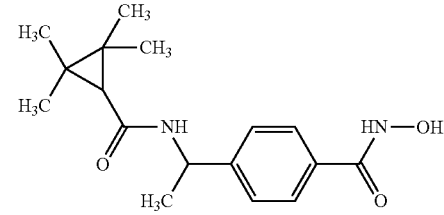
I-373
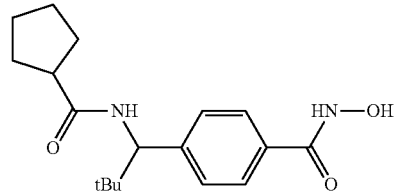

I-374
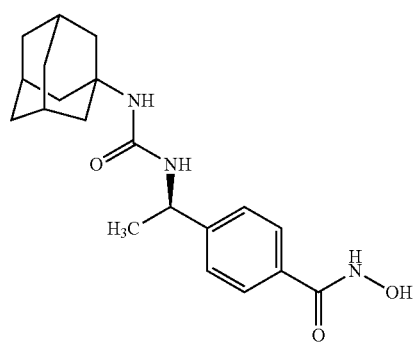
I-375
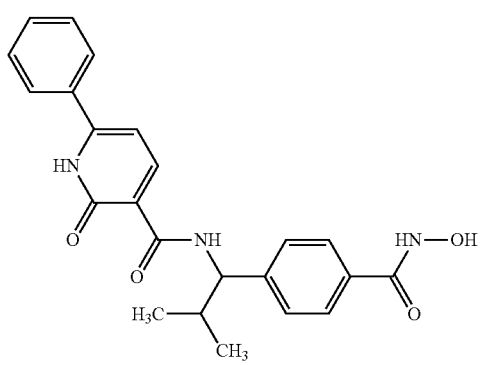
I-376
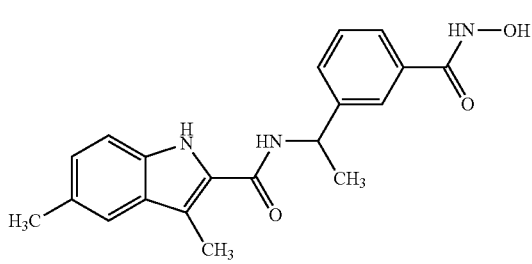
I-377
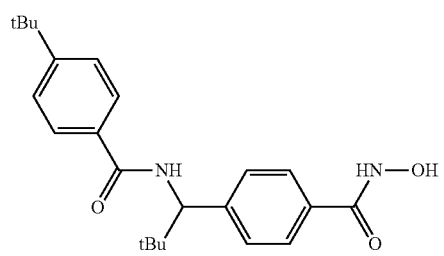
I-378
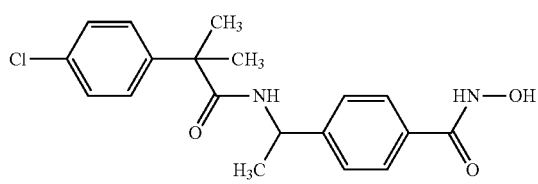
I-379
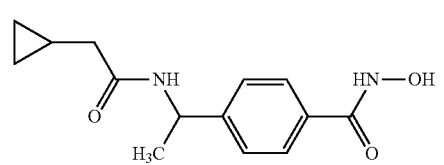
I-380
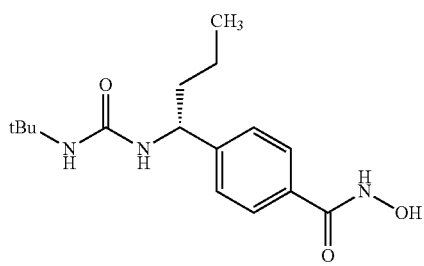
I-381
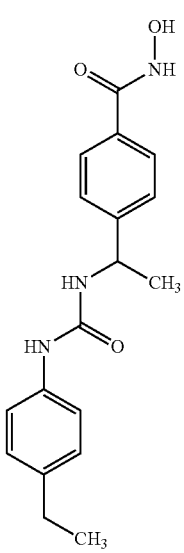
I-382
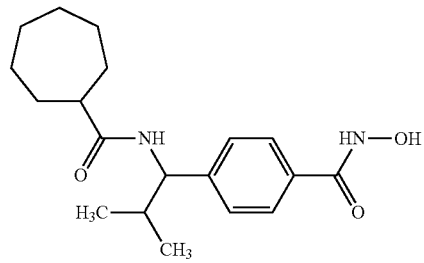
I-383
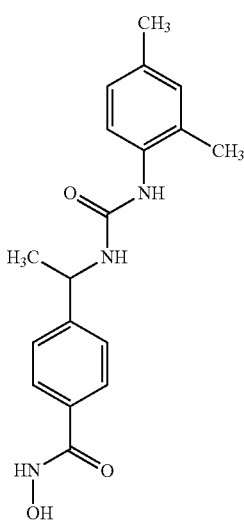

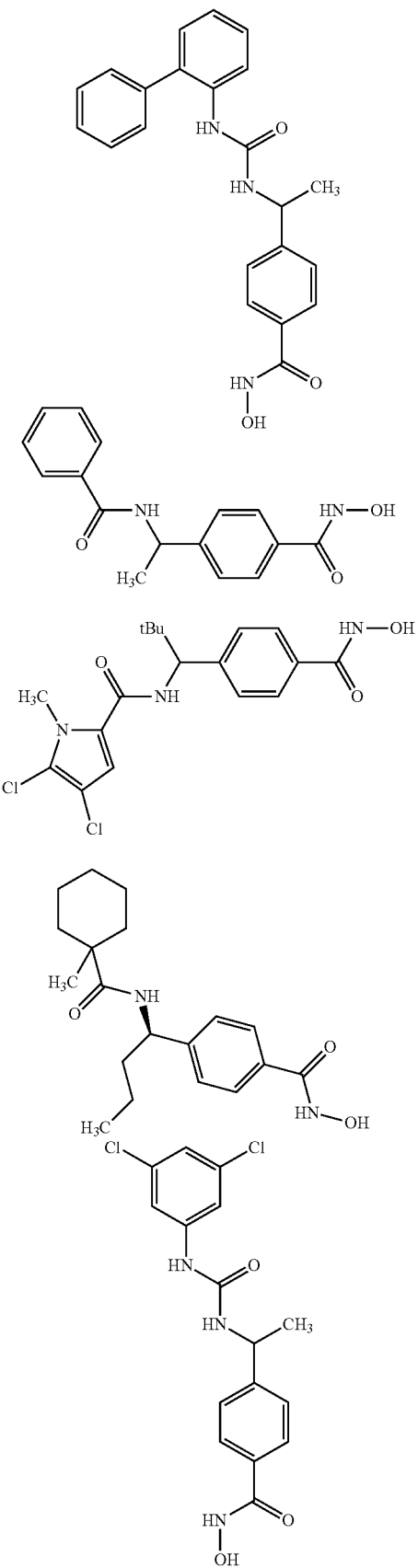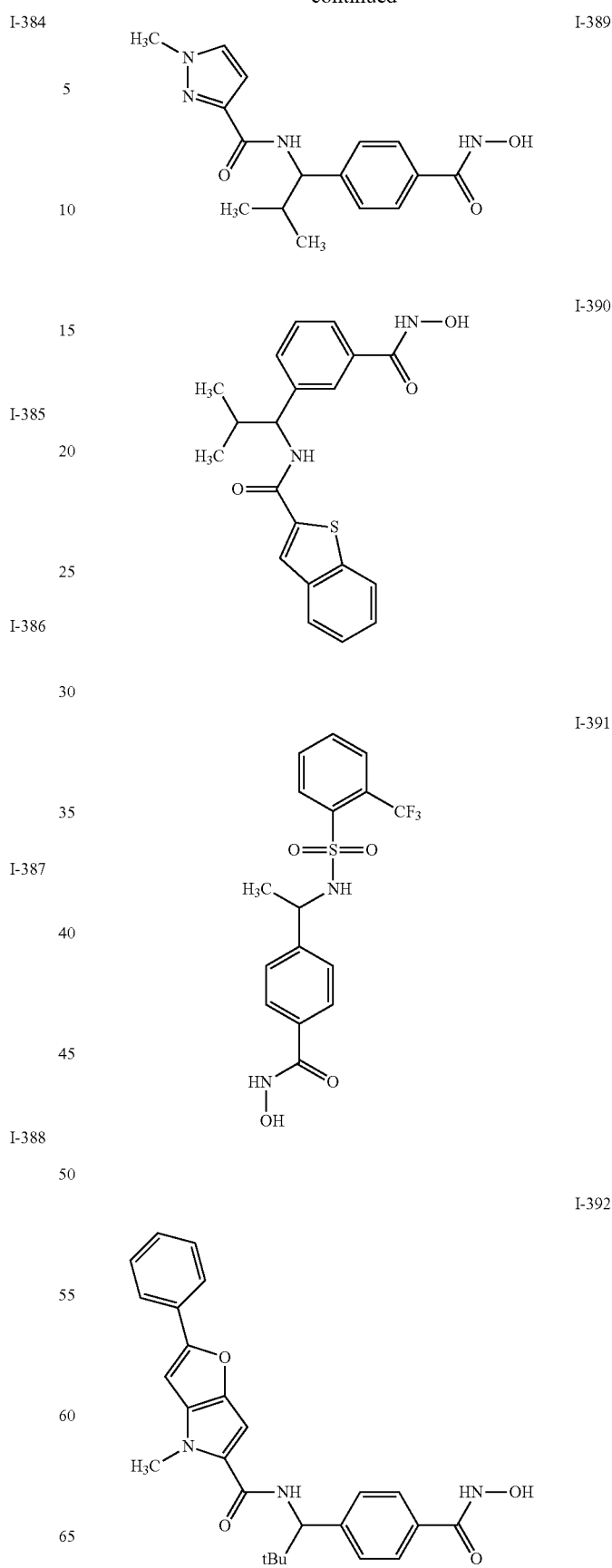

I-393
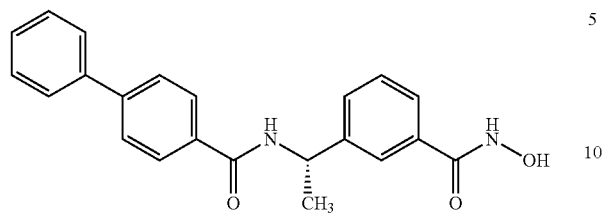
I-394
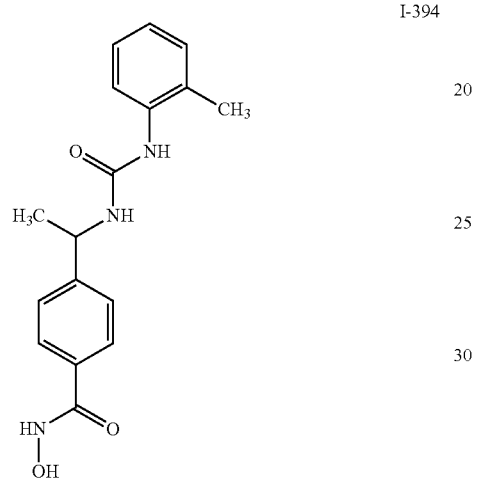
I-395
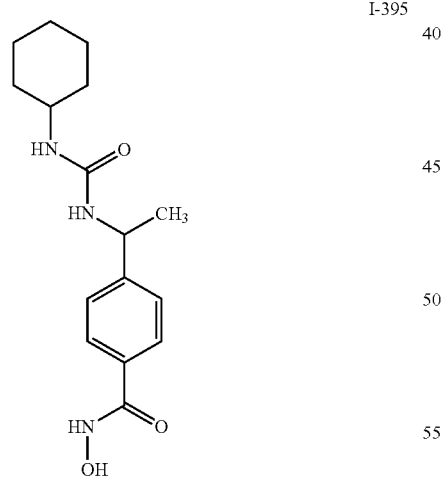
I-396
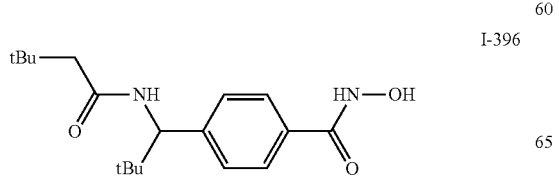
I-397
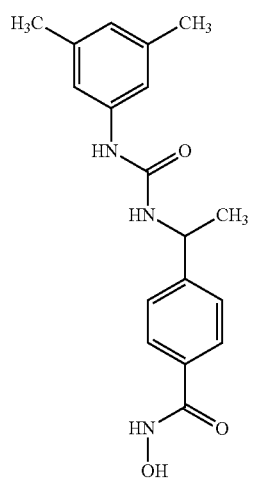
I-398
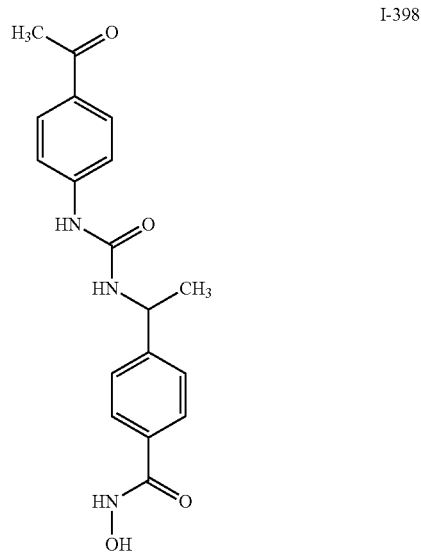
I-399
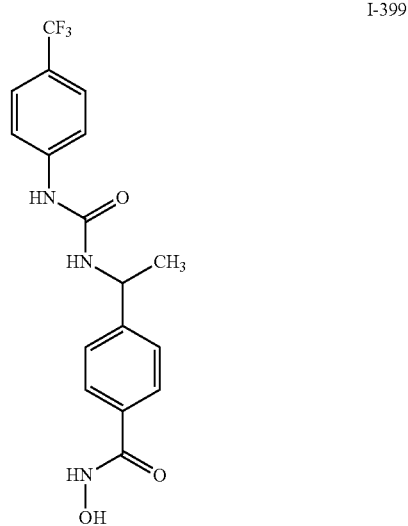

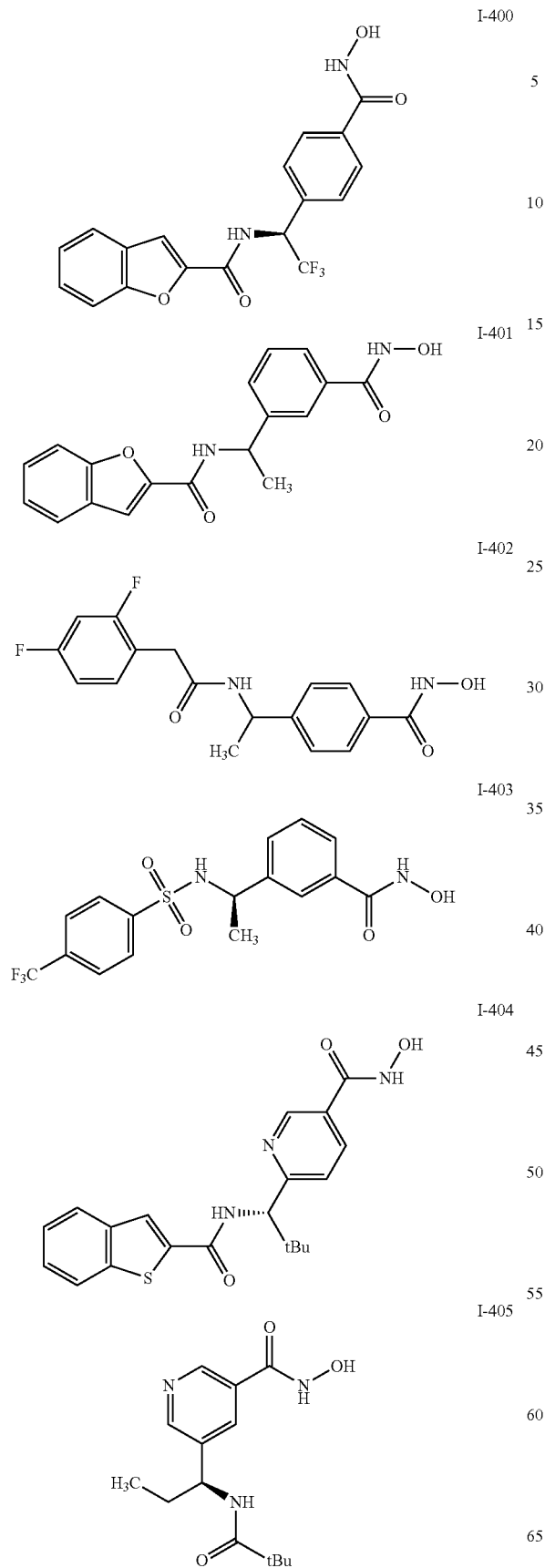
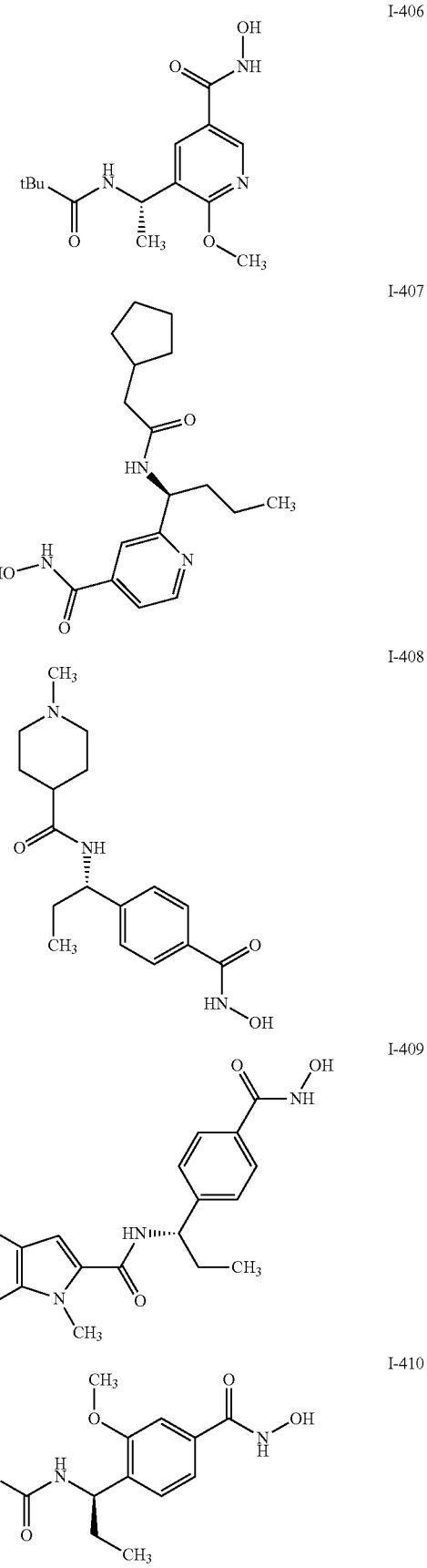

I-411 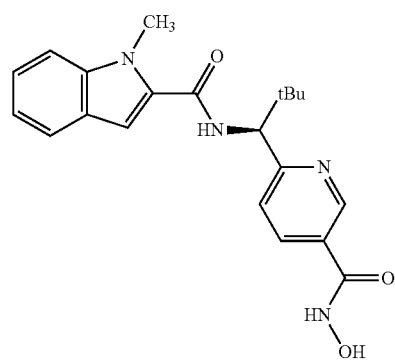
I-412 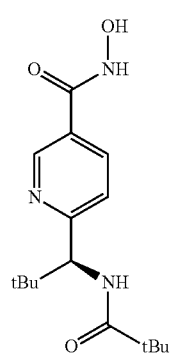
I-413 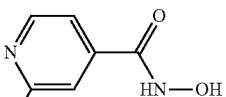 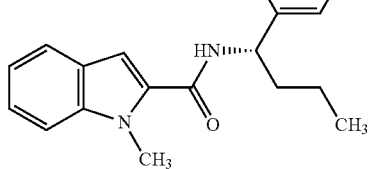
I-414 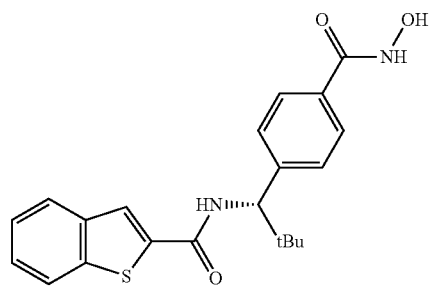
I-415 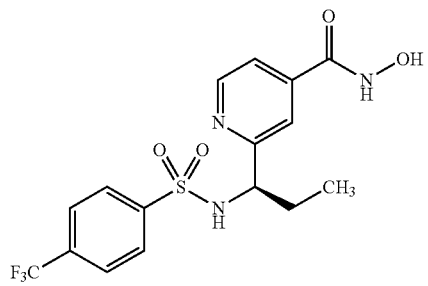
I-416 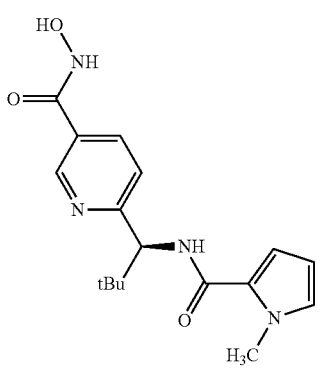
I-417 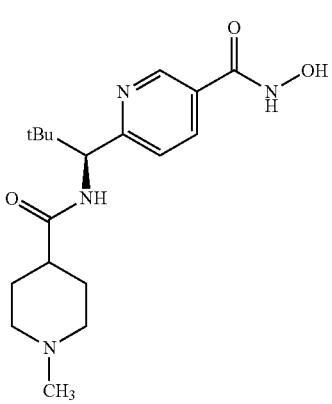
I-418 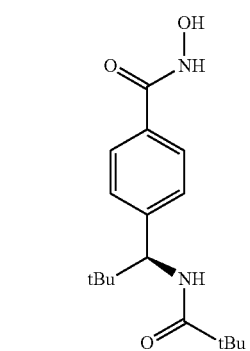
I-419 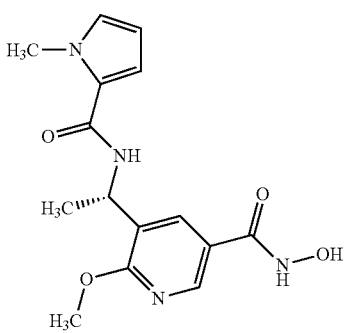

I-420
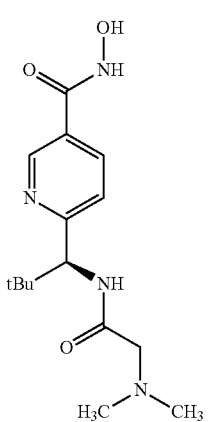
I-421
I-422
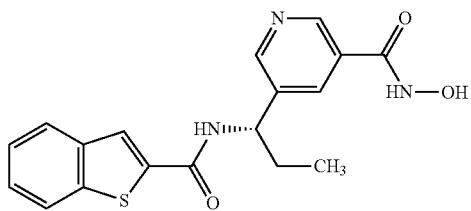
I-423
I-424
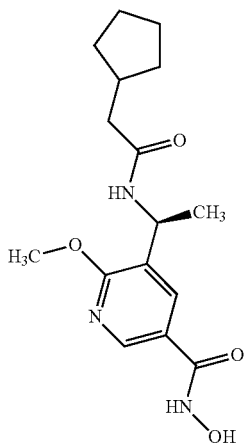
I-425
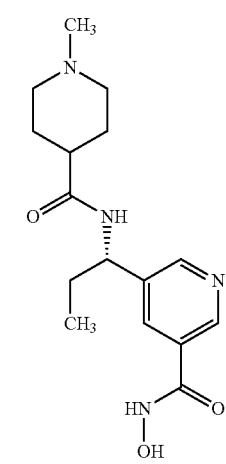
I-426
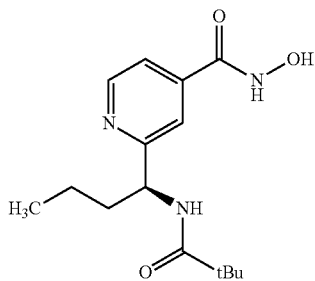
I-427
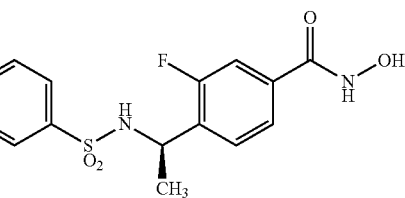

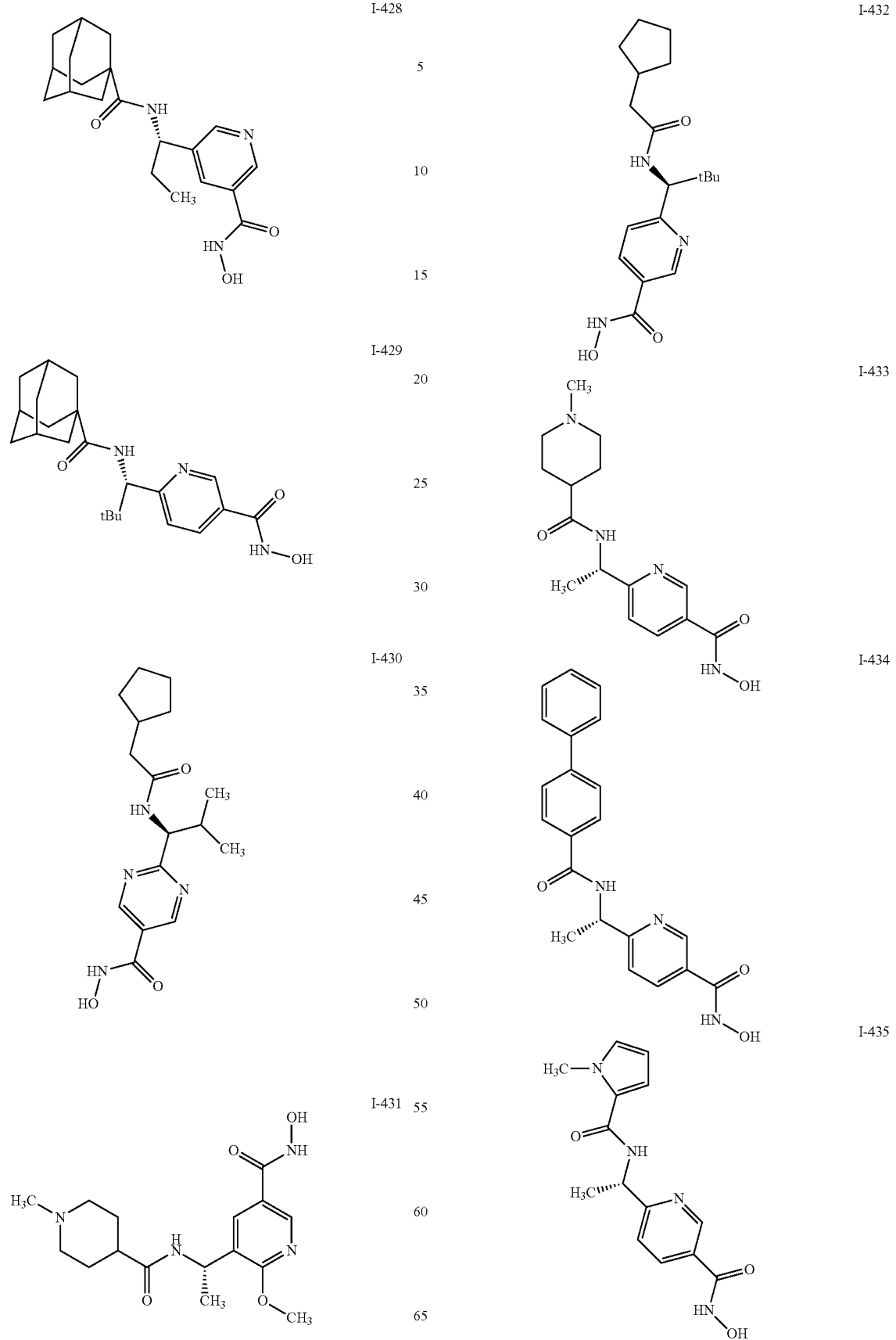

I-436 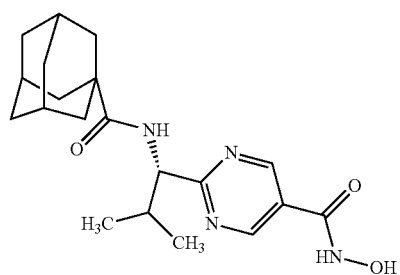
I-437 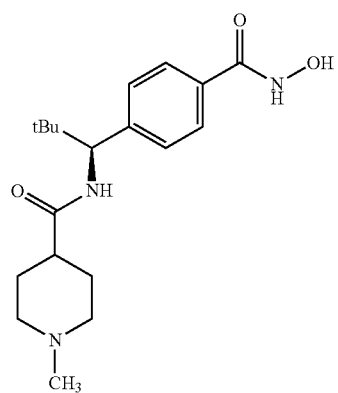
I-438 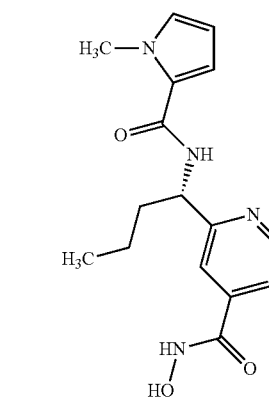
I-439 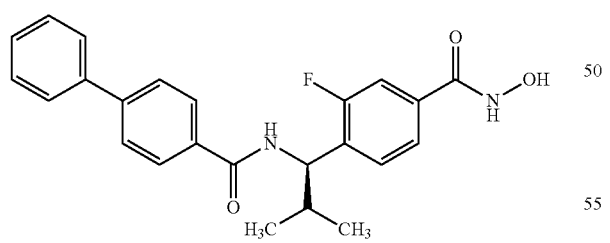
I-440 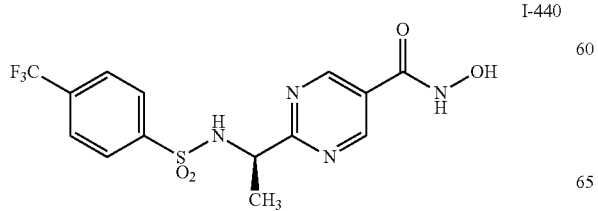
I-441 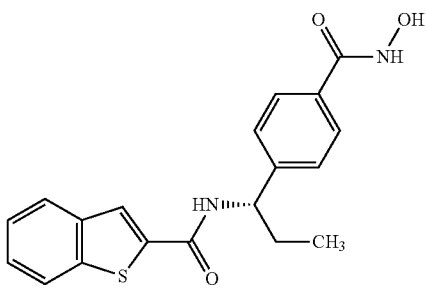
I-442 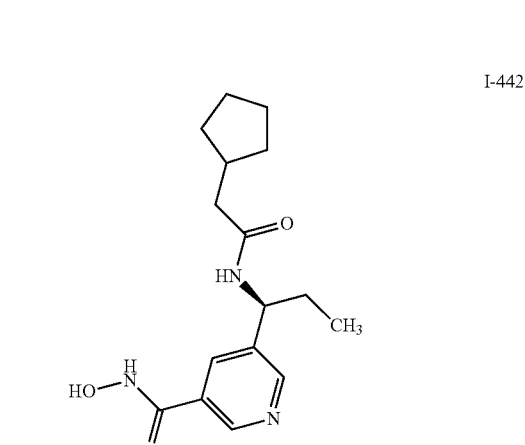
I-443 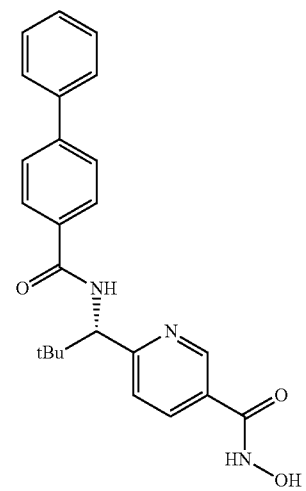
I-444 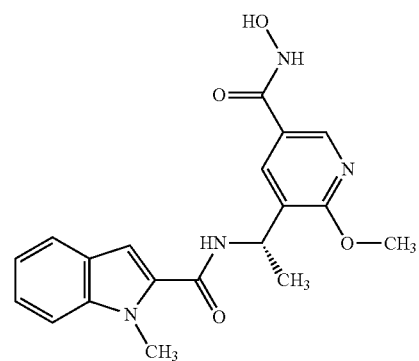

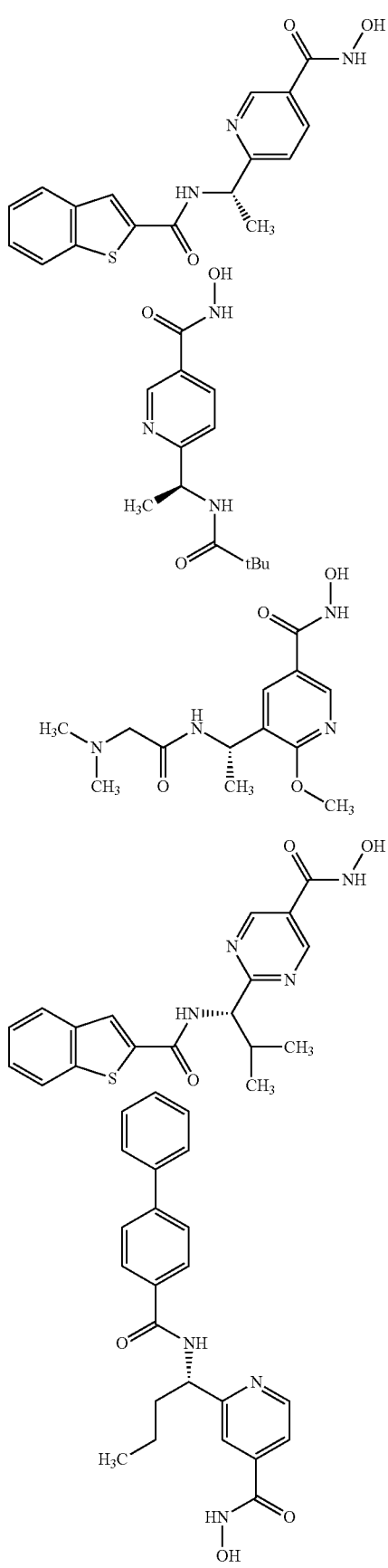
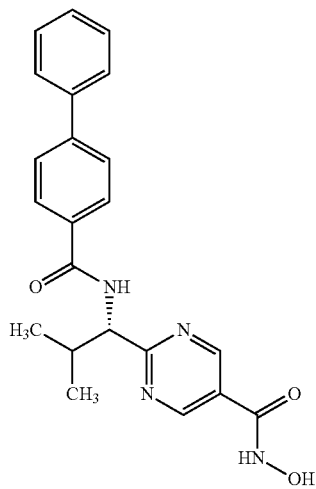
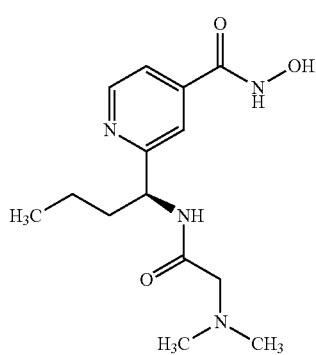
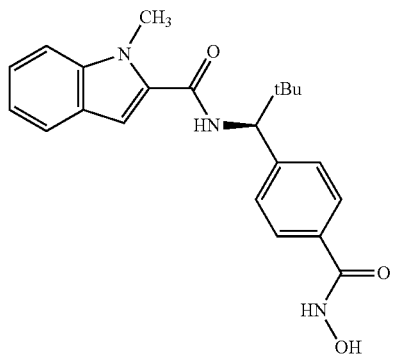
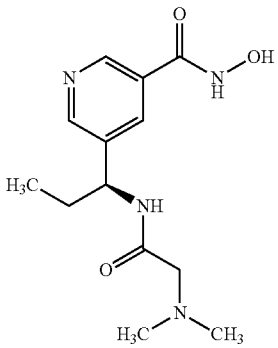

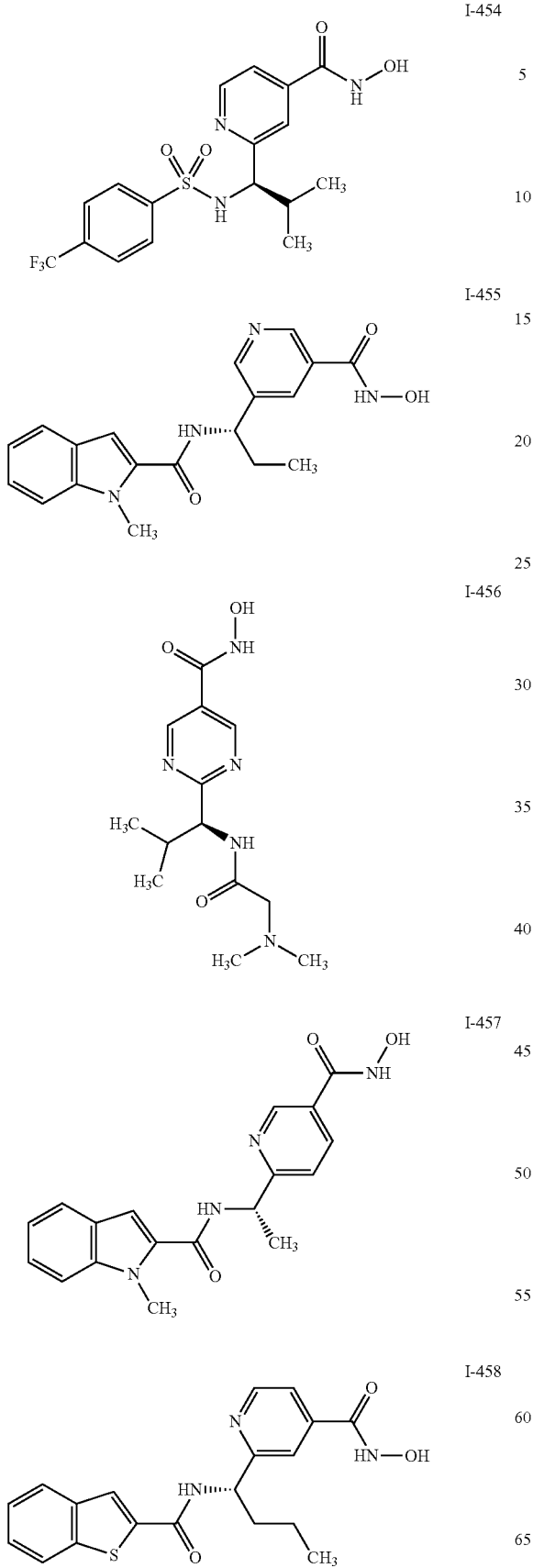
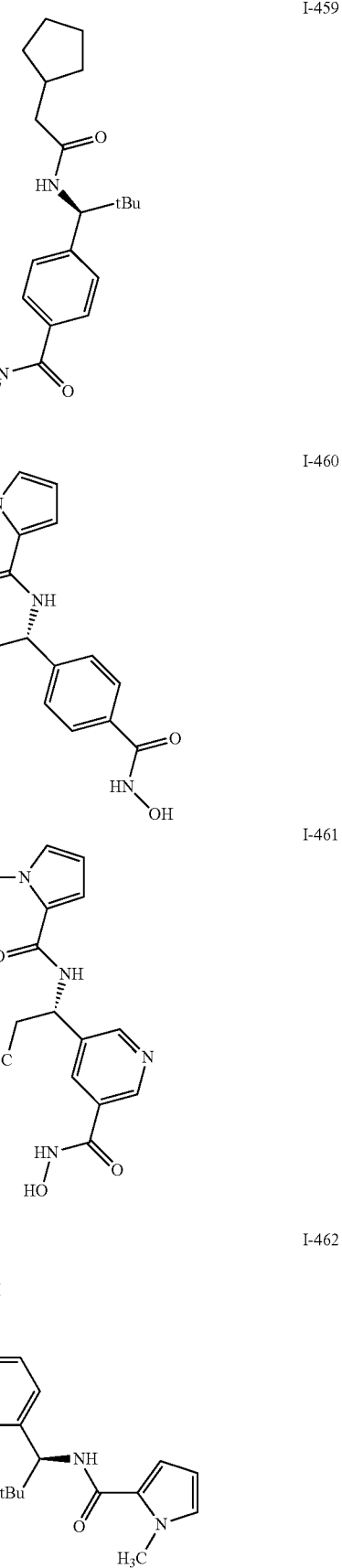

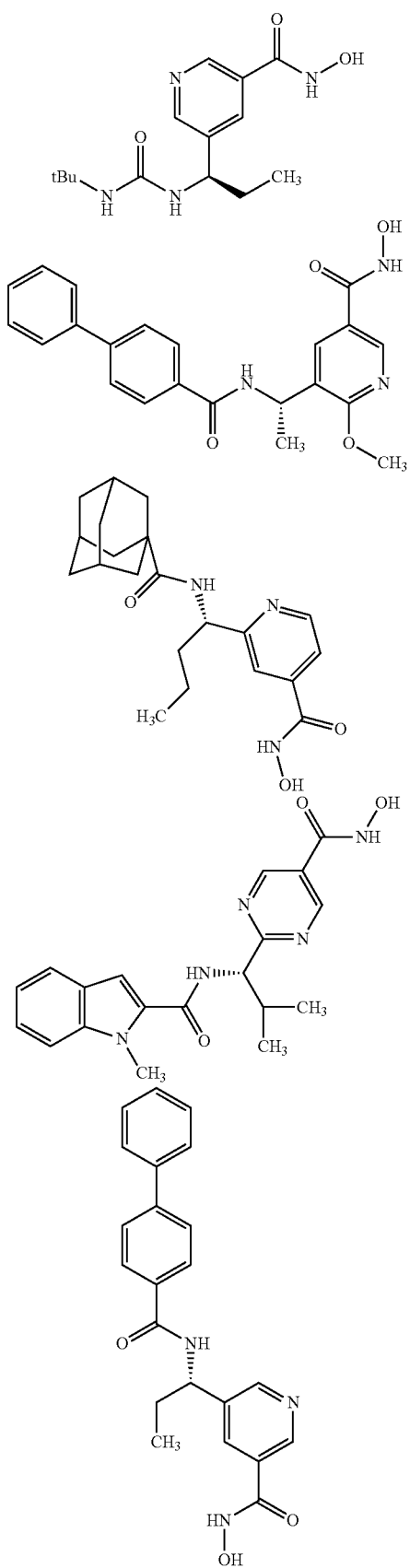
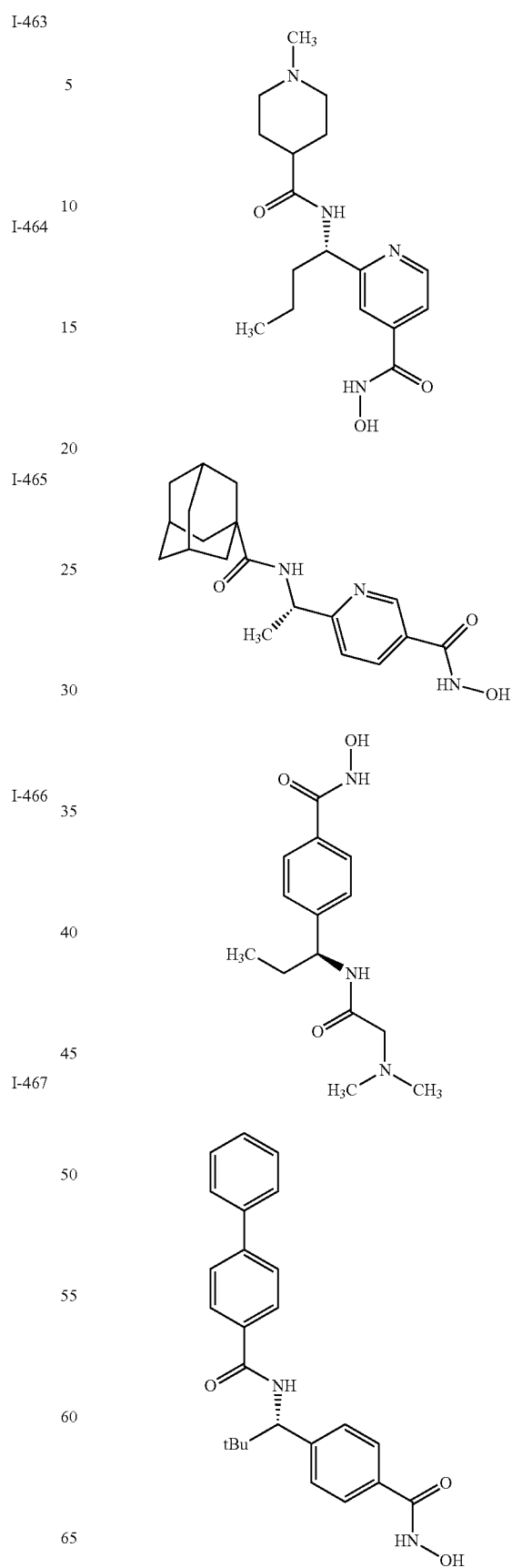

-continued
I-472
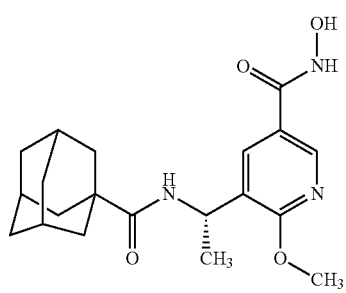
I-473
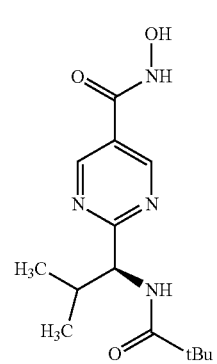
I-474
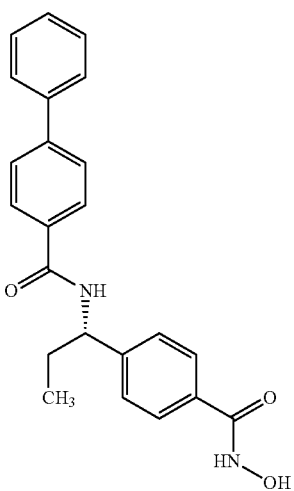
I-475
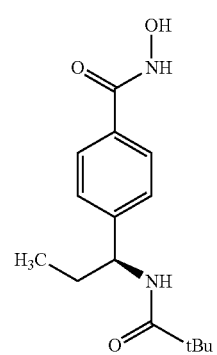
-continued
I-476
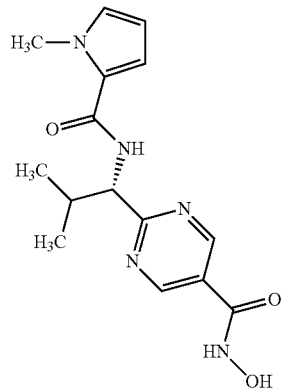
I-477
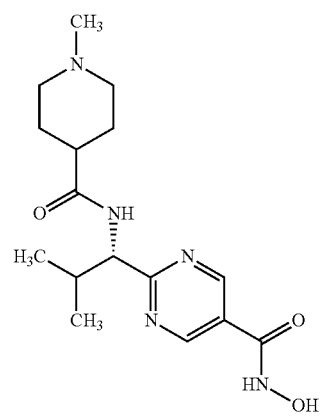
I-478
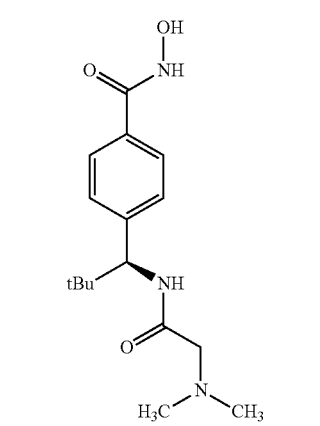
I-479
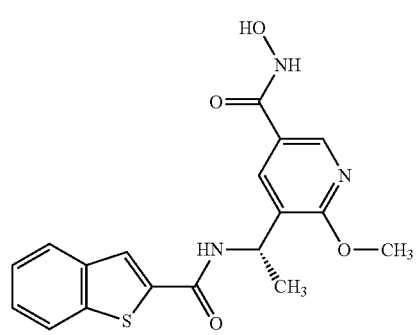

-continued
I-480
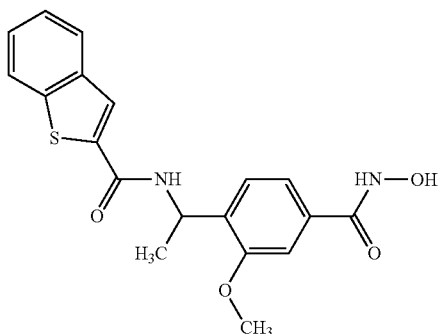
I-481
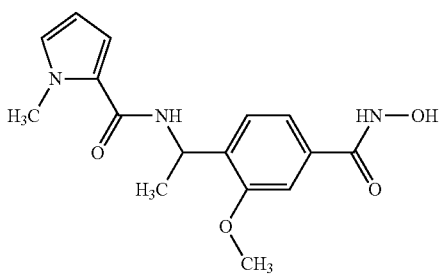
I-482
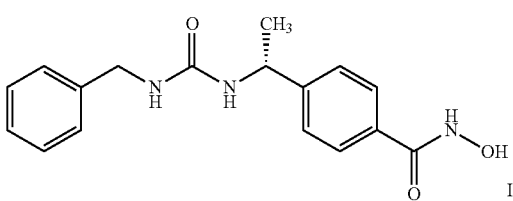
I-483
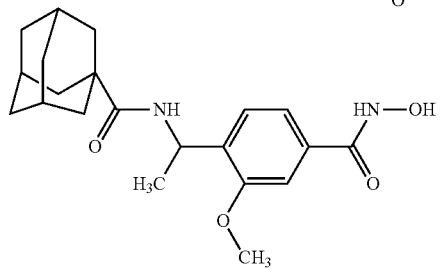
I-484
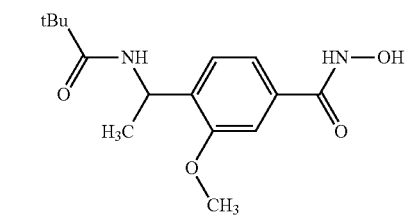
I-485
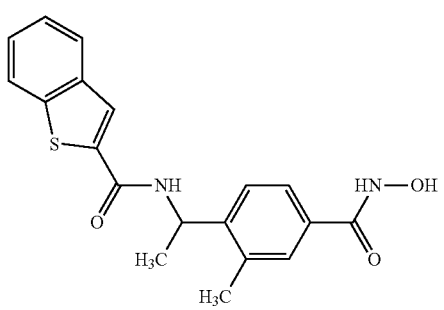
I-486
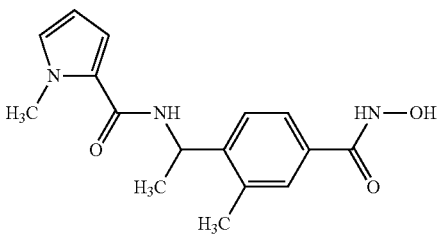
I-487
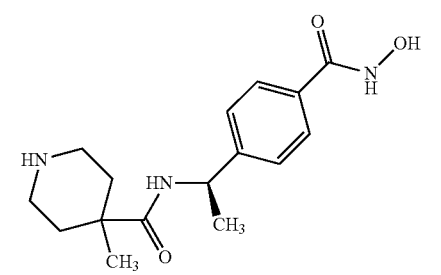
I-488
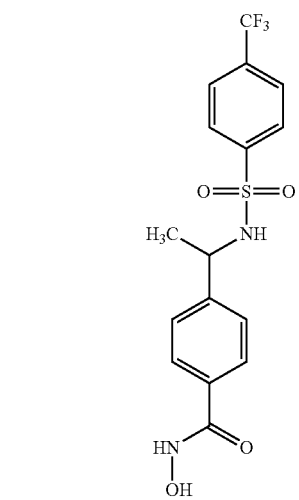
I-489
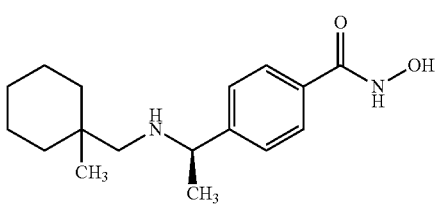
I-490
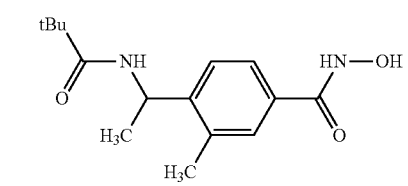

I-491
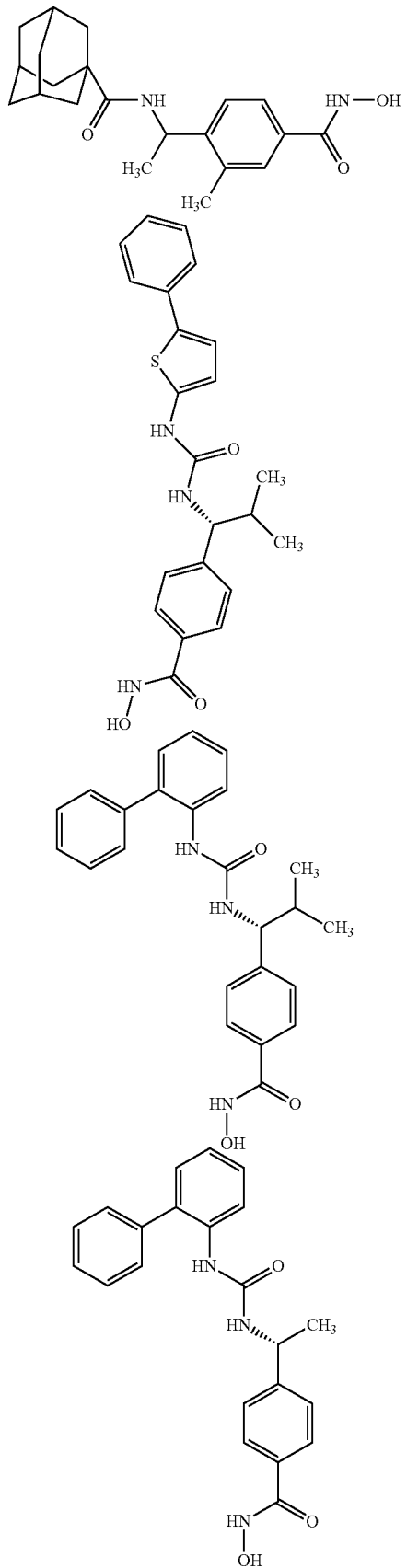
I-492
I-493
I-494
I-495
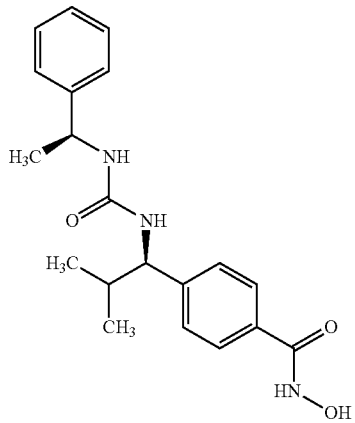
I-496
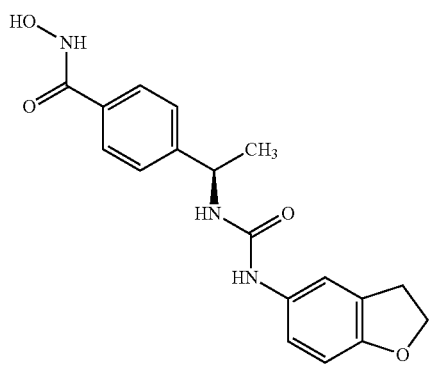
I-497
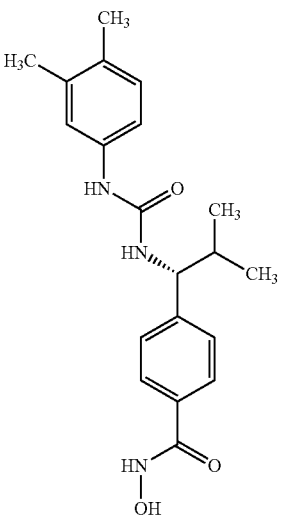

-continued
I-498
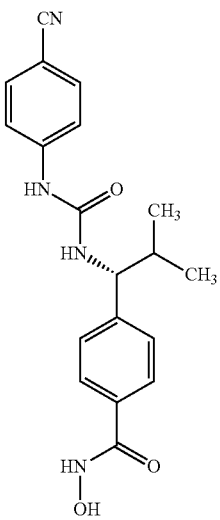
I-499
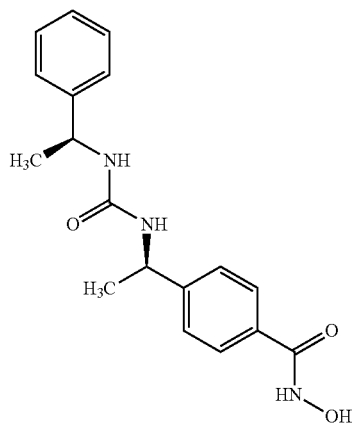
I-500
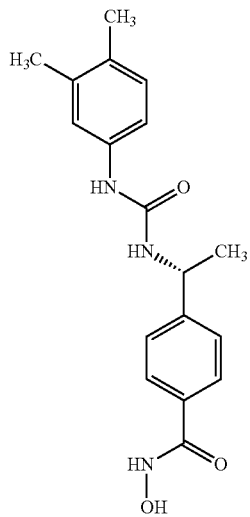
-continued
I-501
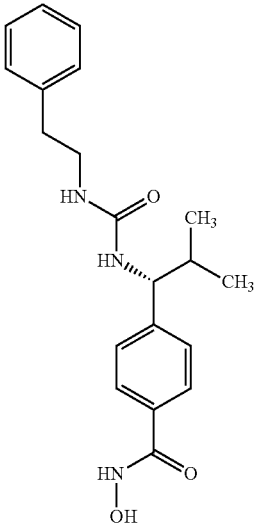
I-502
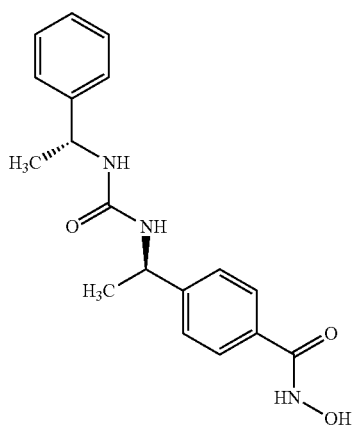
I-503
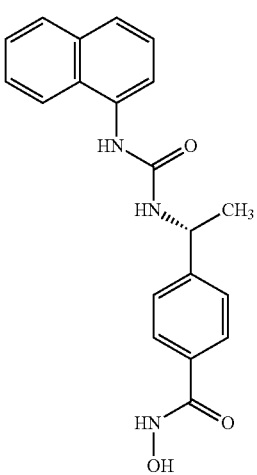

I-504
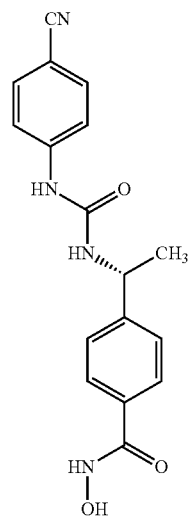
I-505
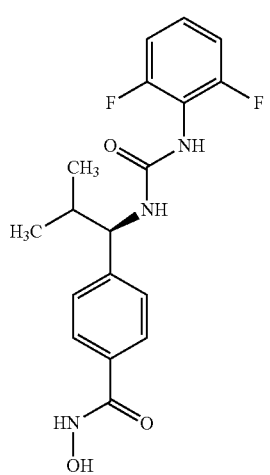
I-506
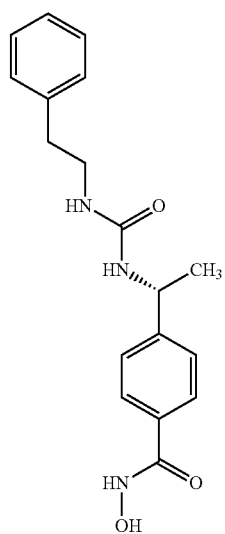
I-507
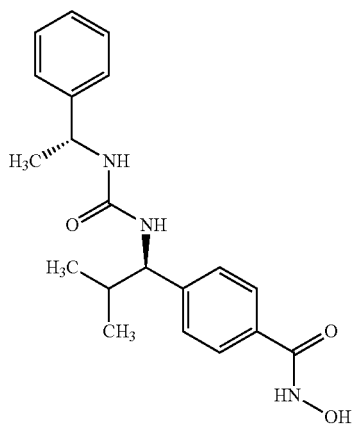
I-508
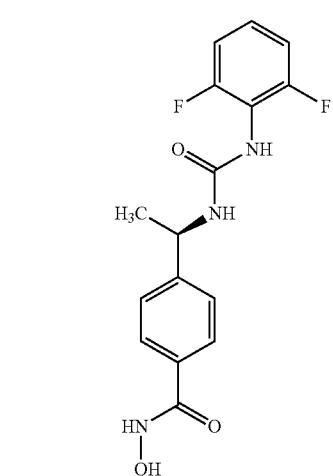
I-509
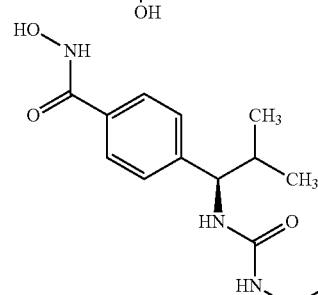
I-510
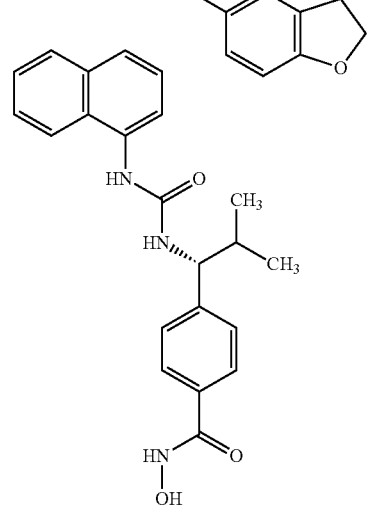

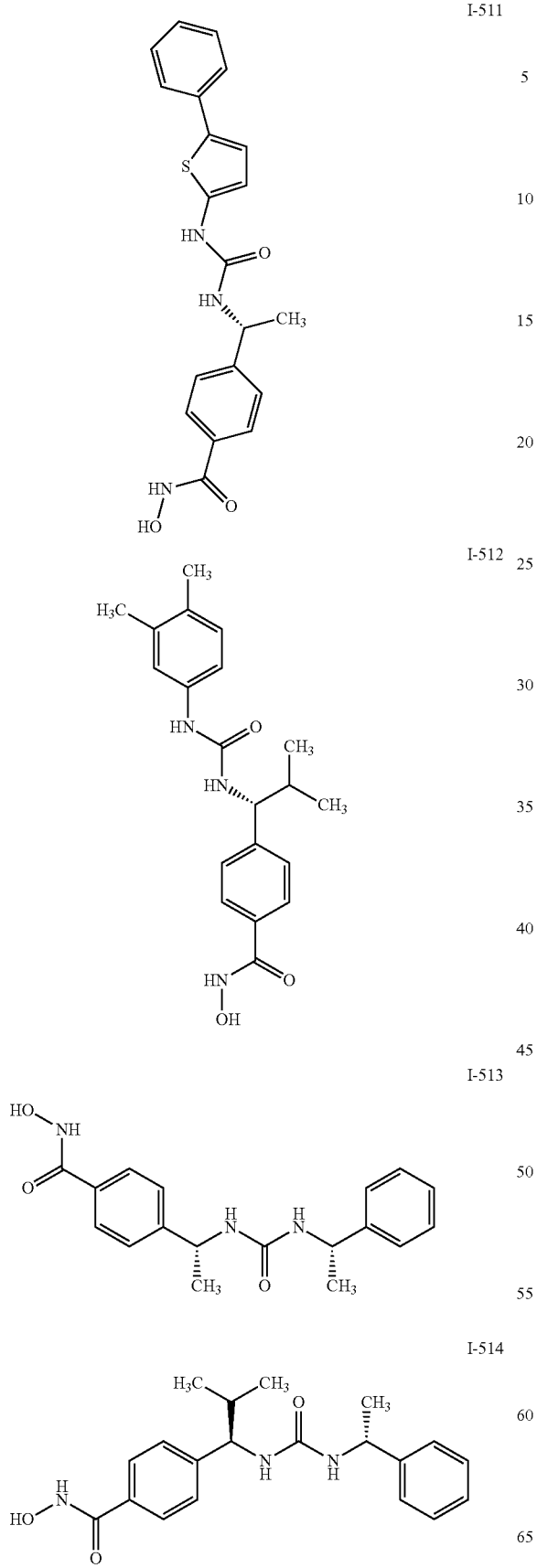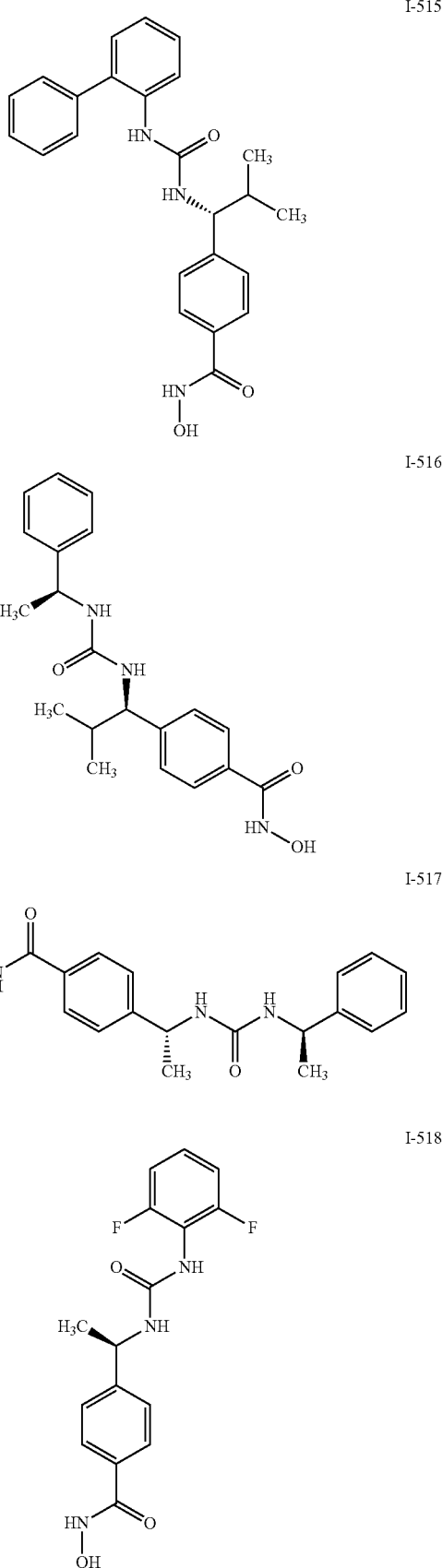

I-519
I-520
I-521
I-522
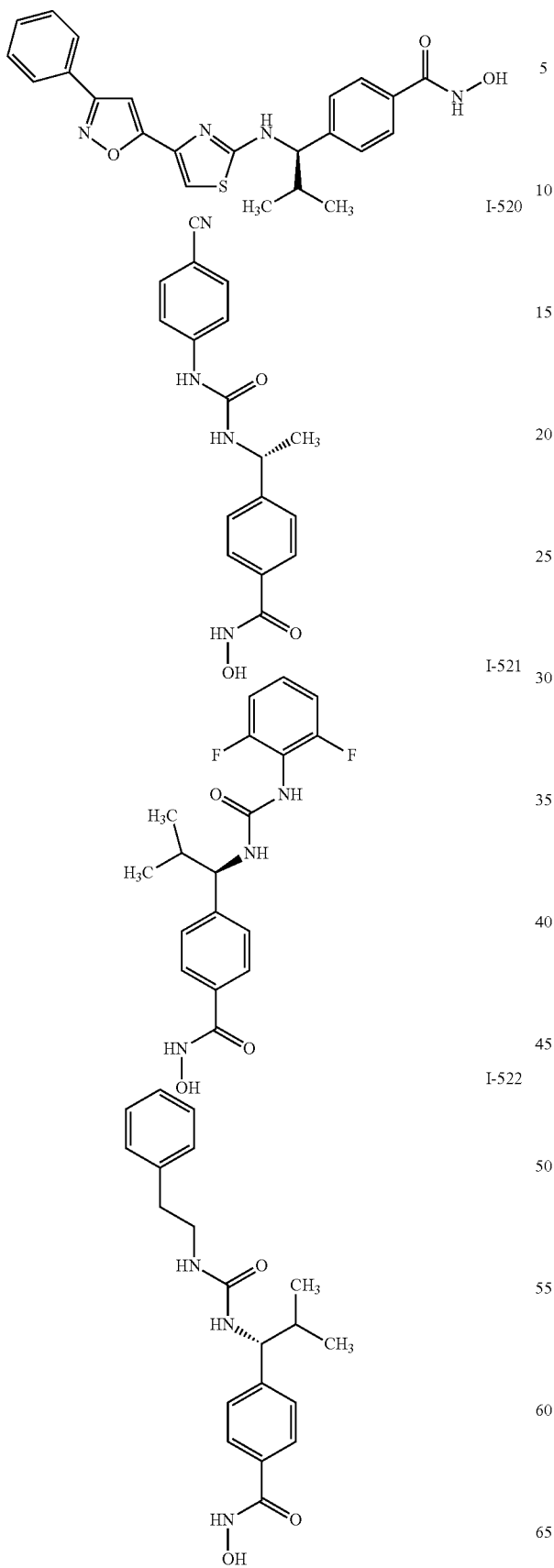
I-523
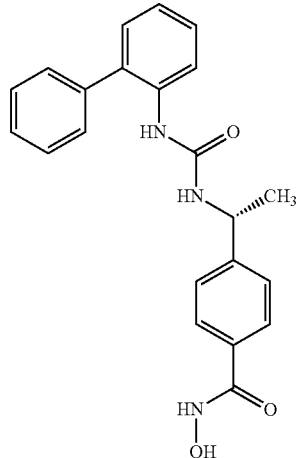
I-524
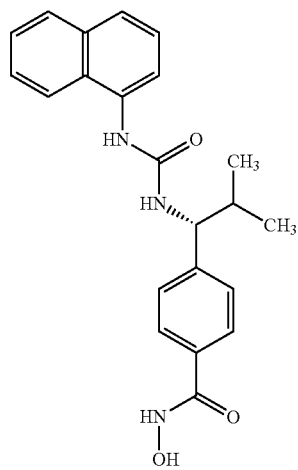
I-525
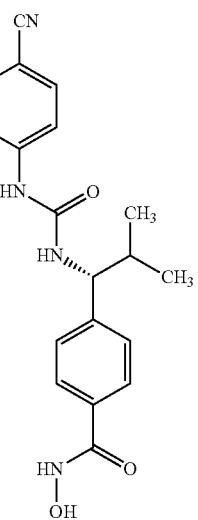

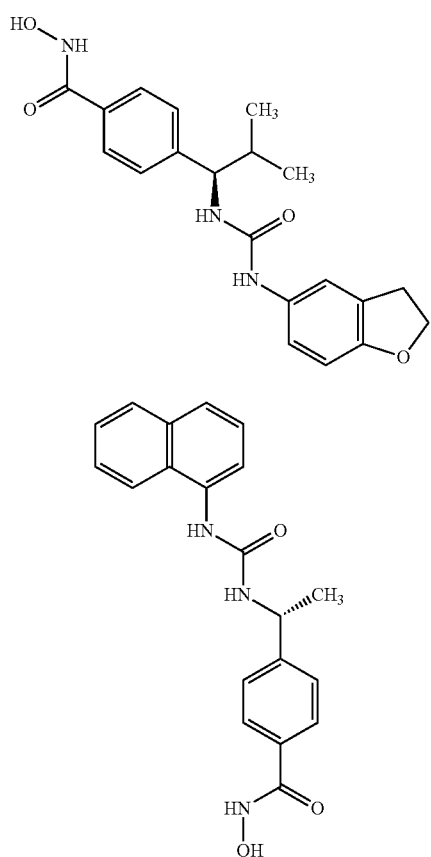
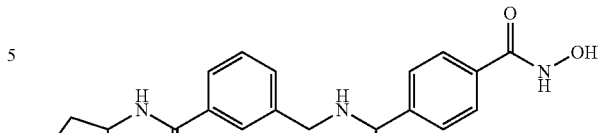
I-526
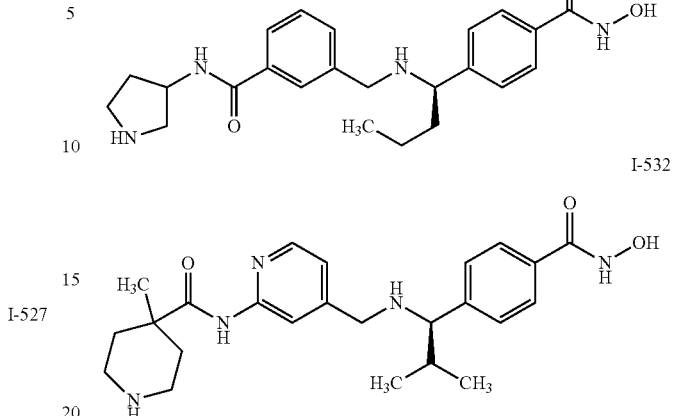
I-527
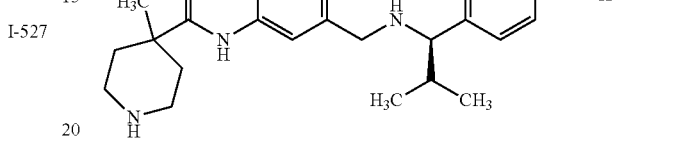
I-528
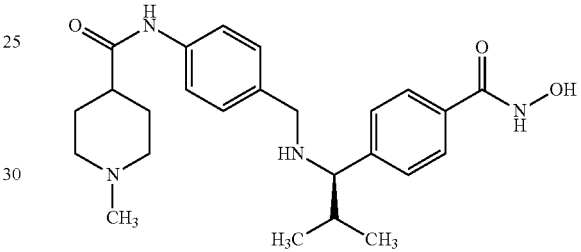
I-529
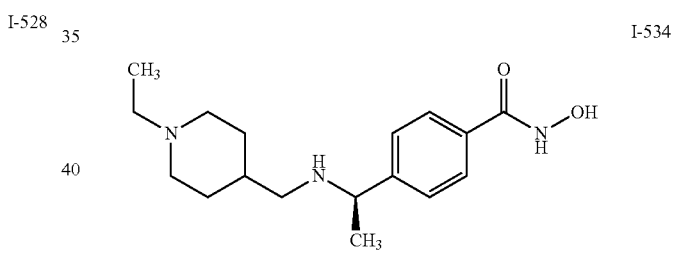
I-530
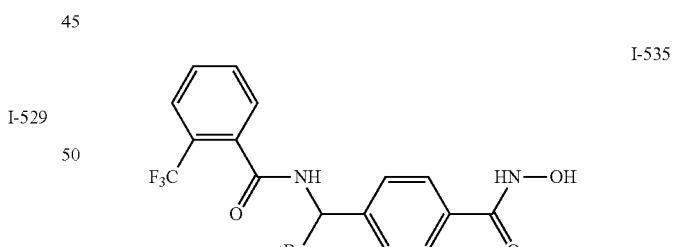
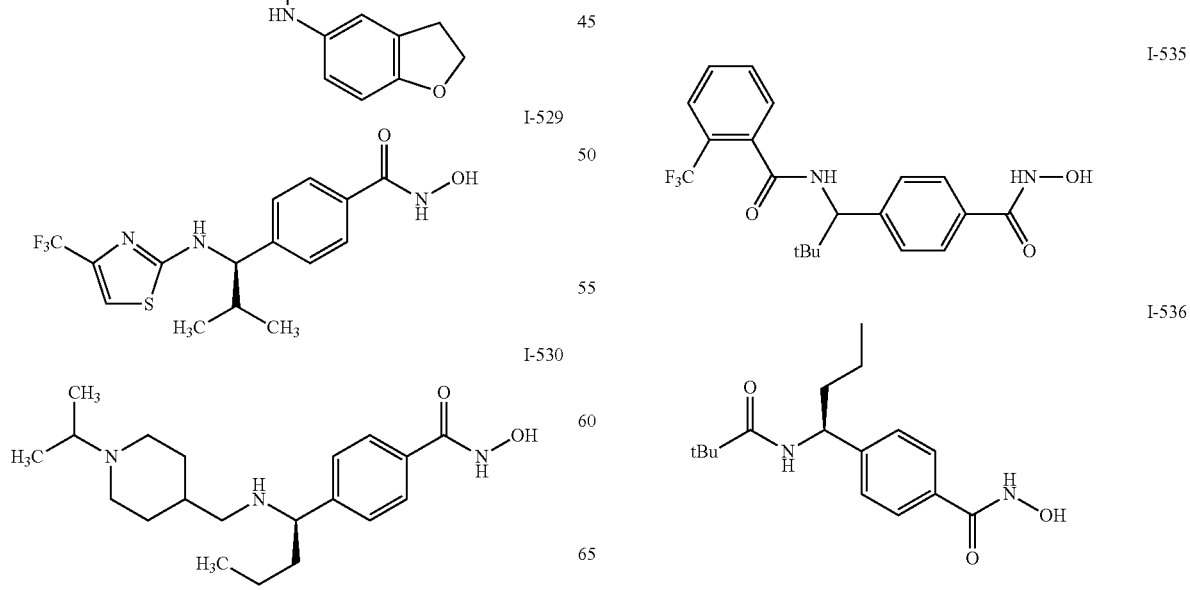

The compounds in Table 1 above may also be identified by the following chemical names:

I-1   4-{1-[(ethylsulfonyl)amino]ethyl}-N-hydroxybenzamide
I-2   4-(1-{[(4-fluorophenyl)sulfonyl]amino}ethyl)-N-hydroxybenzamide
I-3   N-(1-{4-[(hydroxyamino)carbonyl]phenyl}ethyl)adamantane-1-carboxamide
I-4   N-(1-{4-[(hydroxyamino)carbonyl]phenyl}-2,2-dimethylpropyl)-1-benzofuran-2-carboxamide
I-5   N-((1R)-1-{4-[(hydroxyamino)carbonyl]phenyl}ethyl)-4-methyl-2-phenyl-4H-furo[3,2-b]pyrrole-5-carboxamide
I-6   N-hydroxy-4-(1-{[(1-naphthylamino)carbonyl]amino}ethyl)benzamide
I-7   N-(1-{4-[(hydroxyamino)carbonyl]phenyl}ethyl)-3-methyl-1-benzofuran-2-carboxamide
I-8   2-fluoro-N-(1-{4-[(hydroxyamino)carbonyl]phenyl}ethyl)-5-methylbenzamide
I-9   N-(1-{4-[(hydroxyamino)carbonyl]phenyl}-2,2-dimethylpropyl)-2,5-dimethyl-3-furamide
I-10  N-(1-{3-[(hydroxyamino)carbonyl]phenyl}ethyl)-1H-indole-3-carboxamide
I-11  N-(1-{4-[(hydroxyamino)carbonyl]phenyl}-2-methylpropyl)biphenyl-4-carboxamide
I-12  N-((1R)-1-{4-[(hydroxyamino)carbonyl]phenyl}ethyl)-3-methyl-1-benzothiophene-2-carboxamide
I-13  3-(1-{[(5-chloro-1-benzothien-3-yl)acetyl]amino}ethyl)-N-hydroxybenzamide
I-14  4-((1R)-1-{[(tert-butylamino)carbonyl]amino}ethyl)-N-hydroxybenzamide
I-15  N-((1R)-1-{4-[(hydroxyamino)carbonyl]phenyl}butyl)adamantane-1-carboxamide
I-16  N-((1R)-1-{3-[(hydroxyamino)carbonyl]phenyl}ethyl)-4-methyl-2-phenyl-4H-furo[3,2-b]pyrrole-5-carboxamide
I-17  N-(1-{4-[(hydroxyamino)carbonyl]phenyl}-2-methylpropyl)-4-methyl-2-phenylpyrimidine-5-carboxamide
I-18  4-[(1R)-1-({[1-adamantylamino]carbonyl}amino)butyl]-N-hydroxybenzamide
I-19  N-((1R)-1-{4-[(hydroxyamino)carbonyl]phenyl}-2-methylpropyl)-4-methoxybenzamide
I-20  N-hydroxy-4-[1-({[(4-phenoxyphenyl)amino]carbonyl}amino)ethyl]benzamide
I-21  4-{1-[(cyclobutylcarbonyl)amino]ethyl}-N-hydroxybenzamide
I-22  N-((1R)-1-{4-[(hydroxyamino)carbonyl]phenyl}-2-methylpropyl)-1-benzofuran-2-carboxamide
I-23  N-hydroxy-4-(1-{[(3-methoxyphenyl)sulfonyl]amino}ethyl)benzamide
I-24  4-(1-{[(2-chloro-6-fluorophenyl)acetyl]amino}ethyl)-N-hydroxybenzamide
I-25  N-((1S)-1-{4-[(hydroxyamino)carbonyl]phenyl}ethyl)-1-methyl-1H-pyrrole-2-carboxamide
I-26  N-hydroxy-4-((1R)-1-{[(1-methylcyclohexyl)carbonyl]amino}ethyl)benzamide
I-27  4-[1-({[(3-fluorophenyl)amino]carbonyl}amino)ethyl]-N-hydroxybenzamide
I-28  N-hydroxy-4-{1-[(mesitylacetyl)amino]-2-methylpropyl}benzamide
I-29  N-(1-{3-[(hydroxyamino)carbonyl]phenyl}ethyl)-2-methyl-1,3-thiazole-4-carboxamide
I-30  N-(1-{4-[(hydroxyamino)carbonyl]phenyl}-2-methylpropyl)-1-methyl-1H-pyrrole-2-carboxamide
I-31  N-hydroxy-4-[1-({[(2-phenoxyphenyl)amino]carbonyl}amino)ethyl]benzamide
I-32  N-(1-{4-[(hydroxyamino)carbonyl]phenyl}-2-methylpropyl)-1-benzofuran-2-carboxamide
I-33  N-hydroxy-4-{1-[(propylsulfonyl)amino]ethyl}benzamide
I-34  N-hydroxy-4-(1-{[(2-methoxyphenyl)acetyl]amino}ethyl)benzamide
I-35  6-chloro-N-(1-{4-[(hydroxyamino)carbonyl]phenyl}ethyl)imidazo[1,2-a]pyridine-2-carboxamide
I-36  N-hydroxy-4-[1-(isobutyrylamino)ethyl]benzamide
I-37  4-[1-({[(4-fluorophenyl)amino]carbonyl}amino)ethyl]-N-hydroxybenzamide
I-38  N-(1-{4-[(hydroxyamino)carbonyl]phenyl}ethyl)-4-isopropoxybenzamide
I-39  4,5-dichloro-N-(1-{3-[(hydroxyamino)carbonyl]phenyl}ethyl)-1-methyl-1H-pyrrole-2-carboxamide
I-40  4-fluoro-N-(1-{4-[(hydroxyamino)carbonyl]phenyl}-2-methylpropyl)benzamide
I-41  4-[1-({[1-(4-chlorophenyl)cyclopropyl]carbonyl}amino)-2,2-dimethylpropyl]-N-hydroxybenzamide
I-42  N-(1-{4-[(hydroxyamino)carbonyl]phenyl}-2,2-dimethylpropyl)-2-methyl-1,3-thiazole-4-carboxamide
I-43  N-(1-{4-[(hydroxyamino)carbonyl]phenyl}-2-methylpropyl)-1,3-benzothiazole-6-carboxamide
I-44  4-[1-({[(2,4-dimethoxyphenyl)amino]carbonyl}amino)ethyl]-N-hydroxybenzamide
I-45  N-hydroxy-4-{1-[(3-phenylpropanoyl)amino]ethyl}benzamide
I-46  N-((R)-cyclopropyl{4-[(hydroxyamino)carbonyl]phenyl}methyl)adamantane-1-carboxamide
I-47  N-hydroxy-4-(1-{[(4-methoxyphenyl)sulfonyl]amino}ethyl)benzamide
I-48  N-hydroxy-4-(2-methyl-1-{[(5-methyl-2-phenyl-1,3-oxazol-4-yl)acetyl]amino}propyl)benzamide
I-49  N-hydroxy-4-(1-{[(2-oxo-2H-chromen-6-yl)sulfonyl]amino}ethyl)benzamide
I-50  4-{(1R)-1-[(2,2-dimethylpropanoyl)amino]-2,2,2-trifluoroethyl}-N-hydroxybenzamide
I-51  4-(1-{[(2,5-dimethylphenyl)sulfonyl]amino}ethyl)-N-hydroxybenzamide
I-52  N-(1-{4-[(hydroxyamino)carbonyl]phenyl}-2,2-dimethylpropyl)-3,5-bis(trifluoromethyl)benzamide
I-53  N-((1S)-1-{4-[(hydroxyamino)carbonyl]phenyl}ethyl)-1-benzothiophene-2-carboxamide
I-54  4-(1-{[(1,2-dimethyl-1H-imidazol-4-yl)sulfonyl]amino}ethyl)-N-hydroxybenzamide
I-55  4-[1-({[(3,4-dimethylphenyl)amino]carbonyl}amino)ethyl]-N-hydroxybenzamide
I-56  N-(1-{4-[(hydroxyamino)carbonyl]phenyl}ethyl)cinnoline-4-carboxamide
I-57  N-(1-{3-[(hydroxyamino)carbonyl]phenyl}ethyl)-2-(trifluoromethyl)benzamide
I-58  N-(1-{4-[(hydroxyamino)carbonyl]phenyl}-2-methylpropyl)adamantane-1-carboxamide
I-59  4-{1-[(2,2-dimethylpropanoyl)amino]ethyl}-N-hydroxybenzamide
I-60  N-hydroxy-4-(1-{[(1,3,5-trimethyl-1H-pyrazol-4-yl)sulfonyl]amino}ethyl)benzamide
I-61  4-(1-{[(4-fluoro-2-methylphenyl)sulfonyl]amino}ethyl)-N-hydroxybenzamide
I-62  N-((1R)-1-{4-[(hydroxyamino)carbonyl]phenyl}butyl)-3-methyl-1-benzothiophene-2-carboxamide
I-63  N-(1-{4-[(hydroxyamino)carbonyl]phenyl}ethyl)-4-(1H-pyrrol-1-yl)benzamide
I-64  4-(1-{[(4-chlorobenzyl)sulfonyl]amino}ethyl)-N-hydroxybenzamide
I-65  N-((1R)-1-{4-[(hydroxyamino)carbonyl]phenyl}-2-methylpropyl)-1-methyl-1H-pyrrole-2-carboxamide
I-66  N-(1-{4-[(hydroxyamino)carbonyl]phenyl}-2,2-dimethylpropyl)-1-methyl-1H-pyrazole-3-carboxamide -continued

| | |
|---|---|
| I-67 | N-((1S)-1-{4-[(hydroxyamino)carbonyl]phenyl}-2-methylpropyl)-1-benzothiophene-2-carboxamide |
| I-68 | N-((1R)-1-{4-[(hydroxyamino)carbonyl]phenyl}-2-methylpropyl)-1H-indole-2-carboxamide |
| I-69 | N-(1-{4-[(hydroxyamino)carbonyl]phenyl}-2-methylpropyl)-5-methyl-1H-indole-2-carboxamide |
| I-70 | N-hydroxy-4-(1-{[4-(4-methoxyphenyl)butanoyl]amino}ethyl)benzamide |
| I-71 | 4-(1-{[(1,3-benzodioxol-5-ylamino)carbonyl]amino}ethyl)-N-hydroxybenzamide |
| I-72 | N-(1-{3-[(hydroxyamino)carbonyl]phenyl}ethyl)-4-methyl-2-[4-(trifluoromethyl)phenyl]-4H-furo[3,2-b]pyrrole-5-carboxamide |
| I-73 | 4-{(1R)-1-[(2,2-dimethylpropanoyl)amino]ethyl}-N-hydroxybenzamide |
| I-74 | 4-[1-({[(2-fluorophenyl)amino]carbonyl}amino)ethyl]-N-hydroxybenzamide |
| I-75 | N-(1-{4-[(hydroxyamino)carbonyl]phenyl}-2,2-dimethylpropyl)-3-(methylsulfonyl)benzamide |
| I-76 | N-hydroxy-4-[1-({[(2-methylbenzyl)amino]carbonyl}amino)ethyl]benzamide |
| I-77 | 1-benzyl-3-tert-butyl-N-(1-{4-[(hydroxyamino)carbonyl]phenyl}-2-methylpropyl)-1H-pyrazole-5-carboxamide |
| I-78 | 4-(1-{[(2,4-dimethylphenyl)sulfonyl]amino}ethyl)-N-hydroxybenzamide |
| I-79 | N-((1R)-1-{4-[(hydroxyamino)carbonyl]phenyl}butyl)-1-benzofuran-2-carboxamide |
| I-80 | 4-(2,2-dimethyl-1-{[(5-methyl-2-phenyl-1,3-oxazol-4-yl)acetyl]amino}propyl)-N-hydroxybenzamide |
| I-81 | N-(1-{3-[(hydroxyamino)carbonyl]phenyl}ethyl)-1-methyl-1H-pyrazole-3-carboxamide |
| I-82 | 4-{1-[(2,3-dihydro-1,4-benzodioxin-6-ylsulfonyl)amino]ethyl}-N-hydroxybenzamide |
| I-83 | N-(1-{3-[(hydroxyamino)carbonyl]phenyl}ethyl)adamantane-1-carboxamide |
| I-84 | N-(1-{3-[(hydroxyamino)carbonyl]phenyl}ethyl)-1,5-dimethyl-1H-pyrazole-3-carboxamide |
| I-85 | N-hydroxy-4-[1-({[(3-methylphenyl)amino]carbonyl}amino)ethyl]benzamide |
| I-86 | N-(1-{4-[(hydroxyamino)carbonyl]phenyl}-2,2-dimethylpropyl)-1,3-dimethyl-1H-pyrazole-4-carboxamide |
| I-87 | N-(1-{4-[(hydroxyamino)carbonyl]phenyl}-2,2-dimethylpropyl)pyrazine-2-carboxamide |
| I-88 | 4-{1-[(cyclopentylcarbonyl)amino]ethyl}-N-hydroxybenzamide |
| I-89 | 4-[1-({[(2,5-dichlorophenyl)amino]carbonyl}amino)ethyl]-N-hydroxybenzamide |
| I-90 | 4-(1-{[(3,4-difluorophenyl)sulfonyl]amino}ethyl)-N-hydroxybenzamide |
| I-91 | N-(1-{3-[(hydroxyamino)carbonyl]phenyl}ethyl)-3,5-dimethyl-1H-pyrrole-2-carboxamide |
| I-92 | N-((1R)-1-{4-[(hydroxyamino)carbonyl]phenyl}ethyl)biphenyl-4-carboxamide |
| I-93 | N-(1-{3-[(hydroxyamino)carbonyl]phenyl}-2-methylpropyl)-3-methyl-1-benzofuran-2-carboxamide |
| I-94 | N-(1-{4-[(hydroxyamino)carbonyl]phenyl}-2-methylpropyl)-1-benzothiophene-2-carboxamide |
| I-95 | N-hydroxy-4-{1-[(1-naphthylsulfonyl)amino]ethyl}benzamide |
| I-96 | 4,5-dichloro-N-((1R)-1-{4-[(hydroxyamino)carbonyl]phenyl}-2-methylpropyl)-1-methyl-1H-pyrrole-2-carboxamide |
| I-97 | N-(1-{3-[(hydroxyamino)carbonyl]phenyl}ethyl)-1-benzothiophene-2-carboxamide |
| I-98 | N-(1-{4-[(hydroxyamino)carbonyl]phenyl}ethyl)-1-methyl-1H-indole-2-carboxamide |
| I-99 | N-[(R)-{4-[(hydroxyamino)carbonyl]phenyl}(phenyl)methyl]-1-benzothiophene-2-carboxamide |
| I-100 | N-(1-{3-[(hydroxyamino)carbonyl]phenyl}ethyl)-1-methyl-1H-benzimidazole-2-carboxamide |
| I-101 | N-(1-{3-[(hydroxyamino)carbonyl]phenyl}ethyl)-2-methyl-4,5,6,7-tetrahydro-2H-indazole-3-carboxamide |
| I-102 | N-((1R)-1-{4-[(hydroxyamino)carbonyl]phenyl}ethyl)-1-methyl-1H-pyrrole-2-carboxamide |
| I-103 | 4-[1-({[(3-chloro-4-methylphenyl)amino]carbonyl}amino)ethyl]-N-hydroxybenzamide |
| I-104 | N-(1-{3-[(hydroxyamino)carbonyl]phenyl}ethyl)-2,5-dimethyl-3-furamide |
| I-105 | 4-((1R)-1-{[(1-adamantylamino)carbonyl]amino}-2,2,2-trifluoroethyl)-N-hydroxybenzamide |
| I-106 | N-((1R)-1-{4-[(hydroxyamino)carbonyl]phenyl}butyl)-1-methyl-1H-indole-2-carboxamide |
| I-107 | N-(1-{4-[(hydroxyamino)carbonyl]phenyl}-2,2-dimethylpropyl)-1-methyl-1H-indole-3-carboxamide |
| I-108 | 4,5-dichloro-1-methyl-N-((1S)-2,2,2-trifluoro-1-{4-[(hydroxyamino)carbonyl]phenyl}ethyl)-1H-pyrrole-2-carboxamide |
| I-109 | N-(1-{4-[(hydroxyamino)carbonyl]phenyl}ethyl)-3-phenyl-1H-pyrazole-5-carboxamide |
| I-110 | 4-[1-({[1-(4-chlorophenyl)cyclobutyl]carbonyl}amino)ethyl]-N-hydroxybenzamide |
| I-111 | N-hydroxy-4-{1-[(3-methylbutanoyl)amino]ethyl}benzamide |
| I-112 | N-(1-{4-[(hydroxyamino)carbonyl]phenyl}-2-methylpropyl)thiophene-2-carboxamide |
| I-113 | N-((1R)-1-{3-[(hydroxyamino)carbonyl]phenyl}ethyl)-3-methyl-1-benzothiophene-2-carboxamide |
| I-114 | N-(1-{4-[(hydroxyamino)carbonyl]phenyl}ethyl)-2-methyl-4,5,6,7-tetrahydro-2H-indazole-3-carboxamide |
| I-115 | N-((1R)-1-{4-[(hydroxyamino)carbonyl]phenyl}ethyl)-1-methyl-1H-indole-2-carboxamide |
| I-116 | 2,4,5-trifluoro-N-(1-{4-[(hydroxyamino)carbonyl]phenyl}-2-methylpropyl)benzamide |
| I-117 | N-(1-{3-[(hydroxyamino)carbonyl]phenyl}ethyl)-1-benzothiophene-3-carboxamide |
| I-118 | 4-(1-{[(3-chloro-4-methylphenyl)sulfonyl]amino}ethyl)-N-hydroxybenzamide |
| I-119 | 1-methyl-N-((1R)-2,2,2-trifluoro-1-{4-[(hydroxyamino)carbonyl]phenyl}ethyl)-1H-pyrrole-2-carboxamide |
| I-120 | 4-[1-({[(3-fluoro-4-methylphenyl)amino]carbonyl}amino)ethyl]-N-hydroxybenzamide |
| I-121 | N-((1R)-1-{3-[(hydroxyamino)carbonyl]phenyl}ethyl)biphenyl-4-carboxamide |
| I-122 | 4-methoxy-N-((1S)-2,2,2-trifluoro-1-{4-[(hydroxyamino)carbonyl]phenyl}ethyl)benzamide |
| I-123 | N-(1-{4-[(hydroxyamino)carbonyl]phenyl}-2,2-dimethylpropyl)-1,3-thiazole-4-carboxamide |
| I-124 | N-[(S)-{4-[(hydroxyamino)carbonyl]phenyl}(phenyl)methyl]-1-benzothiophene-2-carboxamide |
| I-125 | N-(1-{4-[(hydroxyamino)carbonyl]phenyl}ethyl)imidazo[1,2-a]pyridine-2-carboxamide |
| I-126 | N-hydroxy-4-((1R)-2-methyl-1-{[(1-methylcyclohexyl)carbonyl]amino}propyl)benzamide |
| I-127 | N-(1-{4-[(hydroxyamino)carbonyl]phenyl}-2,2-dimethylpropyl)-1H-indole-2-carboxamide |
| I-128 | N-(1-{4-[(hydroxyamino)carbonyl]phenyl}ethyl)quinoline-2-carboxamide |
| I-129 | N-(1-{4-[(hydroxyamino)carbonyl]phenyl}-2,2-dimethylpropyl)-5-methyl-1H-indole-2-carboxamide |
| I-130 | 5-chloro-N-(1-{4-[(hydroxyamino)carbonyl]phenyl}-2-methylpropyl)-1-benzofuran-2-carboxamide |

-continued

| | |
|---|---|
| I-131 | 4-(1-{[(4-tert-butylphenyl)sulfonyl]amino}ethyl)-N-hydroxybenzamide |
| I-132 | N-hydroxy-4-(1-{[(1-methylcyclohexyl)carbonyl]amino}ethyl)benzamide |
| I-133 | N-(1-{4-[(hydroxyamino)carbonyl]phenyl}-2,2-dimethylpropyl)-1-methyl-1H-pyrrole-2-carboxamide |
| I-134 | N-(1-{4-[(hydroxyamino)carbonyl]phenyl}ethyl)-2,3-dihydro-1-benzofuran-7-carboxamide |
| I-135 | N-(1-{4-[(hydroxyamino)carbonyl]phenyl}-2-methylpropyl)-2,1,3-benzothiadiazole-5-carboxamide |
| I-136 | 4-chloro-N-(1-{4-[(hydroxyamino)carbonyl]phenyl}ethyl)benzamide |
| I-137 | 3,5-difluoro-N-(1-{3-[(hydroxyamino)carbonyl]phenyl}ethyl)benzamide |
| I-138 | N-(1-{4-[(hydroxyamino)carbonyl]phenyl}ethyl)-4-(1,3-oxazol-5-yl)benzamide |
| I-139 | N-(1-{4-[(hydroxyamino)carbonyl]phenyl}-2-methylpropyl)-2-methyl-4-(trifluoromethyl)-1,3-thiazole-5-carboxamide |
| I-140 | 4-[1-({[(4-tert-butylphenyl)amino]carbonyl}amino)ethyl]-N-hydroxybenzamide |
| I-141 | N-hydroxy-4-{1-[({[4-(trifluoromethoxy)phenyl]amino}carbonyl)amino]ethyl}benzamide |
| I-142 | N-(1-{3-[(hydroxyamino)carbonyl]phenyl}ethyl)biphenyl-4-carboxamide |
| I-143 | 4'-fluoro-N-(1-{4-[(hydroxyamino)carbonyl]phenyl}-2-methylpropyl)biphenyl-4-carboxamide |
| I-144 | 4-{1-[(3,3-dimethylbutanoyl)amino]ethyl}-N-hydroxybenzamide |
| I-145 | N-(1-{4-[(hydroxyamino)carbonyl]phenyl}-2,2-dimethylpropyl)-1-methyl-1H-indole-5-carboxamide |
| I-146 | N-((1R)-1-{4-[(hydroxyamino)carbonyl]phenyl}butyl)-4-methoxybenzamide |
| I-147 | N-(1-{4-[(hydroxyamino)carbonyl]phenyl}ethyl)-5-methylthiophene-2-carboxamide |
| I-148 | 4-(1-{[(2,3-dihydro-1-benzofuran-5-ylamino)carbonyl]amino}ethyl)-N-hydroxybenzamide |
| I-149 | 3-{1-[(cyclohexylcarbonyl)amino]ethyl}-N-hydroxybenzamide |
| I-150 | 4-{1-[({[4-(difluoromethoxy)phenyl]amino}carbonyl)amino]ethyl}-N-hydroxybenzamide |
| I-151 | N-hydroxy-3-(1-{[4-(trifluoromethyl)benzoyl]amino}ethyl)benzamide |
| I-152 | 4-(1-{[(2,5-difluorophenyl)sulfonyl]amino}ethyl)-N-hydroxybenzamide |
| I-153 | 4-(1-{[(3-fluoro-4-methoxyphenyl)sulfonyl]amino}ethyl)-N-hydroxybenzamide |
| I-154 | N-hydroxy-4-(1-{[(1-methylcyclopropyl)carbonyl]amino}ethyl)benzamide |
| I-155 | N-(1-{4-[(hydroxyamino)carbonyl]phenyl}-2-methylpropyl)-2,5-bis(trifluoromethyl)benzamide |
| I-156 | 4-[1-({[(2,6-dimethylphenyl)amino]carbonyl}amino)ethyl]-N-hydroxybenzamide |
| I-157 | N-((1S)-1-{4-[(hydroxyamino)carbonyl]phenyl}-2-methylpropyl)adamantane-1-carboxamide |
| I-158 | N-(1-{4-[(hydroxyamino)carbonyl]phenyl}-2,2-dimethylpropyl)-1-benzothiophene-3-carboxamide |
| I-159 | N-hydroxy-4-(1-{[(4-methoxyphenyl)acetyl]amino}ethyl)benzamide |
| I-160 | N-(1-{4-[(hydroxyamino)carbonyl]phenyl}ethyl)-5,7-dimethylpyrazolo[1,5-a]pyrimidine-2-carboxamide |
| I-161 | 4-{1-[(2,1,3-benzoxadiazol-4-ylsulfonyl)amino]ethyl}-N-hydroxybenzamide |
| I-162 | N-(1-{4-[(hydroxyamino)carbonyl]phenyl}-2,2-dimethylpropyl)adamantane-1-carboxamide |
| I-163 | 4-{1-[({[2-chloro-4-(trifluoromethyl)phenyl]amino}carbonyl)amino]ethyl}-N-hydroxybenzamide |
| I-164 | 4-fluoro-N-(1-{4-[(hydroxyamino)carbonyl]phenyl}ethyl)-3-methoxybenzamide |
| I-165 | N-(1-{3-[(hydroxyamino)carbonyl]phenyl}ethyl)pyrazine-2-carboxamide |
| I-166 | N-hydroxy-4-[1-({[3-(trifluoromethyl)phenyl]sulfonyl}amino)ethyl]benzamide |
| I-167 | N-(1-{3-[(hydroxyamino)carbonyl]phenyl}ethyl)-1,3-dimethyl-1H-pyrazole-4-carboxamide |
| I-168 | N-hydroxy-4-[1-({[(3-methyl-5-phenylisoxazol-4-yl)amino]carbonyl}amino)ethyl]benzamide |
| I-169 | N-((1R)-1-{3-[(hydroxyamino)carbonyl]phenyl}ethyl)-3-methyl-1-benzofuran-2-carboxamide |
| I-170 | N-hydroxy-4-{1-[(isoquinolin-5-ylsulfonyl)amino]ethyl}benzamide |
| I-171 | N-hydroxy-4-[(1R)-1-({[4-(trifluoromethyl)phenyl]sulfonyl}amino)butyl]benzamide |
| I-172 | N-(1-{4-[(hydroxyamino)carbonyl]phenyl}-2-methylpropyl)-2-phenyl-1,3-thiazole-4-carboxamide |
| I-173 | N-(1-{4-[(hydroxyamino)carbonyl]phenyl}-2-methylpropyl)-3,5-bis(trifluoromethyl)benzamide |
| I-174 | N-hydroxy-4-(2-methyl-1-{[(2-methyl-1H-indol-3-yl)acetyl]amino}propyl)benzamide |
| I-175 | 4-[1-({[(2,3-dimethylphenyl)amino]carbonyl}amino)ethyl]-N-hydroxybenzamide |
| I-176 | N-hydroxy-4-{1-[(mesitylsulfonyl)amino]ethyl}benzamide |
| I-177 | 3-{(1R)-1-[(2,2-dimethylpropanoyl)amino]ethyl}-N-hydroxybenzamide |
| I-178 | N-hydroxy-4-[1-({[4-(1,3-oxazol-5-yl)phenyl]sulfonyl}amino)ethyl]benzamide |
| I-179 | N-(1-{3-[(hydroxyamino)carbonyl]phenyl}ethyl)-1,3-thiazole-4-carboxamide |
| I-180 | N-(1-{3-[(hydroxyamino)carbonyl]phenyl}ethyl)-4-methyl-2-phenyl-4H-furo[3,2-b]pyrrole-5-carboxamide |
| I-181 | N-(1-{3-[(hydroxyamino)carbonyl]phenyl}ethyl)-2,5-dimethyl-1H-pyrrole-3-carboxamide |
| I-182 | N-(1-{4-[(hydroxyamino)carbonyl]phenyl}-2,2-dimethylpropyl)-5-methyl-1-phenyl-1H-pyrazole-4-carboxamide |
| I-183 | 3-[1-({[1-(4-chlorophenyl)cyclopropyl]carbonyl}amino)ethyl]-N-hydroxybenzamide |
| I-184 | N-((1R)-1-{4-[(hydroxyamino)carbonyl]phenyl}ethyl)-1-benzothiophene-2-carboxamide |
| I-185 | N-(1-{4-[(hydroxyamino)carbonyl]phenyl}ethyl)-4-(1H-pyrazol-1-yl)benzamide |
| I-186 | N-(1-{4-[(hydroxyamino)carbonyl]phenyl}ethyl)-3-isopropyl-1-methyl-1H-pyrazole-5-carboxamide |
| I-187 | N-((1R)-1-{4-[(hydroxyamino)carbonyl]phenyl}-2-methylpropyl)-3-methyl-1-benzofuran-2-carboxamide |
| I-188 | 4-(1-{[(2-chloro-6-methylphenyl)sulfonyl]amino}ethyl)-N-hydroxybenzamide |
| I-189 | N-hydroxy-4-[(1R)-2-methyl-1-({[4-(trifluoromethyl)phenyl]sulfonyl}amino)propyl]benzamide |
| I-190 | N-(1-{4-[(hydroxyamino)carbonyl]phenyl}-2-methylpropyl)quinoxaline-2-carboxamide |
| I-191 | N-(1-{4-[(hydroxyamino)carbonyl]phenyl}-2-methylpropyl)-1,3-benzothiazole-2-carboxamide |
| I-192 | 4-tert-butyl-N-(1-{4-[(hydroxyamino)carbonyl]phenyl}-2-methylpropyl)benzamide |
| I-193 | N-hydroxy-3-{(1R)-1-[(4-methoxybenzoyl)amino]ethyl}benzamide |
| I-194 | N-(1-{4-[(hydroxyamino)carbonyl]phenyl}-2-methylpropyl)-1-benzofuran-5-carboxamide |
| I-195 | N-hydroxy-4-[2-methyl-1-({[3-(trifluoromethyl)phenyl]acetyl}amino)propyl]benzamide |
| I-196 | N-hydroxy-4-[1-({[(1-phenylethyl)amino]carbonyl}amino)ethyl]benzamide |
| I-197 | 4-(1-{[(3-chlorophenyl)sulfonyl]amino}ethyl)-N-hydroxybenzamide |

-continued

| | |
|---|---|
| I-198 | 4-(1-{[(4-fluorobenzyl)sulfonyl]amino}ethyl)-N-hydroxybenzamide |
| I-199 | N-(1-{3-[(hydroxyamino)carbonyl]phenyl}ethyl)-3-(methylsulfonyl)benzamide |
| I-200 | N-(1-{4-[(hydroxyamino)carbonyl]phenyl}-2,2-dimethylpropyl)-3,5-dimethylisoxazole-4-carboxamide |
| I-201 | N-((1R)-1-{3-[(hydroxyamino)carbonyl]phenyl}ethyl)-1-benzofuran-2-carboxamide |
| I-202 | N-hydroxy-3-{1-[(4-methoxybenzoyl)amino]ethyl}benzamide |
| I-203 | N-(1-{4-[(hydroxyamino)carbonyl]phenyl}-2-methylpropyl)pyrazine-2-carboxamide |
| I-204 | 4-{1-[(diphenylacetyl)amino]-2-methylpropyl}-N-hydroxybenzamide |
| I-205 | 4-(1-{[(5-fluoro-2-methylphenyl)sulfonyl]amino}ethyl)-N-hydroxybenzamide |
| I-206 | 4-(1-{[(5-chloro-1-benzothien-3-yl)acetyl]amino}-2-methylpropyl)-N-hydroxybenzamide |
| I-207 | N-(1-{4-[(hydroxyamino)carbonyl]phenyl}ethyl)-1-benzofuran-2-carboxamide |
| I-208 | 4-{1-[(cyclohexylcarbonyl)amino]ethyl}-N-hydroxybenzamide |
| I-209 | N-((1R)-1-{4-[(hydroxyamino)carbonyl]phenyl}ethyl)adamantane-1-carboxamide |
| I-210 | N-hydroxy-4-[1-({[(2-phenylethyl)amino]carbonyl}amino)ethyl]benzamide |
| I-211 | N-(1-{4-[(hydroxyamino)carbonyl]phenyl}-2,2-dimethylpropyl)-2-methyl-4,5,6,7-tetrahydro-2H-indazole-3-carboxamide |
| I-212 | 4-(1-{[(1-adamantylacetyl)amino}ethyl)-N-hydroxybenzamide |
| I-213 | N-(1-{4-[(hydroxyamino)carbonyl]phenyl}ethyl)cycloheptanecarboxamide |
| I-214 | N-((1R)-1-{4-[(hydroxyamino)carbonyl]phenyl}-2-methylpropyl)-1-benzothiophene-2-carboxamide |
| I-215 | N-(1-{4-[(hydroxyamino)carbonyl]phenyl}-2,2-dimethylpropyl)thiophene-2-carboxamide |
| I-216 | 3-ethyl-N-(1-{3-[(hydroxyamino)carbonyl]phenyl}ethyl)-1-methyl-1H-pyrazole-5-carboxamide |
| I-217 | 4-(1-{[(2,5-dimethyl-1,3-thiazol-4-yl)acetyl]amino}ethyl)-N-hydroxybenzamide |
| I-218 | N-(1-{3-[(hydroxyamino)carbonyl]phenyl}ethyl)-3,5-dimethylisoxazole-4-carboxamide |
| I-219 | N-(1-{3-[(hydroxyamino)carbonyl]phenyl}ethyl)-1-methyl-1H-indole-2-carboxamide |
| I-220 | N-hydroxy-4-(2-methyl-1-{[(2,4,7-trimethyl-1H-indol-3-yl)acetyl]amino}propyl)benzamide |
| I-221 | N-hydroxy-4-(1-{[(4-isopropylphenyl)sulfonyl]amino}ethyl)benzamide |
| I-222 | N-((1R)-1-{4-[(hydroxyamino)carbonyl]phenyl}butyl)-4-methyl-2-phenyl-4H-furo[3,2-b]pyrrole-5-carboxamide |
| I-223 | 3-hydroxy-N-((1R)-1-{4-[(hydroxyamino)carbonyl]phenyl}-2-methylpropyl)adamantane-1-carboxamide |
| I-224 | N-(1-{4-[(hydroxyamino)carbonyl]phenyl}ethyl)-2H-chromene-3-carboxamide |
| I-225 | N-(1-{4-[(hydroxyamino)carbonyl]phenyl}ethyl)-3-methoxybenzamide |
| I-226 | 5-chloro-N-(1-{3-[(hydroxyamino)carbonyl]phenyl}ethyl)-1-benzofuran-2-carboxamide |
| I-227 | N-(1-{3-[(hydroxyamino)carbonyl]phenyl}ethyl)-1H-indole-2-carboxamide |
| I-228 | N-(1-{4-[(hydroxyamino)carbonyl]phenyl}ethyl)-3-(1H-pyrrol-1-yl)thiophene-2-carboxamide |
| I-229 | N-((R)-cyclopropyl{4-[(hydroxyamino)carbonyl]phenyl}methyl)-1-benzothiophene-2-carboxamide |
| I-230 | N-(1-{4-[(hydroxyamino)carbonyl]phenyl}ethyl)-2-methyl-1,3-benzothiazole-5-carboxamide |
| I-231 | 4-methyl-2-phenyl-N-((1S)-2,2,2-trifluoro-1-{4-[(hydroxyamino)carbonyl]phenyl}ethyl)-4H-furo[3,2-b]pyrrole-5-carboxamide |
| I-232 | N-hydroxy-4-(1-{[(2-methylphenyl)sulfonyl]amino}ethyl)benzamide |
| I-233 | N-(1-{4-[(hydroxyamino)carbonyl]phenyl}ethyl)-2,1,3-benzothiadiazole-5-carboxamide |
| I-234 | N-hydroxy-3-(1-{[(5-methyl-2-phenyl-1,3-oxazol-4-yl)acetyl]amino}ethyl)benzamide |
| I-235 | 4-(1-{[(2-chloro-4-fluorophenyl)sulfonyl]amino}ethyl)-N-hydroxybenzamide |
| I-236 | 4-[1-({[(4-cyanophenyl)amino]carbonyl}amino)ethyl]-N-hydroxybenzamide |
| I-237 | N-((1R)-1-{4-[(hydroxyamino)carbonyl]phenyl}ethyl)-3-methyl-1-benzofuran-2-carboxamide |
| I-238 | N-(1-{4-[(hydroxyamino)carbonyl]phenyl}-2-methylpropyl)-3,5-dimethylisoxazole-4-carboxamide |
| I-239 | 4-{1-[(cyclopropylcarbonyl)amino]ethyl}-N-hydroxybenzamide |
| I-240 | N-((1S)-1-{3-[(hydroxyamino)carbonyl]phenyl}ethyl)-1-benzothiophene-2-carboxamide |
| I-241 | N-(1-{4-[(hydroxyamino)carbonyl]phenyl}ethyl)-1,5-dimethyl-1H-pyrazole-3-carboxamide |
| I-242 | N-((1R)-1-{4-[(hydroxyamino)carbonyl]phenyl}-2-methylpropyl)-1-methyl-1H-indole-2-carboxamide |
| I-243 | 4-[1-(butyrylamino)ethyl]-N-hydroxybenzamide |
| I-244 | N-(1-{4-[(hydroxyamino)carbonyl]phenyl}ethyl)-1-benzothiophene-3-carboxamide |
| I-245 | 4,5-dichloro-N-((1R)-1-{4-[(hydroxyamino)carbonyl]phenyl}butyl)-1-methyl-1H-pyrrole-2-carboxamide |
| I-246 | N-(1-{4-[(hydroxyamino)carbonyl]phenyl}-2-methylpropyl)quinoline-4-carboxamide |
| I-247 | 5-chloro-N-(1-{4-[(hydroxyamino)carbonyl]phenyl}-2-methylpropyl)-1H-indole-2-carboxamide |
| I-248 | N-(1-{4-[(hydroxyamino)carbonyl]phenyl}-2,2-dimethylpropyl)-4-methyl-2-[4-(trifluoromethyl)phenyl]-4H-furo[3,2-b]pyrrole-5-carboxamide |
| I-249 | N-((S)-cyclopropyl{4-[(hydroxyamino)carbonyl]phenyl}methyl)-1-benzothiophene-2-carboxamide |
| I-250 | 4-[1-({[3,5-bis(trifluoromethyl)phenyl]acetyl}amino)-2-methylpropyl]-N-hydroxybenzamide |
| I-251 | 3,5-difluoro-N-(1-{4-[(hydroxyamino)carbonyl]phenyl}-2,2-dimethylpropyl)benzamide |
| I-252 | N-(1-{4-[(hydroxyamino)carbonyl]phenyl}-2-methylpropyl)-2,5-dimethyl-3-furamide |
| I-253 | N-hydroxy-4-[1-({[(2-methoxy-5-methylphenyl)amino]carbonyl}amino)ethyl]benzamide |
| I-254 | 4-(1-{[(2-chloro-4-cyanophenyl)sulfonyl]amino}ethyl)-N-hydroxybenzamide |
| I-255 | 4-{1-[(cyclopentylcarbonyl)amino]-2-methylpropyl}-N-hydroxybenzamide |
| I-256 | 4-(1-{[(2,5-dimethyl-3-thienyl)sulfonyl]amino}ethyl)-N-hydroxybenzamide |
| I-257 | N-(1-{3-[(hydroxyamino)carbonyl]phenyl}ethyl)-5-methyl-1-phenyl-1H-pyrazole-4-carboxamide |
| I-258 | N-hydroxy-4-(2-methyl-1-{[(1-phenylcyclopentyl)carbonyl]amino}propyl)benzamide |
| I-259 | N-[(S)-{4-[(hydroxyamino)carbonyl]phenyl}(phenyl)methyl]adamantane-1-carboxamide |
| I-260 | N-(1-{4-[(hydroxyamino)carbonyl]phenyl}-2,2-dimethylpropyl)-1,5-dimethyl-1H-pyrazole-3-carboxamide |

-continued

| | |
|---|---|
| I-261 | 4-[1-({[(2,6-difluorophenyl)amino]carbonyl}amino)ethyl]-N-hydroxybenzamide |
| I-262 | N-(1-{4-[(hydroxyamino)carbonyl]phenyl}-2,2-dimethylpropyl)-3,5-dimethyl-1H-pyrrole-2-carboxamide |
| I-263 | N-(1-{3-[(hydroxyamino)carbonyl]phenyl}ethyl)-1-methyl-1H-pyrrole-2-carboxamide |
| I-264 | N-hydroxy-4-[1-({[1-(4-methylphenyl)cyclopropyl]carbonyl}amino)ethyl]benzamide |
| I-265 | 4-{1-[(cyclohexylcarbonyl)amino]-2,2-dimethylpropyl}-N-hydroxybenzamide |
| I-266 | N-hydroxy-4-(1-{[(4-methylphenyl)sulfonyl]amino}ethyl)benzamide |
| I-267 | N-(1-{3-[(hydroxyamino)carbonyl]phenyl}ethyl)thiophene-2-carboxamide |
| I-268 | 3-{1-[(4-tert-butylbenzoyl)amino]ethyl}-N-hydroxybenzamide |
| I-269 | 2-chloro-N-(1-{4-[(hydroxyamino)carbonyl]phenyl}ethyl)benzamide |
| I-270 | 5-chloro-N-(1-{4-[(hydroxyamino)carbonyl]phenyl}-2,2-dimethylpropyl)-1-benzofuran-2-carboxamide |
| I-271 | N-((1R)-1-{3-[(hydroxyamino)carbonyl]phenyl}ethyl)-1-methyl-1H-pyrrole-2-carboxamide |
| I-272 | 4-{1-[(2,1,3-benzothiadiazol-5-ylsulfonyl)amino]ethyl}-N-hydroxybenzamide |
| I-273 | N-hydroxy-4-((1S)-1-{[(1-methylcyclohexyl)carbonyl]amino}ethyl)benzamide |
| I-274 | N-((1R)-1-{4-[(hydroxyamino)carbonyl]phenyl}butyl)biphenyl-4-carboxamide |
| I-275 | 4-[1-({[(3,4-difluorophenyl)amino]carbonyl}amino)ethyl]-N-hydroxybenzamide |
| I-276 | 1-methyl-N-((1R)-2,2,2-trifluoro-1-{4-[(hydroxyamino)carbonyl]phenyl}ethyl)-1H-indole-2-carboxamide |
| I-277 | N-hydroxy-4-[1-({[(4-methylbenzyl)amino]carbonyl}amino)ethyl]benzamide |
| I-278 | N-(1-{4-[(hydroxyamino)carbonyl]phenyl}ethyl)-2-methyl-1,3-thiazole-4-carboxamide |
| I-279 | N-((1S)-1-{4-[(hydroxyamino)carbonyl]phenyl}-2-methylpropyl)-1H-indole-2-carboxamide |
| I-280 | 4-{1-[(1,3-benzodioxol-5-ylacetyl)amino]ethyl}-N-hydroxybenzamide |
| I-281 | N-((1R)-1-{4-[(hydroxyamino)carbonyl]phenyl}butyl)-1-methyl-1H-pyrrole-2-carboxamide |
| I-282 | 3,5-bis(acetylamino)-N-(1-{4-[(hydroxyamino)carbonyl]phenyl}-2-methylpropyl)benzamide |
| I-283 | N-hydroxy-3-((1R)-1-{[(1-methylcyclohexyl)carbonyl]amino}ethyl)benzamide |
| I-284 | N-hydroxy-4-(1-{[(2,3,4-trifluorophenyl)sulfonyl]amino}ethyl)benzamide |
| I-285 | N-hydroxy-4-(1-{[(4-isopropylphenyl)acetyl]amino}ethyl)benzamide |
| I-286 | N-(1-{4-[(hydroxyamino)carbonyl]phenyl}ethyl)-5-isobutylisoxazole-3-carboxamide |
| I-287 | 4-{(1R)-1-[(2,2-dimethylpropanoyl)amino]-2-methylpropyl}-N-hydroxybenzamide |
| I-288 | N-(1-{4-[(hydroxyamino)carbonyl]phenyl}ethyl)-1,3-dimethyl-1H-pyrazole-5-carboxamide |
| I-289 | N-hydroxy-4-{2-methyl-1-[(3-methyl-2-phenylbutanoyl)amino]propyl}benzamide |
| I-290 | 4-((1R)-1-{[(tert-butylamino)carbonyl]amino}-2,2,2-trifluoroethyl)-N-hydroxybenzamide |
| I-291 | 3-tert-butyl-N-(1-{4-[(hydroxyamino)carbonyl]phenyl}-2,2-dimethylpropyl)-1-methyl-1H-pyrazole-5-carboxamide |
| I-292 | 4-(1-{[(2-chlorophenyl)acetyl]amino}ethyl)-N-hydroxybenzamide |
| I-293 | 4-(1-{[(2,1,3-benzothiadiazol-4-ylamino)carbonyl]amino}ethyl)-N-hydroxybenzamide |
| I-294 | N-((1S)-1-{3-[(hydroxyamino)carbonyl]phenyl}ethyl)-1-methyl-1H-indole-2-carboxamide |
| I-295 | N-(1-{4-[(hydroxyamino)carbonyl]phenyl}ethyl)-3-methylbenzamide |
| I-296 | N-((1S)-2,2,2-trifluoro-1-{4-[(hydroxyamino)carbonyl]phenyl}ethyl)biphenyl-4-carboxamide |
| I-297 | N-(1-{4-[(hydroxyamino)carbonyl]phenyl}ethyl)-1,3-benzodioxole-5-carboxamide |
| I-298 | N-hydroxy-4-(1-{[(1-phenylcyclopentyl)carbonyl]amino}ethyl)benzamide |
| I-299 | N-((1R)-1-{4-[(hydroxyamino)carbonyl]phenyl}butyl)-1-benzothiophene-2-carboxamide |
| I-300 | 4-[1-({[1-(4-chlorophenyl)cyclopropyl]carbonyl}amino)-2-methylpropyl]-N-hydroxybenzamide |
| I-301 | 4,5-dichloro-N-((1R)-1-{3-[(hydroxyamino)carbonyl]phenyl}ethyl)-1-methyl-1H-pyrrole-2-carboxamide |
| I-302 | 4-(1-{[(4-chlorophenyl)sulfonyl]amino}ethyl)-N-hydroxybenzamide |
| I-303 | 4-(2,2-dimethyl-1-{[4-(trifluoromethyl)benzoyl]amino}propyl)-N-hydroxybenzamide |
| I-304 | 3-methyl-N-((1S)-2,2,2-trifluoro-1-{4-[(hydroxyamino)carbonyl]phenyl}ethyl)-1-benzofuran-2-carboxamide |
| I-305 | N-hydroxy-4-[1-({[(5-methyl-3-phenylisoxazol-4-yl)amino]carbonyl}amino)ethyl]benzamide |
| I-306 | N-(1-{4-[(hydroxyamino)carbonyl]phenyl}-2-methylpropyl)-7-methoxy-1-benzofuran-2-carboxamide |
| I-307 | N-((1R)-1-{4-[(hydroxyamino)carbonyl]phenyl}-2-methylpropyl)-3-methyl-1-benzothiophene-2-carboxamide |
| I-308 | N-(1-{4-[(hydroxyamino)carbonyl]phenyl}-2,2-dimethylpropyl)-1-benzothiophene-2-carboxamide |
| I-309 | 3-tert-butyl-N-(1-{3-[(hydroxyamino)carbonyl]phenyl}ethyl)-1-methyl-1H-pyrazole-5-carboxamide |
| I-310 | N-(1-{4-[(hydroxyamino)carbonyl]phenyl}-2,2-dimethylpropyl)-2,5-dimethyl-1H-pyrrole-3-carboxamide |
| I-311 | 3-{1-[(cyclopentylcarbonyl)amino]ethyl}-N-hydroxybenzamide |
| I-312 | N-((1R)-1-{3-[(hydroxyamino)carbonyl]phenyl}ethyl)adamantane-1-carboxamide |
| I-313 | N-hydroxy-4-{1-[(tetrahydro-2H-pyran-4-ylacetyl)amino]ethyl}benzamide |
| I-314 | N-hydroxy-3-[1-({[3-(trifluoromethyl)phenyl]acetyl}amino)ethyl]benzamide |
| I-315 | N-hydroxy-4-{1-[(phenylsulfonyl)amino]ethyl}benzamide |
| I-316 | N-hydroxy-4-[1-({[(3-methylbenzyl)amino]carbonyl}amino)ethyl]benzamide |
| I-317 | N-((1R)-1-{4-[(hydroxyamino)carbonyl]phenyl}ethyl)-1-benzofuran-2-carboxamide |
| I-318 | 3-ethyl-N-(1-{4-[(hydroxyamino)carbonyl]phenyl}-2,2-dimethylpropyl)-1-methyl-1H-pyrazole-5-carboxamide |
| I-319 | N-(1-{4-[(hydroxyamino)carbonyl]phenyl}-2,2-dimethylpropyl)-1H-indole-3-carboxamide |
| I-320 | 3-((1R)-1-{[(tert-butylamino)carbonyl]amino}ethyl)-N-hydroxybenzamide |
| I-321 | N-((1R)-1-{3-[(hydroxyamino)carbonyl]phenyl}ethyl)-1-benzothiophene-2-carboxamide |
| I-322 | N-((S)-cyclopropyl{4-[(hydroxyamino)carbonyl]phenyl}methyl)adamantane-1-carboxamide |
| I-323 | N-(1-{3-[(hydroxyamino)carbonyl]phenyl}-2-methylpropyl)biphenyl-4-carboxamide |
| I-324 | 2-(4-tert-butylphenyl)-N-(1-{3-[(hydroxyamino)carbonyl]phenyl}ethyl)-4-methyl-4H-furo[3,2-b]pyrrole-5-carboxamide |
| I-325 | 4-{1-[({[4-chloro-3-(trifluoromethyl)phenyl]amino}carbonyl)amino]ethyl}-N-hydroxybenzamide |

-continued

| | |
|---|---|
| I-326 | N-(1-{4-[(hydroxyamino)carbonyl]phenyl}ethyl)-3,5-dimethylisoxazole-4-carboxamide |
| I-327 | N-(1-{4-[(hydroxyamino)carbonyl]phenyl}ethyl)-2-naphthamide |
| I-328 | N-((1R)-1-{4-[(hydroxyamino)carbonyl]phenyl}-2-methylpropyl)adamantane-1-carboxamide |
| I-329 | N-(1-{4-[(hydroxyamino)carbonyl]phenyl}-2,2-dimethylpropyl)-3,5-dimethyl-1H-indole-2-carboxamide |
| I-330 | N-((1R)-1-{3-[(hydroxyamino)carbonyl]phenyl}ethyl)-1-methyl-1H-indole-2-carboxamide |
| I-331 | N-(1-{4-[(hydroxyamino)carbonyl]phenyl}-2-methylpropyl)-1-naphthamide |
| I-332 | N-((1R)-1-{4-[(hydroxyamino)carbonyl]phenyl}-2-methylpropyl)-4-methyl-2-phenyl-4H-furo[3,2-b]pyrrole-5-carboxamide |
| I-333 | 3-{1-[(3,3-dimethylbutanoyl)amino]ethyl}-N-hydroxybenzamide |
| I-334 | 4-{1-[({[2-fluoro-5-(trifluoromethyl)phenyl]amino}carbonyl)amino]ethyl}-N-hydroxybenzamide |
| I-335 | N-hydroxy-4-(1-{[(1-methyl-1H-imidazol-4-yl)sulfonyl]amino}ethyl)benzamide |
| I-336 | N-[(R)-{4-[(hydroxyamino)carbonyl]phenyl}(phenyl)methyl]adamantane-1-carboxamide |
| I-337 | 2-(4-tert-butylphenyl)-N-(1-{4-[(hydroxyamino)carbonyl]phenyl}-2,2-dimethylpropyl)-4-methyl-4H-furo[3,2-b]pyrrole-5-carboxamide |
| I-338 | 4-{1-[(benzylsulfonyl)amino]ethyl}-N-hydroxybenzamide |
| I-339 | 4-(1-{[(tert-butylamino)carbonyl]amino}ethyl)-N-hydroxybenzamide |
| I-340 | 4-(1-{[(2-cyanophenyl)sulfonyl]amino}ethyl)-N-hydroxybenzamide |
| I-341 | N-((1R)-1-{4-[(hydroxyamino)carbonyl]phenyl}-2-methylpropyl)biphenyl-4-carboxamide |
| I-342 | N-(1-{3-[(hydroxyamino)carbonyl]phenyl}ethyl)-5-methyl-1H-indole-2-carboxamide |
| I-343 | 3-[(1R)-1-({[1-adamantylamino]carbonyl}amino)ethyl]-N-hydroxybenzamide |
| I-344 | 4-{1-[(cyclohexylcarbonyl)amino]-2-methylpropyl}-N-hydroxybenzamide |
| I-345 | 4-(1-{[(5-chloro-1-benzothien-3-yl)acetyl]amino}-2,2-dimethylpropyl)-N-hydroxybenzamide |
| I-346 | N-(1-{4-[(hydroxyamino)carbonyl]phenyl}-2-methylpropyl)-4-methoxybenzamide |
| I-347 | 4-(1-{[(5-chloro-2-methoxyphenyl)sulfonyl]amino}ethyl)-N-hydroxybenzamide |
| I-348 | 4-{1-[(cyclohex-3-en-1-ylcarbonyl)amino]ethyl}-N-hydroxybenzamide |
| I-349 | N-(1-{4-[(hydroxyamino)carbonyl]phenyl}ethyl)-1-benzofuran-5-carboxamide |
| I-350 | 4-tert-butyl-N-(1-{4-[(hydroxyamino)carbonyl]phenyl}ethyl)benzamide |
| I-351 | N-hydroxy-4-[(1R)-1-({[4-(trifluoromethyl)phenyl]sulfonyl}amino)ethyl]benzamide |
| I-352 | N-(1-{4-[(hydroxyamino)carbonyl]phenyl}-2,2-dimethylpropyl)-4-methoxybenzamide |
| I-353 | N-(1-{3-[(hydroxyamino)carbonyl]phenyl}ethyl)-1-methyl-1H-indole-3-carboxamide |
| I-354 | 4-[(1R)-1-({[1-adamantylamino]carbonyl}amino)-2-methylpropyl]-N-hydroxybenzamide |
| I-355 | N-(1-{4-[(hydroxyamino)carbonyl]phenyl}-2,2-dimethylpropyl)biphenyl-4-carboxamide |
| I-356 | N-(1-{4-[(hydroxyamino)carbonyl]phenyl}ethyl)-1-methyl-1H-pyrrole-2-carboxamide |
| I-357 | 4-{1-[(2,3-dihydro-1H-inden-2-ylacetyl)amino]ethyl}-N-hydroxybenzamide |
| I-358 | 4-[1-({[(3-acetylphenyl)amino]carbonyl}amino)ethyl]-N-hydroxybenzamide |
| I-359 | 4,5-dichloro-N-((1R)-1-{4-[(hydroxyamino)carbonyl]phenyl}ethyl)-1-methyl-1H-pyrrole-2-carboxamide |
| I-360 | N-(1-{4-[(hydroxyamino)carbonyl]phenyl}ethyl)-1,3-benzothiazole-6-carboxamide |
| I-361 | 4-(1-{[(2-chlorophenyl)sulfonyl]amino}ethyl)-N-hydroxybenzamide |
| I-362 | 3-[1-({[3,5-bis(trifluoromethyl)phenyl]acetyl}amino)ethyl]-N-hydroxybenzamide |
| I-363 | N-hydroxy-4-{1-[(quinolin-8-ylsulfonyl)amino]ethyl}benzamide |
| I-364 | N-(1-{4-[(hydroxyamino)carbonyl]phenyl}-2,2-dimethylpropyl)-1-methyl-1H-indole-2-carboxamide |
| I-365 | 4-{(1R)-1-[(2,2-dimethylpropanoyl)amino]butyl}-N-hydroxybenzamide |
| I-366 | 2,6-dichloro-N-(1-{3-[(hydroxyamino)carbonyl]phenyl}ethyl)benzamide |
| I-367 | N-((1R)-1-{4-[(hydroxyamino)carbonyl]phenyl}butyl)-3-methyl-1-benzofuran-2-carboxamide |
| I-368 | 4-((1R)-1-{[(tert-butylamino)carbonyl]amino}-2-methylpropyl)-N-hydroxybenzamide |
| I-369 | 4-{1-[(1-benzothien-2-ylsulfonyl)amino]ethyl}-N-hydroxybenzamide |
| I-370 | 4-{1-[(cyclopentylacetyl)amino]ethyl}-N-hydroxybenzamide |
| I-371 | N-hydroxy-4-[1-({[3-(trifluoromethyl)phenyl]amino}carbonyl)amino]ethyl}benzamide |
| I-372 | N-hydroxy-4-(1-{[(2,2,3,3-tetramethylcyclopropyl)carbonyl]amino}ethyl)benzamide |
| I-373 | 4-{1-[(cyclopentylcarbonyl)amino]-2,2-dimethylpropyl}-N-hydroxybenzamide |
| I-374 | 4-[(1R)-1-({[1-adamantylamino]carbonyl}amino)ethyl]-N-hydroxybenzamide |
| I-375 | N-(1-{4-[(hydroxyamino)carbonyl]phenyl}-2-methylpropyl)-2-oxo-6-phenyl-1,2-dihydropyridine-3-carboxamide |
| I-376 | N-(1-{3-[(hydroxyamino)carbonyl]phenyl}ethyl)-3,5-dimethyl-1H-indole-2-carboxamide |
| I-377 | 4-tert-butyl-N-(1-{4-[(hydroxyamino)carbonyl]phenyl}-2,2-dimethylpropyl)benzamide |
| I-378 | 4-(1-{[2-(4-chlorophenyl)-2-methylpropanoyl]amino}ethyl)-N-hydroxybenzamide |
| I-379 | 4-{1-[(cyclopropylacetyl)amino]ethyl}-N-hydroxybenzamide |
| I-380 | 4-((1R)-1-{[(tert-butylamino)carbonyl]amino}butyl)-N-hydroxybenzamide |
| I-381 | 4-[1-({[(4-ethylphenyl)amino]carbonyl}amino)ethyl]-N-hydroxybenzamide |
| I-382 | N-(1-{4-[(hydroxyamino)carbonyl]phenyl}-2-methylpropyl)cycloheptanecarboxamide |
| I-383 | 4-[1-({[(2,4-dimethylphenyl)amino]carbonyl}amino)ethyl]-N-hydroxybenzamide |
| I-384 | 4-(1-{[(biphenyl-2-ylamino)carbonyl]amino}ethyl)-N-hydroxybenzamide |
| I-385 | 4-[1-(benzoylamino)ethyl]-N-hydroxybenzamide |
| I-386 | 4,5-dichloro-N-(1-{4-[(hydroxyamino)carbonyl]phenyl}-2,2-dimethylpropyl)-1-methyl-1H-pyrrole-2-carboxamide |
| I-387 | N-hydroxy-4-((1R)-1-{[(1-methylcyclohexyl)carbonyl]amino}butyl)benzamide |
| I-388 | 4-[1-({[(3,5-dichlorophenyl)amino]carbonyl}amino)ethyl]-N-hydroxybenzamide |
| I-389 | N-(1-{4-[(hydroxyamino)carbonyl]phenyl}-2-methylpropyl)-1-methyl-1H-pyrazole-3-carboxamide |
| I-390 | N-(1-{3-[(hydroxyamino)carbonyl]phenyl}-2-methylpropyl)-1-benzothiophene-2-carboxamide |
| I-391 | N-hydroxy-4-[1-({[2-(trifluoromethyl)phenyl]sulfonyl}amino)ethyl]benzamide |
| I-392 | N-(1-{4-[(hydroxyamino)carbonyl]phenyl}-2,2-dimethylpropyl)-4-methyl-2-phenyl-4H-furo[3,2-b]pyrrole-5-carboxamide |
| I-393 | N-((1S)-1-{3-[(hydroxyamino)carbonyl]phenyl}ethyl)biphenyl-4-carboxamide |
| I-394 | N-hydroxy-4-[1-({[(2-methylphenyl)amino]carbonyl}amino)ethyl]benzamide |
| I-395 | 4-(1-{[(cyclohexylamino)carbonyl]amino}ethyl)-N-hydroxybenzamide |

-continued

| | |
|---|---|
| I-396 | 4-{1-[(3,3-dimethylbutanoyl)amino]-2,2-dimethylpropyl}-N-hydroxybenzamide |
| I-397 | 4-[1-({[(3,5-dimethylphenyl)amino]carbonyl}amino)ethyl]-N-hydroxybenzamide |
| I-398 | 4-[1-({[(4-acetylphenyl)amino]carbonyl}amino)ethyl]-N-hydroxybenzamide |
| I-399 | N-hydroxy-4-{1-[({[4-(trifluoromethyl)phenyl]amino}carbonyl)amino]ethyl}benzamide |
| I-400 | N-((1S)-2,2,2-trifluoro-1-{4-[(hydroxyamino)carbonyl]phenyl}ethyl)-1-benzofuran-2-carboxamide |
| I-401 | N-(1-{3-[(hydroxyamino)carbonyl]phenyl}ethyl)-1-benzofuran-2-carboxamide |
| I-402 | 4-(1-{[(2,4-difluorophenyl)acetyl]amino}ethyl)-N-hydroxybenzamide |
| I-403 | N-hydroxy-3-[(1R)-1-({[4-(trifluoromethyl)phenyl]sulfonyl}amino)ethyl]benzamide |
| I-404 | 6-{(1S)-1-[(1-benzothien-2-ylcarbonyl)amino]-2,2-dimethylpropyl}-N-hydroxynicotinamide |
| I-405 | 5-{(1S)-1-[(2,2-dimethylpropanoyl)amino]propyl}-N-hydroxynicotinamide |
| I-406 | 5-{(1S)-1-[(2,2-dimethylpropanoyl)amino]ethyl}-N-hydroxy-6-methoxynicotinamide |
| I-407 | 2-{(1S)-1-[(cyclopentylacetyl)amino]butyl}-N-hydroxyisonicotinamide |
| I-408 | N-((1S)-1-{4-[(hydroxyamino)carbonyl]phenyl}propyl)-1-methylpiperidine-4-carboxamide |
| I-409 | N-((1S)-1-{4-[(hydroxyamino)carbonyl]phenyl}propyl)-1-methyl-1H-indole-2-carboxamide |
| I-410 | 4-{(1R)-1-[(2,2-dimethylpropanoyl)amino]propyl}-N-hydroxy-3-methoxybenzamide |
| I-411 | N-((1S)-1-{5-[(hydroxyamino)carbonyl]pyridin-2-yl}-2,2-dimethylpropyl)-1-methyl-1H-indole-2-carboxamide |
| I-412 | 6-{(1S)-1-[(2,2-dimethylpropanoyl)amino]-2,2-dimethylpropyl}-N-hydroxynicotinamide |
| I-413 | N-((1S)-1-{4-[(hydroxyamino)carbonyl]pyridin-2-yl}butyl)-1-methyl-1H-indole-2-carboxamide |
| I-414 | N-((1S)-1-{4-[(hydroxyamino)carbonyl]phenyl}-2,2-dimethylpropyl)-1-benzothiophene-2-carboxamide |
| I-415 | N-hydroxy-2-[(1R)-1-({[4-(trifluoromethyl)phenyl]sulfonyl}amino)propyl]isonicotinamide |
| I-416 | 6-((1S)-2,2-dimethyl-1-{[(1-methyl-1H-pyrrol-2-yl)carbonyl]amino}propyl)-N-hydroxynicotinamide |
| I-417 | 6-((1S)-2,2-dimethyl-1-{[(1-methylpiperidin-4-yl)carbonyl]amino}propyl)-N-hydroxynicotinamide |
| I-418 | 4-{(1S)-1-[(2,2-dimethylpropanoyl)amino]-2,2-dimethylpropyl}-N-hydroxybenzamide |
| I-419 | N-hydroxy-6-methoxy-5-((1S)-1-{[(1-methyl-1H-pyrrol-2-yl)carbonyl]amino}ethyl)nicotinamide |
| I-420 | 6-((1S)-1-{[(dimethylamino)acetyl]amino}-2,2-dimethylpropyl)-N-hydroxynicotinamide |
| I-421 | 6-((1S)-1-{[(dimethylamino)acetyl]amino}ethyl)-N-hydroxynicotinamide |
| I-422 | 4-{(1S)-1-[(cyclopentylacetyl)amino]propyl}-N-hydroxybenzamide |
| I-423 | 5-{(1S)-1-[(1-benzothien-2-ylcarbonyl)amino]propyl}-N-hydroxynicotinamide |
| I-424 | 5-{(1S)-1-[(cyclopentylacetyl)amino]ethyl}-N-hydroxy-6-methoxynicotinamide |
| I-425 | N-hydroxy-5-((1S)-1-{[(1-methylpiperidin-4-yl)carbonyl]amino}propyl)nicotinamide |
| I-426 | 2-{(1S)-1-[(2,2-dimethylpropanoyl)amino]butyl}-N-hydroxyisonicotinamide |
| I-427 | 3-fluoro-N-hydroxy-4-[(1R)-1-({[4-(trifluoromethyl)phenyl]sulfonyl}amino)ethyl]benzamide |
| I-428 | 5-{(1S)-1-[(1-adamantylcarbonyl)amino]propyl}-N-hydroxynicotinamide |
| I-429 | 6-{(1S)-1-[(1-adamantylcarbonyl)amino]-2,2-dimethylpropyl}-N-hydroxynicotinamide |
| I-430 | 2-{(1S)-1-[(cyclopentylacetyl)amino]-2-methylpropyl}-N-hydroxypyrimidine-5-carboxamide |
| I-431 | N-hydroxy-6-methoxy-5-((1S)-1-{[(1-methylpiperidin-4-yl)carbonyl]amino}ethyl)nicotinamide |
| I-432 | 6-{(1S)-1-[(cyclopentylacetyl)amino]-2,2-dimethylpropyl}-N-hydroxynicotinamide |
| I-433 | N-hydroxy-6-((1S)-1-{[(1-methylpiperidin-4-yl)carbonyl]amino}ethyl)nicotinamide |
| I-434 | 6-{(1S)-1-[(biphenyl-4-ylcarbonyl)amino]ethyl}-N-hydroxynicotinamide |
| I-435 | N-hydroxy-6-((1S)-1-{[(1-methyl-1H-pyrrol-2-yl)carbonyl]amino}ethyl)nicotinamide |
| I-436 | 2-{(1S)-1-[(1-adamantylcarbonyl)amino]-2-methylpropyl}-N-hydroxypyrimidine-5-carboxamide |
| I-437 | N-((1S)-1-{4-[(hydroxyamino)carbonyl]phenyl}-2,2-dimethylpropyl)-1-methylpiperidine-4-carboxamide |
| I-438 | N-hydroxy-2-((1S)-1-{[(1-methyl-1H-pyrrol-2-yl)carbonyl]amino}butyl)isonicotinamide |
| I-439 | N-((1R)-1-{2-fluoro-4-[(hydroxyamino)carbonyl]phenyl}-2-methylpropyl)biphenyl-4-carboxamide |
| I-440 | N-hydroxy-2-[(1R)-1-({[4-(trifluoromethyl)phenyl]sulfonyl}amino)ethyl]pyrimidine-5-carboxamide |
| I-441 | N-((1S)-1-{4-[(hydroxyamino)carbonyl]phenyl}propyl)-1-benzothiophene-2-carboxamide |
| I-442 | 5-{(1S)-1-[(cyclopentylacetyl)amino]propyl}-N-hydroxynicotinamide |
| I-443 | 6-{(1S)-1-[(biphenyl-4-ylcarbonyl)amino]-2,2-dimethylpropyl}-N-hydroxynicotinamide |
| I-444 | N-((1S)-1-{5-[(hydroxyamino)carbonyl]-2-methoxypyridin-3-yl}ethyl)-1-methyl-1H-indole-2-carboxamide |
| I-445 | 6-{(1S)-1-[(1-benzothien-2-ylcarbonyl)amino]ethyl}-N-hydroxynicotinamide |
| I-446 | 6-{(1S)-1-[(2,2-dimethylpropanoyl)amino]ethyl}-N-hydroxynicotinamide |
| I-447 | 5-((1S)-1-{[(dimethylamino)acetyl]amino}ethyl)-N-hydroxy-6-methoxynicotinamide |
| I-448 | 2-{(1S)-1-[(1-benzothien-2-ylcarbonyl)amino]-2-methylpropyl}-N-hydroxypyrimidine-5-carboxamide |
| I-449 | 2-{(1S)-1-[(biphenyl-4-ylcarbonyl)amino]butyl}-N-hydroxyisonicotinamide |
| I-450 | 2-{(1S)-1-[(biphenyl-4-ylcarbonyl)amino]-2-methylpropyl}-N-hydroxypyrimidine-5-carboxamide |
| I-451 | 2-((1S)-1-{[(dimethylamino)acetyl]amino}butyl)-N-hydroxyisonicotinamide |
| I-452 | N-((1S)-1-{4-[(hydroxyamino)carbonyl]phenyl}-2,2-dimethylpropyl)-1-methyl-1H-indole-2-carboxamide |
| I-453 | 5-((1S)-1-{[(dimethylamino)acetyl]amino}propyl)-N-hydroxynicotinamide |
| I-454 | N-hydroxy-2-[(1R)-2-methyl-1-({[4-(trifluoromethyl)phenyl]sulfonyl}amino)propyl]isonicotinamide |
| I-455 | N-((1S)-1-{5-[(hydroxyamino)carbonyl]pyridin-3-yl}propyl)-1-methyl-1H-indole-2-carboxamide |
| I-456 | 2-((1S)-1-{[(dimethylamino)acetyl]amino}-2-methylpropyl)-N-hydroxypyrimidine-5-carboxamide |
| I-457 | N-((1S)-1-{5-[(hydroxyamino)carbonyl]pyridin-2-yl}ethyl)-1-methyl-1H-indole-2-carboxamide |
| I-458 | 2-{(1S)-1-[(1-benzothien-2-ylcarbonyl)amino]butyl}-N-hydroxyisonicotinamide |

| | |
|---|---|
| I-459 | 4-{(1S)-1-[(cyclopentylacetyl)amino]-2,2-dimethylpropyl}-N-hydroxybenzamide |
| I-460 | N-((1S)-1-{4-[(hydroxyamino)carbonyl]phenyl}propyl)-1-methyl-1H-pyrrole-2-carboxamide |
| I-461 | N-hydroxy-5-((1S)-1-{[(1-methyl-1H-pyrrol-2-yl)carbonyl]amino}propyl)nicotinamide |
| I-462 | N-((1S)-1-{4-[(hydroxyamino)carbonyl]phenyl}-2,2-dimethylpropyl)-1-methyl-1H-pyrrole-2-carboxamide |
| I-463 | 5-((1R)-1-{[(tert-butylamino)carbonyl]amino}propyl)-N-hydroxynicotinamide |
| I-464 | 5-{(1S)-1-[(biphenyl-4-ylcarbonyl)amino]ethyl}-N-hydroxy-6-methoxynicotinamide |
| I-465 | 2-{(1S)-1-[(1-adamantylcarbonyl)amino]butyl}-N-hydroxyisonicotinamide |
| I-466 | N-((1S)-1-{5-[(hydroxyamino)carbonyl]pyrimidin-2-yl}-2-methylpropyl)-1-methyl-1H-indole-2-carboxamide |
| I-467 | 5-{(1S)-1-[(biphenyl-4-ylcarbonyl)amino]propyl}-N-hydroxynicotinamide |
| I-468 | N-hydroxy-2-((1S)-1-{[(1-methylpiperidin-4-yl)carbonyl]amino}butyl)isonicotinamide |
| I-469 | 6-{(1S)-1-[(1-adamantylcarbonyl)amino]ethyl}-N-hydroxynicotinamide |
| I-470 | 4-((1S)-1-{[(dimethylamino)acetyl]amino}propyl)-N-hydroxybenzamide |
| I-471 | N-((1S)-1-{4-[(hydroxyamino)carbonyl]phenyl}-2,2-dimethylpropyl)biphenyl-4-carboxamide |
| I-472 | 5-{(1S)-1-[(1-adamantylcarbonyl)amino]ethyl}-N-hydroxy-6-methoxynicotinamide |
| I-473 | 2-{(1S)-1-[(2,2-dimethylpropanoyl)amino]-2-methylpropyl}-N-hydroxypyrimidine-5-carboxamide |
| I-474 | N-((1S)-1-{4-[(hydroxyamino)carbonyl]phenyl}propyl)biphenyl-4-carboxamide |
| I-475 | 4-{(1S)-1-[(2,2-dimethylpropanoyl)amino]propyl}-N-hydroxybenzamide |
| I-476 | N-hydroxy-2-((1S)-2-methyl-1-{[(1-methyl-1H-pyrrol-2-yl)carbonyl]amino}propyl)pyrimidine-5-carboxamide |
| I-477 | N-hydroxy-2-((1S)-2-methyl-1-{[(1-methylpiperidin-4-yl)carbonyl]amino}propyl)pyrimidine-5-carboxamide |
| I-478 | 4-((1S)-1-{[(dimethylamino)acetyl]amino}-2,2-dimethylpropyl)-N-hydroxybenzamide |
| I-479 | 5-{(1S)-1-[(1-benzothien-2-ylcarbonyl)amino]ethyl}-N-hydroxy-6-methoxynicotinamide |
| I-480 | N-(1-{4-[(hydroxyamino)carbonyl]-2-methoxyphenyl}ethyl)-1-benzothiophene-2-carboxamide |
| I-481 | N-(1-{4-[(hydroxyamino)carbonyl]-2-methoxyphenyl}ethyl)-1-methyl-1H-pyrrole-2-carboxamide |
| I-482 | 4-((1R)-1-{[(benzylamino)carbonyl]amino}ethyl)-N-hydroxybenzamide |
| I-483 | N-(1-{4-[(hydroxyamino)carbonyl]-2-methoxyphenyl}ethyl)adamantane-1-carboxamide |
| I-484 | 4-{1-[(2,2-dimethylpropanoyl)amino]ethyl}-N-hydroxy-3-methoxybenzamide |
| I-485 | N-(1-{4-[(hydroxyamino)carbonyl]-2-methylphenyl}ethyl)-1-benzothiophene-2-carboxamide |
| I-486 | N-(1-{4-[(hydroxyamino)carbonyl]-2-methylphenyl}ethyl)-1-methyl-1H-pyrrole-2-carboxamide |
| I-487 | N-((1R)-1-{4-[(hydroxyamino)carbonyl]phenyl}ethyl)-4-methylpiperidine-4-carboxamide |
| I-488 | N-hydroxy-4-[1-({[4-(trifluoromethyl)phenyl]sulfonyl}amino)ethyl]benzamide |
| I-489 | N-hydroxy-4-((1R)-1-{[(1-methylcyclohexyl)methyl]amino}ethyl)benzamide |
| I-490 | 4-{1-[(2,2-dimethylpropanoyl)amino]ethyl}-N-hydroxy-3-methylbenzamide |
| I-491 | N-(1-{4-[(hydroxyamino)carbonyl]-2-methylphenyl}ethyl)adamantane-1-carboxamide |
| I-492 | N-hydroxy-4-[(1R)-2-methyl-1-({[(5-phenyl-2-thienyl)amino]carbonyl}amino)propyl]benzamide |
| I-493 | 4-((1R)-1-{[(biphenyl-2-ylamino)carbonyl]amino}-2-methylpropyl)-N-hydroxybenzamide |
| I-494 | 4-((1R)-1-{[(biphenyl-2-ylamino)carbonyl]amino}ethyl)-N-hydroxybenzamide |
| I-495 | N-hydroxy-4-{(1R)-2-methyl-1-[({[(1S)-1-phenylethyl]amino}carbonyl)amino]propyl}benzamide |
| I-496 | 4-((1R)-1-{[(2,3-dihydro-1-benzofuran-5-ylamino)carbonyl]amino}ethyl)-N-hydroxybenzamide |
| I-497 | 4-[(1R)-1-({[(3,4-dimethylphenyl)amino]carbonyl}amino)-2-methylpropyl]-N-hydroxybenzamide |
| I-498 | 4-[(1R)-1-({[(4-cyanophenyl)amino]carbonyl}amino)-2-methylpropyl]-N-hydroxybenzamide |
| I-499 | N-hydroxy-4-{(1R)-1-[({[(1S)-1-phenylethyl]amino}carbonyl)amino]ethyl}benzamide |
| I-500 | 4-[(1R)-1-({[(3,4-dimethylphenyl)amino]carbonyl}amino)ethyl]-N-hydroxybenzamide |
| I-501 | N-hydroxy-4-[(1R)-2-methyl-1-({[(2-phenylethyl)amino]carbonyl}amino)propyl]benzamide |
| I-502 | N-hydroxy-4-{(1R)-1-[({[(1R)-1-phenylethyl]amino}carbonyl)amino]ethyl}benzamide |
| I-503 | N-hydroxy-4-((1R)-1-{[(1-naphthylamino)carbonyl]amino}ethyl)benzamide |
| I-504 | 4-[(1R)-1-({[(4-cyanophenyl)amino]carbonyl}amino)ethyl]-N-hydroxybenzamide |
| I-505 | 4-((1R)-1-({[(2,6-difluorophenyl)amino]carbonyl}amino)-2-methylpropyl)-N-hydroxybenzamide |
| I-506 | N-hydroxy-4-[(1R)-1-({[(2-phenylethyl)amino]carbonyl}amino)ethyl]benzamide |
| I-507 | N-hydroxy-4-{(1R)-2-methyl-1-[({[(1R)-1-phenylethyl]amino}carbonyl)amino]propyl}benzamide |
| I-508 | 4-[(1R)-1-({[(2,6-difluorophenyl)amino]carbonyl}amino)ethyl]-N-hydroxybenzamide |
| I-509 | 4-((1R)-1-{[(2,3-dihydro-1-benzofuran-5-ylamino)carbonyl]amino}-2-methylpropyl)-N-hydroxybenzamide |
| I-510 | N-hydroxy-4-((1R)-2-methyl-1-{[(1-naphthylamino)carbonyl]amino}propyl)benzamide |
| I-511 | N-hydroxy-4-[(1R)-1-({[(5-phenyl-2-thienyl)amino]carbonyl}amino)ethyl]benzamide |
| I-512 | 4-[(1R)-1-({[(3,4-dimethylphenyl)amino]carbonyl}amino)-2-methylpropyl]-N-hydroxybenzamide |
| I-513 | N-hydroxy-4-[(1R)-1-({[(1S)-1-phenylethyl]carbamoyl}amino)ethyl]benzamide |
| I-514 | N-hydroxy-4-[(1R)-2-methyl-1-({[(1R)-1-phenylethyl]carbamoyl}amino)propyl]benzamide |
| I-515 | 4-((1R)-1-{[(biphenyl-2-ylamino)carbonyl]amino}-2-methylpropyl)-N-hydroxybenzamide |
| I-516 | N-hydroxy-4-{(1R)-2-methyl-1-[({[(1S)-1-phenylethyl]amino}carbonyl)amino]propyl}benzamide |
| I-517 | N-hydroxy-4-[(1R)-1-({[(1R)-1-phenylethyl]carbamoyl}amino)ethyl]benzamide |
| I-518 | 4-[(1R)-1-({[(2,6-difluorophenyl)amino]carbonyl}amino)ethyl]-N-hydroxybenzamide |
| I-519 | N-hydroxy-4-((1R)-2-methyl-1-{[4-(3-phenylisoxazol-5-yl)-1,3-thiazol-2-yl]amino}propyl)benzamide |
| I-520 | 4-[(1R)-1-({[(4-cyanophenyl)amino]carbonyl}amino)ethyl]-N-hydroxybenzamide |
| I-521 | 4-[(1R)-1-({[(2,6-difluorophenyl)amino]carbonyl}amino)-2-methylpropyl]-N-hydroxybenzamide |
| I-522 | N-hydroxy-4-[(1R)-2-methyl-1-({[(2-phenylethyl)amino]carbonyl}amino)propyl]benzamide |
| I-523 | 4-((1R)-1-{[(biphenyl-2-ylamino)carbonyl]amino}ethyl)-N-hydroxybenzamide |
| I-524 | N-hydroxy-4-((1R)-2-methyl-1-{[(1-naphthylamino)carbonyl]amino}propyl)benzamide |

-continued

I-525  4-[(1R)-1-({[(4-cyanophenyl)amino]carbonyl}amino)-2-methylpropyl]-N-hydroxybenzamide
I-526  4-((1R)-1-{[(2,3-dihydro-1-benzofuran-5-ylamino)carbonyl]amino}-2-methylpropyl)-N-hydroxybenzamide
I-527  N-hydroxy-4-((1R)-1-{[(1-naphthylamino)carbonyl]amino}ethyl)benzamide
I-528  4-((1R)-1-{[(2,3-dihydro-1-benzofuran-5-ylamino)carbonyl]amino}ethyl)-N-hydroxybenzamide
I-529  N-hydroxy-4-((1R)-2-methyl-1-{[4-(trifluoromethyl)-1,3-thiazol-2-yl]amino}propyl)benzamide
I-530  N-hydroxy-4-((1R)-1-{[(1-isopropylpiperidin-4-yl)methyl]amino}butyl)benzamide
I-531  3-{[((1R)-1-{4-[(hydroxyamino)carbonyl]phenyl}butyl)amino]methyl}-N-pyrrolidin-3-ylbenzamide
I-532  N-(4-{[((1R)-1-{4-[(hydroxyamino)carbonyl]phenyl}-2-methylpropyl)amino]methyl}pyridin-2-yl)-4-methylpiperidine-4-carboxamide
I-533  N-(4-{[((1R)-1-{4-[(hydroxyamino)carbonyl]phenyl}-2-methylpropyl)amino]methyl}phenyl)-1-methylpiperidine-4-carboxamide
I-534  4-((1R)-1-{[(1-ethylpiperidin-4-yl)methyl]amino}ethyl)-N-hydroxybenzamide
I-535  N-(1-{4-[(hydroxyamino)carbonyl]phenyl}-2,2-dimethylpropyl)-2-(trifluoromethyl)benzamide
I-536  4-{(1S)-1-[(2,2-dimethylpropanoyl)amino]butyl}-N-hydroxybenzamide

4. General Synthetic Methods and Intermediates

The compounds of the present invention can be prepared by methods known to one of ordinary skill in the art and/or by reference to the schemes shown below and the synthetic examples. Exemplary synthetic routes are set forth in Schemes below, and in the Examples.

As shown in Scheme 1 below, condensation of commercially available methyl 4-acetylbenzoate (xlviii) with hydroxylamine (Method X) affords the resulting oxime xlix which can be reduced by catalytic hydrogenoylsis in the presence of acid (Method Y) to generate racemic compound of formula I. The amine can be further elaborated according to Methods D, H or I, or those described in Scheme 13, followed by treatment with hydroxylamine hydrochloride in the presence of base to generate the corresponding substituted hydroxamate.

Scheme 1: General route to (±) methyl 4-(1-aminoethyl)benzoate hydrochloride

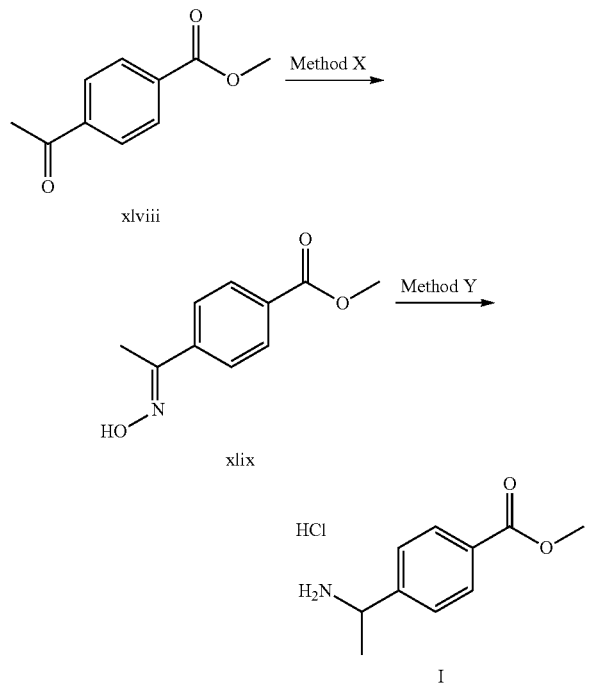

As shown in Scheme 2, aryl bromide Ii can be acylated via a Heck coupling (Method Z) to afford Iii. Application of Methods X-Y as shown in Scheme 1 provides Iii which can then be further elaborated as described herein.

Scheme 2: General route to substituted (±)-methyl 4-(1-aminoethyl)-3-benzoate hydrochloride

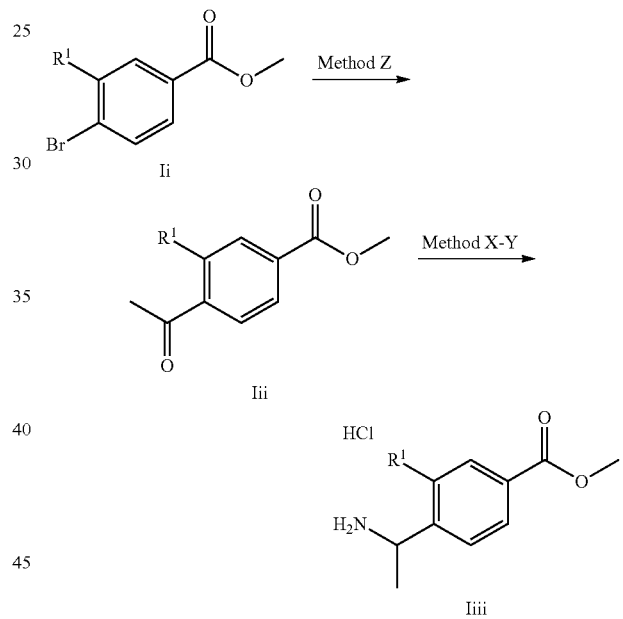

Scheme 3 below shows a general route for the preparation of substituted aminomethyl benzoate compounds of formula iv. Conversion of tert-butyl 4-formylbenzoate i (prepared as described in Adlington et al., *J. Med. Chem.* 2001, 44:1491) to the N-(tert-butanesulfinyl)imine ii is carried out by reaction with one enantiomer of 2-methyl-2-propanesulfinamide under dehydrative conditions (Method A; Ti(OEt)$_4$ or Ti(O$^i$Pr)$_4$, DCM; Ellman et al., *Acc. Chem. Res.* 2002, 35:984; Ellman et al., *J. Org. Chem.* 1999, 64:1278; Ellman et al., *J. Am. Chem. Soc.* 1999, 121:268; Davis et al., *J. Org. Chem.* 1999, 64:1403). Diastereoselective addition of the R$^2$ group by the use of the appropriate Grignard reagent (Method B; as described by Liu et al., *J. Am. Chem. Soc.* 1997, 119: 9913) provides α-branched sulfinamides iii in high diastereomeric ratios. Isolation of single diastereomers by chromatography followed by removal of the chiral auxiliary (1 equiv. HCl; Method C) provides enantiomerically pure amine iv. When R$^2$ is trifluoromethyl, tetra-n-butylammoniumdifluorotriphenylsilicate and (trifluoromethyl)trimethylsilane can be used instead of a Grignard reagent to introduce the trifluoromethyl group to the compound of formula ii, resulting in the compound of formula iii wherein $R^2$ is trifluoromethyl. The synthetic sequence can be repeated with the opposite enantiomer of the 2-methyl-2-propanesulfinamide to generate the other enantiomer of the compound of formula iv. It will also be appreciated that this method can be used to generate the meta-regioisomer of the compounds of formula iv starting from the appropriate starting materials.

The absolute stereochemistry of the chiral primary amines is established by comparison of the $^1$H-NMR spectra of the corresponding Mosher amides as described by Priest et al., *J. Chem. Ed.*, 2008, 85:698.

of formula vi is achieved under acidic conditions, using for example, trifluoracetic acid in DCM or dichloroethane (Method E). Conversion of the acid of formula vi to the corresponding hydroxamate of formula vii (Method F) is achieved by activation of the acid with a coupling reagent such as HATU, in the presence of base such as $Et_3N$, in a solvent such as DMF, followed by treatment with O-(tert-butyldimethylsilyl)hydroxylamine. The silyl protecting group can then be removed by treatment under acidic conditions such as 1% HCl in isopropyl alcohol. Alternatively, the hydroxamate can be introduced by treatment of the acid of formula vi with cyanuric chloride, base and catalytic DMAP followed by hydroxylamine hydrochloride (Method G; Giacomelli et al., *Org. Lett.* 2003, 5:2715).

Scheme 3: General route to single enantiomers of tert-butyl 4-(amino(alkyl)methyl)benzoates

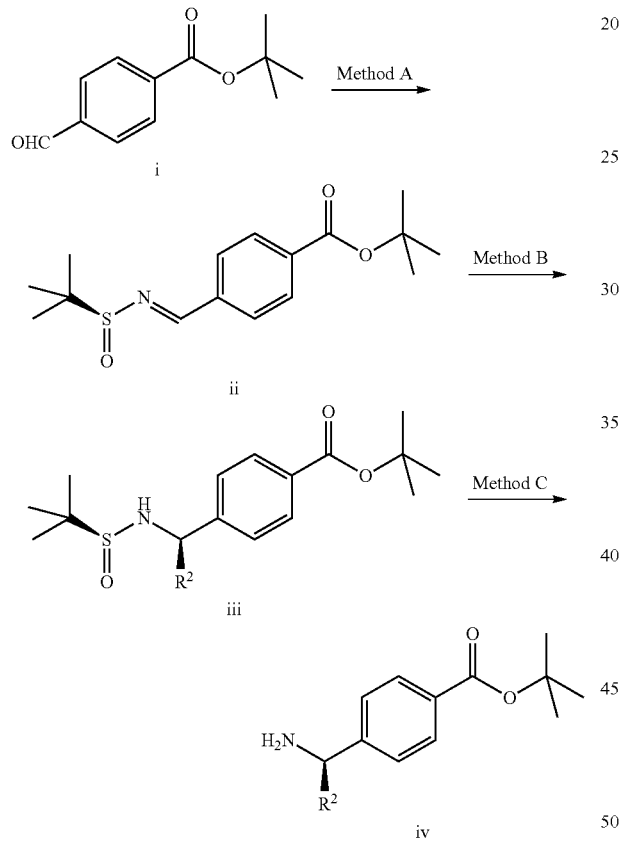

Scheme 4: General route to 4-(substituted-carboxamido(alkyl)methyl)-N-hydroxybenzamide analogs

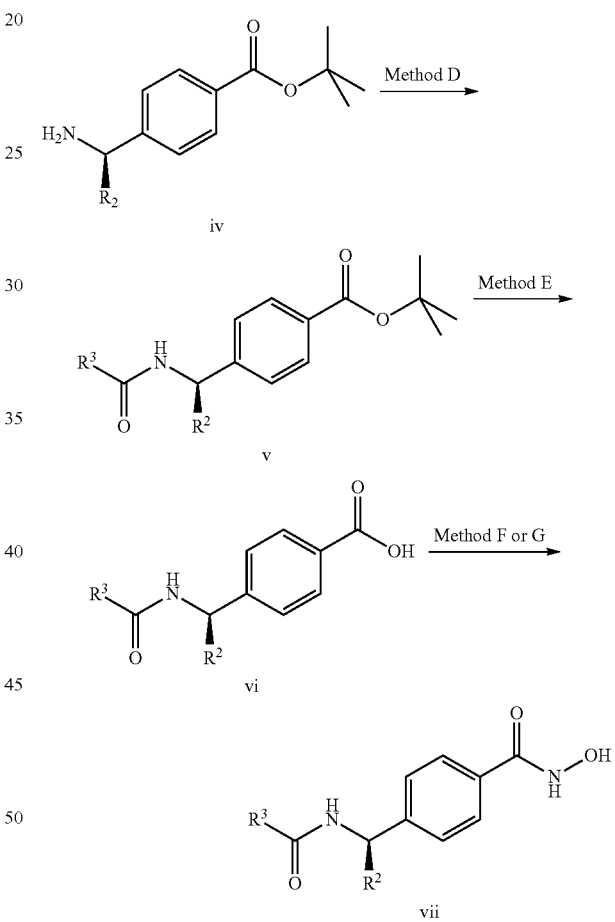

Scheme 4 shows a general route for the elaboration of compounds of formula iv to compounds of formula vii. The primary amine of iv is acylated with a carboxylic acid ($R^3$—$CO_2H$) in the presence of a coupling agent (Method D). Suitable coupling agents include, but are not limited to, 2-(1H-benzotriazole-1-yl)-1,1,3,3-tetramethyluronium hexafluorophosphate (HBTU), or O-(7-azabenzotriazol-1-yl)-1,1,3,3-tetramethyluronium hexafluorophosphate (HATU). Suitable bases for Method D include, but are not limited to, triethylamine ($Et_3N$), N,N'-diisopropylethylamine (DIPEA) and N-methylmorpholine. Suitable solvents for Method D include, but are not limited to, dichloromethane (DCM), tetrahydrofuran (THF), N,N'-dimethylformamide (DMF), N-methylpyrrolidone (NMP) or N,N'-dimethylacetamide. Deprotection of the tert-butyl ester to give compounds Scheme 5 shows a route for the preparation of substituted aminomethyl benzoate compounds of formula x. The primary amine of formula iv is treated with the appropriate sulfonyl chloride, $R^3$—$SO_2Cl$, and DMAP in DMF at ambient temperature to give compounds of formula viii (Method H). Method H may also be carried out in a solvent such as DCM or N,N'-dimethylacetamide. Deprotection of the tert-butyl ester (Method E), and conversion of the acid to the corresponding hydroxamate (Method F or G) can be carried out as described in Scheme 3 above to generate compounds of formula x.

Scheme 5: General route to 4-(substituted-sulfonamido(alkyl)methyl)-N-hydroxybenzamide analogs

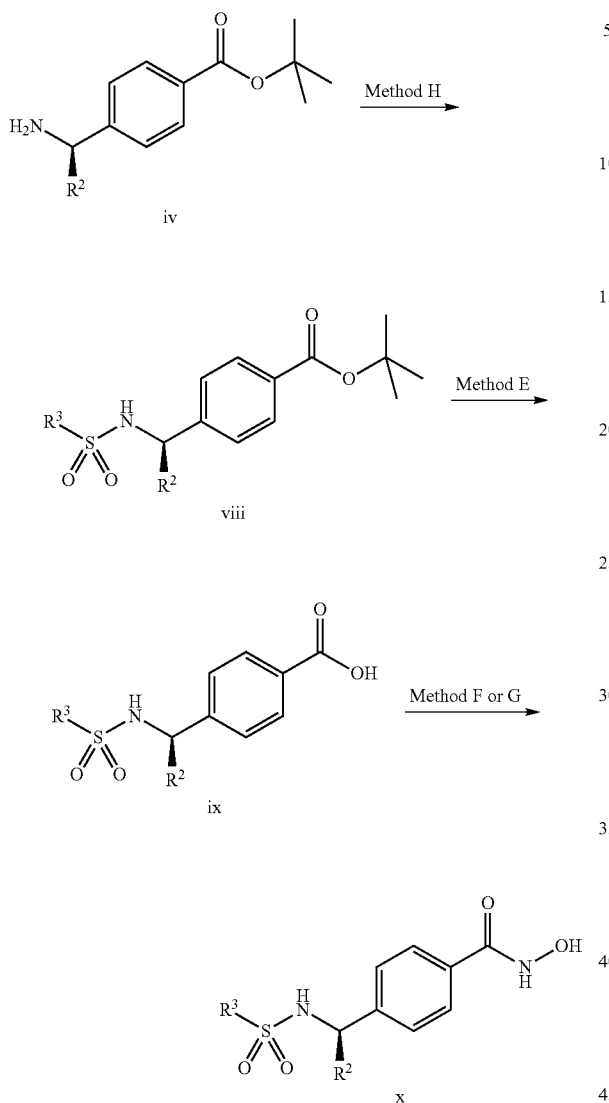

Scheme 6: General route to 4-((3-substituted-ureido(alkyl)methyl)-N-hydroxybenzamide analogs

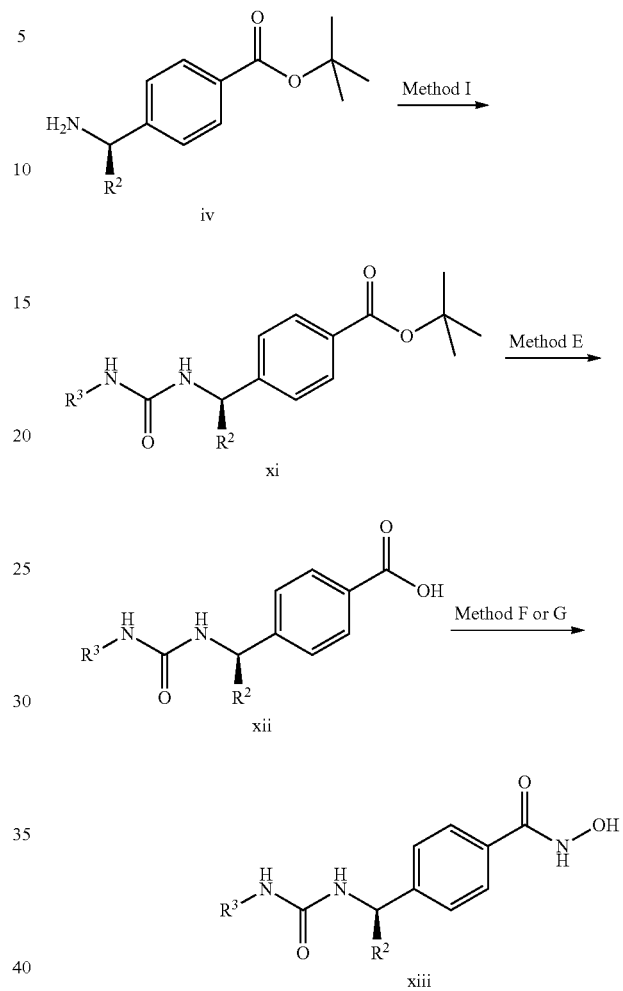

Scheme 6 shows a route for the preparation of substituted aminomethyl benzoate compounds of formula xiii. The primary amine of formula iv is treated with the appropriate isocyanate, ($R^3$—NCO), and base in solvent overnight at ambient or elevated temperature to afford compounds of formula xi (Method I). Suitable bases for Method I include, but are not limited to, $Et_3N$, DIPEA, and N-methylmorpholine. Suitable solvents for Method I include, but are not limited to, DCM, THF, DMF, NMP or N,N'-dimethylacetamide. Deprotection of the tert-butyl ester (Method E), and conversion of the acid to the corresponding hydroxamate (Method F or G) can be carried out as described in Scheme 4 above to give compounds of formula xiii. It will be appreciated that the methods described in Schemes 4, 5 and 6 can be carried out on amines with different substitution at the $R^2$ position and differing ring A structures.

Scheme 7 below shows a route for the preparation of tert-butyl substituted compounds of formula xxiv and xxv. Ketone xv is prepared by reaction of the arylzinc reagent xiv with pivaloyl chloride (Method J; WO 08/156,721). Conversion of xv to the sufinimines xvi and xvii is carried out by reaction with the appropriate sulfinamide under dehydrative conditions (Method A; Ellman et al., *Acc. Chem. Res.* 2002, 35:984; Ellman et al., *J. Org. Chem.* 1999, 64:1278; Ellman et al., *J. Am. Chem. Soc.* 1999, 121:268; Davis et al., *J. Org. Chem.* 1999, 64:1403). Reduction using $NaBH_4$ (Method K; Ellman et al., *Tetrahedron Lett.* 1999, 40:6709; Coyler et al., *J. Org. Chem.* 2006, 71:6859) and subsequent separation of pairs of diastereomers xviii and xix or xx and xxi by normal phase chromatography is followed by removal of the chiral auxiliary (Method C) to give enantiomerically pure amines xxii and xxiii. Further elaboration of the compounds of formula xxiv and xxv is accomplished by reaction with a carboxylic acid as described above in Scheme 4 (Method D), and then conversion to the hydroxamate by treatment with hydroxylamine hydrochloride (Method L; KOH, MeOH). Alternatively, the compounds of formula xxii and xxiii can be further elaborated as described in Schemes 5, 6 or 13 followed by conversion to the corresponding hydroxamates.

Scheme 7: General route to enantiomerically pure 4-(substituted-carboxamido(tert-butyl)methyl)-N-hydroxybenzamide analogs

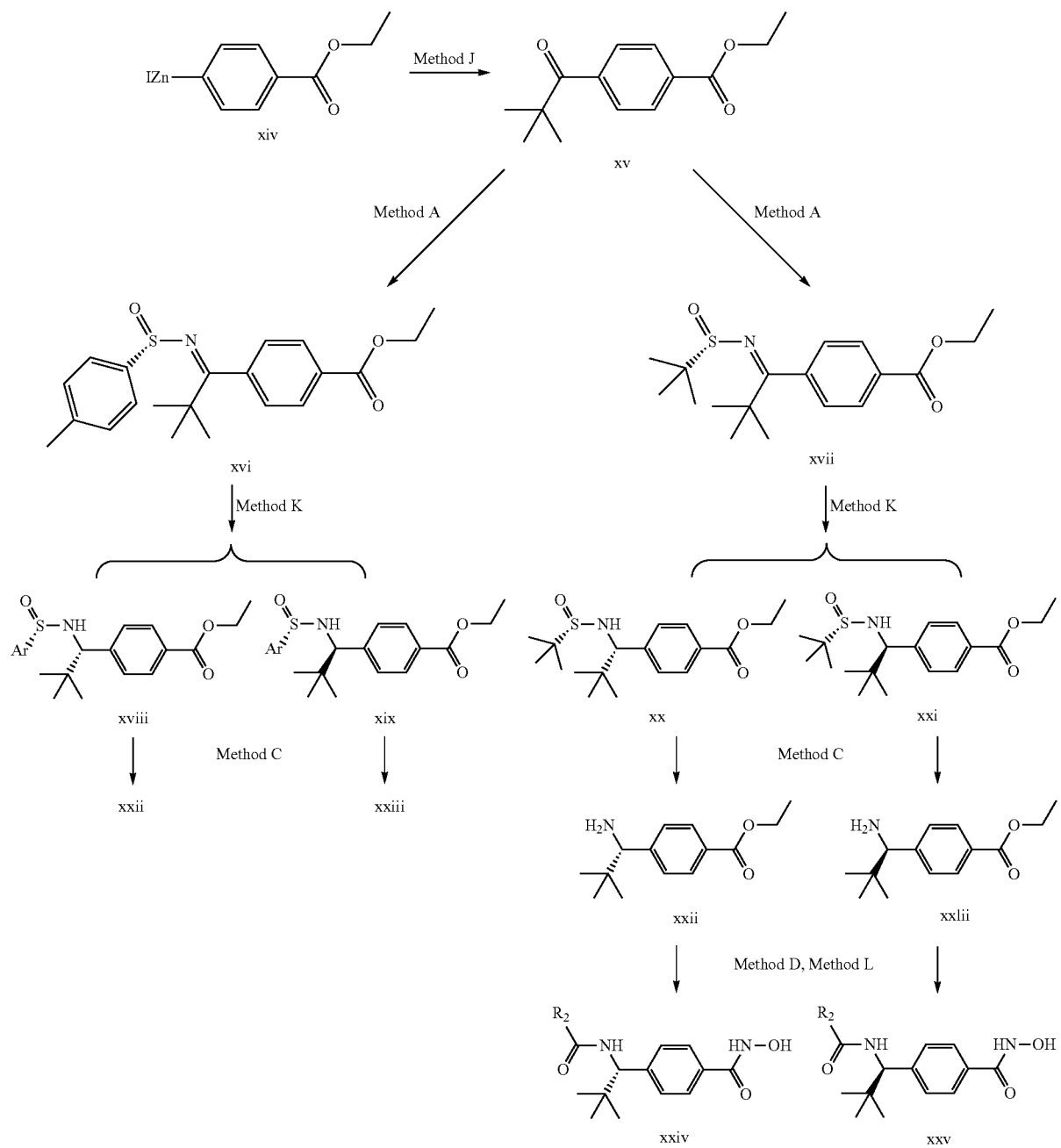

Alternatively, sulfinimine xxvi is prepared as shown in Scheme 8 by condensation of the appropriate sulfinamide with tert-butyl 4-formylbenzoate i (Method M; Yim and Wong, *J. Org. Chem.* 2004, 69:2892); treated with tert-butyl-lithium in THF (Method N) to give xxvii after separation of the resulting diastereomers. Removal of the chiral auxiliary (Method C) followed by elaboration of the resulting amine as described above in Scheme 2 (Method D), and removal of the tert-butyl ester using TFA (Method E) yields the compound of formula xxviii. The compound of formula xxviii is converted to the corresponding hydroxamate of formula xxv using cyanuric chloride, base and catalytic DMAP followed by hydroxylamine hydrochloride (Method G) (Giacomelli, G., et. al. *Org. Lett.* 2003, 5, 2715). Alternatively, following removal of the chiral auxiliary the compound of formula xxvii can be further elaborated as described in Schemes 5, 6 or 13 followed by conversion to the corresponding hydroxamates.

Scheme 8: General route to 4-(substituted-carboxamido(tert-butyl)methyl)-N-hydroxybenzamide analogs

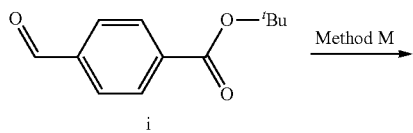

-continued

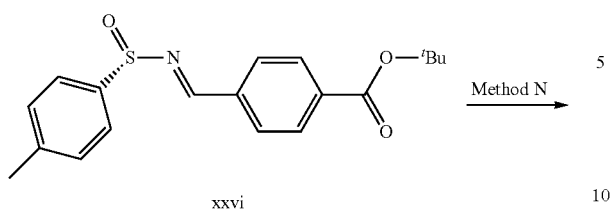

xxvi

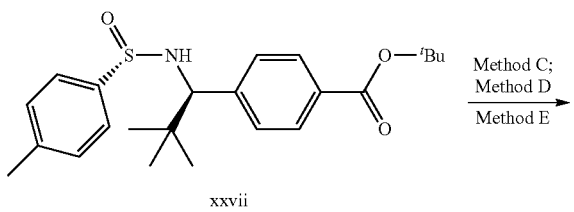

xxvii

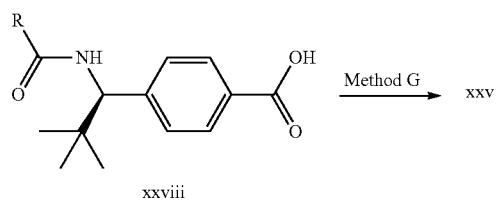

xxviii

Alternatively, as shown in Scheme 9, condensation of pivaloyl aldehyde with S-2-methyl-2-sulfinimide xxix (Method P) gives xxx which can be treated with the aryllithium reagent xxxi (Knochel, *Science of Synthesis* 2004, 3:5-90) in THF at reflux to give compound xxxii (Method Q; Ellman et al *J. Am. Chem. Soc.* 1997, 119:913; *J. Org. Chem.* 2001, 66:8772; WO 02/070492; WO 07/145,568). Compound xxxii can then be further elaborated as described above.

Scheme 9: General route to enantiomerically pure 4-(substituted-carboxamido(tert-butyl)methyl)-N-hydroxybenzamide analogs

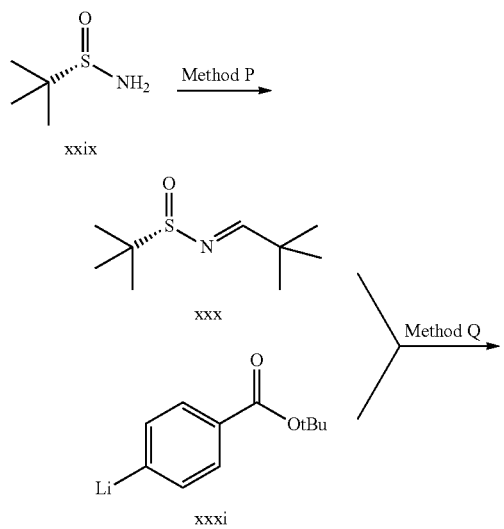

-continued xxxii

Scheme 10 shows another alternative route to enantiomerically pure tert-butyl derivatives. Treatment of pivaloyl chloride xxxiii with 4-carboxymethylphenylmagnesium iodide (prepared according to Wang et al., *Org. Lett.* 2006, 8:305) in the presence of vanadium chloride in DCM affords ketone xxxiv (Method R). Treatment with N-amino-4-benzyl-2-oxazolidinone, and TsOH affords acylhydrazone xxxv (Method S; Friestad et al., *J. Am. Chem. Soc.* 2000, 122:8329). The acylhydrazone is reduced using $Bu_3SnH$ and $BF_3$ in DCM (Method T; Friestad et al., *Tetrahedron* 2003, 59: 6393) to give the compound of formula xxxvi. The compound of formula xxxvi is then acylated using n-BuL$^1$, R$^3$COCl; the chiral auxiliary is removed with $SmI_2$ and HMPA in THF (Method U; Friestad et al., *J. Am. Chem. Soc.* 2000, 122:8329) to afford the compound of formula xxxvii which can then be transformed to the corresponding hydroxamate as described above.

Scheme 10: General route to enantiomerically pure 4-(substituted-carboxamido(tert-butyl)methyl)-N-hydroxybenzamide analogs

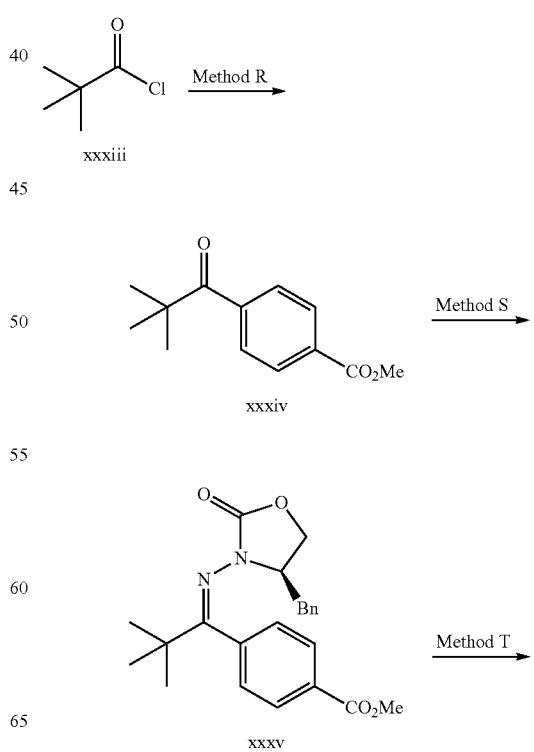

-continued

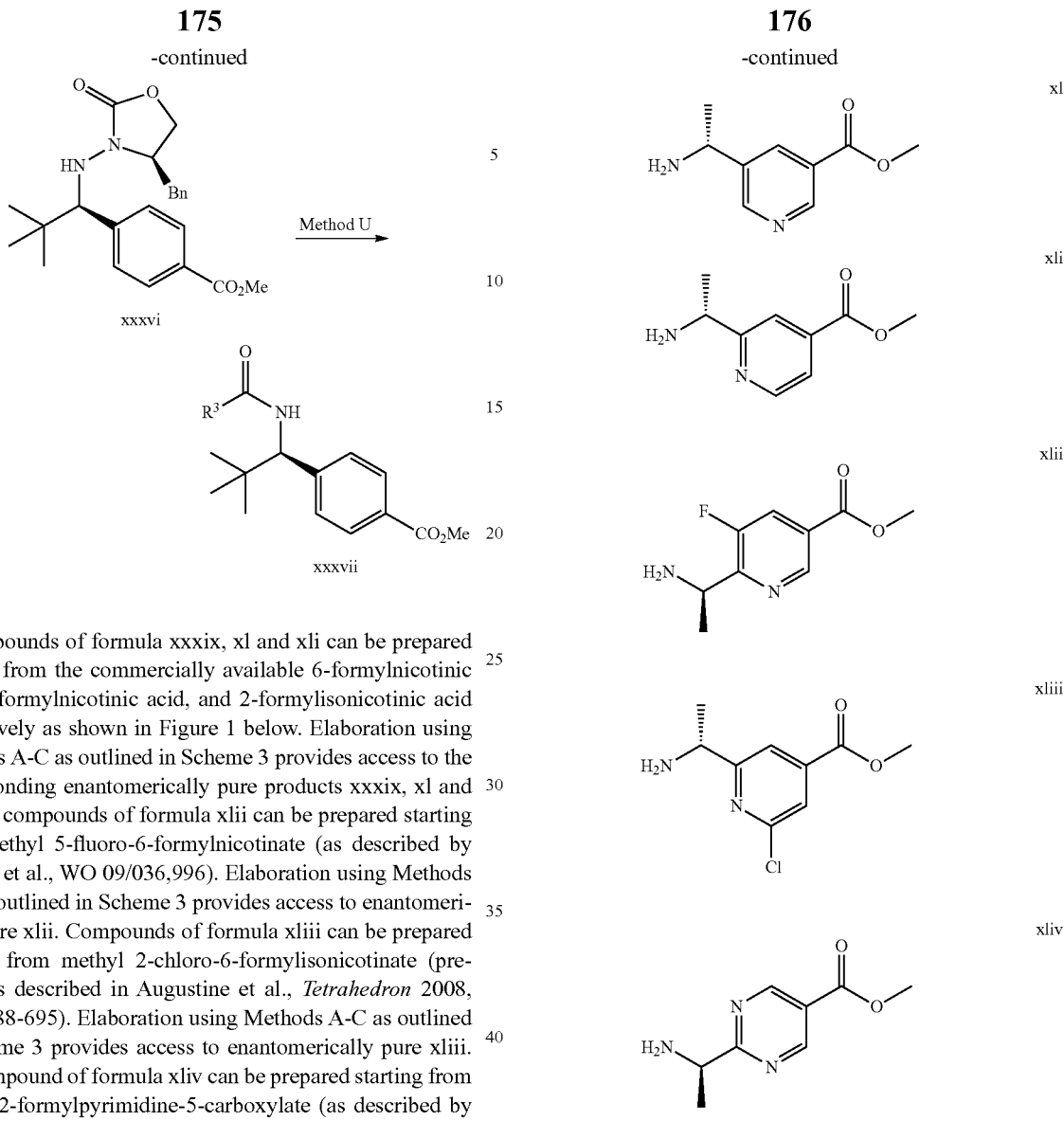

xxxvi xxxvii

Compounds of formula xxxix, xl and xli can be prepared starting from the commercially available 6-formylnicotinic acid, 5-formylnicotinic acid, and 2-formylisonicotinic acid respectively as shown in Figure 1 below. Elaboration using Methods A-C as outlined in Scheme 3 provides access to the corresponding enantiomerically pure products xxxix, xl and xli. The compounds of formula xlii can be prepared starting from methyl 5-fluoro-6-formylnicotinate (as described by Locardi et al., WO 09/036,996). Elaboration using Methods A-C as outlined in Scheme 3 provides access to enantiomerically pure xlii. Compounds of formula xliii can be prepared starting from methyl 2-chloro-6-formylisonicotinate (prepared as described in Augustine et al., *Tetrahedron* 2008, 64(4):688-695). Elaboration using Methods A-C as outlined in Scheme 3 provides access to enantiomerically pure xliii. The compound of formula xliv can be prepared starting from methyl 2-formylpyrimidine-5-carboxylate (as described by Hunt et. al. WO 08/156,715). Elaboration using Methods A-C as outlined in Scheme 3 provides access to enantiomerically pure xliv. It will be appreciated that the other optical isomer of each of the amines shown in Figure 1 will be isolated following column chromatography of the diastereomers prior to removal of the chiral auxiliary. The amines can be further elaborated according to Methods D, H or I, or those described in Scheme 13, followed by treatment with hydroxylamine hydrochloride in the presence of base to generate the substituted hydroxamate.

Scheme 11 shows a general route for the elaboration of compounds of formula xlv to compounds of formula xlvii. Carbonylation of xlv employing carbon monoxide in the presence of a Pd catalyst, as described in WO 05/037214 (Method V) provides xlvi. Elaboration using methods A-C as outlined in Scheme 3 provides access to enantiomerically pure xlvii which can be further elaborated according to Methods D, H or I, or those described in Scheme 13 followed by treatment with hydroxylamine hydrochloride in the presence of base to generate corresponding substituted hydroxamates.

FIG. 1: Examples of enantiomerically pure amines accessible via route outlined in Scheme 3

Scheme 11: General route to single enantiomers of substituted methyl 6-(aminomethyl)-4-methoxynicotinate.

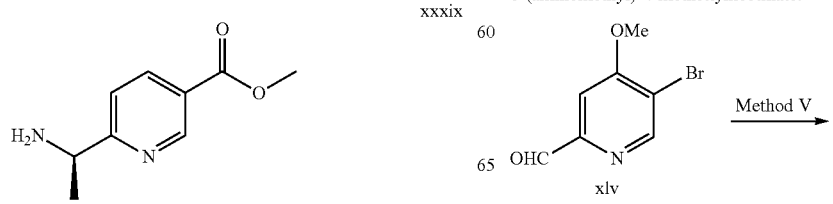

xlv

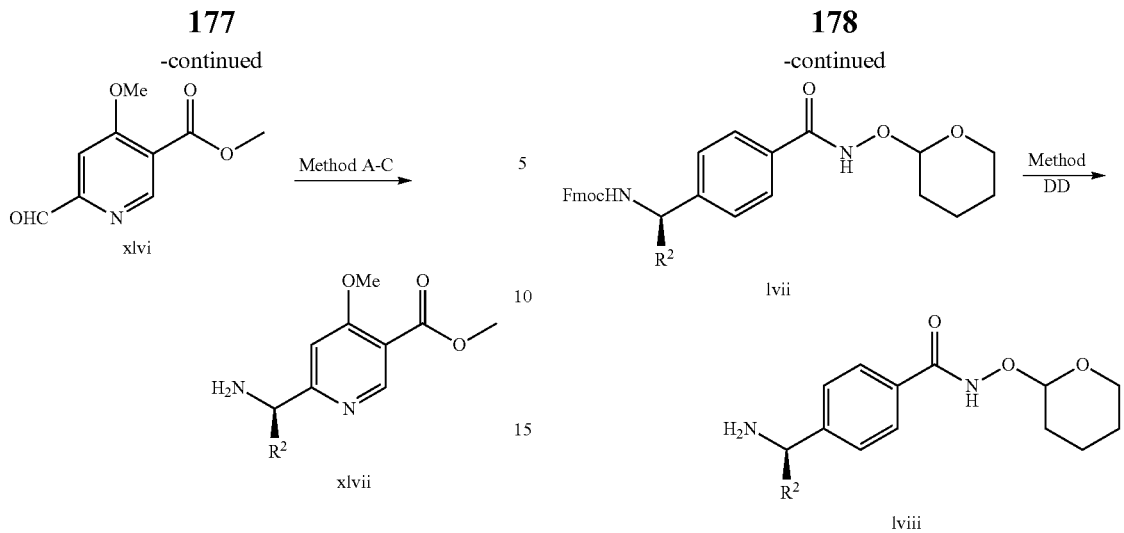

Scheme 12 shows a route for the preparation of substituted (aminomethyl)-N-(tetrahydro-2H-pyran-2-yloxy)benzamides represented by formula lviii. The primary nitrogen of liv can be orthogonally protected with a Fmoc group employing standard conditions using reagents such as Fmoc-Cl (Method Z). Removal of the t-butyl ester under acidic conditions (Method E) followed by coupling of the liberated acid of formula lvi with O-(tetrahydro-2H-pyran-2-yl)hydroxylamine in the presence of an appropriate coupling agent (Method CC) provides lvii. Removal of the Fmoc group is accomplished with piperidine in an appropriate solvent (Method DD) to give compound of formula lviii. The compound of formula lviii can be further functionalized employing transformations such as described in Methods D, H or I or those described in Scheme 13 followed by removal of the THP group under acidic conditons.

Scheme 13 shows a route for the preparation of substituted (R)-4-(1-ethylamino)-N-hydroxybenzamides representated by formula lxii. The compound of formula lix can be selectively converted to the corresponding ester using acid catalyzed Fisher esterification conditons (Method EE). Reductive alkylation resulting from the reaction of an aldehyde (R'CHO) in the presence of an appropriate borohydride such as, but not limited to, sodium cyanoborohydride (Method FF; Jones et al., *Bioorg. & Med. Chem. Lett.* 2008, 18(11):3456-3461) provides the compound of formula lxi. Amine lx may also be arylated using standard nucleophilic aromatic substitution of a suitable eletrophile such as 2-chloro-nitropyridine, in the presence of suitable base, such as DIPEA at elevated temperatures (Method HH). Amine lx may also be N-arylated through a copper(II)-acetate mediated coupling with a suitable arylboronic acid (Method II; Chan et al. *Tetrahedron Lett.* 1998, 39(19):2933). Reaction of the compound of formula lxi with the potassium salt of hydroxylamine (Method GG; Huang et al., *J. Med. Chem.* 2009, 52(21):6757) leads to the formation of the corresponding hydroxamate lxii.

Scheme 12: General route to enantiomerically pure 4-((R)-amino(alkyl)methyl)-N-tetrahydro-2H-pyran-2-yloxy)benzamides

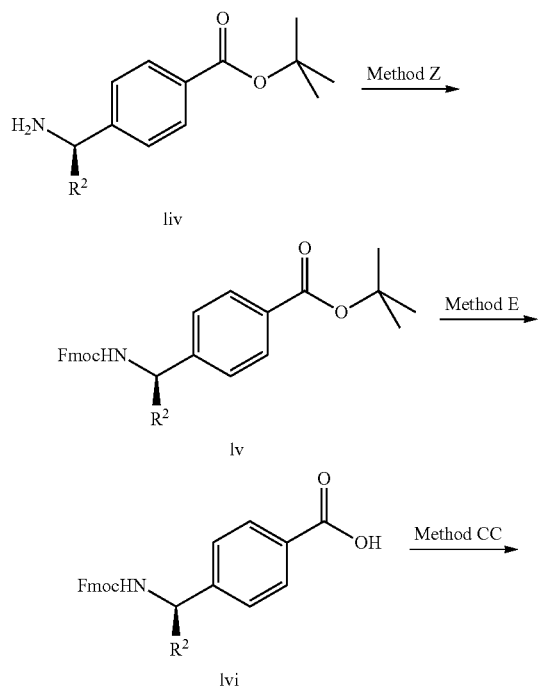

Scheme 13: General route to substituted (R)-4-(1-(ethylamino)alkyl)-N-hydroxybenzamides

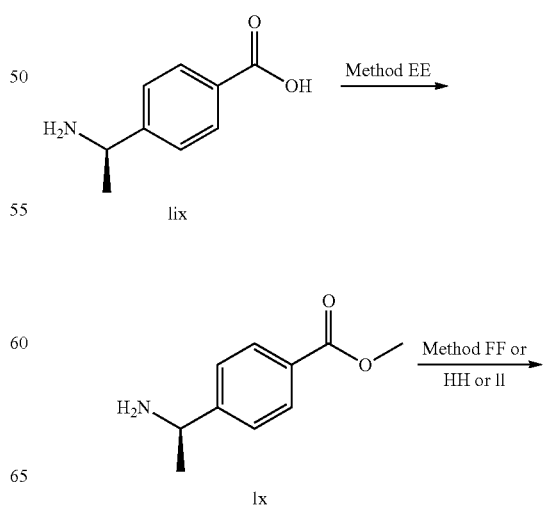

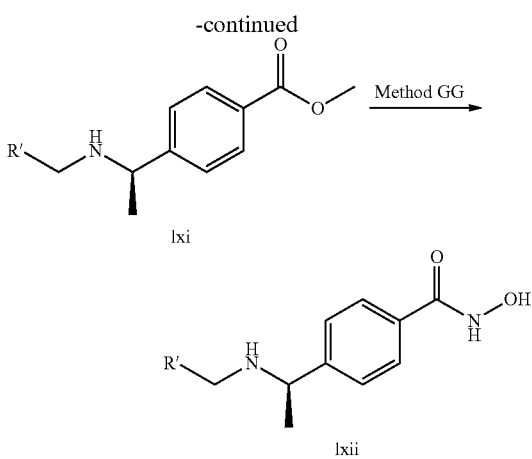

4. Uses, Formulation and Administration

As discussed above, the present invention provides compounds and pharmaceutical compositions that are useful as inhibitors of HDAC enzymes, particularly HDAC6, and thus the present compounds are useful for treating proliferative, inflammatory, infectious, neurological or cardiovascular disorders.

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, compounds of the invention are suitable for the treatment of breast cancer, lung cancer, ovarian cancer, multiple myeloma, acute myeloid leukemia or acute lymphoblastic leukemia.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of HDAC6.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, infectious, neurological or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, infectious, neurological or cardiovascular disorder, or is that amount effective for treating cancer. In other embodiments, an "effective amount" of a compound is an amount which inhibits binding of HDAC6, and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, a compound of formula (I) or a pharmaceutical composition thereof is administered in conjunction with an anticancer agent. As used herein, the term "anticancer agent" refers to any agent that is, administered to a subject with cancer for purposes of treating the cancer. Combination therapy includes administration of the therapeutic agents concurrently or sequentially. Alternatively, the therapeutic agents can be combined into one composition which is administered to the patient.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which down-regulates cell replication. In certain embodiments, a compound of the invention is administered in conjunction with a proteasome inhibitor.

Another aspect of the invention relates to inhibiting HDAC6, activity in a biological sample or a patient, which method comprises administering to the patient, or contacting said biological sample with a compound of formula (I), or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC6 plays a role.

EXPERIMENTAL PROCEDURES

I. Preparation of Exemplary Compounds

Definitions

ATP adenosine triphosphate
DCE dichloroethane
DCM dichloromethane
DIPEA diisopropylethyl amine
DMF N,N-dimethylformamide
DMFDMA N,N-dimethylformamide dimethyl acetal
DMSO dimethylsulfoxide
EDCI N-(3-dimethylaminopropyl)-N-ethylcarbodiimide hydrochloride
EDTA ethylenediaminetetraacetic acid
EtOAc ethyl acetate
EtOH ethanol
FA formic acid
FBS fetal bovine serum
h hours
HATU N,N,N',N'-tetramethyl-o-(7-azabenzotriazole-1-yl) uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
IPA isopropyl alcohol
LAH lithium aluminum hydride
LC-MS liquid chromatography mass spectrum
m/z mass to charge
Me methyl
MEM minimum essential media
MeOH methanol
min minutes
MS mass spectrum
MWI microwave irradiation
NMM N-methyl morpholine
PBS phosphate buffered saline
rt room temperature
TEA triethylamine
TFA trifluoroacetic acid
TFAA trifluoroacetic anhydride
THF tetrahydrofuran Analytical Methods NMR: 1H NMR spectra are run on a 400 MHz Bruker unless otherwise stated.

LCMS: LC-MS spectra are run using an Agilent 1100 LC interfaced to a micromass Waters® Micromass® Zspray™ Mass Detector (ZMD).

HPLC: Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

Example 1 tert-Butyl 4-formylbenzoate

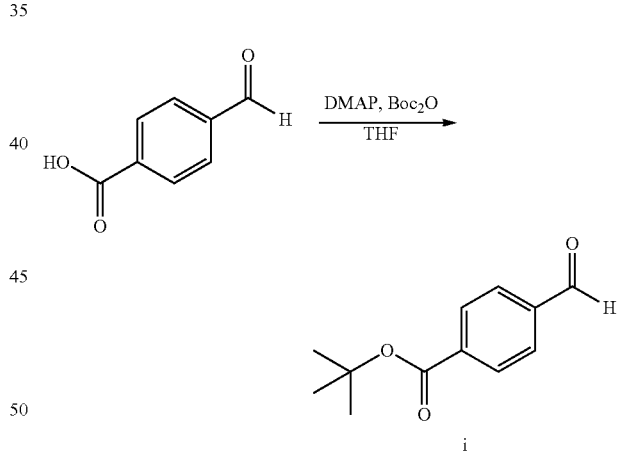

To a 250-mL round-bottom flask was added 4-formylbenzoic acid (5.0 g, 33 mmol), di-tert-butyldicarbonate (14.54 g, 66.6 mmol), N,N-dimethylaminopyridine (0.814 g, 6.66 mmol), and THF (100 mL). The mixture was stirred at rt for 16 h. The solvent was then removed to give a solid. To the residue was added EtOAc (150 mL), sat. NaHCO$_3$ solution (25 mL), and water (25 mL). After separation, the aqueous layer was extracted with EtOAc (2×100 mL). The combined organic phases were washed with brine (50 mL), dried (MgSO$_4$), and concentrated. Purification via flash chromatography (hexanes to 10% EtOAc-hexanes) afforded tert-butyl 4-formylbenzoate (1.90 g, 28%) as a white solid. $^1$H NMR (CDCl$_3$, 400 MHz) δ10.10 (s, 1H), 8.14 (d, J=8.3 Hz, 2H), 7.93 (d, J=8.5 Hz, 2H), 1.61 (s, 9H).

Example 2 tert-Butyl 3-formylbenzoate

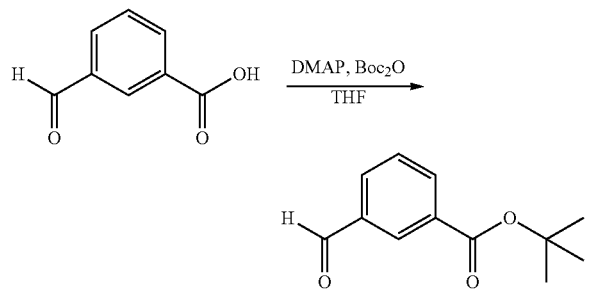

The title compound was prepared in an analogous fashion to that described in Example 1 starting from commercially available 3-formylbenzoic acid. Yield: 92.4%; $^1$H NMR (CDCl$_3$, 400 MHz) δ10.08 (s, 1H), 8.46 (d, J=1.8 Hz, 1H), 8.25 (dd, J=7.6, 1.5 Hz, 1H), 8.05 (dd, J=7.6, 1.5 Hz, 1H), 7.60 (t, J=7.8 Hz, 1H), 1.62 (s, 9H).

Example 3

4-[(E)-{[(S)-tert-butylsulfinyl]imino}methyl]benzoate

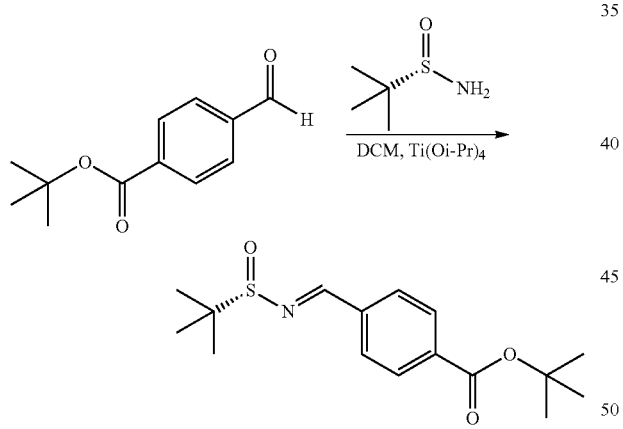

To a 500-mL round-bottom flask was added (S)-(−)-2-methyl-2-propanesulfinamide (1.41 g, 11.6 mmol), tert-butyl 4-formylbenzoate (2.00 g, 9.70 mmol) and DCM (90 mL). The mixture was cooled to 0° C. then titanium tetraisopropoxide (17.2 mL, 58.2 mmol) was added. After the solution was warmed to rt and stirred for 6 h, the reaction mixture was diluted with DCM (200 mL). To the flask was added water (17.2 mL) slowly. The mixture was vigorously stirred at rt for 30 min, then filtered through a pad of Celite. The filtrate was concentrated to give a solid. Purification via flash chromatography (hexanes to 10% EtOAc-hexanes) afforded 4-[(E)-{[(S)-tert-butylsulfinyl]imino}methyl]benzoate (2.42 g, 81%) as a white solid. $[α]_D^{20}$=+52.0 (c=1.0, CHCl$_3$); $^1$H NMR (CDCl$_3$, 400 MHz) δ8.63 (s, 1 μl), 8.08 (d, J=8.5 Hz, 2H), 7.89 (d, J=8.5 Hz, 2H), 1.61 (s, 9H), 1.28 (s, 9H).

Example 4

3-[(E)-{[(S)-tert-butylsulfinyl]imino}methyl]benzoate

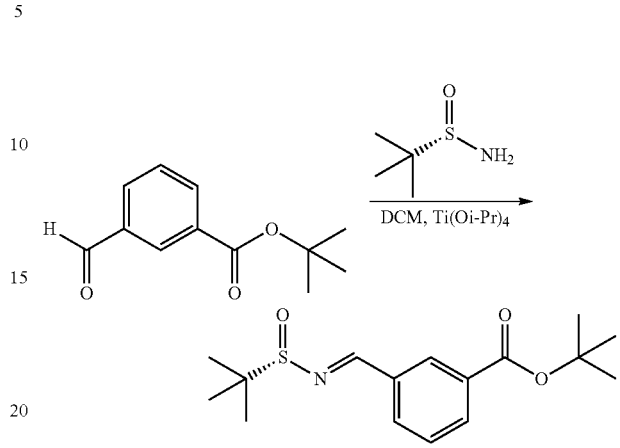

The title compound was prepared in an analogous fashion to that described in Example 3 starting from tert-butyl 3-formylbenzoate. Yield: 83%; $^1$H NMR (CDCl$_3$, 400 MHz) δ8.63 (s, 1H), 8.43 (s, 1H), 8.13 (d, J=7.8 Hz, 1H), 8.03 (dt, J=8.0, 3.0 Hz, 1H), 7.54 (t, J=7.8 Hz, 1H), 1.62 (s, 9H), 1.28 (s, 9H).

Example 5

4-[(E)-{[(R)-tert-butylsulfinyl]imino}methyl]benzoate

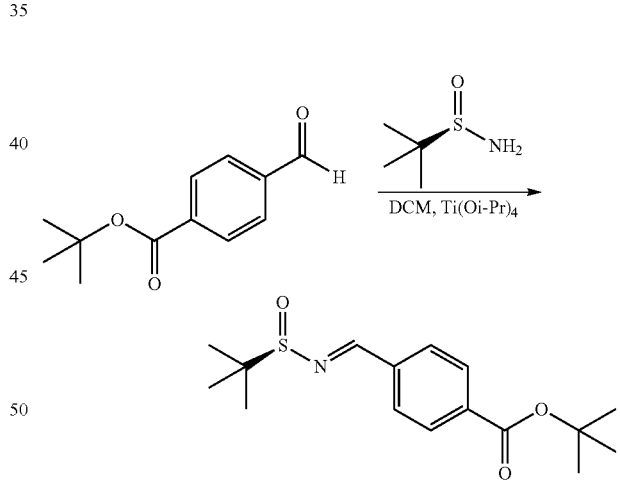

To a 250-mL round-bottom flask was added (R)-(+)-2-methyl-2-propanesulfinamide (0.360 g, 2.97 mmol), tert-butyl 4-formylbenzoate (0.51 g, 2.47 mmol), DCM (20 mL). The mixture was cooled to 0° C., then titanium tetraisopropoxide (4.40 mL, 14.8 mmol) was added. The solution was warmed to rt and stirred overnight. After the reaction was diluted with DCM (100 mL), water (4.4 mL) was added slowly. The mixture was vigorously stirred at rt for 30 min, filtered through a pad of Celite. The filtrate was concentrated to give a solid. Purification via flash chromatography (hexanes to 10% EtOAc-hexanes) afforded 4-[(E)-{[(R)-tert-butylsulfinyl]imino}methyl]benzoate (0.52 g, 68%) as a white solid. $[α]_D^{20}$=−49.6 (c=1.0, CHCl$_3$); $^1$H NMR (CDCl$_3$, 400

MHz) g 8.63 (s, 1H), 8.08 (d, J=8.3 Hz, 2H), 7.89 (d, J=8.3 Hz, 2H), 1.61 (s, 9H), 1.28 (s, 9H).

Example 6

4-[(E)-{[(R)-tert-butylsulfinyl]imino}methyl]benzoate

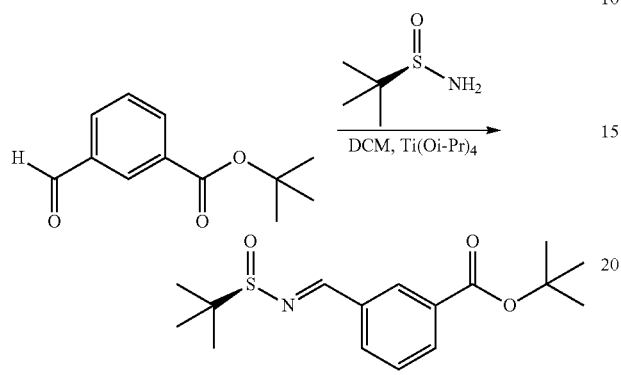

The title compound was prepared in an analogous fashion to that described in Example 5 starting from tert-butyl 3-formylbenzoate. Yield: 83%; [α]$_D^{20}$=−83.6 (c=1.0, CHCl$_3$); $^1$H NMR (CDCl$_3$, 400 MHz) δ8.63 (s, 1H), 8.43 (s, 1H), 8.13 (dd, J=8.0, 3.0 Hz, 1H), 8.03 (d, J=7.8 Hz, 1H), 7.54 (t, J=7.8 Hz, 1H), 1.57 (s, 9 μl), 1.28 (s, 9H).

Example 7 tert-butyl 4-[(1R)-1-{[(S)-tert-butylsulfinyl]amino}ethyl]benzoate and tert-butyl 4-[(1S)-1-{[(S)-tert-butylsulfinyl]amino}ethyl]benzoate

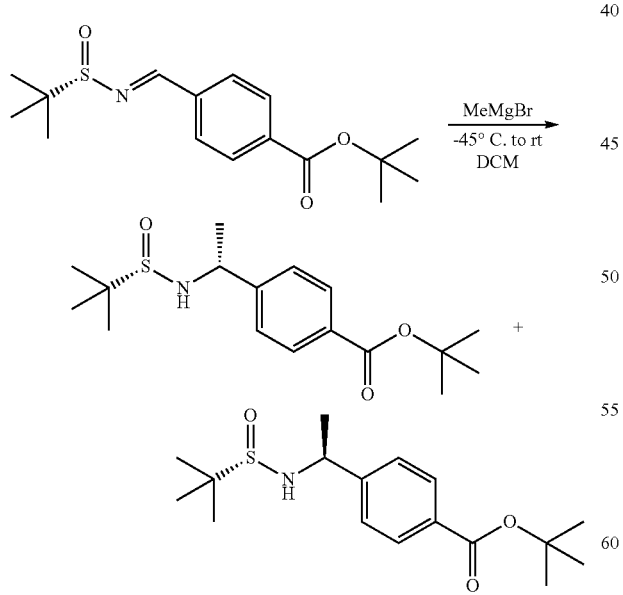

To an oven-dried 100-mL round-bottom flask was added 4-[(E)-{[(S)-tert-butylsulfinyl]imino}methyl]benzoate (0.83 g, 2.68 mmol), and DCM (13.4 mL). The solution was cooled to −45° C. then methylmagnesium bromide (1.78 mL, 5.35 mmol, 3.0 M in ether) was slowly added via syringe. The resulting reaction mixture was stirred at −45° C. for 4 h, then gradually warmed to rt and stirred for 16 h. To the reaction was added DCM (50 mL) and sat. NH$_4$Cl solution (10 mL). After separation, the aqueous layer was extracted with DCM (2×30 mL). The combined organic layers were washed with brine, dried (MgSO$_4$), and concentrated. Purification via flash chromatography (20% EtOAc-hexanes to 50% EtOAc-hexanes) afforded major diastereomer tert-butyl 4-[(1R)-1-{[(S)-tert-butylsulfinyl]amino}ethyl]benzoate (0.656 g, 75%) as a white solid. [α]$_D^{20}$=+86.1 (c=1.0, CHCl$_3$); $^1$H NMR (CDCl$_3$, 400 MHz) g 7.96 (d, J=8.3 Hz, 2H), 7.37 (d, J=8.3 Hz, 2H), 4.62 (m, 1H), 3.33 (d, J=3.0 Hz, 1H), 1.58 (s, 9H), 1.52 (d, J=6.8 Hz, 3H), 1.20 (s, 9H). The minor diastereomer tert-butyl 4-[(1S)-1-{[(S)-tert-butylsulfinyl]amino}ethyl]benzoate (0.065 g, 7.5%) was isolated as a white solid.

Example 8 tert-butyl 3-[(1R)-1-{[(S)-tert-butylsulfinyl]amino}ethyl]benzoate

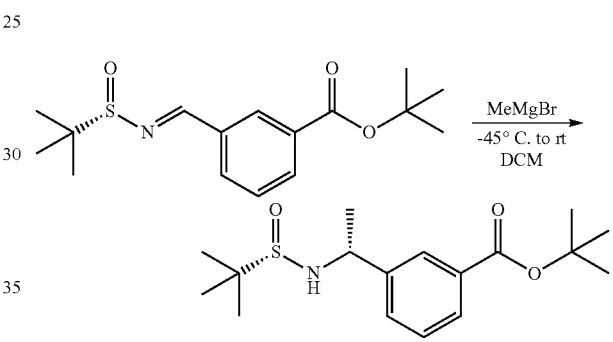

The title compound was prepared in an analogous fashion to that described in Example 7 starting from 3-[(E)-{[(S)-tert-butylsulfinyl]imino}methyl]benzoate. Yield: 74% [α]$_D^{20}$=+90.9 (c=1.0, CHCl$_3$); $^1$H NMR (CDCl$_3$, 400 MHz) δ7.96 (s, 1H), 7.89 (d, J=7.8 Hz, 1H), 7.48 (d, J=7.8, 1H), 7.38 (t, J=7.8 Hz, 1H), 4.63 (m, 1H), 3.35 (d, J=3.3 Hz, 1H), 1.58 (s, 9H), 1.54 (d, J=6.8 Hz, 3H), 1.21 (s, 9H).

Example 9 tert-butyl 3-[(1S)-1-{[(R)-tert-butylsulfinyl]amino}ethyl]benzoate

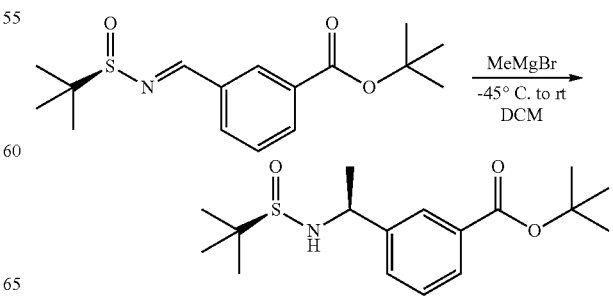

The title compound was prepared in an analogous fashion to that described in Example 7 starting from 3-[(E)-{[(R)-tert-butylsulfinyl]imino}methyl]benzoate. Yield: 58%; $^1$H NMR (CDCl$_3$, 400 MHz) δ7.95 (s, 1H), 7.89 (d, J=7.8 Hz, 1H), 7.48 (d, J=7.8 Hz, 1H), 7.38 (t, J=7.8 Hz, 1H), 4.63 (m, 1H), 3.35 (d, J=3.3 Hz, 1H), 1.58 (s, 9H), 1.54 (d, J=6.8 Hz, 3H), 1.21 (s, 9H).

Example 10 tert-butyl 4-((R)-1-((S)-1,1-dimethylethylsulfina-mido)butyl)benzoate and tert-butyl 4-((S)-1-((S)-1,1-dimethylethylsulfinamido)butyl)benzoate

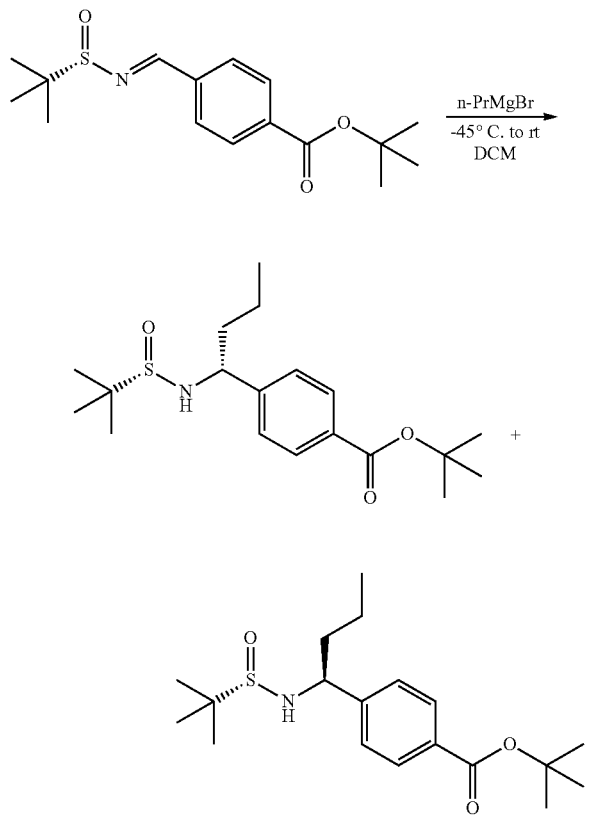

The title compounds were prepared in an analogous fashion to that described in Example 7 starting from 4-[(E)-{[(S)-tert-butylsulfinyl]imino}methyl]benzoate. tert-butyl 4-((R)-1-((S)-1,1-dimethylethylsulfinamido)butyl)benzoate Yield: 39%; $[α]_D^{20}$=+75.2 (c=1.0, CHCl$_3$); $^1$H NMR (CDCl$_3$, 400 MHz) δ7.95 (d, J=8.1 Hz, 2H), 7.34 (d, J=8.3 Hz, 2H), 4.43 (dt, J=7.1, 2.0 Hz, 1H), 3.38 (d, J=2.0 Hz, 1H), 1.77 (m, 2H), 1.59 (s, 9H), 1.26 (m, 2H), 1.17 (s, 9H), 0.88 (t, J=7.4 Hz, 3H). tert-butyl 4-((S)-1-((S)-1,1-dimethylethylsulfinamido)butyl)benzoate Yield: 39%; $[α]_D^{20}$=+34.2 (c=1.0, CHCl$_3$); $^1$H NMR (CDCl$_3$, 400 MHz) δ7.96 (d, J=8.4 Hz, 2H), 7.36 (d, J=8.1 Hz, 2H), 4.39 (m, 1H), 3.37 (d, J=4.0 Hz, 1H), 2.00 (m, 1H), 1.71 (m, 1H), 1.58 (s, 9 μl), 1.22 (s, 9H), 1.17 (m, 2H), 0.87 (t, J=7.4 Hz, 3H).

Example 11 tert-butyl-4-[(R)-{[(R)-tert-butylsulfinyl]amino}(cyclopropyl)methyl]benzoate and tert-butyl 4-[(S)-{[(R)-tert-butylsulfinyl]amino}(cyclopropyl)methyl]benzoate

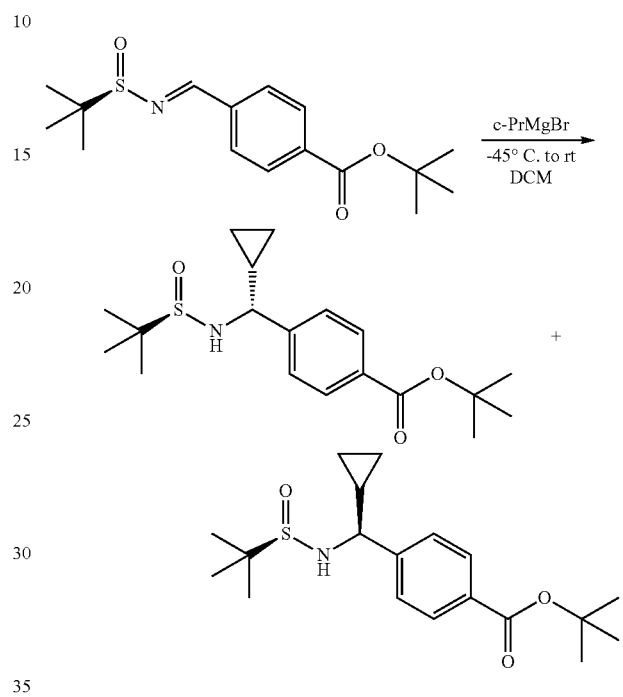

The title compounds were prepared in an analogous fashion to that described in Example 7 starting from 4-[(E)-[(R)-tert-butylsulfinyl]imino methyl]benzoate. tert-butyl-4-[(R)-{[(R)-tert-butylsulfinyl]amino}(cyclopropyl)methyl]benzoate: Yield: 36%; $^1$H NMR (CDCl$_3$, 400 MHz) δ7.97 (d, J=8.5 Hz, 2H), 7.42 (d, J=8.3 Hz, 2H), 3.72 (dd, J=8.8, 3.3 Hz, 1H), 3.54 (d, J=3.0 Hz, 1H), 1.58 (s, 9H), 1.24 (s, 9H), 1.14 (m, 1H), 0.80 (m, 1H), 0.64 (m, 1H), 0.48 (m, 1H), 0.23 (m, 1H). tert-butyl-4-[(S)-{[(R)-tert-butylsulfinyl]amino}(cyclopropyl)methyl]benzoate: Yield: 53%; $^1$H NMR (CDCl$_3$, 400 MHz) δ7.96 (d, J=8.3 Hz, 2H), 7.38 (d, J=8.3 Hz, 2H), 3.61 (m, 1H), 3.58 (d, J=1.8 Hz, 1H), 1.57 (s, 9H), 1.20 (s, 9 μl), 1.17 (m, 1H), 0.67 (m, 1H), 0.48 (m, 2H), 0.38 (m, 1H).

Example 12 tert-butyl 4-[(R)-{[(S)-tert-butylsulfinyl]amino}(phenyl)methyl]benzoate

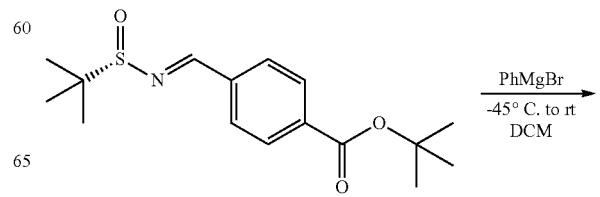

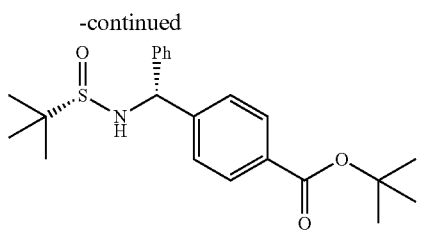

The title compound (dr, 6.0:1) was prepared in an analogous fashion to that described in Example 7 starting from 4-[(E)-{[(S)-tert-butylsulfinyl]imino}methyl]benzoate. Yield: 84%; $^1$H NMR (CDCl$_3$, 400 MHz) δ7.96 (d, J=8.3 Hz, 2H), 7.48 (d, J=8.5 Hz, 2H), 7.37-7.27 (m, 5H), 5.69 (d, J=2.3 Hz, 1H), 3.71 (d, J=2.3 Hz, 1H), 1.57 (s, 9H), 1.27 (s, 9H).

Example 13 tert-butyl 4-[(S)-{[(R)-tert-butylsulfinyl]amino}(phenyl)methyl]benzoate

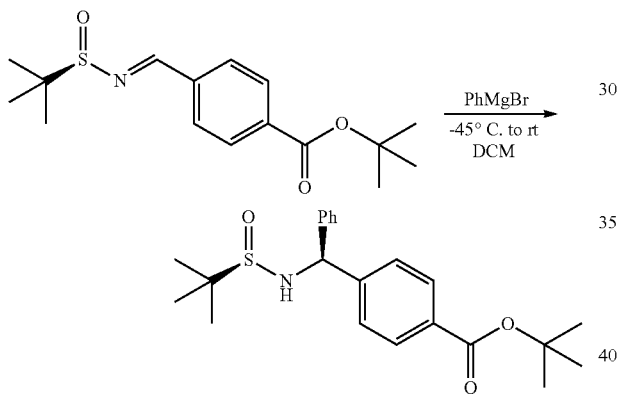

The title compound (dr, 6.3:1) was prepared in an analogous fashion to that described in Example 7 starting from 4-[(E)-{[(R)-tert-butylsulfinyl]imino}methyl]benzoate Yield: 75%; $^1$H NMR (CDCl$_3$, 400 MHz) δ7.96 (d, J=8.5 Hz, 2H), 7.48 (d, J=8.1 Hz, 2H), 7.37-7.27 (m, 5H), 5.69 (d, J=2.3 Hz, 1H), 3.72 (d, J=2.3 Hz, 1H), 1.57 (s, 9H), 1.27 (s, 9H).

Example 14 tert-butyl 4-[(1R)-1-{[(R)-tert-butylsulfinyl]amino}-2-methylpropyl]benzoate

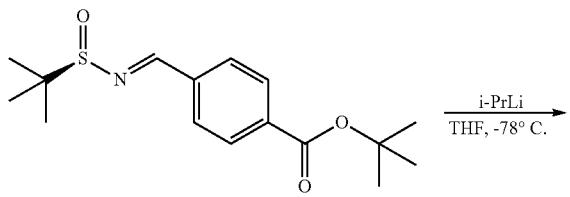

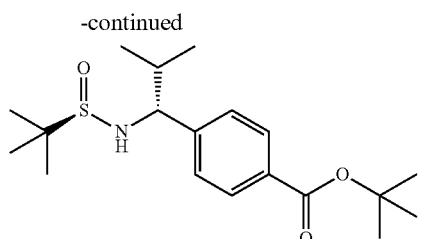

To an oven-dried 50-mL round-bottom flask was added tert-butyl 4-[(E)-{[(R)-tert-butylsulfinyl]imino}methyl]benzoate (3.00 g, 9.70 mmol) and THF (48 mL). The solution was cooled to −78° C. then isopropyllithium (55.4 mL, 38.8 mmol, 0.70 M of in pentane) was slowly added via a syringe pump over 15 min. The resulting reaction mixture was stirred at −78° C. After 1 h, EtOAc (100 mL), sat. NH$_4$Cl solution (20 mL), and water (10 mL) were added to the flask at this temperature. After separation, the aqueous layer was extracted with EtOAc (2×60 mL). Combined organic layers were washed with brine (20 mL), dried (MgSO$_4$), and concentrated. Purification via flash chromatography (20% EtOAc-hexanes to 50% EtOAc-hexanes) afforded major diastereomer tert-butyl 4-[(1R)-1-{[(R)-tert-butylsulfinyl]amino}-2-methylpropyl]benzoate (1.59 g, 46%) as a white solid. [c]$_D^{20}$=−18.9 (c=1.0, CHCl$_3$); $^1$H NMR (CDCl$_3$, 300 MHz) δ 7.96 (d, J=8.5 Hz, 2H), 7.31 (d, J=8.1 Hz, 2H), 4.18 (d, J=6.0 Hz, 1H), 3.45 (d, J=6.0 Hz, 1H), 2.22 (m, 1H), 1.58 (s, 9 μl), 1.24 (s, 9H), 0.94 (d, J=6.8 Hz, 3H), 0.80 (d, J=6.8 Hz, 3H).

Example 15 tert-butyl 4-[(1S)-1-{[(S)-tert-butylsulfinyl]amino}-2-methylpropyl]benzoate

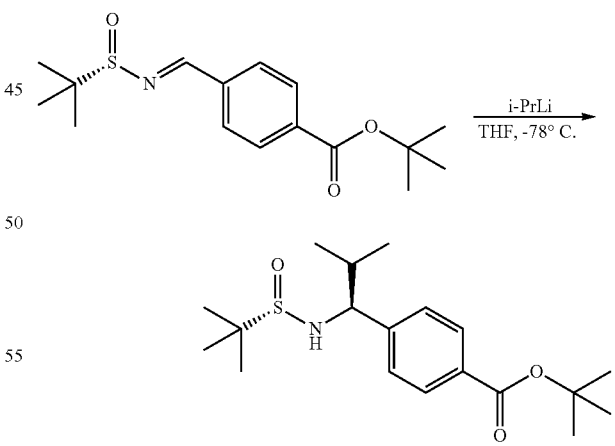

The title compound was prepared in an analogous fashion to that described in Example 14 starting from 4-[(E)-{[(S)-tert-butylsulfinyl]imino}methyl]benzoate. Yield: 47%; $^1$H NMR (CDCl$_3$, 400 MHz) δ7.96 (d, J=8.3 Hz, 2H), 7.31 (d, J=8.3 Hz, 2H), 4.18 (d, J=6.0 Hz, 1H), 3.45 (d, J=5.8 Hz, 1H), 2.22 (m, 1H), 1.58 (s, 9H), 1.24 (s, 9H), 0.94 (d, J=6.8 Hz, 3H), 0.80 (d, J=6.6 Hz, 3H).

Example 16 tert-butyl 4-[(1S)-1-{[(R)-tert-butylsulfinyl]amino}-2,2,2-trifluoroethyl]benzoate

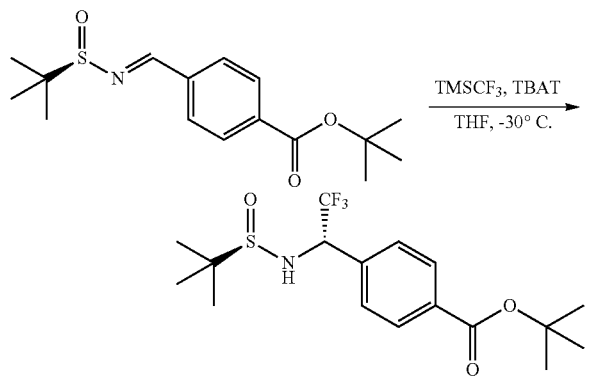

To a 50-mL oven-dried round-bottom flask charged with tert-butyl 4-[(E)-{[(R)-tert-butylsulfinyl]imino}methyl]benzoate (0.16 g, 0.5 mmol), tetra-n-butylammoniumdifluorotriphenylsilicate (0.30 g, 0.55 mmol), THF (8 mL) was slowly added (trifluoromethyl)trimethylsilane (0.94 mL, 0.60 mmol) in THF (2 mL) slowly at −45° C. The mixture was stirred at this temperature for 2 h, then warmed to −30° C. and stirred for 1 h. The reaction was quenched with addition of sat. NH$_4$Cl (5 mL) and EtOAc (10 mL) at −30° C. After warming to rt, the mixture was extracted with EtOAc (2×20 mL). The combined organic phases were washed with brine (10 mL), dried (MgSO$_4$), and concentrated. Purification via flash chromatography (10% EtOAc-hexanes to 20% EtOAc-hexanes) afforded tert-butyl 4-[(1S)-1-{[(R)-tert-butylsulfinyl]amino}-2,2,2-trifluoroethyl]benzoate (0.136 g, 72%) as a white solid. $^1$H NMR (Methanol-d$_4$, 300 MHz) δ 7.98 (d, J=8.5 Hz, 2H), 7.65 (d, J=8.3 Hz, 2H), 5.15 (d, J=7.9 Hz, 1H), 1.59 (s, 9H), 1.23 (s, 9H).

Example 17 tert-butyl 4-[(1R)-1-{[(S)-tert-butylsulfinyl]amino}-2,2,2-trifluoroethyl]benzoate

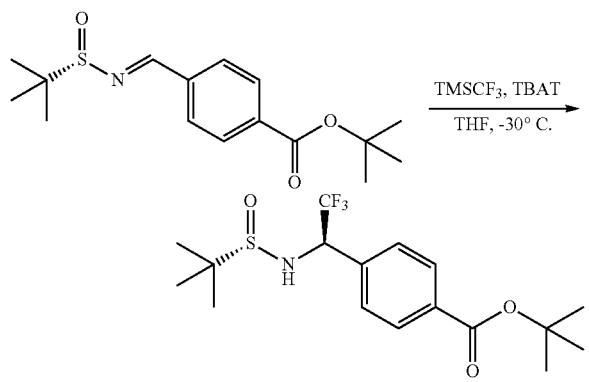

The title compound was prepared in an analogous fashion to that described in Example 16 starting from 4-[(E)-{[(S)-tert-butylsulfinyl]imino}methyl]benzoate. Yield: 47%; [α]$_D^{20}$=+49.3 (c=1.0, CHCl$_3$); $^1$H NMR (CDCl$_3$, 400 MHz) δ 8.03 (d, J=8.3 Hz, 2H), 7.49 (d, J=8.3 Hz, 2H), 4.88 (q, J=7.0 Hz, 1H), 3.67 (d, J=6.5 Hz, 1H), 1.59 (s, 9H), 1.25 (s, 9H).

Example 18

N—((R)-1-{4-[(hydroxyamino)carbonyl]phenyl}ethyl)-1-benzofuran-2-carboxamide Compound I-317

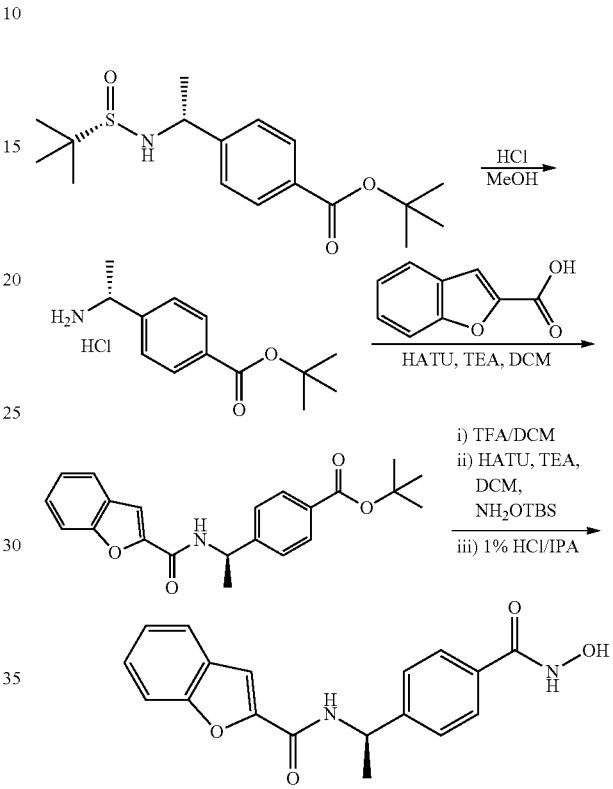

Step 1: tert-butyl-4-[(1R)-1-aminoethyl]benzoate hydrochloride

To a 2-dram vial was added tert-butyl 4-[(1R)-1-{[(S)-tert-butylsulfinyl]amino}ethyl]benzoate (0.0586 g, 0.180 mmol), hydrochloric acid (0.14 mL, 0.54 mmol, 4.0 M in 1,4-dioxane), and methanol (2 mL). The mixture was stirred at rt for 2 h. The solvent was then completely removed to give tert-butyl-4-[(1R)-1-aminoethyl]benzoate hydrochloride as a white solid. LC-MS: (FA) ES+ 222.

Step 2: tert-butyl 4-{(1R)-1-[(1-benzofuran-2-ylcarbonyl)amino]ethyl}benzoate To a 2-dram vial was added triethylamine (0.10 mL, 0.72 mmol), HATU (0.068 g, 0.18 mmol), benzofuran-2-carboxylic acid (0.029 g, 0.18 mmol), and DCM (2 mL). The solution was stirred at rt for 30 min then transferred to another 2-dram vial containing solid tert-butyl-4-[(1R)-1-aminoethyl]benzoate hydrochloride. The mixture was stirred at rt for 16 h. To the reaction was then added DCM (3 mL) and water (1 mL). After separation, the aqueous layer was extracted with DCM (2×3 mL). The combined organic phases were concentrated to dryness to give crude tert-butyl 4-{(1R)-1-[(1-benzofuran-2-ylcarbonyl)amino]ethyl}benzoate as a brown solid. LC-MS: (FA) ES+ 366.

Step 3: N-((1R)-1-{4-[(hydroxyamino)carbonyl]phenyl}ethyl)-1-benzofuran-2-carboxamide To a 2-dram vial containing tert-butyl 4-{(1R)-1-[(1-benzofuran-2-ylcarbonyl)amino]ethyl}benzoate was added DCM (2.5 mL), and trifluoroacetic acid (0.28 mL, 3.60 mmol). The mixture was stirred at rt for 6 h then evaporated to give an oil residue. To the residue was added HATU (0.10 g, 0.27 mmol), triethylamine (0.25 mL, 1.80 mmol), and DCM (2.5 mL). After stirring at rt for 30 min, O-(tert-butyldimethylsilyl)hydroxylamine (0.053 g, 0.360 mmol) was added. The mixture was stirred at rt for 2 h, then the solvent was completely removed to give a sticky brown oil. To this oil residue was added hydrochloric acid (4.0 mL, 1% v/v in IPA). After stirring at rt for 30 min, the solvent was evaporated to dryness to give a solid. To the solid was then added DMSO (1.1 mL). The solution was filtered and purified by Gilson prep-HPLC [25-50% MeCN—$H_2O$] to give N-((1R)-1-{4-[(hydroxyamino)carbonyl]phenyl}ethyl)-1-benzofuran-2-carboxamide (0.0148 g, 24%) as a white solid. LC-MS: (FA) ES+ 325; $^1$H NMR (Methanol-$d_4$, 400 MHz) δ 7.71 (m, 3H), 7.60 (d, J=8.5 Hz, 1H), 7.50 (m, 3H), 7.45 (t, J=7.0 Hz, 1H), 7.31 (t, J=7.8 Hz, 1H), 5.30 (q, J=7.2 Hz, 1H), 1.61 (d, J=7.0 Hz, 3H).

Example 19

N-((1R)-1-{4-[(hydroxyamino)carbonyl]phenyl}ethyl)-1-methyl-1H-pyrrole-2-carboxamide Compound I-102

The title compound was prepared in an analogous fashion to that described in Example 18 starting from tert-butyl 4-[(1R)-1-{[(S)-tert-butylsulfinyl]amino}ethyl]benzoate. Yield: 38%; LC-MS: (FA) ES+ 288; $^1$H NMR (Methanol-$d_4$, 400 MHz) δ8.06 (s, 1H), 7.70 (d, J=8.5 Hz, 2H), 7.46 (d, J=8.5 Hz, 2H), 6.86 (dd, J=4.0, 1.8 Hz, 1H), 6.80 (t, J=2.3 Hz, 1H), 6.05 (dd, J=4.0, 2.8 Hz, 1H), 5.17 (q, J=7.0 Hz, 1H), 3.82 (s, 3H), 1.52 (d, J=7.3 Hz, 3H).

Example 20

N-((1R)-1-{4-[(hydroxyamino)carbonyl]phenyl}ethyl)-1-benzothiophene-2-carboxamide Compound I-184

The title compound was prepared in an analogous fashion to that described in Example 18 starting from tert-butyl 4-[(1R)-1-{[(S)-tert-butylsulfinyl]amino}ethyl]benzoate. Yield: 38%; LC-MS: (FA) ES+ 341; $^1$H NMR (Methanol-$d_4$, 400 MHz) δ8.04 (s, 1H), 7.88 (m, 2H), 7.73 (d, J=8.0 Hz, 2 µl), 7.50 (d, J=8.3 Hz, 2H), 7.42 (m, 2H), 5.26 (q, J=7.3 Hz, 1H), 1.60 (d, J=7.3 Hz, 3H).

Example 21

N-hydroxy-4-((1R)-1-{[(1-methylcyclohexyl)carbonyl]amino}ethyl)benzamide Compound I-26

The title compound was prepared in an analogous fashion to that described in Example 18 starting from tert-butyl 4-[(1R)-1-{[(S)-tert-butylsulfinyl]amino}ethyl]benzoate. Yield: 27%; LC-MS: (FA) ES+ 305; $^1$H NMR (Methanol-$d_4$, 400 MHz) δ7.81 (d, J=7.8 Hz, 1H), 7.69 (d, J=8.3 Hz, 2H), 7.41 (d, J=8.0 Hz, 2H), 5.08 (q, J=7.3 Hz, 1H), 2.02 (m, 2H), 1.53 (m, 2H), 1.47 (d, J=7.0 Hz, 3H), 1.30 (m, 6H), 1.12 (s, 3H).

Example 22

N-((1R)-1-{4-[(hydroxyamino)carbonyl]phenyl}ethyl)biphenyl-4-carboxamide Compound I-92

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 361.

Example 23

N—((R)-1-{4-[(hydroxyamino)carbonyl]phenyl}ethyl)-3-methyl-1-benzothiophene-2-carboxamide Compound I-12

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 355.

Example 24

4,5-dichloro-N-((1R)-1-{4-[(hydroxyamino)carbonyl]phenyl}ethyl)-1-methyl-1H-pyrrole-2-carboxamide Compound I-359

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 356.

Example 25

N-((1R)-1-{4-[(hydroxyamino)carbonyl]phenyl}ethyl)-4-methyl-2-phenyl-4H-furo[3,2-b]pyrrole-5-carboxamide Compound I-5

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 404.

Example 26

N-((1R)-1-{4-[(hydroxyamino)carbonyl]phenyl}ethyl)adamantane-1-carboxamide Compound I-209

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 343.

Example 27

N-((1R)-1-{4-[(hydroxyamino)carbonyl]phenyl}ethyl)-3-methyl-1-benzofuran-2-carboxamide Compound I-237

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 339.

Example 28

N-((1R)-1-{4-[(hydroxyamino)carbonyl]phenyl}ethyl)-1-methyl-1H-indole-2-carboxamide Compound I-115

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 338.

Example 29

N-hydroxy-4-[(1R)-1-({[4-(trifluoromethyl)phenyl]sulfonyl}amino)ethyl]benzamide Compound I-351

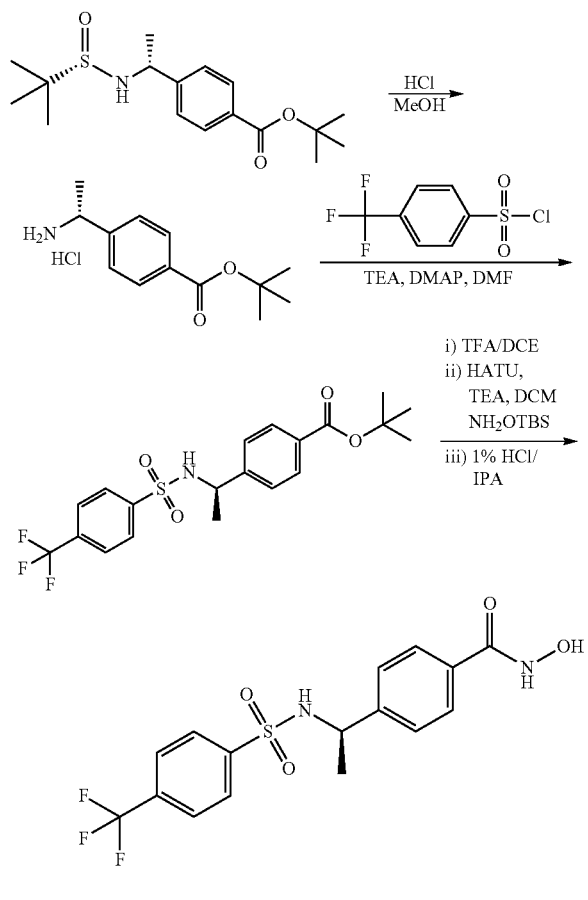

Step 1: tert-butyl-4-[(1R)-1-aminoethyl]benzoate hydrochloride

To a microwave vial containing tert-butyl 4-[(1R)-1-{[(S)-tert-butylsulfinyl]amino}ethyl]benzoate (0.052 g, 0.16 mmol) was added hydrochloric acid (0.08 mL, 0.32 mmol, 4.0 M of in 1,4-dioxane), and methanol (2 mL). This mixture was stirred at rt for 2 h, and then evaporated to dryness to afford tert-butyl-4-[(1R)-1-aminoethyl]benzoate hydrochloride as a white solid. LC-MS: (FA) ES+ 222.

Step 2: (R)-tert-butyl 4-(1-(4-(trifluoromethyl)phenylsulfonamido)ethyl)benzoate To a vial containing tert-butyl-4-[(1R)-1-aminoethyl]benzoate hydrochloride from Step 1 was added N,N-dimethylaminopyridine (3.91 mg, 0.032 mmol), 4-(trifluoromethyl)benzenesulfonyl chloride (0.059 g, 0.24 mmol), N,N-dimethylformamide (2 mL), and triethylamine (0.18 mL, 1.28 mmol). The mixture was stirred at rt for 16 h, after which the solvent was fully evaporated. To the residue was added 1,2-dichloroethane (3 mL), sat. NaHCO$_3$ solution (0.5 mL), and water (0.5 mL). After separation, the aqueous layer was extracted with 1,2-dichloroethane (2×3 mL). The combined organic phases were evaporated to dryness to give (R)-tert-butyl 4-(1-(4-(trifluoromethyl)phenylsulfonamido)ethyl)benzoate as a brown solid. LC-MS: (FA) ES+ 430.

Step 3: N-hydroxy-4-[(1R)-1-({[4-(trifluoromethyl)phenyl]sulfonyl}amino)ethyl]benzamide To a 2-dram vial containing (R)-tert-butyl 4-(1-(4-(trifluoromethyl)phenylsulfonamido)ethyl)benzoate was added 1,2-dichloroethane (2 mL), and trifluoroacetic acid (0.246 mL, 3.20 mmol). After shaking at rt for 4 h, the mixture was evaporated to dryness to give a residue which was azetroped with toluene (2×5 mL). To the solid residue in another vial was added HATU (0.091 g, 0.24 mmol), N,N-dimethylformamide (1.5 mL), triethylamine (0.18 mL, 1.28 mmol). The mixture was stirred for 10 min then O-(tert-butyldimethylsilyl)hydroxylamine (0.047 g, 0.32 mmol) in DCM (0.5 mL) was added. The solution was shaken at rt for 2 h, after which the solvent was then completely removed to afford a brown oil. To this oil in another vial was added hydrochloric acid (3.5 mL, 1% in IPA). After shaking at rt for 30 min, solid NaHCO$_3$ was added to quench the excess acid, and the solvent was then removed. To the solid residue was added DMSO (1.2 mL). After filtration, the DMSO solution was purified by Gilson prep-HPLC to give the title compound (0.091 g, 15%) as a white solid. LC-MS: (FA) ES− 387; $^1$H NMR (Methanol-d$_4$, 400 MHz) δ7.79 (d, J=8.3 Hz, 2H), 7.66 (d, J=8.3 Hz, 2H), 7.51 (d, J=8.5 Hz, 2H), 7.19 (d, J=8.5 Hz, 2H), 4.53 (q, J=7.0 Hz, 1H), 1.36 (d, J=7.0 Hz, 3H).

Example 30

4-((1R)-1-{[(tert-butylamino)carbonyl]amino}ethyl)-N-hydroxybenzamide Compound I-14

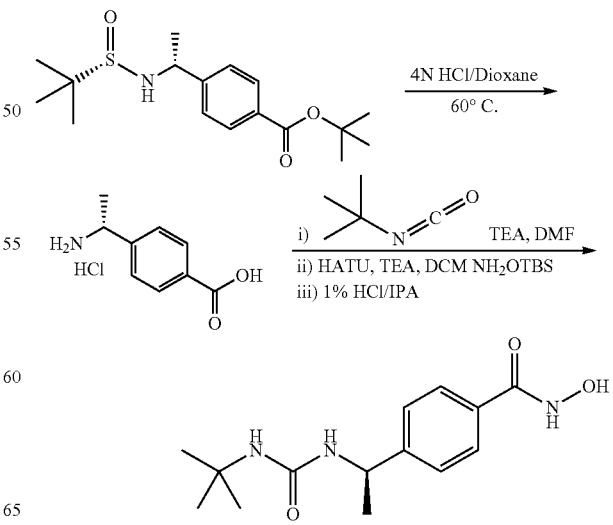

Step 1: (R)-4-(1-aminoethyl)benzoic acid hydrochloride

To a vial containing tert-butyl 4-[(1R)-1-{[(S)-tert-butylsulfinyl]amino}ethyl]benzoate (0.065 g, 0.20 mmol) was added hydrochloric acid (2.0 mL, 8.0 mmol, 4.0 M in 1,4-dioxane). This vial was capped and heated at 60° C. for 2 h, and then completely evaporated to afford (R)-4-(1-aminoethyl)benzoic acid hydrochloride as a white solid. LC-MS: (FA) ES+ 166.

Step 2: 4-((1R)-1-{[(tert-butylamino)carbonyl]amino}ethyl)-N-hydroxybenzamide

To the vial containing (R)-4-(1-aminoethyl)benzoic acid hydrochloride was added tert-butyl isocyanate (0.023 mL, 0.198 mmol), N,N dimethylformamide (3.0 mL), and triethylamine (0.22 mL, 1.59 mmol). After the reaction was stirred at rt for 16 h, HATU (0.075 g, 0.198 mmol) in N,N-dimethylformamide (0.5 mL) was added, immediately followed by the addition of O-(tert-butyldimethylsilyl)hydroxylamine (0.044 g, 0.30 mmol) in DCM (1 mL). This mixture was shaken at rt for 1 hr, after which the mixture was evaporated to dryness. To the residue was added hydrochloric acid (4 mL, 1% in IPA). After shaking at rt for 30 min, solid $NaHCO_3$ was added to quench the excess acid, and the mixture was evaporated to dryness to give a solid residue. This solid was dissolved in DMSO (1.2 mL), and filtered; then purified via Gilson prep-HPLC [15-38% MeCN—$H_2O$] to give the title compound (0.026 g, 47%) as a white solid. LC-MS: (FA) ES+ 280; $^1$H NMR (Methanol-$d_4$, 400 MHz) 87.69 (d, J=8.3 Hz, 2H), 7.37 (d, J=8.3 Hz, 2H), 4.80 (q, J=7.0 Hz, 1H), 1.37 (d, J=7.0 Hz, 3H), 1.26 (s, 9H).

Example 31

4-[(1R)-1-({[1-adamantylamino]carbonyl}amino)ethyl]-N-hydroxybenzamide Compound I-374

The title compound was prepared in an analogous fashion to that described in Example 30 starting from tert-butyl 4-[(1R)-1-{[(S)-tert-butylsulfinyl]amino}ethyl]benzoate. LC-MS: (FA) ES+ 358.

Example 32

N-((1S)-1-{4-[(hydroxyamino)carbonyl]phenyl}ethyl)-1-methyl-1H-pyrrole-2-carboxamide Compound I-25

The title compound was prepared in an analogous fashion to that described in Example 18 starting from tert-butyl 4-[(1S)-1-{[(R)-tert-butylsulfinyl]amino}ethyl]benzoate. Yield: 44.8%; LC-MS: (FA) ES+ 288; $^1$H NMR (Methanol-$d_4$, 400 MHz) δ7.70 (d, J=8.3 Hz, 2H), 7.46 (d, J=8.0 Hz, 2H), 6.86 (m, 1H), 6.80 (m, 1H), 6.05 (dd, J=4.0, 2.7 Hz, 1H), 5.17 (q, J=7.0 Hz, 1H), 3.82 (s, 3H), 1.52 (d, J=7.3 Hz, 3H).

Example 33

N-((1S)-1-{4-[(hydroxyamino)carbonyl]phenyl}ethyl)-1-benzothiophene-2-carboxamide Compound I-53

The title compound was prepared in an analogous fashion to that described in Example 18 starting from tert-butyl 4-[(1S)-1-{[(R)-tert-butylsulfinyl]amino}ethyl]benzoate. Yield: 42.5%; %; LC-MS: (FA) ES+ 341; $^1$H NMR (Methanol-$d_4$, 400 MHz) δ8.04 (s, 1H), 7.88 (m, 2H), 7.73 (d, J=8.0 Hz, 2H), 7.50 (d, J=8.3 Hz, 2H), 7.42 (m, 2H), 5.26 (q, J=7.3 Hz, 1H), 1.60 (d, J=7.3 Hz, 3H).

Example 34

N-hydroxy-4-((1S)-1-{[(1-methylcyclohexyl)carbonyl]amino}ethyl)benzamide Compound I-273

The title compound was prepared in an analogous fashion to that described in Example 18 starting from tert-butyl 4-[(1S)-1-{[(R)-tert-butylsulfinyl]amino}ethyl]benzoate. Yield: 18.2%; LC-MS: (FA) ES+ 305.

Example 35

N-((1R)-1-{4-[(hydroxyamino)carbonyl]phenyl}butyl)-1-methyl-1H-pyrrole-2-carboxamide Compound I-281

The title compound was prepared in an analogous fashion to that described in Example 18 starting from tert-butyl 4-((R)-1-((S)-1,1-dimethylethylsulfinamido)butyl)benzoate. LC-MS: (FA) ES+ 316.

Example 36

N-((1R)-1-{4-[(hydroxyamino)carbonyl]phenyl}butyl)-1-benzothiophene-2-carboxamide Compound I-299

The title compound was prepared in an analogous fashion to that described in Example 18 starting from tert-butyl 4-((R)-1-(S)-1,1-dimethylethylsulfinamido)butyl)benzoate. LC-MS: (FA) ES+ 369.

Example 37

4-{(1R)-1-[(2,2-dimethylpropanoyl)amino]butyl}-N-hydroxybenzamide Compound I-365

The title compound was prepared in an analogous fashion to that described in Example 18 starting from tert-butyl 4-((R)-1-((S)-1,1-dimethylethylsulfinamido)butyl)benzoate. LC-MS: (FA) ES+ 293; $^1$H NMR (Methanol-$d_4$, 400 MHz) δ7.75 (d, J=8.0 Hz, 1H), 7.69 (d, J=8.5 Hz, 2H), 7.39 (d, J=8.3 Hz, 2H), 4.91 (m, 1H), 1.85-1.69 (m, 2H), 1.45-1.27 (m, 2H), 1.18 (s, 9H), 0.94 (d, J=7.5 Hz, 3H).

Example 38

N-((1R)-1-{4-[(hydroxyamino)carbonyl]phenyl}butyl)-4-methyl-2-phenyl-4H-furo[3,2-b]pyrrole-5-carboxamide Compound I-222

The title compound was prepared in an analogous fashion to that described in Example 18 starting from tert-butyl 4-((R)-1-((S)-1,1-dimethylethylsulfinamido)butyl)benzoate. LC-MS: (FA) ES+ 432.

Example 39

N-((1R)-1-{4-[(hydroxyamino)carbonyl]phenyl}butyl)-3-methyl-1-benzothiophene-2-carboxamide Compound I-62

The title compound was prepared in an analogous fashion to that described in Example 18 starting from tert-butyl 4-((R)-1-((S)-1,1-dimethylethylsulfinamido)butyl)benzoate. LC-MS: (FA) ES+ 383.

Example 40

N-((1R)-1-{4-[(hydroxyamino)carbonyl]phenyl}butyl)biphenyl-4-carboxamide Compound I-274

The title compound was prepared in an analogous fashion to that described in Example 18 starting from tert-butyl 4-((R)-1-((S)-1,1-dimethylethylsulfinamido)butyl)benzoate. LC-MS: (FA) ES+ 389.

Example 41

N-((1R)-1-{4-[(hydroxyamino)carbonyl]phenyl}butyl)-4-methoxybenzamide Compound I-146

The title compound was prepared in an analogous fashion to that described in Example 18 starting from tert-butyl 4-((R)-1-((S)-1,1-dimethylethylsulfinamido)butyl)benzoate. LC-MS: (FA) ES+ 343.

Example 42

N-((1R)-1-{4-[(hydroxyamino)carbonyl]phenyl}butyl)-1-methyl-1H-indole-2-carboxamide Compound I-106

The title compound was prepared in an analogous fashion to that described in Example 18 starting from tert-butyl 4-((R)-1-((S)-1,1-dimethylethylsulfinamido)butyl)benzoate. LC-MS: (FA) ES+ 366.

Example 43

N-hydroxy-4-((1R)-1-{[(1-methylcyclohexyl)carbonyl]amino}butyl)benzamide Compound I-387

The title compound was prepared in an analogous fashion to that described in Example 18 starting from tert-butyl 4-((R)-1-((S)-1,1-dimethylethylsulfinamido)butyl)benzoate. LC-MS: (FA) ES+ 333.

Example 44

4,5-dichloro-N-((1R)-1-{4-[(hydroxyamino)carbonyl]phenyl}butyl)-1-methyl-1H-pyrrole-2-carboxamide Compound I-245

The title compound was prepared in an analogous fashion to that described in Example 18 starting from tert-butyl 4-((R)-1-((S)-1,1-dimethylethylsulfinamido)butyl)benzoate. LC-MS: (FA) ES+ 384.

Example 45

N-((1R)-1-{4-[(hydroxyamino)carbonyl]phenyl}butyl)adamantane-1-carboxamide Compound I-15

The title compound was prepared in an analogous fashion to that described in Example 18 starting from tert-butyl 4-((R)-1-((S)-1,1-dimethylethylsulfinamido)butyl)benzoate. LC-MS: (FA) ES+ 371; $^1$H NMR (Methanol-$d_4$, 400 MHz) δ7.68 (d, J=8.3 Hz, 2H), 7.38 (d, J=8.0 Hz, 2H), 4.91 (m, 1H), 2.01 (m, 3H), 1.87 (m, 6H), 1.75 (m, 6H), 1.81-1.71 (m, 2H), 1.45-1.27 (m, 2H), 0.94 (d, J=7.5 Hz, 3H).

Example 46

N-((1R)-1-{4-[(hydroxyamino)carbonyl]phenyl}butyl)-3-methyl-1-benzofuran-2-carboxamide Compound I-367

The title compound was prepared in an analogous fashion to that described in Example 18 starting from tert-butyl 4-((R)-1-((S)-1,1-dimethylethylsulfinamido)butyl)benzoate. LC-MS: (FA) ES+ 367.

Example 47

N-((1R)-1-{4-[(hydroxyamino)carbonyl]phenyl}butyl)-1-benzofuran-2-carboxamide Compound I-79

The title compound was prepared in an analogous fashion to that described in Example 18 starting from tert-butyl 4-((R)-1-((S)-1,1-dimethylethylsulfinamido)butyl)benzoate. LC-MS: (FA) ES+ 353.

Example 48

N-hydroxy-4-[(1R)-1-({[4-(trifluoromethyl)phenyl]sulfonyl}amino)butyl]benzamide Compound I-171

The title compound was prepared in an analogous fashion to that described in Example 29 starting from tert-butyl 4-((R)-1-((S)-1,1-dimethylethylsulfinamido)butyl)benzoate. LC-MS: (FA) ES− 415; $^1$H NMR (Methanol-$d_4$, 400 MHz) δ7.72 (d, J=8.7 Hz, 2H), 7.58 (d, J=8.0 Hz, 2H), 7.47 (d, J=8.5 Hz, 2H), 7.11 (d, J=8.3 Hz, 2H), 4.36 (m, 1H), 1.71 (m, 1H), 1.58 (m, 1H), 1.32 (m, 1H), 1.21 (m, 1H), 0.85 (d, J=7.5 Hz, 3H).

Example 49

4-((1R)-1-{[(tert-butylamino)carbonyl]amino}butyl)-N-hydroxybenzamide Compound I-380

The title compound was prepared in an analogous fashion to that described in Example 30 starting from tert-butyl 4-((R)-1-((S)-1,1-dimethylethylsulfinamido)butyl)benzoate. LC-MS: (FA) ES+ 308.

Example 50

4-[(1R)-1-({[(1S,3R,5R,7S)-1-adamantylamino]carbonyl}amino)butyl]-N-hydroxybenzamide Compound I-18

The title compound was prepared in an analogous fashion to that described in Example 30 starting from tert-butyl 4-((R)-1-((S)-1,1-dimethylethylsulfinamido)butyl)benzoate. LC-MS: (FA) ES+ 386.

Example 51

N-((1R)-1-{4-[(hydroxyamino)carbonyl]phenyl}-2-methylpropyl)-1-benzothiophene-2-carboxamide Compound I-214

The title compound was prepared in an analogous fashion to that described in Example 18 starting from tert-butyl 4-[(1R)-1-{[(R)-tert-butylsulfinyl]amino}-2-methylpropyl]benzoate. Yield: 17%; LC-MS: (FA) ES+ 369; $^1$H NMR (Methanol-$d_4$, 400 MHz) δ8.03 (s, 1H), 7.89 (m, 2H), 7.73 (d, J=8.3 Hz, 2H), 7.50 (d, J=8.3 Hz, 2H), 7.42 (m, 2H), 4.73 (d, J=10.0 Hz, 1H), 2.25 (m, 1H), 1.30 (t, J=7.3 Hz, 1H), 1.14 (d, J=6.6 Hz, 3H), 0.81 (d, J=6.8 Hz, 3H).

Example 52

N-((1R)-1-{4-[(hydroxyamino)carbonyl]phenyl}-2-methylpropyl)adamantane-1-carboxamide Compound I-328

The title compound was prepared in an analogous fashion to that described in Example 18 starting from tert-butyl 4-[(1R)-1-{[(R)-tert-butylsulfinyl]amino}-2-methylpropyl]benzoate. Yield: 27.4%; LC-MS: (FA) ES+ 371.

Example 53

N-((1R)-1-{4-[(hydroxyamino)carbonyl]phenyl}-2-methylpropyl)-1H-indole-2-carboxamide Compound I-68

The title compound was prepared in an analogous fashion to that described in Example 18 starting from tert-butyl 4-[(1R)-{[(R)-tert-butylsulfinyl]amino}-2-methylpropyl]benzoate. Yield: 15.0%; LC-MS: (FA) ES+ 352; $^1$H NMR (Methanol-$d_4$, 400 MHz) δ8.63 (d, J=8.8 Hz, 1H), 7.72 (d, J=8.3 Hz, 2H), 7.60 (d, J=8.0 Hz, 1H), 7.50 (d, J=8.3 Hz, 2H), 7.41 (d, J=8.0 Hz, 1H), 7.19 (m, 2H), 7.04 (t, J=7.3 Hz, 1H), 4.77 (t, J=9.3 Hz, 1H), 2.23 (m, 1H), 1.12 (d, J=6.8 Hz, 3H), 0.81 (d, J=6.8 Hz, 3H).

Example 54

N-((1R)-1-{4-[(hydroxyamino)carbonyl]phenyl}-2-methylpropyl)-3-methyl-1-benzothiophene-2-carboxamide Compound I-307

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 383.

Example 55

4-{(1R)-1-[(2,2-dimethylpropanoyl)amino]-2-methylpropyl}-N-hydroxybenzamide Compound I-287

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 293.

Example 56

N-((1R)-1-{4-[(hydroxyamino)carbonyl]phenyl}-2-methylpropyl)-4-methyl-2-phenyl-4H-furo[3,2-b]pyrrole-5-carboxamide Compound I-332

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 432.

Example 57

N-((1R)-1-{4-[(hydroxyamino)carbonyl]phenyl}-2-methylpropyl)-3-methyl-1-benzofuran-2-carboxamide Compound I-187

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 367.

Example 58

N-hydroxy-4-((R)-2-methyl-1-{[(1-methylcyclohexyl)carbonyl]amino}propyl)benzamide Compound I-126

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 333.

Example 59

4,5-dichloro-N-((1R)-1-{4-[(hydroxyamino)carbonyl]phenyl}-2-methylpropyl)-1-methyl-1H-pyrrole-2-carboxamide Compound I-96

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 385.

Example 60

N—((R)-1-{4-[(hydroxyamino)carbonyl]phenyl}-2-methylpropyl)-1-methyl-1H-indole-2-carboxamide Compound I-242

The title compound was prepared in an analogous fashion to that described in Example 18 starting from tert-butyl 4-[(1R)-1-{[(R)-tert-butylsulfinyl]amino}-2-methylpropyl]benzoate. LC-MS: (FA) ES+ 366.

Example 61

N—((R)-1-{4-[(hydroxyamino)carbonyl]phenyl}-2-methylpropyl)biphenyl-4-carboxamide Compound I-341

The title compound was prepared in an analogous fashion to that described in Example 18 starting from tert-butyl 4-[(1R)-1-{[(R)-tert-butylsulfinyl]amino}-2-methylpropyl] benzoate. LC-MS: (FA) ES+ 389.

Example 62

N-((1R)-1-{4-[(hydroxyamino)carbonyl]phenyl}-2-methylpropyl)-4-methoxybenzamide Compound I-19

The title compound was prepared in an analogous fashion to that described in Example 18 starting from tert-butyl 4-[(1R)-1-{[(R)-tert-butylsulfinyl]amino}-2-methylpropyl] benzoate. LC-MS: (FA) ES+ 343.

Example 63

N-((1R)-1-{4-[(hydroxyamino)carbonyl]phenyl}-2-methylpropyl)-1-methyl-1H-pyrrole-2-carboxamide Compound I-65

The title compound was prepared in an analogous fashion to that described in Example 18 starting from tert-butyl 4-[(1R)-1-{[(R)-tert-butylsulfinyl]amino}-2-methylpropyl] benzoate. LC-MS: (FA) ES+ 316.

Example 64

N-((1R)-1-{4-[(hydroxyamino)carbonyl]phenyl}-2-methylpropyl)-1-benzofuran-2-carboxamide Compound I-22

The title compound was prepared in an analogous fashion to that described in Example 18 starting from tert-butyl 4-[(1R)-1-{[(R)-tert-butylsulfinyl]amino}-2-methylpropyl] benzoate. LC-MS: (FA) ES+ 353.

Example 65

N-hydroxy-4-[(1R)-2-methyl-1-({[4-(trifluoromethyl)phenyl]sulfonyl}amino)propyl]benzamide Compound I-189

The title compound was prepared in an analogous fashion to that described in Example 29 starting from tert-butyl 4-[(1R)-1-{[(R)-tert-butylsulfinyl]amino}-2-methylpropyl] benzoate. LC-MS: (FA) ES− 415; $^1$H NMR (Methanol-d$_4$, 400 MHz) δ7.68 (d, J=8.3 Hz, 2H), 7.54 (d, J=8.3 Hz, 2H), 7.45 (d, J=8.5 Hz, 2H), 7.06 (d, J=8.1 Hz, 2H), 4.04 (d, J=8.5 Hz, 1H), 1.89 (m, 1H), 1.02 (d, J=6.8 Hz, 3H), 0.69 (d, J=6.8 Hz, 3H).

Example 66

4-((1R)-1-[(tert-butylamino)carbonyl]amino-2-methylpropyl)-N-hydroxybenzamide Compound I-368

The title compound was prepared in an analogous fashion to that described in Example 30 starting from tert-butyl 4-[(1R)-1-{[(R)-tert-butylsulfinyl]amino}-2-methylpropyl] benzoate. LC-MS: (FA) ES+ 308.

Example 67

4-[(1R)-1-({[1-adamantylamino]carbonyl}amino)-2-methylpropyl]-N-hydroxybenzamide Compound I-354

The title compound was prepared in an analogous fashion to that described in Example 30 starting from tert-butyl 4-[(1R)-1-{[(R)-tert-butylsulfinyl]amino}-2-methylpropyl] benzoate. LC-MS: (FA) ES+ 386.

Example 68

N-((1S)-1-{4-[(hydroxyamino)carbonyl]phenyl}-2-methylpropyl)-1-benzothiophene-2-carboxamide Compound I-67

The title compound was prepared in an analogous fashion to that described in Example 18 starting from tert-butyl 4-[(1S)-1-{[(S)-tert-butylsulfinyl]amino}-2-methylpropyl] benzoate. Yield: 25.3%; LC-MS: (FA) ES+ 369; $^1$H NMR (Methanol-d$_4$, 400 MHz) δ8.03 (s, 1H), 7.89 (m, 2H), 7.73 (d, J=8.3 Hz, 2H), 7.50 (d, J=8.3 Hz, 2H), 7.42 (m, 2H), 4.73 (d, J=10.0 Hz, 1H), 2.25 (m, 1H), 1.30 (t, J=7.3 Hz, 1H), 1.14 (d, J=6.6 Hz, 3H), 0.81 (d, J=6.8 Hz, 3H).

Example 69

N-((1S)-1-{4-[(hydroxyamino)carbonyl]phenyl}-2-methylpropyl)adamantane-1-carboxamide Compound I-157

The title compound was prepared in an analogous fashion to that described in Example 18 starting from tert-butyl 4-[(1S)-1-{[(S)-tert-butylsulfinyl]amino}-2-methylpropyl] benzoate. Yield: 33.4%; LC-MS: (FA) ES+ 371.

Example 70

N-((1S)-1-{4-[(hydroxyamino)carbonyl]phenyl}-2-methylpropyl)-1H-indole-2-carboxamide Compound I-279

The title compound was prepared in an analogous fashion to that described in Example 18 starting from tert-butyl 4-[(1S)-1-{[(S)-tert-butylsulfinyl]amino}-2-methylpropyl] benzoate. Yield: 11%; LC-MS: (FA) ES+ 352; $^1$H NMR (Methanol-d$_4$, 300 MHz) δ8.63 (d, J=8.8 Hz, 1H), 7.72 (d, J=8.3 Hz, 2H), 7.60 (d, J=8.0 Hz, 1H), 7.50 (d, J=8.3 Hz, 2H), 7.41 (d, J=8.0 Hz, 1H), 7.19 (m, 2H), 7.04 (t, J=7.3 Hz, 1H), 4.77 (t, J=9.3 Hz, 1H), 2.23 (m, 1H), 1.12 (d, J=6.8 Hz, 3H), 0.81 (d, J=6.8 Hz, 3H).

Example 71

N-((1R)-1-{3-[(hydroxyamino)carbonyl]phenyl}ethyl)-1-methyl-1H-indole-2-carboxamide Compound I-330

The title compound was prepared in an analogous fashion to that described in Example 18 starting from tert-butyl 3-[(1R)-1-{[(S)-tert-butylsulfinyl]amino}ethyl]benzoate. Yield: 31.3%; LC-MS: (FA) ES+ 338; $^1$H NMR (Methanol-d$_4$, 300 MHz) δ7.82 (s, 1H), 7.61 (m, 3H), 7.42 (m, 2H), 7.27 (t, J=7.8 Hz, 1H), 7.11 (s, 1H), 7.09 (d, J=7.5 Hz, 1H), 5.25 (q, J=6.8 Hz, 1H), 3.93 (s, 3H), 1.59 (d, J=7.0 Hz, 3H).

Example 72

N—((R)-1-{3-[(hydroxyamino)carbonyl]phenyl}ethyl)biphenyl-4-carboxamide Compound I-121

The title compound was prepared in an analogous fashion to that described in Example 18 starting from tert-butyl 3-[(1R)-1-{[(S)-tert-butylsulfinyl]amino}ethyl]benzoate. Yield: 43.9%; LC-MS: (FA) ES+ 361; $^1$H NMR (Methanol-$d_4$, 400 MHz) δ7.93 (d, J=8.0 Hz, 2H), 7.82 (s, 1H), 7.71 (d, J=8.3 Hz, 2H), 7.65 (d, J=8.3 Hz, 2H), 7.61 (t, J=7.3 Hz, 2H), 7.45 (q, J=7.8 Hz, 2H), 7.37 (t, J=7.8 Hz, 2H), 5.29 (q, J=6.8 Hz, 1H), 1.61 (d, J=7.0 Hz, 3H).

Example 73

N-((1R)-1-{3-[(hydroxyamino)carbonyl]phenyl}ethyl)-1-benzothiophene-2-carboxamide Compound I-321

The title compound was prepared in an analogous fashion to that described in Example 18 starting from tert-butyl 3-[(1R)-1-{[(S)-tert-butylsulfinyl]amino}ethyl]benzoate. Yield: 40.9%; LC-MS: (FA) ES+ 341.

Example 74

3-{(1R)-1-[(2,2-dimethylpropanoyl)amino]ethyl}-N-hydroxybenzamide Compound I-177

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 265.

Example 75

N-hydroxy-3-((1R)-1-{[(1-methylcyclohexyl)carbonyl]amino}ethyl)benzamide Compound I-283

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 305.

Example 76

N-((1R)-1-{3-[(hydroxyamino)carbonyl]phenyl}ethyl)-3-methyl-1-benzofuran-2-carboxamide Compound I-169

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 339.

Example 77

N-((1R)-1-{3-[(hydroxyamino)carbonyl]phenyl}ethyl)-3-methyl-1-benzothiophene-2-carboxamide Compound I-113

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 355.

Example 78

N-((1R)-1-{3-[(hydroxyamino)carbonyl]phenyl}ethyl)-1-methyl-1H-pyrrole-2-carboxamide Compound I-271

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 288.

Example 79

N-((1R)-1-{3-[(hydroxyamino)carbonyl]phenyl}ethyl)-1-benzofuran-2-carboxamide Compound I-201

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 325.

Example 80

N-((1R)-1-{3-[(hydroxyamino)carbonyl]phenyl}ethyl)adamantane-1-carboxamide Compound I-312

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 343.

Example 81

N-((1R)-1-{3-[(hydroxyamino)carbonyl]phenyl}ethyl)-4-methyl-2-phenyl-4H-furo[3,2-b]pyrrole-5-carboxamide Compound I-16

The title compound was prepared in an analogous fashion to that described in Example 8 starting from tert-butyl 3-[(1R)-1-{[(S)-tert-butylsulfinyl]amino}ethyl]benzoate. LC-MS: (FA) ES+ 404.

Example 82

4,5-dichloro-N-((1R)-1-{3-[(hydroxyamino)carbonyl]phenyl}ethyl)-1-methyl-1H-pyrrole-2-carboxamide Compound I-301

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 356.

Example 83

N-hydroxy-3-{(1R)-1-[(4-methoxybenzoyl)amino]ethyl}benzamide Compound I-193

The title compound was prepared in an analogous fashion to that described in Example 18 starting from tert-butyl 3-[(1R)-1-{[(S)-tert-butylsulfinyl]amino}ethyl]benzoate. LC-MS: (FA) ES+ 315.

Example 84

N-hydroxy-3-[(1R)-1-{[4-(trifluoromethyl)phenyl] sulfonyl}amino)ethyl]benzamide Compound I-403

The title compound was prepared in an analogous fashion to that described in Example 29 starting from tert-butyl 3-[(1R)-1-{[(S)-tert-butylsulfinyl]amino}-2-methylpropyl] benzoate. LC-MS: (FA) ES− 387.

Example 85

3-((1R)-1-{[(tert-butylamino)carbonyl]amino}ethyl)-N-hydroxybenzamide Compound I-320

The title compound was prepared in an analogous fashion to that described in Example 30 starting from tert-butyl 3-[(1R)-1-{[(S)-tert-butylsulfinyl]amino}-2-methylpropyl] benzoate. LC-MS: (FA) ES+ 280.

Example 86

3-[(1R)-1-({[1-adamantylamino]carbonyl}amino) ethyl]-N-hydroxybenzamide Compound I-343

The title compound was prepared in an analogous fashion to that described in Example 30 starting from tert-butyl 3-[(1R)-1-{[(S)-tert-butylsulfinyl]amino}-2-methylpropyl] benzoate. LC-MS: (FA) ES+ 358.

Example 87

N-((1S)-1-{3-[(hydroxyamino)carbonyl] phenyl}ethyl)-1-methyl-1H-indole-2-carboxamide Compound I-294

The title compound was prepared in an analogous fashion to that described in Example 18 starting from tert-butyl 3-[(15)-1-{[(R)-tert-butylsulfinyl]amino}ethyl]benzoate. Yield: 22.7%; LC-MS: (FA) ES+ 338; $^1$H NMR (Methanol-$d_4$, 300 MHz) δ7.82 (s, 1H), 7.61 (m, 3H), 7.42 (m, 2H), 7.27 (t, J=7.8 Hz, 1H), 7.11 (s, 1H), 7.09 (d, J=7.5 Hz, 1H), 5.25 (q, J=6.8 Hz, 1H), 3.93 (s, 3H), 1.59 (d, J=7.0 Hz, 3H).

Example 88

N-((1S)-1-{3-[(hydroxyamino)carbonyl] phenyl}ethyl)biphenyl-4-carboxamide Compound I-393

The title compound was prepared in an analogous fashion to that described in Example 18 starting from tert-butyl 3-[(1S)-1-{[(R)-tert-butylsulfinyl]amino}ethyl]benzoate. Yield: 40.4%; LC-MS: (FA) ES+ 361; $^1$H NMR (Methanol-$d_4$, 300 MHz) δ7.93 (d, J=8.0 Hz, 2H), 7.82 (s, 1H), 7.71 (d, J=8.3 Hz, 2H), 7.65 (d, J=8.3 Hz, 2H), 7.61 (t, J=7.3 Hz, 2H), 7.45 (q, J=7.8 Hz, 2H), 7.37 (t, J=7.8 Hz, 2H), 5.29 (q, J=6.8 Hz, 1H), 1.61 (d, J=7.0 Hz, 3H).

Example 89

N-((1S)-1-{3-[(hydroxyamino)carbonyl] phenyl}ethyl)-1-benzothiophene-2-carboxamide Compound I-240

The title compound was prepared in an analogous fashion to that described in Example 18 starting from tert-butyl 3-[(1S)-1-{[(R)-tert-butylsulfinyl]amino}ethyl]benzoate. Yield: 48.1%; LC-MS: (FA) ES+ 341; $^1$H NMR (Methanol-$d_4$, 300 MHz) δ8.04 (s, 1H), 7.88 (m, 2H), 7.82 (s, 1H), 7.60 (m, 2H), 7.46-7.38 (m, 3H), 5.26 (q, J=7.2 Hz, 1H), 1.61 (d, J=7.2 Hz, 3H).

Example 90

N-((1S)-2,2,2-trifluoro-1-{4-[(hydroxyamino)carbonyl]phenyl}ethyl)biphenyl-4-carboxamide Compound I-296

The title compound was prepared in an analogous fashion to that described in Example 18 starting from tert-butyl 4-[(1S)-1-{[(R)-tert-butylsulfinyl]amino}-2,2,2-trifluoroethyl]benzoate. LC-MS: (FA) ES− 413; $^1$H NMR (DMSO-$d_6$, 400 MHz) δ11.26 (s, 1H), 9.59 (d, J=9.5 Hz, 1H), 9.10 (s, 1H), 8.01 (d, J=8.5 Hz, 2H), 7.82-7.75 (m, 4H), 7.73 (m, 2H), 7.50 (m, 2H), 7.41 (m, 1H), 6.15 (d, J=9.2 Hz, 1H).

Example 91

N-((1S)-2,2,2-trifluoro-1-{4-[(hydroxyamino)carbonyl]phenyl}ethyl)-1-benzofuran-2-carboxamide Compound I-400

The title compound was prepared in an analogous fashion to that described in Example 18 starting from tert-butyl 4-[(1S)-1-{[(R)-tert-butylsulfinyl]amino}-2,2,2-trifluoroethyl]benzoate. LC-MS: (FA) ES− 377.

Example 92

4,5-dichloro-1-methyl-N-((1S)-2,2,2-trifluoro-1-{4-[(hydroxyamino)carbonyl]phenyl}ethyl)-1H-pyrrole-2-carboxamide Compound I-108

The title compound was prepared in an analogous fashion to that described in Example 18 starting from tert-butyl 4-[(1S)-1-{[(R)-tert-butylsulfinyl]amino}-2,2,2-trifluoroethyl]benzoate. LC-MS: (FA) ES− 409.

Example 93

4-methyl-2-phenyl-N-((1S)-2,2,2-trifluoro-1-{4-[(hydroxyamino)carbonyl]phenyl}ethyl)-4H-furo[3,2]pyrrole-5-carboxamide Compound I-231

The title compound was prepared in an analogous fashion to that described in Example 18 starting from tert-butyl 4-[(1S)-1-{[(R)-tert-butylsulfinyl]amino}-2,2,2-trifluoroethyl]benzoate. LC-MS: (FA) ES− 456.

Example 94

4-methoxy-N-((1S)-2,2,2-trifluoro-1-{4-[(hydroxyamino)carbonyl]phenyl}ethyl)benzamide Compound I-122

The title compound was prepared in an analogous fashion to that described in Example 18 starting from tert-butyl 4-[(15)-1-{[(R)-tert-butylsulfinyl]amino}-2,2,2-trifluoroethyl]benzoate. LC-MS: (FA) ES− 367.

Example 95

3-methyl-N-((1S)-2,2,2-trifluoro-1-{4-[hydroxyamino)carbonyl]phenyl}ethyl)-1-benzofuran-2-carboxamide Compound I-304

The title compound was prepared in an analogous fashion to that described in Example 18 starting from tert-butyl 4-[(1S)-1-{[(R)-tert-butylsulfinyl]amino}-2,2,2-trifluoroethyl]benzoate. LC-MS: (FA) ES– 391.

Example 96

4-{(1R)-1-[(2,2-dimethylpropanoyl)amino]-2,2,2-trifluoroethyl}-N-hydroxybenzamide Compound I-50

The title compound was prepared in an analogous fashion to that described in Example 18 starting from tert-butyl 4-[(1R)-1-{[(S)-tert-butylsulfinyl]amino}-2,2,2-trifluoroethyl]benzoate. LC-MS: (FA) ES– 317.

Example 97

1-methyl-N-((1R)-2,2,2-trifluoro-1-{4-[hydroxyamino)carbonyl]phenyl}ethyl)-1H-pyrrole-2-carboxamide Compound I-119

The title compound was prepared in an analogous fashion to that described in Example 18 starting from tert-butyl 4-[(1R)-1-{[(S)-tert-butylsulfinyl]amino}-2,2,2-trifluoroethyl]benzoate. LC-MS: (FA) ES– 340.

Example 98

1-methyl-N-((1R)-2,2,2-trifluoro-1-{4-[hydroxyamino)carbonyl]phenyl}ethyl)-1H-indole-2-carboxamide Compound I-276

The title compound was prepared in an analogous fashion to that described in Example 18 starting from tert-butyl 4-[(1R)-1-{[(S)-tert-butylsulfinyl]amino}-2,2,2-trifluoroethyl]benzoate. LC-MS: (FA) ES– 390.

Example 99

4-((1R)-1-{[(tert-butylamino)carbonyl]amino}-2,2,2-trifluoroethyl)-N-hydroxybenzamide Compound I-290

The title compound was prepared in an analogous fashion to that described in Example 30 starting from tert-butyl 4-[(1R)-1-{[(S)-tert-butylsulfinyl]amino}-2,2,2-trifluoroethyl]benzoate. LC-MS: (FA) ES– 332.

Example 100

4-((1R)-1-{[(1-adamantylamino)carbonyl]amino}-2,2,2-trifluoroethyl)-N-hydroxybenzamide Compound I-105

The title compound was prepared in an analogous fashion to that described in Example 30 starting from tert-butyl 4-[(1R)-1-{[(S)-tert-butylsulfinyl]amino}-2,2,2-trifluoroethyl]benzoate. LC-MS: (FA) ES– 410.

Example 101

N—((R)-cyclopropyl{4-[(hydroxyamino)carbonyl]phenyl}methyl)-1-benzothiophene-2-carboxamide Compound I-229

The title compound was prepared in an analogous fashion to that described in Example 18 starting from tert-butyl-4-[(R)-{[(R)-tert-butylsulfinyl]amino}(cyclopropyl)methyl]benzoate. Yield: 26.8%; LC-MS: (FA) ES+ 367.

Example 102

N—((R)-cyclopropyl{4-[(hydroxyamino)carbonyl]phenyl}methyl)adamantane-1-carboxamide Compound I-46

The title compound was prepared in an analogous fashion to that described in Example 18 starting from tert-butyl-4-[(R)-{[(R)-tert-butylsulfinyl]amino}(cyclopropyl)methyl]benzoate. Yield: 29.6%; LC-MS: (FA) ES+ 369.

Example 103

N—((S)-cyclopropyl{4-[(hydroxyamino)carbonyl]phenyl}methyl)-1-benzothiophene-2-carboxamide Compound I-249

The title compound was prepared in an analogous fashion to that described in Example 18 starting from tert-butyl-4-[(S)-{[(R)-tert-butylsulfinyl]amino}(cyclopropyl)methyl]benzoate. Yield: 27.8%; LC-MS: (FA) ES+ 367; $^1$H NMR (Methanol-$d_4$, 300 MHz) δ8.06 (s, 1H), 7.89 (m, 2H), 7.73 (d, J=8.3 Hz, 2H), 7.56 (d, J=8.3 Hz, 2H), 7.42 (m, 2H), 4.42 (m, 1H), 1.39 (m, 1H), 0.68 (d, J=7.7 Hz, 2H), 0.49 (t, J=4.5 Hz, 2H).

Example 104

N—((S)-cyclopropyl{4-[(hydroxyamino)carbonyl]phenyl}methyl)adamantane-1-carboxamide Compound I-322

The title compound was prepared in an analogous fashion to that described in Example 18 starting from tert-butyl-4-[(S)-{[(R)-tert-butylsulfinyl]amino}(cyclopropyl)methyl]benzoate. Yield: 48.1%; LC-MS: (FA) ES+ 369; $^1$H NMR (Methanol-$d_4$, 300 MHz) δ7.69 (d, J=8.3 Hz, 2H), 7.45 (d, J=8.3 Hz, 2H), 4.21 (m, 1 µl), 2.02 (m, 3H), 1.89 (m, 6H), 1.76 (m, 6H), 1.26 (m, 1H), 0.61 (d, J=7.9 Hz, 2H), 0.38 (t, J=4.4 Hz, 2H).

Example 105

N—[(R)-{4-[(hydroxyamino)carbonyl]phenyl}(phenyl)methyl]-1-benzothiophene-2-carboxamide Compound I-99

The title compound (er, 6.0:1) was prepared in an analogous fashion to that described in Example 18 starting from tert-butyl 4-[(R)-{[(S)-tert-butylsulfinyl]amino}(phenyl)methyl]benzoate. Yield: 32.4%; LC-MS: (FA) ES+ 403.

Example 106

N—[(R)-{4-[(hydroxyamino)carbonyl]phenyl}(phenyl)methyl]adamantane-1-carboxamide Compound I-336

The title compound (er, 6.0:1) was prepared in an analogous fashion to that described in Example 18 starting from tert-butyl 4-[(R)-{[(S)-tert-butylsulfinyl]amino}(phenyl)methyl]benzoate. Yield: 57.7%; LC-MS: (FA) ES+ 405.

Example 107

N—[(S)-{4-[(hydroxyamino)carbonyl]phenyl}(phenyl)methyl]-1-benzothiophene-2-carboxamide Compound I-124

The title compound (er, 6.3:1) was prepared in an analogous fashion to that described in Example 18 starting from tert-butyl-4-[(S)-{[(R)-tert-butylsulfinyl]amino}(cyclopropyl)methyl]benzoate. Yield: 31.0%; LC-MS: (FA) ES+ 403; $^1$H NMR (Methanol-$d_4$, 300 MHz) δ8.09 (s, 1H), 7.89 (m, 2H), 7.74 (d, J=7.9 Hz, 2H), 7.47-7.25 (m, 9H), 6.48 (d, J=8.5 Hz, 1H).

Example 108

N—[(S)-{4-[(hydroxyamino)carbonyl]phenyl}(phenyl)methyl]adamantane-1-carboxamide Compound I-259

The title compound (er, 6.3:1) was prepared in an analogous fashion to that described in Example 18 starting from tert-butyl-4-[(S)-{[(R)-tert-butylsulfinyl]amino}(cyclopropyl)methyl]benzoate. Yield: 29.9%; LC-MS: (FA) ES+ 405; $^1$H NMR (Methanol-$d_4$, 300 MHz) δ8.01 (d, J=8.1 Hz, 1H), 7.70 (d, J=8.3 Hz, 2H), 7.36-7.18 (m, 6H), 6.27 (d, J=8.1 Hz, 1H), 2.01 (m, 3H), 1.91 (m, 6H), 1.76 (m, 6H).

Example 109

4-{(1R)-1-[(2,2-dimethylpropanoyl)amino]ethyl}-N-hydroxybenzamide Compound I-73

The title compound was prepared in an analogous fashion to that described in Example 18 starting from tert-butyl 4-[(1R)-1-{[(S)-tert-butylsulfinyl]amino}ethyl]benzoate. LC-MS: (FA) ES+ 265.

Example 110 ethyl 4-(1-amino-2-methylpropyl)benzoate

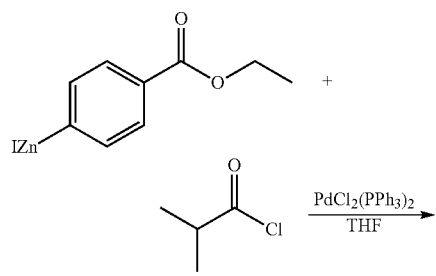

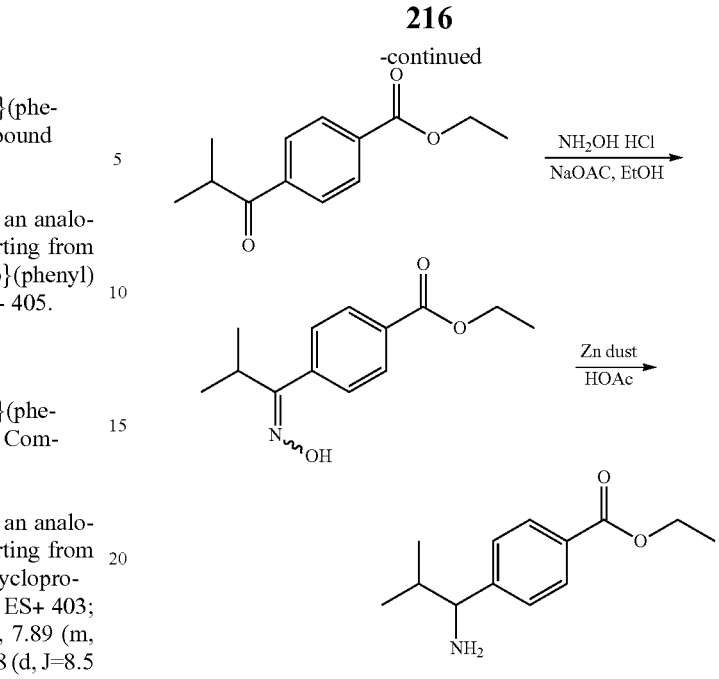

Step 1: ethyl 4-isobutyrylbenzoate

To a 100-mL round-bottom flask was added THF (25 mL). The solvent was bubbled with nitrogen for a few minutes then cooled to 0° C. and added bis(triphenylphosphine)palladium (II) chloride (0.44 g, 0.63 mmol) followed by 4-(ethoxycarbonyl)phenylzinciodide (25.0 mL, 12.5 mmol; 0.50 M in THF). After stirred at at 0° C. for 15 min, isobutyryl chloride (1.32 mL, 12.5 mmol) was added and the resulting mixture was stirred at 0° C. for 2 h. The reaction was quenched with slow addition of 1 N HCl and extracted with EtOAc (3×100 mL). After separation, combined organic extracts were washed with sat. NaHCO$_3$, water, brine, dried (MgSO$_4$), and concentrated. Flash column chromatography (EtOAc:hexanes, 0:1 to 1:9) afforded ethyl 4-isobutyrylbenzoate (2.49 g, 90%) as a slight-brown oil. LC-MS: (FA) ES+ 221; $^1$H NMR (CDCl$_3$, 400 MHz) δ8.13 (d, J=8.5 Hz, 2H), 7.99 (d, J=8.5 Hz, 2H), 4.40 (q, J=7.2 Hz, 2H), 3.56 (m, 1H), 1.42 (t, J=7.2 Hz, 3H), 1.23 (d, J=7.2 Hz, 6H).

Step 2: ethyl 4-(1-(hydroxyimino)-2-methylpropyl)benzoate

A mixture of ethyl 4-isobutyrylbenzoate (0.56 g, 2.54 mmol), hydroxylamine hydrochloride (1.06 g, 15.2 mmol), and sodium acetate (1.25 g, 15.2 mmol) in ethanol (36 mL) was heated to 36° C. for 2 h. The reaction was then concentrated and the residue was dissolved in EtOAc (200 mL). The organic phase was washed with water (2×20 mL), brine, dried (MgSO$_4$), and concentrated to give crude ethyl 4-(1-(hydroxyimino)-2-methylpropyl)benzoate as a slight-yellow solid. LC-MS: (FA) ES+ 236.

Step 3: ethyl 4-(1-amino-2-methylpropyl)benzoate

To the crude ethyl 4-(1-(hydroxyimino)-2-methylpropyl)benzoate in a 100-mL round-bottom flask was added acetic acid (8 mL) and zinc dust (1.33 g, 20.3 mmol). The mixture was stirred at rt for 1 h, then filtered through a pad of Celite. The pad was rinsed with ethanol (50 mL). Combined filtrate was concentrated to give a solid. To the solid residue was added ammonium hydroxide (20 mL) and DCM (50 mL). The solution was stirred at rt for 10 min. After separation, the aqueous layer was extracted with DCM (2×50 mL). Combined organic phases were washed with brine, dried (MgSO$_4$), and concentrated to give an oil. Flash column chromatography (EtOAc:hexanes:TEA, 20:80:2 to 100:0:2) afforded ethyl 4-(1-amino-2-methylpropyl)benzoate (0.563 g, 55%) as a clear oil. LC-MS: (FA) ES+ 222; $^1$H NMR (CDCl$_3$, 300 MHz) δ7.99 (d, J=8.3 Hz, 2H), 7.36 (d, J=8.5 Hz, 2H), 4.37 (q, J=7.2 Hz, 2 μl), 3.68 (d, J=7.0 Hz, 1H), 1.86 (m, 1H), 1.39 (t, J=7.0 Hz, 3H), 0.96 (d, J=7.0 Hz, 3H), 0.77 (d, J=7.0 Hz, 3H).

Example 111 ethyl 4-(1-amino-2,2-dimethylpropyl)benzoate

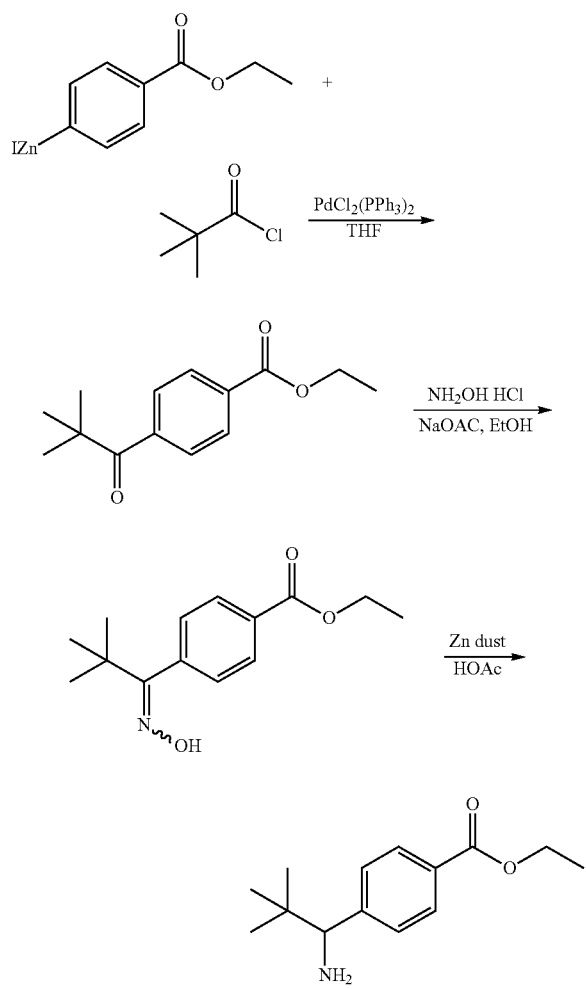

The title compound was prepared in an analogous fashion to that described in Example 110 starting from (4-(ethoxycarbonyl)phenyl)zinc(II) iodide and pivaloyl chloride. Yield: 63%; LC-MS: (FA) ES+ 236; $^1$H NMR (CDCl$_3$, 300 MHz) δ7.97 (d, J=8.3 Hz, 2H), 7.37 (d, J=8.3 Hz, 2H), 4.37 (q, J=7.0 Hz, 2H), 3.77 (s, 1H), 1.86 (m, 1H), 1.39 (t, J=7.3 Hz, 3H), 0.90 (s, 9H).

Example 112

N-(1-{4-[(hydroxyamino)carbonyl]phenyl}-2-methylpropyl)adamantane-1-carboxamide Compound I-58

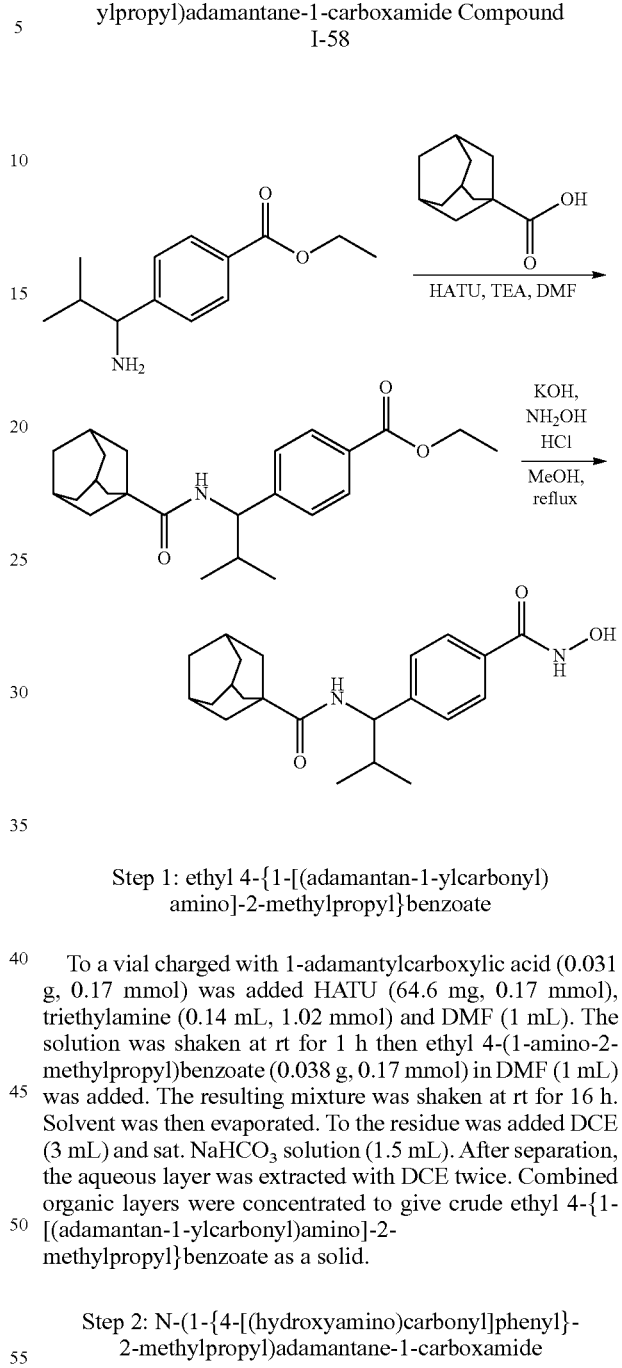

Step 1: ethyl 4-{1-[(adamantan-1-ylcarbonyl)amino]-2-methylpropyl}benzoate

To a vial charged with 1-adamantylcarboxylic acid (0.031 g, 0.17 mmol) was added HATU (64.6 mg, 0.17 mmol), triethylamine (0.14 mL, 1.02 mmol) and DMF (1 mL). The solution was shaken at rt for 1 h then ethyl 4-(1-amino-2-methylpropyl)benzoate (0.038 g, 0.17 mmol) in DMF (1 mL) was added. The resulting mixture was shaken at rt for 16 h. Solvent was then evaporated. To the residue was added DCE (3 mL) and sat. NaHCO$_3$ solution (1.5 mL). After separation, the aqueous layer was extracted with DCE twice. Combined organic layers were concentrated to give crude ethyl 4-{1-[(adamantan-1-ylcarbonyl)amino]-2-methylpropyl}benzoate as a solid.

Step 2: N-(1-{4-[(hydroxyamino)carbonyl]phenyl}-2-methylpropyl)adamantane-1-carboxamide To the crude ethyl 4-{1-[(adamantan-1-ylcarbonyl)amino]-2-methylpropyl}benzoate in a vial was added potassium hydroxide (0.11 g, 1.87 mmol), hydroxylamine hydrochloride (0.047 g, 0.68 mmol), and methanol (2 mL). The reaction was capped and heated at 80° C. for 1 h. After cooled to rt, acetic acid (0.097 mL, 1.7 mmol was added to neutralize the excess base. The solvent was then completely evaporated. To the solid was added DMSO (1.3 mL). The solution was then filtered and purified by prep-HPLC purification to give the title compound (0.009 g, 15%) as a white solid. LC-MS: (FA) ES+ 371.

Example 113

5-chloro-N-(1-{4-[(hydroxyamino)carbonyl]phenyl}-2-methylpropyl)-1-benzofuran-2-carboxamide Compound I-130

The title compound was prepared in an analogous fashion to that described in Example 112 starting from ethyl 4-(1-amino-2-methylpropyl)benzoate. LC-MS: (FA) ES+ 387.

Example 114

N-(1-{4-[(hydroxyamino)carbonyl]phenyl}-2-methylpropyl)pyrazine-2-carboxamide Compound I-203

The title compound was prepared in an analogous fashion to that described in Example 112 starting from ethyl 4-(1-amino-2-methylpropyl)benzoate. LC-MS: (FA) ES+ 315.

Example 115

N-(1-{4-[(hydroxyamino)carbonyl]phenyl}-2-methylpropyl)-5-methyl-1H-indole-2-carboxamide Compound I-69

The title compound was prepared in an analogous fashion to that described in Example 112 starting from ethyl 4-(1-amino-2-methylpropyl)benzoate. LC-MS: (FA) ES+ 366.

Example 116

N-hydroxy-4-[2-methyl-1-({[3-(trifluoromethyl)phenyl]acetyl}amino)propyl]benzamide Compound I-195

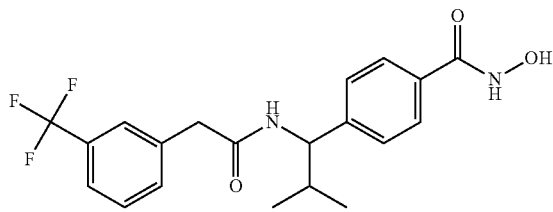 [SMILES: CC(C)C(NC(=O)Cc1cccc(C(F)(F)F)c1)c1ccc(C(=O)NO)cc1]

The title compound was prepared in an analogous fashion to that described in Example 111 starting from ethyl 4-(1-amino-2-methylpropyl)benzoate. LC-MS: (FA) ES- 393.

Example 117

N-(1-{4-[(hydroxyamino)carbonyl]phenyl}-2-methylpropyl)quinoxaline-2-carboxamide Compound I-190

The title compound was prepared in an analogous fashion to that described in Example 112 starting from ethyl 4-(1-amino-2-methylpropyl)benzoate. LC-MS: (FA) ES+ 365.

Example 118

N-(1-{4-[(hydroxyamino)carbonyl]phenyl}-2-methylpropyl)-2,1,3-benzothiadiazole-5-carboxamide Compound I-135

The title compound was prepared in an analogous fashion to that described in Example 112 starting from ethyl 4-(1-amino-2-methylpropyl)benzoate. LC-MS: (FA) ES+ 371.

Example 119

4'-fluoro-N-(1-{4-[(hydroxyamino)carbonyl]phenyl}-2-methylpropyl)biphenyl-4-carboxamide Compound I-143

The title compound was prepared in an analogous fashion to that described in Example 112 starting from ethyl 4-(1-amino-2-methylpropyl)benzoate. LC-MS: (FA) ES- 405.

Example 120

2,4,5-trifluoro-N-(1-{4-[(hydroxyamino)carbonyl]phenyl}-2-methylpropyl)benzamide Compound I-116

The title compound was prepared in an analogous fashion to that described in Example 112 starting from ethyl 4-(1-amino-2-methylpropyl)benzoate. LC-MS: (FA) ES- 365.

Example 121

N-(1-{4-[(hydroxyamino)carbonyl]phenyl}-2-methylpropyl)-1-benzofuran-2-carboxamide Compound I-32

The title compound was prepared in an analogous fashion to that described in Example 112 starting from ethyl 4-(1-amino-2-methylpropyl)benzoate. LC-MS: (FA) ES+ 353.

Example 122

N-(1-{4-[(hydroxyamino)carbonyl]phenyl}-2-methylpropyl)-4-methyl-2-phenylpyrimidine-5-carboxamide Compound I-17

The title compound was prepared in an analogous fashion to that described in Example 112 starting from ethyl 4-(1-amino-2-methylpropyl)benzoate. LC-MS: (FA) ES+ 405.

Example 123

N-(1-{4-[(hydroxyamino)carbonyl]phenyl}-2-methylpropyl)cycloheptanecarboxamide Compound I-382

The title compound was prepared in an analogous fashion to that described in Example 112 starting from ethyl 4-(1-amino-2-methylpropyl)benzoate. LC-MS: (FA) ES+ 333.

Example 124

N-(1-{4-[(hydroxyamino)carbonyl]phenyl}-2-methylpropyl)-1,3-benzothiazole-6-carboxamide Compound I-43

The title compound was prepared in an analogous fashion to that described in Example 112 starting from ethyl 4-(1-amino-2-methylpropyl)benzoate. LC-MS: (FA) ES+ 370.

Example 125

N-(1-[4-{(hydroxyamino)carbonyl]phenyl}-2-methylpropyl)-3,5-dimethylisoxazole-4-carboxamide Compound I-238

The title compound was prepared in an analogous fashion to that described in Example 112 starting from ethyl 4-(1-amino-2-methylpropyl)benzoate. LC-MS: (FA) ES+ 332.

Example 126

N-(1-{4-[(hydroxyamino)carbonyl]phenyl}-2-methylpropyl)-1,3-benzothiazole-2-carboxamide Compound I-191

The title compound was prepared in an analogous fashion to that described in Example 112 starting from ethyl 4-(1-amino-2-methylpropyl)benzoate. LC-MS: (FA) ES+ 370.

Example 127

N-(1-{4-[(hydroxyamino)carbonyl]phenyl}-2-methylpropyl)-1-naphthamide Compound I-331

The title compound was prepared in an analogous fashion to that described in Example 112 starting from ethyl 4-(1-amino-2-methylpropyl)benzoate. LC-MS: (FA) ES+ 363.

Example 128

N-hydroxy-4-(2-methyl-1-{[(5-methyl-2-phenyl-1,3-oxazol-4-yl)acetyl]amino}propyl)benzamide Compound I-48

The title compound was prepared in an analogous fashion to that described in Example 112 starting from ethyl 4-(1-amino-2-methylpropyl)benzoate. LC-MS: (FA) ES+ 408.

Example 129

4-[1-({[1-(4-chlorophenyl)cyclopropyl]carbonyl}amino)-2-methylpropyl]N-hydroxybenzamide Compound I-300

The title compound was prepared in an analogous fashion to that described in Example 112 starting from ethyl 4-(1-amino-2-methylpropyl)benzoate. LC-MS: (FA) ES+ 387.

Example 130

N-(1-[4-[(hydroxyamino)carbonyl]phenyl]-2-methylpropyl)thiophene-2-carboxamide Compound I-112

The title compound was prepared in an analogous fashion to that described in Example 112 starting from ethyl 4-(1-amino-2-methylpropyl)benzoate. LC-MS: (FA) ES+ 319.

Example 131

5-chloro-N-(1-{-4-[(hydroxyamino)carbonyl]phenyl}-2-methylpropyl)-1H-indole-2-carboxamide Compound I-247

The title compound was prepared in an analogous fashion to that described in Example 112 starting from ethyl 4-(1-amino-2-methylpropyl)benzoate. LC-MS: (FA) ES+ 386.

Example 132

N-(1-{4-[(hydroxyamino)carbonyl]phenyl}-2-methylpropyl)-1-benzofuran-5-carboxamide Compound I-194

The title compound was prepared in an analogous fashion to that described in Example 112 starting from ethyl 4-(1-amino-2-methylpropyl)benzoate. LC-MS: (FA) ES+ 353.

Example 133

4-{1-[(cyclohexylcarbonyl)amino]-2-methylpropyl}-N-hydroxybenzamide Compound I-344

The title compound was prepared in an analogous fashion to that described in Example 112 starting from ethyl 4-(1-amino-2-methylpropyl)benzoate. LC-MS: (FA) ES+ 319.

Example 134

N-(1-{4-[(hydroxyamino)carbonyl]phenyl}-2-methylpropyl)quinoline-4-carboxamide Compound I-246

The title compound was prepared in an analogous fashion to that described in Example 112 starting from ethyl 4-(1-amino-2-methylpropyl)benzoate. LC-MS: (FA) ES+ 364.

Example 135

N-(1-{4-[(hydroxyamino)carbonyl]phenyl}-2-methylpropyl)biphenyl-4-carboxamide Compound I-11

The title compound was prepared in an analogous fashion to that described in Example 112 starting from ethyl 4-(1-amino-2-methylpropyl)benzoate. LC-MS: (FA) ES+ 389.

Example 136

N-(1-{4-[(hydroxyamino)carbonyl]phenyl}-2-methylpropyl)-2,5-bis(trifluoromethyl)benzamide Compound I-155

The title compound was prepared in an analogous fashion to that described in Example 112 starting from ethyl 4-(1-amino-2-methylpropyl)benzoate. LC-MS: (FA) ES– 447.

Example 137

N-(1-{4-[(hydroxyamino)carbonyl]phenyl}-2-methylpropyl)-7-methoxy-1-benzofuran-2-carboxamide Compound I-306

The title compound was prepared in an analogous fashion to that described in Example 112 starting from ethyl 4-(1-amino-2-methylpropyl)benzoate. LC-MS: (FA) ES+ 383.

Example 138

N-(1-{4-[(hydroxyamino)carbonyl]phenyl}-2-methylpropyl)-3,5-bis(trifluoromethyl)benzamide Compound I-173

The title compound was prepared in an analogous fashion to that described in Example 112 starting from ethyl 4-(1-amino-2-methylpropyl)benzoate. LC-MS: (FA) ES– 447.

Example 139

4-{1-[(diphenylacetyl)amino]-2-methylpropyl}-N-hydroxybenzamide Compound I-204

The title compound was prepared in an analogous fashion to that described in Example 112 starting from ethyl 4-(1-amino-2-methylpropyl)benzoate. LC-MS: (FA) ES+ 403.

Example 140

4-tert-butyl-N-(1-{4-[(hydroxyamino)carbonyl]phenyl}-2-methylpropyl)benzamide Compound I-192

The title compound was prepared in an analogous fashion to that described in Example 112 starting from ethyl 4-(1-amino-2-methylpropyl)benzoate. LC-MS: (FA) ES+ 369.

Example 141

3,5-bis(acetylamino)-N-(1-{4-[(hydroxyamino)carbonyl]phenyl}-2-methylpropyl)benzamide Compound I-282

The title compound was prepared in an analogous fashion to that described in Example 112 starting from ethyl 4-(1-amino-2-methylpropyl)benzoate. LC-MS: (FA) ES+ 427.

Example 142

N-hydroxy-4-{2-methyl-1-[(3-methyl-2-phenylbutanoyl)amino]propyl}benzamide Compound I-289

The title compound was prepared in an analogous fashion to that described in Example 112 starting from ethyl 4-(1-amino-2-methylpropyl)benzoate. LC-MS: (FA) ES+ 369.

Example 143

N-(1-(4-(hydroxycarbamoyl)phenyl)-2-methylpropyl)-2,5-dimethylfuran-3-carboxamide Compound I-252

The title compound was prepared in an analogous fashion to that described in Example 112 starting from ethyl 4-(1-amino-2-methylpropyl)benzoate. LC-MS: (FA) ES+ 331.

Example 144

N-hydroxy-4-(2-methyl-1-(2-(2,4,7-trimethyl-1H-indol-3-yl)acetamido)propyl)benzamide Compound I-220

The title compound was prepared in an analogous fashion to that described in Example 112 starting from ethyl 4-(1-amino-2-methylpropyl)benzoate. LC-MS: (FA) ES+ 408.

Example 145

N-hydroxy-4-(1-(4-methoxybenzamido)-2-methylpropyl)benzamide Compound I-346

The title compound was prepared in an analogous fashion to that described in Example 112 starting from ethyl 4-(1-amino-2-methylpropyl)benzoate. LC-MS: (FA) ES+ 343.

Example 146

N-(1-(4-(hydroxycarbamoyl)phenyl)-2-methylpropyl)-2-methyl-4-(trifluoromethyl)thiazole-5-carboxamide Compound I-139

The title compound was prepared in an analogous fashion to that described in Example 112 starting from ethyl 4-(1-amino-2-methylpropyl)benzoate. LC-MS: (FA) ES– 400.

Example 147

N-(1-(4-(hydroxycarbamoyl)phenyl)-2-methylpropyl)-2-phenylthiazole-4-carboxamide Compound I-172

The title compound was prepared in an analogous fashion to that described in Example 112 starting from ethyl 4-(1-amino-2-methylpropyl)benzoate. LC-MS: (FA) ES+ 396.

Example 148

1-benzyl-3-tert-butyl-N-(1-[4-{(hydroxyamino)carbonyl]phenyl}-2-methylpropyl)-1H-pyrazole-5-carboxamide Compound I-77

The title compound was prepared in an analogous fashion to that described in Example 112 starting from ethyl 4-(1-amino-2-methylpropyl)benzoate. LC-MS: (FA) ES+ 449.

Example 149

N-hydroxy-4-{1-[(mesitylacetyl)amino]-2-methylpropyl}benzamide Compound I-28

The title compound was prepared in an analogous fashion to that described in Example 112 starting from ethyl 4-(1-amino-2-methylpropyl)benzoate. LC-MS: (FA) ES+ 369.

Example 150

N-(1-{4-[(hydroxyamino)carbonyl]phenyl}-2-methylpropyl)-2-oxo-6-phenyl-1,2-dihydropyridine-3-carboxamide Compound I-375

The title compound was prepared in an analogous fashion to that described in Example 112 starting from ethyl 4-(1-amino-2-methylpropyl)benzoate. LC-MS: (FA) ES+ 406.

Example 151

N-(1-{4-[(hydroxyamino)carbonyl]phenyl}-2-methylpropyl)-1-methyl-1H-pyrazole-3-carboxamide Compound I-389

The title compound was prepared in an analogous fashion to that described in Example 112 starting from ethyl 4-(1-amino-2-methylpropyl)benzoate. LC-MS: (FA) ES+ 317.

Example 152

4-[1-({[3,5-bis(trifluoromethyl)phenyl]acetyl}amino)-2-methylpropyl]-N-hydroxybenzamide Compound I-250

The title compound was prepared in an analogous fashion to that described in Example 112 starting from ethyl 4-(1-amino-2-methylpropyl)benzoate. LC-MS: (FA) ES+ 461.

Example 153

N-(1-{4-[(hydroxyamino)carbonyl]phenyl}-2-methylpropyl)-1-benzothiophene-2-carboxamide Compound I-94

The title compound was prepared in an analogous fashion to that described in Example 112 starting from ethyl 4-(1-amino-2-methylpropyl)benzoate. LC-MS: (FA) ES+ 369.

Example 154

4-{1-[(cyclopentylcarbonyl)amino]-2-methylpropyl}-N-hydroxybenzamide Compound I-255

The title compound was prepared in an analogous fashion to that described in Example 112 starting from ethyl 4-(1-amino-2-methylpropyl)benzoate. LC-MS: (FA) ES+ 305.

Example 155

N-hydroxy-4-(2-methyl-1-{[(1-phenylcyclopentyl)carbonyl]amino}propyl)benzamide Compound I-258

The title compound was prepared in an analogous fashion to that described in Example 112 starting from ethyl 4-(1-amino-2-methylpropyl)benzoate. LC-MS: (FA) ES+ 381.

Example 156

N-hydroxy-4-(2-methyl-1-{[(2-methyl-1H-indol-3-yl)acetyl]amino}propyl)benzamide Compound I-174

The title compound was prepared in an analogous fashion to that described in Example 112 starting from ethyl 4-(1-amino-2-methylpropyl)benzoate. LC-MS: (FA) ES+ 380.

Example 157

4-(1-{[(5-chloro-1-benzothien-3-yl)acetyl]amino}-2-methylpropyl)-N-hydroxybenzamide Compound I-206

The title compound was prepared in an analogous fashion to that described in Example 112 starting from ethyl 4-(1-amino-2-methylpropyl)benzoate. LC-MS: (FA) ES+ 417.

Example 158

4-fluoro-N-(1-{4-[(hydroxyamino)carbonyl]phenyl}-2-methylpropyl)benzamide Compound I-40

The title compound was prepared in an analogous fashion to that described in Example 112 starting from ethyl 4-(1-amino-2-methylpropyl)benzoate. LC-MS: (FA) ES− 329.

Example 159

N-(1-{4-[(hydroxyamino)carbonyl]phenyl}-2,2-dimethylpropyl)adamantane-1-carboxamide Compound I-162

The title compound was prepared in an analogous fashion to that described in Example 112 starting from ethyl 4-(1-amino-2,2-dimethylpropyl)benzoate. LC-MS: (FA) ES+ 385.

Example 160

N-(1-{4-[(hydroxyamino)carbonyl]phenyl}-2,2-dimethylpropyl)-1-methyl-1H-pyrazole-3-carboxamide Compound I-66

The title compound was prepared in an analogous fashion to that described in Example 112 starting from ethyl 4-(1-amino-2,2-dimethylpropyl)benzoate. LC-MS: (FA) ES+ 331.

Example 161

N-(1-{4-[(hydroxyamino)carbonyl]phenyl}-2,2-dimethylpropyl)-1-benzothiophene-2-carboxamide Compound I-308

The title compound was prepared in an analogous fashion to that described in Example 112 starting from ethyl 4-(1-amino-2,2-dimethylpropyl)benzoate. LC-MS: (FA) ES+ 383.

Example 162

4-(1-{[(5-chloro-1-benzothien-3-yl)acetyl]amino}-2,2-dimethylpropyl)-N-hydroxybenzamide Compound I-345

The title compound was prepared in an analogous fashion to that described in Example 112 starting from ethyl 4-(1-amino-2,2-dimethylpropyl)benzoate. LC-MS: (FA) ES+ 431.

Example 163

5-chloro-N-(1-{4-[(hydroxyamino)carbonyl]phenyl}-2,2-dimethylpropyl)-1-benzofuran-2-carboxamide Compound I-270

The title compound was prepared in an analogous fashion to that described in Example 112 starting from ethyl 4-(1-amino-2,2-dimethylpropyl)benzoate. LC-MS: (FA) ES+ 401.

Example 164

N-(1-{4-[(hydroxyamino)carbonyl]phenyl}-2,2-dimethylpropyl)-4-methoxybenzamide Compound I-352

The title compound was prepared in an analogous fashion to that described in Example 112 starting from ethyl 4-(1-amino-2,2-dimethylpropyl)benzoate. LC-MS: (FA) ES+ 357.

Example 165

4-(2,2-dimethyl-1-{[4-(trifluoromethyl)benzoyl]amino}propyl)-N-hydroxybenzamide Compound I-303

The title compound was prepared in an analogous fashion to that described in Example 112 starting from ethyl 4-(1-amino-2,2-dimethylpropyl)benzoate. LC-MS: (FA) ES− 393.

Example 166

3-ethyl-N-(1-{4-[(hydroxyamino)carbonyl]phenyl}-2,2-dimethylpropyl)-1-methyl-1H-pyrazole-5-carboxamide Compound I-318

The title compound was prepared in an analogous fashion to that described in Example 112 starting from ethyl 4-(1-amino-2,2-dimethylpropyl)benzoate. LC-MS: (FA) ES+ 359.

Example 167

N-(1-{4-[hydroxyamino)carbonyl]phenyl}-2,2-dimethylpropyl)-1-methyl-1H-pyrrole-2-carboxamide Compound I-133

The title compound was prepared in an analogous fashion to that described in Example 112 starting from ethyl 4-(1-amino-2,2-dimethylpropyl)benzoate. LC-MS: (FA) ES+ 330.

Example 168

N-(1-{4-[hydroxyamino)carbonyl]phenyl}-2,2-dimethylpropyl)-1,3-dimethyl-1H-pyrazole-4-carboxamide Compound I-86

The title compound was prepared in an analogous fashion to that described in Example 112 starting from ethyl 4-(1-amino-2,2-dimethylpropyl)benzoate. LC-MS: (FA) ES+ 345.

Example 169

4-[1-({[1-(4-chlorophenyl)cyclopropyl]carbonyl}amino)-2,2-dimethylpropyl]-N-hydroxybenzamide Compound I-41

The title compound was prepared in an analogous fashion to that described in Example 112 starting from ethyl 4-(1-amino-2,2-dimethylpropyl)benzoate. LC-MS: (FA) ES+ 401.

Example 170

N-(1-{4-[(hydroxyamino)carbonyl]phenyl}-2,2-dimethylpropyl)-3,5-dimethyl-1H-pyrrole-2-carboxamide Compound I-262

The title compound was prepared in an analogous fashion to that described in Example 112 starting from ethyl 4-(1-amino-2,2-dimethylpropyl)benzoate. LC-MS: (FA) ES+ 344.

Example 171

N-(1-{4-[(hydroxyamino)carbonyl]phenyl}-2,2-dimethylpropyl)-1-methyl-1H-indole-2-carboxamide Compound I-364

The title compound was prepared in an analogous fashion to that described in Example 112 starting from ethyl 4-(1-amino-2,2-dimethylpropyl)benzoate. LC-MS: (FA) ES+ 385.

Example 172

N-(1-{4-[(hydroxyamino)carbonyl]phenyl}-2,2-dimethylpropyl)pyrazine-2-carboxamide Compound I-87

The title compound was prepared in an analogous fashion to that described in Example 112 starting from ethyl 4-(1-amino-2,2-dimethylpropyl)benzoate. LC-MS: (FA) ES+ 329.

Example 173

N-(1-{4-[(hydroxyamino)carbonyl]phenyl}-2,2-dimethylpropyl)-2-methyl-4,5,6,7-tetrahydro-2H-indazole-3-carboxamide Compound I-211

The title compound was prepared in an analogous fashion to that described in Example 112 starting from ethyl 4-(1-amino-2,2-dimethylpropyl)benzoate. LC-MS: (FA) ES+ 385.

Example 174

N-(1-(4-(hydroxycarbamoyl)phenyl)-2,2-dimethylpropyl)-2-(trifluoromethyl)benzamide Compound I-535

The title compound was prepared in an analogous fashion to that described in Example 112 starting from ethyl 4-(1-amino-2,2-dimethylpropyl)benzoate. LC-MS: (FA) ES– 393.

Example 175

4-(2,2-dimethyl-1-{[(5-methyl-2-phenyl-1,3-oxazol-4-yl)acetyl]amino}propyl)-N-hydroxybenzamide Compound I-80

The title compound was prepared in an analogous fashion to that described in Example 111 starting from ethyl 4-(1-amino-2,2-dimethylpropyl)benzoate. LC-MS: (FA) ES+ 422.

Example 176

3,5-difluoro-N-(1-{4-[(hydroxyamino)carbonyl]phenyl}-2,2-dimethylpropyl)benzamide Compound I-251

The title compound was prepared in an analogous fashion to that described in Example 112 starting from ethyl 4-(1-amino-2,2-dimethylpropyl)benzoate. LC-MS: (FA) ES– 361.

Example 177

N-(1-{4-[(hydroxyamino)carbonyl]phenyl}-2,2-dimethylpropyl)-2,5-dimethyl-3-furamide Compound I-9

The title compound was prepared in an analogous fashion to that described in Example 112 starting from ethyl 4-(1-amino-2,2-dimethylpropyl)benzoate. LC-MS: (FA) ES+ 345.

Example 178

N-(1-{4-[(hydroxyamino)carbonyl]phenyl}-2,2-dimethylpropyl)-2,5-dimethyl-1H-pyrrole-3-carboxamide Compound I-310

The title compound was prepared in an analogous fashion to that described in Example 112 starting from ethyl 4-(1-amino-2,2-dimethylpropyl)benzoate. LC-MS: (FA) ES+ 344.

Example 179

N-(1-{4-[(hydroxyamino)carbonyl]phenyl}-2,2-dimethylpropyl)thiophene-2-carboxamide Compound I-215

The title compound was prepared in an analogous fashion to that described in Example 112 starting from ethyl 4-(1-amino-2,2-dimethylpropyl)benzoate. LC-MS: (FA) ES+ 333.

Example 180

N-(1-{4-[(hydroxyamino)carbonyl]phenyl}-2,2-dimethylpropyl)-1-benzothiophene-3-carboxamide Compound I-158

The title compound was prepared in an analogous fashion to that described in Example 112 starting from ethyl 4-(1-amino-2,2-dimethylpropyl)benzoate. LC-MS: (FA) ES+ 383.

Example 181

4-tert-butyl-N-(1-{4-[(hydroxyamino)carbonyl]phenyl}-2,2-dimethylpropyl)benzamide Compound I-377

The title compound was prepared in an analogous fashion to that described in Example 112 starting from ethyl 4-(1-amino-2,2-dimethylpropyl)benzoate. LC-MS: (FA) ES+ 383.

Example 182

N-(1-{4-[(hydroxyamino)carbonyl]phenyl}-2,2-dimethylpropyl)-3,5-dimethyl-1H-indole-2-carboxamide Compound I-329

The title compound was prepared in an analogous fashion to that described in Example 112 starting from ethyl 4-(1-amino-2,2-dimethylpropyl)benzoate. LC-MS: (FA) ES+ 394.

Example 183

N-(1-{4-[(hydroxyamino)carbonyl]phenyl}-2,2-dimethylpropyl)-1,5-dimethyl-1H-pyrazole-3-carboxamide Compound I-260

The title compound was prepared in an analogous fashion to that described in Example 112 starting from ethyl 4-(1-amino-2,2-dimethylpropyl)benzoate. LC-MS: (FA) ES+ 345.

Example 184

4-{1-[(3,3-dimethylbutanoyl)amino]-2,2-dimethylpropyl}-N-hydroxybenzamide Compound I-396

The title compound was prepared in an analogous fashion to that described in Example 112 starting from ethyl 4-(1-amino-2,2-dimethylpropyl)benzoate. LC-MS: (FA) ES+ 307.

Example 185

N-(1-{4-[(hydroxyamino)carbonyl]phenyl}-2,2-dimethylpropyl)-1H-indole-3-carboxamide Compound I-319

The title compound was prepared in an analogous fashion to that described in Example 112 starting from ethyl 4-(1-amino-2,2-dimethylpropyl)benzoate. LC-MS: (FA) ES+ 366.

Example 186

3-tert-butyl-N-(1-{4-[(hydroxyamino)carbonyl]phenyl}-2,2-dimethylpropyl)-1-methyl-1H-pyrazole-5-carboxamide Compound I-291

The title compound was prepared in an analogous fashion to that described in Example 112 starting from ethyl 4-(1-amino-2,2-dimethylpropyl)benzoate. LC-MS: (FA) ES+ 387.

Example 187

N-(1-{4-[(hydroxyamino)carbonyl]phenyl}-2,2-dimethylpropyl)-1-benzofuran-2-carboxamide Compound I-4

The title compound was prepared in an analogous fashion to that described in Example 112 starting from ethyl 4-(1-amino-2,2-dimethylpropyl)benzoate. LC-MS: (FA) ES+ 367.

Example 188

N-(1-{4-[(hydroxyamino)carbonyl]phenyl}-2,2-dimethylpropyl)-3,5-dimethylisoxazole-4-carboxamide Compound I-200

The title compound was prepared in an analogous fashion to that described in Example 112 starting from ethyl 4-(1-amino-2,2-dimethylpropyl)benzoate. LC-MS: (FA) ES+ 346.

Example 189

N-(1-{4-[(hydroxyamino)carbonyl]phenyl}-2,2-dimethylpropyl)-5-methyl-1H-indole-2-carboxamide Compound I-129

The title compound was prepared in an analogous fashion to that described in Example 112 starting from ethyl 4-(1-amino-2,2-dimethylpropyl)benzoate. LC-MS: (FA) ES+ 380.

Example 190

N-(1-{4-[(hydroxyamino)carbonyl]phenyl}-2,2-dimethylpropyl)biphenyl-4-carboxamide Compound I-355

The title compound was prepared in an analogous fashion to that described in Example 112 starting from ethyl 4-(1-amino-2,2-dimethylpropyl)benzoate. LC-MS: (FA) ES+ 403.

Example 191

N-(1-{4-[(hydroxyamino)carbonyl]phenyl}-2,2-dimethylpropyl)-1-methyl-1H-indole-5-carboxamide Compound I-145

The title compound was prepared in an analogous fashion to that described in Example 112 starting from ethyl 4-(1-amino-2,2-dimethylpropyl)benzoate. LC-MS: (FA) ES+ 380.

Example 192

N-(1-{4-[(hydroxyamino)carbonyl]phenyl}-2,2-dimethylpropyl)-1,3-thiazole-4-carboxamide Compound I-123

The title compound was prepared in an analogous fashion to that described in Example 112 starting from ethyl 4-(1-amino-2,2-dimethylpropyl)benzoate. LC-MS: (FA) ES+ 334.

Example 193

4-{1-[(cyclohexylcarbonyl)amino]-2,2-dimethylpropyl}-N-hydroxybenzamide Compound I-265

The title compound was prepared in an analogous fashion to that described in Example 112 starting from ethyl 4-(1-amino-2,2-dimethylpropyl)benzoate. LC-MS: (FA) ES+ 333.

Example 194

N-(1-{4-[(hydroxyamino)carbonyl]phenyl}-2,2-dimethylpropyl)-2-methyl-1,3-thiazole-4-carboxamide Compound I-42

The title compound was prepared in an analogous fashion to that described in Example 112 starting from ethyl 4-(1-amino-2,2-dimethylpropyl)benzoate. LC-MS: (FA) ES+ 348.

Example 195

N-(1-{4-[(hydroxyamino)carbonyl]phenyl}-2,2-dimethylpropyl)-5-methyl-1-phenyl-1H-pyrazole-4-carboxamide Compound I-182

The title compound was prepared in an analogous fashion to that described in Example 112 starting from ethyl 4-(1-amino-2,2-dimethylpropyl)benzoate. LC-MS: (FA) ES+ 407.

Example 196

N-(1-{4-[(hydroxyamino)carbonyl]phenyl}-2,2-dimethylpropyl)-1-methyl-1H-indole-3-carboxamide Compound I-107

The title compound was prepared in an analogous fashion to that described in Example 112. starting from ethyl 4-(1-amino-2,2-dimethylpropyl)benzoate. LC-MS: (FA) ES+ 380.

Example 197

N-(1-[4-{(hydroxyamino)carbonyl]phenyl}-2,2-dimethylpropyl)-1H-indole-2-carboxamide Compound I-127

The title compound was prepared in an analogous fashion to that described in Example 112 starting from ethyl 4-(1-amino-2,2-dimethylpropyl)benzoate. LC-MS: (FA) ES+ 366.

Example 198

4-{1-[(cyclopentylcarbonyl)amino]-2,2-dimethylpropyl}-N-hydroxybenzamide Compound I-373

The title compound was prepared in an analogous fashion to that described in Example 112 starting from ethyl 4-(1-amino-2,2-dimethylpropyl)benzoate. LC-MS: (FA) ES+ 319.

Example 199

N-(1-{4-[(hydroxyamino)carbonyl]phenyl}-2,2-dimethylpropyl)-3,5-bis(trifluoromethyl)benzamide Compound I-52

The title compound was prepared in an analogous fashion to that described in Example 112 starting from ethyl 4-(1-amino-2,2-dimethylpropyl)benzoate. LC-MS: (FA) ES− 461.

Example 200

N-(1-{4-[(hydroxyamino)carbonyl]phenyl}-2,2-dimethylpropyl)-3-(methylsulfonyl)benzamide Compound I-75

The title compound was prepared in an analogous fashion to that described in Example 112 starting from ethyl 4-(1-amino-2,2-dimethylpropyl)benzoate. LC-MS: (FA) ES+ 405.

Example 201 methyl 4-(1-(hydroxyimino)ethyl)benzoate

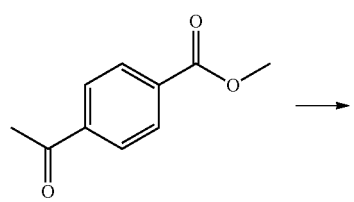

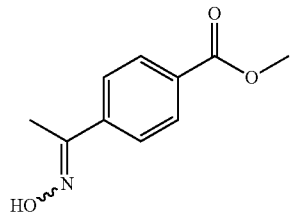

A mixture of 4-acetylbenzoic acid methyl ester (1.0 g, 5.6 mmol), hydroxylamine hydrochloride (3.1 g, 45 mmol) and sodium acetate (3.7 g, 45 mmol) in methanol (50 mL) was heated at 40° C. for 2 hours. The mixture was evaporated to dryness and the residue partitioned between EtOAc (40 mL) and water (40 mL). The organic layer was washed with brine (40 mL), dried over anhydrous $MgSO_4$ and evaporated to dryness to afford the title compound as a white solid (1.04 g, 96%). LC-MS: (FA) ES+ 194; $^1$H NMR (400 MHz, MeOD) δ 8.02-7.98 (m, 2H), 7.78-7.75 (m, 2H), 3.90 (s, 3H), 2.24 (s, 3H).

Example 202 methyl 4-(1-aminoethyl)benzoate hydrochloride

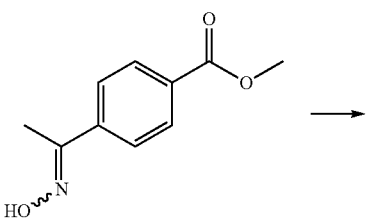

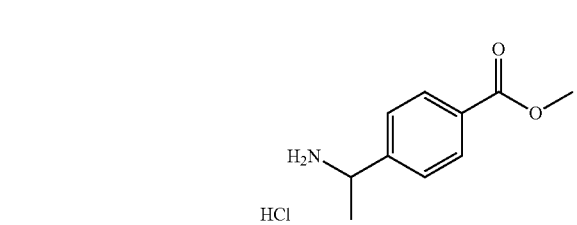

To a degassed solution of methyl 4-(1-(hydroxyimino)ethyl)benzoate (1.1 g, 5.6 mmol) and 12.0 M of hydrochloric acid in water (0.6 mL, 7.3 mmol) in methanol (50 mL) was added 10% palladium on carbon (0.20 g, 0.18 mmol). The reaction mixture was stirred overnight at room temperature. All insolubles were removed via filtration through celite and subsequent evaporation of the filtrate to dryness afforded the title compound as a white solid (1.12 g, 83%). LC-MS: (FA) ES+ 180; $^1$H NMR (400 MHz, MeO D) δ 8.09 (d, J=8.4 Hz, 1H), 7.58 (d, J=8.4 Hz, 1H), 4.55 (q, J=6.8 Hz, 1H), 3.91 (s, 3H), 1.65 (d, J=6.9 Hz, 3H).

Example 203 methyl 4-acetyl-3-methylbenzoate

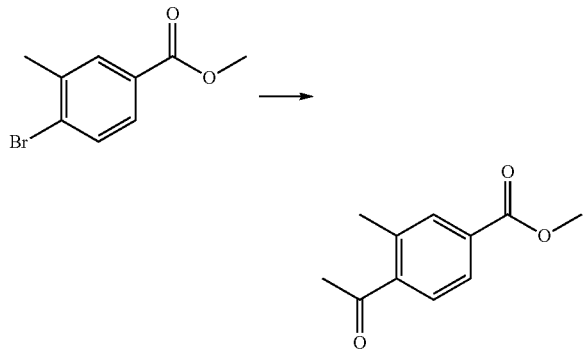

Methyl 4-bromo-methylbenzoate (2.146 g, 9.368 mmol), 1,3-bis(diphenylphosphino)propane (0.21 g, 0.52 mmol), sodium carbonate (2.19 g, 20.6 mmol) and palladium (II) acetate (0.10 g, 0.47 mmol) were combined in a vial and purged with argon. Methanol (10.7 mL, 265 mmol) and n-butyl vinyl ether (4.83 mL, 37.5 mmol) were added by syringe. The resulting mixture was further sonicated under argon flow for several minutes then heated at 90° C. overnight. Upon cooling to room temperature, the reaction was diluted with methanol (10 mL). Celite (2 g) was added, the mixture thoroughly homogenized and filtered. The filter cake was washed with several mL of methanol. To the red/brown methanolic filtrate was added 6M aqueous HCl (6.5 mL). The solution turned yellow and then turbid white over stirring at room temperature (0.3 h). The solvent was removed under reduced pressure and the residue obtained was partitioned between ethyl acetate (75 mL) and water (30 mL). The aqueous phase was extracted with ethyl acetate (30 mL). The extracts were combined, washed with saturated aqueous sodium bicarbonate then brine, dried over sodium sulfate, filtered and concentrated under reduced pressure. The crude residue was dried in vacuo to remove butanol. The residue was purified by silica gel chromatography (5-20% EtOAC/hexanes gradient) to afford the title compound as an off-white solid (1.49 g, 83%). LC-MS: (FA) ES+ 193; $^1$H NMR (400 MHz, DMSO) δ 7.89-7.83 (m, 3H), 3.86 (s, 3H), 2.57 (s, 3H), 2.44 (s, 3H).

Example 204 methyl 4-(1-(hydroxyimino)ethyl)-3-methylbenzoate

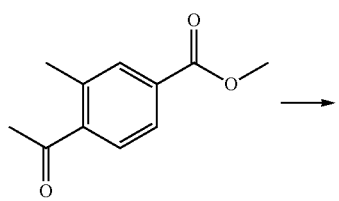

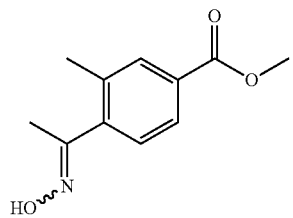

Methyl 4-acetyl-3-methylbenzoate (1.49 g, 7.76 mmol), hydroxylamine hydrochloride (4.18 g, 60.1 mmol), and sodium acetate (4.93 g, 60.1 mmol) were suspended in methanol (40 mL) and the reaction mixture heated at 40° C. for 2 h. Upon cooling to room temperature the solvent was removed under reduced pressure. The residue obtained was partitioned between ethyl acetate (75 mL) and water (30 mL). The organic extract was washed with water (20 mL) and brine. The washed extract was dried over sodium sulfate, filtered and concentrated under reduced pressure to afford the title compound as a solid (1.61 g, 100%). LC-MS: (FA) ES+ 208; $^1$H NMR (300 MHz, MeO D) δ 7.91-7.77 (m, 2H), 7.31 (d, J=8.0 Hz, 0.7H), 7.16 (d, J=7.9 Hz, 0.3H), 3.89 (s, 3H), 2.37 (s, 2H), 2.28 (s, 1H), 2.17 (s, 2H), 2.10 (s, 1H).

Example 205

Methyl 4-(1-aminoethyl)-3-methylbenzoate hydrochloride

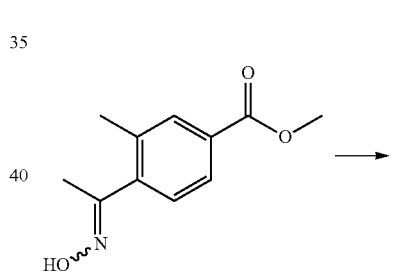

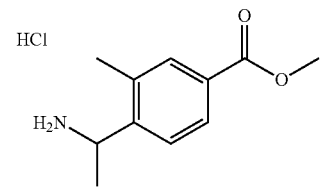

To a degassed solution of methyl 4-[N-hydroxyethanimidoyl]-3-methylbenzoate (0.348 g, 1.68 mmol) and 12.0 M aqueous hydrochloric acid (0.35 mL, 4.20 mmol) in methanol (15 mL) was added 10% palladium on carbon (0.11 g, 0.101 mmol). The reaction mixture was stirred under a balloon atmosphere of H$_2$ overnight. All insolubles were then removed via filtration through celite and the filtrate was evaporated to dryness. The residue was redissolved in methanol/toluene and concentrated under reduced pressure to afford a white solid (0.385 g, 100%). LC-MS: (FA) ES+ 195; $^1$H NMR (300 MHz, DMSO) δ 7.15 (m Hz, 2H), 6.73 (d, J=8.1 Hz, 1H), 6.45-6.26 (m, 1H), 3.96 (dd, J=13.7, 6.9 Hz, 1H), 3.10 (s, 3H), 1.67 (s, 3H), 0.80 (d, J=6.8 Hz, 3H).

Example 206 methyl 4-acetyl-3-methoxybenzoate

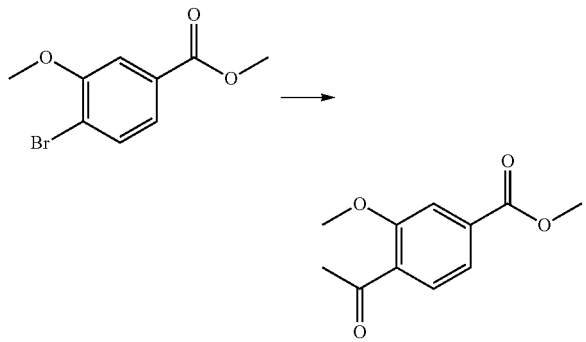

Methyl 4-bromo-3-methoxybenzoate (0.53 g, 2.2 mmol), 1,3-bis(diphenylphosphino)propane (0.050 g, 0.12 mmol), sodium carbonate (0.510 g, 4.81 mmol) and palladium (II) acetate (0.024 g, 0.11 mmol) were combined in a 5 mL microwave vial. The vial was sealed and purged with argon. Methanol (2.50 mL, 61.7 mmol) and n-butyl vinyl ether (1.12 mL, 8.74 mmol) were added by syringe, and the mixture was sonicated under argon flow for several minutes, then heated to 90° C. over night. Upon cooling to room temperature, celite (1 g) was added. The mixture was diluted with methanol (5 mL) and the slurry was then filtered. The filter cake was washed with methanol and to the pale red/brown methanolic filtrate was added 6M aqueous HCl (2.5 mL). The solution turned yellow and then turbid white over stirring at room temperature (0.5 h). The solvent was removed under reduced pressure and the residue obtained was partitioned between ethyl acetate (50 mL) and half-saturated aqueous sodium bicarbonate solution (25 mL). The aqueous phase was extracted with ethyl acetate (30 mL). The organic extracts were combined, washed with brine, dried over sodium sulfate, filtered and concentrated under reduced pressure. The residue was purified by silica gel chromatography (15-85% EtOAc/hexanes gradient) to afford the title compound (0.396 g, 87%). LC-MS: (FA) ES+ 209; $^1$H NMR (300 MHz, DMSO) δ 7.69-7.53 (m, 3H), 3.94 (s, 3H), 3.88 (s, 3H), 2.54 (s, 3H).

Example 207 methyl 4-(1-(hydroxyimino)ethyl)-3-methoxybenzoate

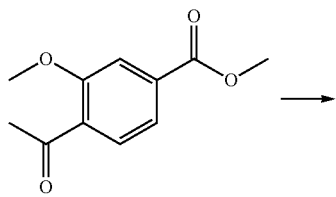

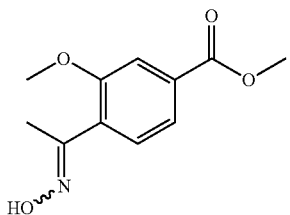

Methyl 4-acetyl-3-methoxybenzoate (0.396 g, 1.90 mmol), hydroxylamine hydrochloride (1.02 g, 14.7 mmol), and sodium acetate (1.21 g, 14.7 mmol) were suspended in methanol (10 mL) and the reaction mixture heated at 40° C. for 4 h. Upon cooling to room temperature the solvent was removed under reduced pressure. The residue obtained was partitioned between ethyl acetate (80 mL) and water (30 mL). The organic extract was washed with water (25 mL) and brine. The washed extract was dried over sodium sulfate, filtered and concentrated under reduced pressure to afford the title compound as a solid (0.417 g, 98%). LC-MS: (FA) ES+ 224; $^1$H NMR (400 MHz, DMSO) δ 11.22 (s, 1H), 7.61-7.49 (m, 2H), 7.34 (d, J=7.7 Hz, 1H), 3.86 (s, 6H), 2.05 (s, 3H).

Example 208 methyl 4-(1-aminoethyl)-3-methoxybenzoate hydrochloride

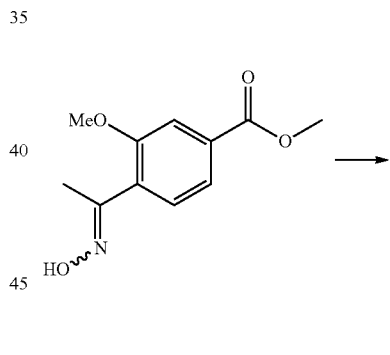

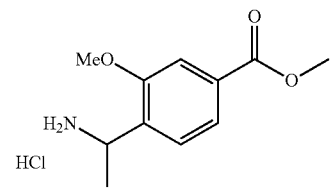

To a degassed solution of methyl 4-(1-(hydroxyimino)ethyl)-3-methoxybenzoate (0.417 g, 1.87 mmol) in methanol (17 mL) was added 12.0 M aqueous hydrochloric acid (0.389 mL, 4.67 mmol) and 10% palladium on carbon (0.120 g, 0.113 mmol). The reaction mixture was stirred under a balloon atmosphere of H$_2$ overnight. The catalyst was removed via filtration through celite and evaporation of the filtrate to dryness afforded the title compound (0.471 g, 100%). LC-MS: (FA) ES+ 209; $^1$H NMR (300 MHz, DMSO) δ 8.20 (s, 3H), 7.64 (m, 1H), 7.55 (s, 2H), 4.60 (m, 1H), 3.91 (s, 3H), 3.86 (s, 3H), 1.46 (d, J=6.9 Hz, 3H).

Example 209

N-(1-{4-[(hydroxyamino)carbonyl]phenyl}ethyl)-1-methyl-1H-pyrrole-2-carboxamide Compound I-356

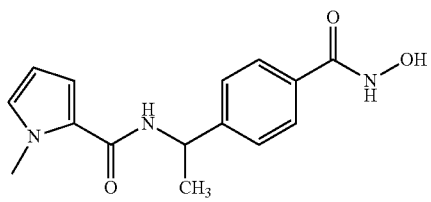 [SMILES: CC(NC(=O)c1cccn1C)c1ccc(C(=O)NO)cc1]

To a solution of N-methylpyrrole-2-carboxylic acid (0.032 g, 0.26 mmol) and methyl 4-(1-aminoethyl)benzoate hydrochloride (50 mg, 0.23 mmol) in methylene chloride (2 mL) was added N,N,N',N'-tetramethyl-O-(7-azabenzotriazol-1-yl)uronium hexafluorophosphate (0.106 g, 0.278 mmol) and N-methylmorpholine (0.0586 g, 0.58 mmol) respectively. The resulting mixture was stirred at room temperature overnight. The reaction was evaporated to dryness and the residue obtained was partitioned between DCE (3 mL) and saturated aqueous NaHCO₃ (1 mL). The layers were seperated and the aqueous layer was washed with additional DCE (3 mL). The combined organic layers were concentrated. The residue was taken up in anhydrous methanol (2 mL) to which was added potassium hydroxide (0.10 g, 1.8 mmol) and hydroxylamine hydrochloride (0.0805 g, 1.16 mmol). The mixture was stirred at room temperature for 30 minutes then heated to 80° C. for 5 hours. The reaction was neutralized by the addition of formic acid (0.0673 mL, 1.78 mmol) and the solution purified using prep-HPLC. Concentration of fractions containing desired product afforded the title compound as a white solid (11.3 mg, 17%). LC-MS: (FA) ES+ 288; $^1$H NMR (400 MHz, DMSO) δ 11.10 (s, 1H), 9.00 (s, 1H), 8.31 (d, J=8.0 Hz, 1H), 7.68 (d, J=8.3 Hz, 2H), 7.41 (d, J=8.2 Hz, 2H), 6.92 (dd, J=3.9, 1.7 Hz, 1H), 6.88 (t, J=2.1 Hz, 1H), 6.01 (dd, J=3.9, 2.5 Hz, 1H), 3.77 (s, 3H), 1.43 (d, J=7.1 Hz, 3H).

The following compounds were prepared in an analogous fashion to Example 209.

4-{1-[(2,2-dimethylpropanoyl)amino]ethyl}-N-hydroxybenzamide Compound I-59: LCMS: (FA) ES+ 265

6-chloro-N-(1-{4-[(hydroxyamino)carbonyl]phenyl}ethyl) imidazo[1,2-a]pyridine-2-carboxamide Compound I-35: LCMS: (FA) ES+ 360

4-[1-({[1-(4-chlorophenyl)cyclobutyl]carbonyl}amino) ethyl]-N-hydroxybenzamide Compound I-110: LCMS: (FA) ES+ 374

N-(1-{4-[(hydroxyamino)carbonyl]phenyl}ethyl)-3-phenyl-1H-pyrazole-5-carboxamide Compound I-109: LCMS: (FA) ES+ 351

N-hydroxy-4-{1-[(3-phenylpropanoyl)amino] ethyl}benzamide Compound I-45: LCMS: (FA) ES+ 313

Example 210

N-(1-[4-{(hydroxyamino)carbonyl]phenyl}ethyl)-3-isopropyl-1-methyl-1H-pyrazole-5-carboxamide Compound I-186

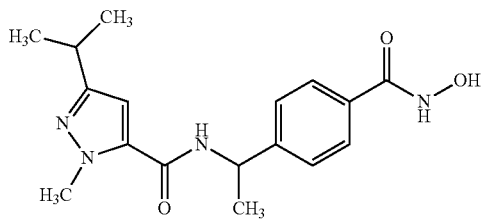 [SMILES: CC(C)c1cc(C(=O)NC(C)c2ccc(C(=O)NO)cc2)n(C)n1]

A solution of N,N,N',N'-tetramethyl-O-(7-azabenzotriazol-1-yl)uronium hexafluorophosphate (41.8 mg, 0.110 mmol), 3-isopropyl-1-methyl-1H-pyrazole-5-carboxylic acid (20.2 mg, 0.12 mmol) and N,N-diisopropylethylamine (52.2 µL, 0.3 mmol) in DMF (1.0 mL, 13 mmol) was stirred at room temperature for 30 minutes. Methyl 4-(1-aminoethyl) benzoate hydrochloride (21.6 mg, 0.10 mmol) and N,N-diisopropylethylamine (17.4 µL, 0.10 mmol) in DMF (1 mL) was then added and the reaction solution was stirred at room temperature overnight. The solution was evaporated to dryness and the residue obtained was partitioned between DCE (2 mL) and half-saturated aqueous sodium bicarbonate solution (2 mL). The aqueous layer was washed with additional DCE (2 mL) and the combined organic layers concentrated. The residue was dissolved in a mixture of MeOH (0.5 mL) and THF (2 mL); 1.0M aqueous NaOH (0.5 mL) was added and the solution heated to 40° C. overnight. Upon cooling to room temperature, the solution was neutralized by the addition of 1.0M aqueous HCl (0.5 mL) and evaporated to dryness. The residue obtained was taken up in DMF (2.0 mL) and to the solution was added N,N,N',N'-tetramethyl-O-(7-azabenzotriazol-1-yl)uronium hexafluorophosphate (41.8 mg, 0.11 mmol), O-(tetrahydropyran-2-yl)hydroxylamine (14.0 mg, 0.120 mmol) and N,N-diisopropylethylamine (52 µL, 0.3 mmol). The reaction solution was stirred at room temperature overnight. The solution was evaporated to dryness and the residue obtained was partitioned between DCE (2 mL) and half-saturated aqueous sodium bicarbonate solution (2 mL). The aqueous layer was washed with additional DCE (2 mL) and the combined organic layers concentrated. The material obtained was dissolved in MeOH (1 mL), 2.0 M HCl in dioxane (52.2 uL, 0.30 mmol) was added and the solution stirred at room temperature for 1 hour. The solvents were evaporated and the resulting material was dissolved in DMSO and purified on Agilent 1100 LC/MSD instrument to afford the title compound as a white solid (5.3 mg, 16%). LC-MS: (FA) ES+ 331.

The following compounds were prepared in an analogous fashion to Example 210.

4-(1-{[(2-chlorophenyl)acetyl]amino}ethyl)-N-hydroxybenzamide Compound I-292: LCMS: (FA) ES+ 334;

N-hydroxy-4-(1-{[(1-phenylcyclopentyl)carbonyl] amino}ethyl)benzamide Compound I-198: LCMS: (FA) ES+ 353;

N-(1-{4-[(hydroxyamino)carbonyl]phenyl}ethyl)-2-methyl-4,5,6,7-tetrahydro-2H-indazole-3-carboxamide Compound I-114: LCMS: (FA) ES+ 343;

N-(1-{4-[(hydroxyamino)carbonyl]phenyl}ethyl)-5-isobutylisoxazole-3-carboxamide Compound I-286: LCMS: (FA) ES+ 332;

N-(1-{4-[(hydroxyamino)carbonyl]phenyl}ethyl)-1-benzothiophene-3-carboxamide Compound I-244: LCMS: (FA) ES+ 341;

4-{1-[(2,3-dihydro-1H-inden-2-ylacetyl)amino]ethyl}-N-hydroxybenzamide Compound I-357: LCMS: (FA) ES+ 339;

N-hydroxy-4-(1-{[(4-isopropylphenyl)acetyl]amino}ethyl) benzamide Compound I-285: LCMS: (FA) ES+ 341;

N-(1-{4-[(hydroxyamino)carbonyl]phenyl}ethyl)cinnoline-4-carboxamide Compound I-56: LCMS: (FA) ES+ 337;

N-hydroxy-4-(1-{[4-(4-methoxyphenyl)butanoyl]amino}ethyl)benzamide Compound I-70: LCMS: (FA) ES+ 357;

4-(1-{[(2,5-dimethyl-1,3-thiazol-4-yl)acetyl]amino}ethyl)-N-hydroxybenzamide Compound I-217: LCMS: (FA) ES+ 334;

N-(1-{4-[hydroxyamino)carbonyl]phenyl}ethyl)-4-(1H-pyrazol-1-yl)benzamide Compound I-185: LCMS: (FA) ES+ 351;

4-tert-butyl-N-(1-{4-[(hydroxyamino)carbonyl]phenyl}ethyl)benzamide Compound I-350: LCMS: (FA) ES+ 341;

N-(1-{4-[(hydroxyamino)carbonyl]phenyl}ethyl)-2-naphthamide Compound I-327: LCMS: (FA) ES+ 335;

4-{1-[(1,3-benzodioxol-5-ylacetyl)amino]ethyl}-N-hydroxybenzamide Compound I-280: LCMS: (FA) ES+ 343;

N-hydroxy-4-[1-({[1-(4-methylphenyl)cyclopropyl]carbonyl}amino)ethyl]benzamide Compound I-264: LCMS: (FA) ES+ 339;

N-(1-{4-[(hydroxyamino)carbonyl]phenyl}ethyl)-3-methyl-1-benzofuran-2-carboxamide Compound I-7: LCMS: (FA) ES+ 339;

N-(1-{4-[(hydroxyamino)carbonyl]phenyl}ethyl)-2H-chromene-3-carboxamide Compound I-224: LCMS: (FA) ES+ 339;

4-(1-{[(2,4-difluorophenyl)acetyl]amino}ethyl)-N-hydroxybenzamide Compound I-402: LCMS: (FA) ES+ 335;

N-(1-{4-[(hydroxyamino)carbonyl]phenyl}ethyl)quinoline-2-carboxamide Compound I-128: LCMS: (FA) ES+ 336;

N-(1-{4-[(hydroxyamino)carbonyl]phenyl}ethyl)-2,1,3-benzothiadiazole-5-carboxamide Compound I-233: LCMS: (FA) ES+ 343;

N-(1-{4-[(hydroxyamino)carbonyl]phenyl}ethyl)-4-(1,3-oxazol-5-yl)benzamide Compound I-138: LCMS: (FA) ES+ 352;

N-(1-{4-[(hydroxyamino)carbonyl]phenyl}ethyl)-4-isopropoxybenzamide Compound I-38: LCMS: (FA) ES+ 343;

N-(1-{4-[(hydroxyamino)carbonyl]phenyl}ethyl)-5,7-dimethylpyrazolo[1,5-a]pyrimidine-2-carboxamide Compound I-160: LCMS: (FA) ES+ 354;

4-(1-{[(2-chloro-6-fluorophenyl)acetyl]amino}ethyl)-N-hydroxybenzamide Compound I-24: LCMS: (FA) ES+ 352;

N-(1-{4-[(hydroxyamino)carbonyl]phenyl}ethyl)adamantane-1-carboxamide Compound I-3: LCMS: (FA) ES+ 343;

4-fluoro-N-(1-{4-[(hydroxyamino)carbonyl]phenyl}ethyl)-3-methoxybenzamide Compound I-164: LCMS: (FA) ES+ 333;

N-(1-{4-[(hydroxyamino)carbonyl]phenyl}ethyl)-1-methyl-1H-indole-2-carboxamide Compound I-98: LCMS: (FA) ES+ 338;

N-(1-{4-[(hydroxyamino)carbonyl]phenyl}ethyl)-3-(1H-pyrrol-1-yl)thiophene-2-carboxamide Compound I-228: LCMS: (FA) ES+ 356;

4-(1-{[2-(4-chlorophenyl)-2-methylpropanoyl]amino}ethyl)-N-hydroxybenzamide Compound I-378: LCMS: (FA) ES+ 362;

N-(1-{4-[(hydroxyamino)carbonyl]phenyl}ethyl)-2-methyl-1,3-benzothiazole-5-carboxamide Compound I-230: LCMS: (FA) ES+ 356;

4-(1-{[1-adamantylacetyl]amino}ethyl)-N-hydroxybenzamide Compound I-212: LCMS: (FA) ES+ 357;

N-(1-{4-[(hydroxyamino)carbonyl]phenyl}ethyl)-4-(1H-pyrrol-1-yl)benzamide Compound I-63: LCMS: (FA) ES+ 350;

N-(1-{4-[(hydroxyamino)carbonyl]phenyl}ethyl)-1,3-benzothiazole-6-carboxamide Compound I-360: LCMS: (FA) ES+ 342;

N-(1-{4-[(hydroxyamino)carbonyl]phenyl}ethyl)imidazo[1,2-a]pyridine-2-carboxamide Compound I-125: LCMS: (FA) ES+ 325;

4-{1-[(cyclopropylcarbonyl)amino]ethyl}-N-hydroxybenzamide Compound I-239: LCMS: (FA) ES+ 249;

4-{1-[(cyclopropylacetyl)amino]ethyl}-N-hydroxybenzamide Compound I-379: LCMS: (FA) ES+ 263;

N-hydroxy-4-(1-{[(2-methoxyphenyl)acetyl]amino}ethyl) benzamide Compound I-34: LCMS: (FA) ES+ 329;

N-(1-{4-[(hydroxyamino)carbonyl]phenyl}ethyl)-2,3-dihydro-1-benzofuran-7-carboxamide Compound I-134: LCMS: (FA) ES+ 327;

N-(1-{4-[(hydroxyamino)carbonyl]phenyl}ethyl)-1,3-dimethyl-1H-pyrazole-5-carboxamide Compound I-288: LCMS: (FA) ES+ 303;

4-chloro-N-(1-{4-[(hydroxyamino)carbonyl]phenyl}ethyl) benzamide Compound I-136: LCMS: (FA) ES+ 320;

N-(1-{4-[(hydroxyamino)carbonyl]phenyl}ethyl)-2-methyl-1,3-thiazole-4-carboxamide Compound I-278: LCMS: (FA) ES+ 306;

N-(1-{4-[(hydroxyamino)carbonyl]phenyl}ethyl)-1,3-benzodioxole-5-carboxamide Compound I-297: LCMS: (FA) ES+ 329;

2-chloro-N-(1-{4-[(hydroxyamino)carbonyl]phenyl}ethyl) benzamide Compound I-269: LCMS: (FA) ES+ 320;

4-[1-(butyrylamino)ethyl]-N-hydroxybenzamide Compound I-243: LCMS: (FA) ES+ 251;

N-hydroxy-4-(1-{[(4-methoxyphenyl)acetyl]amino}ethyl) benzamide Compound I-159: LCMS: (FA) ES+ 329;

N-(1-{4-[(hydroxyamino)carbonyl]phenyl}ethyl)-1,5-dimethyl-1H-pyrazole-3-carboxamide Compound I-241: LCMS: (FA) ES+ 303;

N-(1-{4-[(hydroxyamino)carbonyl]pheny}ethyl)-1-benzofuran-5-carboxamide Compound I-349: LCMS: (FA) ES+ 325;

N-(1-{4-[hydroxyamino)carbonyl]phenyl}ethyl)-3,5-dimethylisoxazole-4-carboxamide Compound I-326: LCMS: (FA) ES+ 304;

4-{1-[(cyclopentylcarbonyl)amino]ethyl}-N-hydroxybenzamide Compound I-88: LCMS: (FA) ES+ 277;

4-{1-[(cyclobutylcarbonyl)amino]ethyl}-N-hydroxybenzamide Compound I-21: LCMS: (FA) ES+ 263;

N-(1-{4-[(hydroxyamino)carbonyl]phenyl}ethyl)-5-methylthiophene-2-carboxamide Compound I-147: LCMS: (FA) ES+ 305;

4-{1-[(3,3-dimethylbutanoyl)amino]ethyl}-N-hydroxybenzamide Compound I-144: LCMS: (FA) ES+ 279;

N-(1-{4-[(hydroxyamino)carbonyl]phenyl}ethyl)-1-benzofuran-2-carboxamide Compound I-207: LCMS: (FA) ES+ 325;

N-(1-{4-[(hydroxyamino)carbonyl]phenyl}ethyl)-3-methylbenzamide Compound I-295: LCMS: (FA) ES+ 299;

4-{1-[cyclohexylcarbonyl)amino]ethyl}-N-hydroxybenzamide Compound I-208: LCMS: (FA) ES+ 291;

N-hydroxy-4-[1-(isobutyrylamino)ethyl]benzamide Compound I-36: LCMS: (FA) ES+ 251;

N-hydroxy-4-{1-[(tetrahydro-2H-pyran-4-ylacetyl)amino]ethyl}benzamide Compound I-313: LCMS: (FA) ES+ 307;

N-hydroxy-4-(1-{[(2,2,3,3-tetramethylcyclopropyl)carbonyl]amino}ethyl)benzamide Compound I-372: LCMS: (FA) ES+ 305;

4-{1-[(cyclohex-3-en-1-ylcarbonyl)amino]ethyl}-N-hydroxybenzamide Compound I-348: LCMS: (FA) ES+ 289;

4-{1-[(cyclopentylacetyl)amino]ethyl}-N-hydroxybenzamide Compound I-370: LCMS: (FA) ES+ 291;

2-fluoro-N-(1-{4-[(hydroxyamino)carbonyl]phenyl}ethyl)-5-methylbenzamide Compound I-8: LCMS: (FA) ES+ 317;

N-(1-{4-[(hydroxyamino)carbonyl]phenyl}ethyl)cycloheptanecarboxamide Compound I-213: LCMS: (FA) ES+ 305;

N-hydroxy-4-{1-[(3-methylbutanoyl)amino]ethyl}benzamide Compound I-111: LCMS: (FA) ES+ 265;

N-hydroxy-4-(1-{[(1-methylcyclohexyl)carbonyl]amino}ethyl)benzamide Compound I-132: LCMS: (FA) ES+ 305;

N-hydroxy-4-(1-{[(1-methylcyclopropyl)carbonyl]amino}ethyl)benzamide Compound I-154: LCMS: (FA) ES+ 263;

4-[1-(benzoylamino)ethyl]-N-hydroxybenzamide Compound I-385: LCMS: (FA) ES+ 285;

N-(1-{4-[(hydroxyamino)carbonyl]phenyl}ethyl)-3-methoxybenzamide Compound I-225: LCMS: (FA) ES+ 315;

The following compounds were prepared in an analogous fashion to Example 210 using methyl 4-(1-aminoethyl)-3-methoxybenzoate hydrochloride as the starting material:

N-(1-{4-[(hydroxyamino)carbonyl]-2-methoxyphenyl}ethyl)-1-methyl-4H-pyrrole-2-carboxamide Compound I-481: LCMS: (FA) ES+ 318;

4-{1-[(2,2-dimethylpropanoyl)amino]ethyl}-N-hydroxy-3-methoxybenzamide Compound I-484: LCMS: (FA) ES+ 295;

N-(1-{4-[(hydroxyamino)carbonyl]-2-methoxyphenyl}ethyl)adamantane-1-carboxamide Compound I-483: LCMS: (FA) ES+ 373;

N-(1-{4-[(hydroxyamino)carbonyl]-2-methoxyphenyl}ethyl)-1-benzothiophene-2-carboxamide Compound I-480: LCMS: (FA) ES+ 371.

The following compounds were prepared in an analogous fashion to Example 210 using methyl 4-(1-aminoethyl)-3-methylbenzoate hydrochloride: as the starting material:

N-(1-{4-[(hydroxyamino)carbonyl]-2-methylphenyl}ethyl)-1-benzothiophene-2-carboxamide Compound I-485: LCMS: (FA) ES+ 355;

N-(1-{4-[(hydroxyamino)carbonyl]-2-methylphenyl}ethyl)-1-methyl-1H-pyrrole-2-carboxamide Compound I-486: LCMS: (FA) ES+ 302;

4-{1-[(2,2-dimethylpropanoyl)amino]ethyl}-N-hydroxy-3-methylbenzamide Compound I-490: LCMS: (FA) ES+ 279;

N-(1-{4-[(hydroxyamino)carbonyl]-2-methylphenyl}ethyl)adamantane-1-carboxamide Compound I-491: LCMS: (FA) ES+ 357.

Example 211

4-[1-({[(4-cyanophenyl)amino]carbonyl}amino)ethyl]-N-hydroxybenzamide Compound I-236

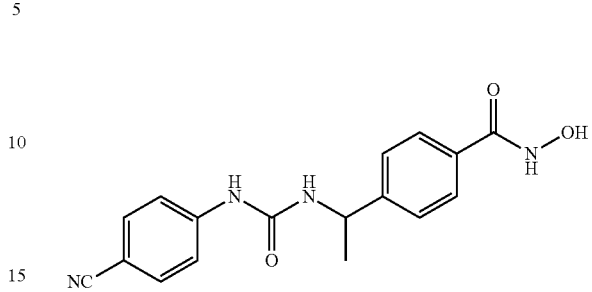

To a solution of methyl 4-(1-aminoethyl)benzoate hydrochloride (32.4 mg, 0.15 mmol) and N,N-diisopropylethylamine (125 µL, 0.718 mmol) in 1,2-dichloroethane (1 mL) was added 4-isocyanatobenzonitrile (32.4 g, 0.23 mmol). The reaction solution was stirred at room temperature overnight. The solution was evaporated to dryness and the residue was partitioned between DCE (2 mL) and half-saturated aqueous sodium bicarbonate solution (2 mL). The aqueous layer was washed with additional DCE (2 mL) and the combined organic layers concentrated. The material thus obtained was dissolved in a mixture of MeOH (0.5 mL) and THF (2 mL); 1.0M aqueous NaOH (0.5 mL) was added and the solution heated at 40° C. overnight. Upon cooling to room temperature, the solution was neutralized by the addition of 1.0M aqueous HCl (0.5 mL) and evaporated to dryness. The residue was taken up in DMF (2 mL) and to the solution was added N,N,N',N$^1$-tetramethyl-O-(7-azabenzotriazol-1-yl)uronium hexafluorophosphate (62.7 mg, 0.165 mmol), O-(tetrahydro-pyran-2-yl)hydroxylamine (14 mg, 0.12 mmol) and N,N-diisopropylethylamine (104 µL, 0.6 mmol). The reaction solution was heated at 45° C. overnight. The reaction mixture was then evaporated to dryness and the residue obtained was partitioned between DCE (2 mL) and half-saturated aqueous sodium bicarbonate solution (2 mL). The aqueous layer was washed with additional DCE (2 mL) and the combined organic layers concentrated. The residue obtained was dissolved in MeOH (1 mL), and 2.0 M HCl in dioxane (52.2 µL, 0.30 mmol) was added and the solution stirred at room temperature for 1 hour. The solvent was evaporated and the resulting material was dissolved in DMSO and purified using an Agilent 1100 LC/MSD instrument to afford the title compound as a white solid (8.1 mg, 25%). LC-MS: (FA) ES+ 325.

The following compounds were prepared in an analogous fashion to Example 211.

4-[1-({[(3-fluoro-4-methylphenyl)amino]carbonyl}amino)ethyl]-N-hydroxybenzamide Compound I-120: LCMS: (FA) ES+ 332;

4-[1-({[(3-chloro-4-methylphenyl)amino]carbonyl}amino)ethyl]-N-hydroxybenzamide Compound I-103: LCMS: (FA) ES+ 349;

N-hydroxy-4-[1-({[(4-phenoxyphenyl)amino]carbonyl}amino)ethyl]benzamide Compound I-20: LCMS: (FA) ES+ 392;

4-[1-({[(2,4-dimethylphenyl)amino]carbonyl}amino)ethyl]-N-hydroxybenzamide Compound I-383: LCMS: (FA) ES+ 328;

4-[1-({[(3,4-dimethylphenyl)amino]carbonyl}amino)ethyl]-N-hydroxybenzamide Compound I-55: LCMS: (FA) ES+ 328;

4-[1-({[(3-acetylphenyl)amino]carbonyl}amino)ethyl]-N-hydroxybenzamide Compound I-358: LCMS: (FA) ES+ 342;

4-(1-{[(biphenyl-2-ylamino)carbonyl]amino}ethyl)-N-hydroxybenzamide Compound I-384: LCMS: (FA) ES+ 376;

N-hydroxy-4-[1-({[(2-methylbenzyl)amino]carbonyl}amino)ethyl]benzamide Compound I-76: LCMS: (FA) ES+ 328;

4-(1-{[(2,1,3-benzothiadiazol-4-ylamino)carbonyl]amino}ethyl)-N-hydroxybenzamide Compound I-293: LCMS: (FA) ES+ 358;

N-hydroxy-4-[1-({[(2-phenoxyphenyl)amino]carbonyl}amino)ethyl]benzamide Compound I-31: LCMS: (FA) ES+ 392;

4-{1-[({[2-fluoro-5-(trifluoromethyl)phenyl]amino}carbonyl)amino]ethyl}-N-hydroxybenzamide Compound I-334: LCMS: (FA) ES+ 386;

4-[1-({[(2,3-dimethylphenyl)amino]carbonyl}amino)ethyl]-N-hydroxybenzamide Compound I-175: LCMS: (FA) ES+ 328;

N-hydroxy-4-{1-[({[4-(trifluoromethyl)phenyl]amino}carbonyl)amino]ethyl}benzamide Compound I-399: LCMS: (FA) ES+ 368;

N-hydroxy-4-[1-({[(2-methoxy-5-methylphenyl)amino]carbonyl}amino)ethyl]benzamide Compound I-253: LCMS: (FA) ES+ 344

4-{1-[({[2-chloro-4-(trifluoromethyl)phenyl]amino}carbonyl)amino]ethyl}-N-hydroxybenzamide Compound I-163: LCMS: (FA) ES+ 403;

4-[1-({[(2,6-dimethylphenyl)amino]carbonyl}amino)ethyl]-N-hydroxybenzamide Compound I-156: LCMS: (FA) ES+ 328

4-[1-({[(2,6-difluorophenyl)amino]carbonyl}amino)ethyl]-N-hydroxybenzamide Compound I-261: LCMS: (FA) ES+ 336

N-hydroxy-4-[1-({[(3-methylbenzyl)amino]carbonyl}amino)ethyl]benzamide Compound I-316: LCMS: (FA) ES+ 328

4-[1-({[(4-ethylphenyl)amino]carbonyl}amino)ethyl]-N-hydroxybenzamide Compound I-381: LCMS: (FA) ES+ 328

N-hydroxy-4-[1-({[(2-phenylethyl)amino]carbonyl}amino)ethyl]benzamide Compound I-210: LCMS: (FA) ES+ 328

4-{1-[({[4-(difluoromethoxy)phenyl]amino}carbonyl)amino]ethyl}-N-hydroxybenzamide Compound I-150: LCMS: (FA) ES+ 366

4-[1-({[(2,5-dichlorophenyl)amino]carbonyl}amino)ethyl]-N-hydroxybenzamide Compound I-89: LCMS: (FA) ES+ 369

N-hydroxy-4-(1-{[(1-naphthylamino)carbonyl]amino}ethyl)benzamide Compound I-6: LCMS: (FA) ES+ 350

4-(1-{[(1,3-benzodioxol-5-ylamino)carbonyl]amino}ethyl)-N-hydroxybenzamide Compound I-71: LCMS: (FA) ES+ 344

4-[1-({[(2,4-dimethoxyphenyl)amino]carbonyl}amino)ethyl]-N-hydroxybenzamide Compound I-44: LCMS: (FA) ES+ 360

4-[1-({[(4-fluorophenyl)amino]carbonyl}amino)ethyl]-N-hydroxybenzamide Compound I-37: LCMS: (FA) ES+ 318

4-[1-({[(4-tert-butylphenyl)amino]carbonyl}amino)ethyl]-N-hydroxybenzamide Compound I-140: LCMS: (FA) ES+ 356

4-(1-{[(2,3-dihydro-1-benzofuran-5-ylamino)carbonyl]amino}ethyl)-N-hydroxybenzamide Compound I-148: LCMS: (FA) ES+ 342

4-[1-({[(2-fluorophenyl)amino]carbonyl}amino)ethyl]-N-hydroxybenzamide Compound I-74: LCMS: (FA) ES+ 318

N-hydroxy-4-[1-({[(3-methylphenyl)amino]carbonyl}amino)ethyl]benzamide Compound I-85: LCMS: (FA) ES+ 314

4-[1-({[(3,4-difluorophenyl)amino]carbonyl}amino)ethyl]-N-hydroxybenzamide Compound I-275: LCMS: (FA) ES+ 336

4-[1-({[(3,5-dimethylphenyl)amino]carbonyl}amino)ethyl]-N-hydroxybenzamide Compound I-397: LCMS: (FA) ES+ 328

N-hydroxy-4-[1-({[(4-methylbenzyl)amino]carbonyl}amino)ethyl]benzamide Compound I-277: LCMS: (FA) ES+ 328

4-[1-({[(3,5-dichlorophenyl)amino]carbonyl}amino)ethyl]-N-hydroxybenzamide Compound I-388: LCMS: (FA) ES+ 369

N-hydroxy-4-{1-[({[3-(trifluoromethyl)phenyl]amino}carbonyl)amino]ethyl}benzamide Compound I-371: LCMS: (FA) ES+ 368

N-hydroxy-4-[1-({[(3-methyl-5-phenylisoxazol-4-yl)amino]carbonyl}amino)ethyl]benzamide Compound I-168: LCMS: (FA) ES+ 381

N-hydroxy-4-{1-[({[4-(trifluoromethoxy)phenyl]amino}carbonyl)amino]ethyl}benzamide Compound I-141: LCMS: (FA) ES+ 384

4-[1-({[(4-acetylphenyl)amino]carbonyl}amino)ethyl]-N-hydroxybenzamide Compound I-398: LCMS: (FA) ES+ 342

N-hydroxy-4-[1-({[(5-methyl-3-phenylisoxazol-4-yl)amino]carbonyl}amino)ethyl]benzamide Compound I-305: LCMS: (FA) ES+ 381

4-{1-[({[4-chloro-3-(trifluoromethyl)phenyl]amino}carbonyl)amino]ethyl}-N-hydroxybenzamide Compound I-325: LCMS: (FA) ES+ 403

N-hydroxy-4-[1-({[(1-phenylethyl)amino]carbonyl}amino)ethyl]benzamide Compound I-196: LCMS: (FA) ES+ 328

N-hydroxy-4-[1-({[(2-methylphenyl)amino]carbonyl}amino)ethyl]benzamide Compound I-394: LCMS: (FA) ES+ 314

4-(1-{[(cyclohexylamino)carbonyl]amino}ethyl)-N-hydroxybenzamide Compound I-395: LCMS: (FA) ES+ 306

4-[1-({[(3-fluorophenyl)amino]carbonyl}amino)ethyl]-N-hydroxybenzamide Compound I-27: LCMS: (FA) ES+ 318.

Example 212

4-(1-{[(2,4-dimethylphenyl)sulfonyl]amino}ethyl)-N-hydroxybenzamide Compound I-78

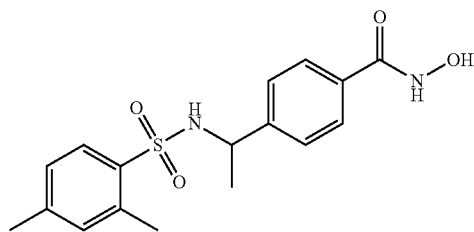 [SMILES: Cc1ccc(S(=O)(=O)NC(C)c2ccc(C(=O)NO)cc2)c(C)c1]

To a solution of methyl 4-(1-aminoethyl)benzoate hydrochloride (32.4 mg, 0.15 mmol) and N,N-diisopropylethylamine (125 µL, 0.72 mmol) in 1,2-dichloroethane (1 mL)

was added 2,4-dimethylbenzenesulfonyl chloride (46 mg, 0.23 mmol). The reaction was stirred at room temperature overnight. The solution was evaporated to dryness and the residue was partitioned between DCE (2 mL) and half-saturated aqueous sodium bicarbonate solution (2 mL). The aqueous layer was washed with additional DCE (2 mL) and the combined organic layers concentrated. The residue was dissolved in a mixture of MeOH (0.5 mL) and THF (2 mL); then 1.0M aqueous NaOH (0.5 mL) was added and the solution heated at 40° C. overnight. Upon cooling to room temperature, the solution was neutralized with 1.0M aqueous HCl (0.5 mL) and evaporated to dryness. The resulting solid was taken up in DMF (2 mL) and to the resulting solution was added N,N,N',N'-tetramethyl-O-(7-azabenzotriazol-1-yOuronium hexafluorophosphate (62.7 mg, 0.165 mmol), O-(tetrahydropyran-2-yl)hydroxylamine (19.3 mg, 0.165 mmol) and N,N-diisopropylethylamine (104 µL, 0.60 mmol). The reaction solution was stirred at 45° C. overnight. The reaction mixture was evaporated to dryness and the residue obtained was partitioned between DCE (2 mL) and half-saturated aqueous sodium bicarbonate solution (2 mL). The aqueous layer was washed with additional DCE (2 mL) and the combined organic layers concentrated. The residue obtained was dissolved in MeOH (1 mL), 2.0 M HCl in dioxane (52 µL, 0.3 mmol) was added and the solution stirred at room temperature for 1 hour. The solvent was evaporated and the resulting material was dissolved in DMSO and purified using an Agilent 1100 LC/MSD instrument to afford the title compounds as a white solid (23.3 mg, 45%). LC-MS: (FA) ES+ 349.

The following compounds were prepared in an analogous fashion to Example 212.

N-hydroxy-4-{1-[(propylsulfonyl)amino]ethyl}benzamide Compound I-33: LCMS: (FA) ES+ 287;

4-{1-[(ethylsulfonyl)amino]ethyl}-N-hydroxybenzamide Compound I-1: LCMS: (FA) ES+ 273;

4-{1-[(benzylsulfonyl)amino]ethyl}-N-hydroxybenzamide Compound I-338: LCMS: (FA) ES+ 335;

4-(1-{[(4-fluorophenyl)sulfonyl]amino}ethyl)-N-hydroxybenzamide Compound I-2: LCMS: (FA) ES+ 339;

N-hydroxy-4-(1-{[(4-methylphenyl)sulfonyl]amino}ethyl)benzamide Compound I-266: LCMS: (FA) ES+ 335;

N-hydroxy-4-(1-{[(2-methylphenyl)sulfonyl]amino}ethyl)benzamide Compound I-232: LCMS: (FA) ES+ 335;

N-hydroxy-4-(1-{[(1-methyl-1H-imidazol-4-yl)sulfonyl]amino}ethyl)benzamide Compound I-335: LCMS: (FA) ES+ 325;

N-hydroxy-4-{1-[(phenylsulfonyl)amino]ethyl}benzamide Compound I-315: LCMS: (FA) ES+ 321;

N-hydroxy-4-[1-({[4-(trifluoromethyl)phenyl]sulfonyl}amino)ethyl]benzamide Compound I-488: LCMS: (FA) ES+ 389;

4-(1-{[(tert-butylamino)carbonyl]amino}ethyl)-N-hydroxybenzamide Compound I-339: LCMS: (FA) ES+ 280;

N-hydroxy-4-{1-[(mesitylsulfonyl)amino]ethyl}benzamide Compound I-176: LCMS: (FA) ES+ 363;

N-hydroxy-4-[1-({[3-(trifluoromethyl)phenyl]sulfonyl}amino)ethyl]benzamide Compound I-166: LCMS: (FA) ES+ 389;

N-hydroxy-4-[1-({[4-(1,3-oxazol-5-yl)phenyl]sulfonyl}amino)ethyl]benzamide Compound I-178: LCMS: (FA) ES+ 388;

4-(1-{[(5-fluoro-2-methylphenyl)sulfonyl]amino}ethyl)-N-hydroxybenzamide Compound I-205: LCMS: (FA) ES+ 353;

4-{1-[(1-benzothien-2-ylsulfonyl)amino]ethyl}-N-hydroxybenzamide Compound I-369: LCMS: (FA) ES+ 377;

4-(1-{[(2-cyanophenyl)sulfonyl]amino}ethyl)-N-hydroxybenzamide Compound I-340: LCMS: (FA) ES+ 346;

N-hydroxy-4-(1-{[(4-isopropylphenyl)sulfonyl]amino}ethyl)benzamide Compound I-221: LCMS: (FA) ES+ 363;

4-(1-{[(2,5-difluorophenyl)sulfonyl]amino}ethyl)-N-hydroxybenzamide Compound I-152: LCMS: (FA) ES+ 357;

4-(1-{[(2,5-dimethyl-3-thienyl)sulfonyl]amino}ethyl)-N-hydroxybenzamide Compound I-256: LCMS: (FA) ES+ 355;

4-(1-{[(3-chlorophenyl)sulfonyl]amino}ethyl)-N-hydroxybenzamide Compound I-197: LCMS: (FA) ES+ 356;

4-(1-{[(2-chloro-4-fluorophenyl)sulfonyl]amino}ethyl)-N-hydroxybenzamide Compound I-235: LCMS: (FA) ES+ 374;

4-{1-[(2,3-dihydro-1,4-benzodioxin-6-ylsulfonyl)amino]ethyl}-N-hydroxybenzamide Compound I-82: LCMS: (FA) ES+ 379;

N-hydroxy-4-(1-{[(2-oxo-2H-chromen-6-ylsulfonyl]amino}ethyl)benzamide Compound I-49: LCMS: (FA) ES+ 389;

4-(1-{[(5-chloro-2-methoxyphenyl)sulfonyl]amino}ethyl)-N-hydroxybenzamide Compound I-347: LCMS: (FA) ES+ 386;

4-(1-{[(4-chlorophenyl)sulfonyl]amino}ethyl)-N-hydroxybenzamide Compound I-302: LCMS: (FA) ES+ 356;

N-hydroxy-4-{1-[(isoquinolin-5-ylsulfonyl)amino]ethyl}benzamide Compound I-170: LCMS: (FA) ES+ 372;

N-hydroxy-4-(1-{[(3-methoxyphenyl)sulfonyl]amino}ethyl)benzamide Compound I-23: LCMS: (FA) ES+ 351;

N-hydroxy-4-{1-[(1-naphthylsulfonyl)amino]ethyl}benzamide Compound I-95: LCMS: (FA) ES+ 371;

4-(1-{[(1,2-dimethyl-1H-imidazol-4-yl)sulfonyl]amino}ethyl)-N-hydroxybenzamide Compound I-54: LCMS: (FA) ES+ 339;

4-(1-{[(2-chloro-4-cyanophenyl)sulfonyl]amino}ethyl)-N-hydroxybenzamide Compound I-254: LCMS: (FA) ES+ 381;

N-hydroxy-4-(1-{[(1,3,5-trimethyl-1H-pyrazol-4-yl)sulfonyl]amino}ethyl)benzamide Compound I-60: LCMS: (FA) ES+ 353;

4-(1-{[(3,4-difluorophenyl)sulfonyl]amino}ethyl)-N-hydroxybenzamide Compound I-90: LCMS: (FA) ES+ 357;

4-(1-{[(3-chloro-4-methylphenyl)sulfonyl]amino}ethyl)-N-hydroxybenzamide Compound I-118: LCMS: (FA) ES+ 370;

4-(1-{[(4-tert-butylphenyl)sulfonyl]amino}ethyl)-N-hydroxybenzamide Compound I-131: LCMS: (FA) ES+ 377;

4-(1-{[(2-chlorophenyl)sulfonyl]amino}ethyl)-N-hydroxybenzamide Compound I-361: LCMS: (FA) ES+ 356;

N-hydroxy-4-{1-[(quinolin-8-ylsulfonyl)amino]ethyl}benzamide Compound I-363: LCMS: (FA) ES+ 372;

4-{1-[(2,1,3-benzoxadiazol-4-ylsulfonyl)amino]ethyl}-N-hydroxybenzamide Compound I-161: LCMS: (FA) ES+ 363;

4-(1-{[(4-chlorobenzyl)sulfonyl]amino}ethyl)-N-hydroxybenzamide Compound I-64: LCMS: (FA) ES+ 370;

4-{1-[(2,1,3-benzothiadiazol-5-ylsulfonyl)amino]ethyl}-N-hydroxybenzamide Compound I-272: LCMS: (FA) ES+ 379;

4-(1-{[(4-fluoro-2-methylphenyl)sulfonyl]amino}ethyl)-N-hydroxybenzamide Compound I-61: LCMS: (FA) ES+ 353;

4-(1-{[(3-fluoro-4-methoxyphenyl)sulfonyl]amino}ethyl)-N-hydroxybenzamide Compound I-153: LCMS: (FA) ES+ 369;

4-(1-{[(2-chloro-6-methylphenyl)sulfonyl]amino}ethyl)-N-hydroxybenzamide Compound I-188: LCMS: (FA) ES+ 370;

N-hydroxy-4-[1-({[2-(trifluoromethyl)phenyl]sulfonyl}amino)ethyl]benzamide Compound I-391: LCMS: (FA) ES+ 389;

4-(1-{[(4-fluorobenzyl)sulfonyl]amino}ethyl)-N-hydroxybenzamide Compound I-198: LCMS: (FA) ES+ 353;

N-hydroxy-4-(1-{[(4-methoxyphenyl)sulfonyl]amino}ethyl)benzamide Compound I-47: LCMS: (FA) ES+ 351;

N-hydroxy-4-(1-{[(2,3,4-trifluorophenyl)sulfonyl]amino}ethyl)benzamide Compound I-284: LCMS: (FA) ES+ 375;

4-(1-{[(2,5-dimethylphenyl)sulfonyl]amino}ethyl)-N-hydroxybenzamide Compound I-51: LCMS: (FA) ES+ 349;

4-(1-{[(2,4-dimethylphenyl)sulfonyl]amino}ethyl)-N-hydroxybenzamide Compound I-78: LCMS: (FA) ES+ 349.

Example 213 tert-butyl 4-methyl-4-({[(1R)-1-(4-{[(tetrahydro-2H-pyran-2-yloxy)amino]carbonyl}phenyl)ethyl]amino}carbonyl)piperidine-1-carboxylate

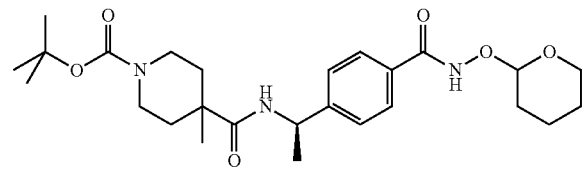 [SMILES: C[C@@H](NC(=O)C1(C)CCN(C(=O)OC(C)(C)C)CC1)c1ccc(C(=O)NOC2CCCCO2)cc1]

To a solution of 4-methyl-4-carboxy-1-N-butoxycarbonyl-piperidine (0.250 g, 1.03 mmol) in N,N-dimethylformamide (1.85 mL) was added N,N-diisopropylethylamine (0.537 mL, 3.08 mmol) and fluoro-N,N,N',N'-tetramethylformamidinium hexafluorophosphate (0.298 g, 1.13 mmol). The reaction mixture was stirred for 15 minutes whereupon (R)-4-(1-amino-ethyl)-benzoic acid hydrochloride (0.200 g, 0.99 mmol) was added and further stirred at room temperature overnight. Water was added and the mixture extracted into ethyl acetate. Upon separation of the layers, the organic layer was dried over anhydrous MgSO₄ and evaporated to dryness. LC-MS: (FA) ES+ 391.

To a mixture of this material and N,N-diisopropylethylamine (0.518 mL, 2.97 mmol) in N,N-dimethylformamide (2 mL) was added fluoro-N,N,N',N'-tetramethylformamidinium hexafluorophosphate (0.288 g, 1.09 mmol) and O-(tetrahydropyran-2-yl)hydroxylamine (0.139 g, 1.19 mmol). The resulting solution was stirred at room temperature overnight. Upon quenching the reaction with the addition of water, the solution was extracted into ethyl acetate, the organic layer washed with brine and the solvent evaporated to dryness. The residue obtained was purified via silica chromatography (0-5% MeOH/DCM) to afford the title compound as a white solid (86.0 mg, 18%). LC-MS: (FA) ES+ 490.

Example 214

N-((1R)-1-{4-[(hydroxyamino)carbonyl]phenyl}ethyl)-4-methylpiperidine-4-carboxamide Compound I-487

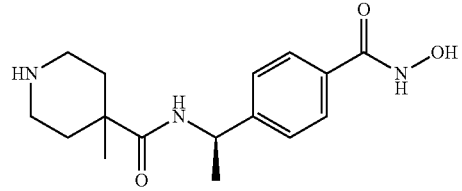 [SMILES: C[C@@H](NC(=O)C1(C)CCNCC1)c1ccc(C(=O)NO)cc1]

To a solution of tert-butyl 4-methyl-4-({[(1R)-1-(4-{[(tetrahydro-2H-pyran-2-yloxy)amino]carbonyl}phenyl)ethyl]amino}carbonyl)piperidine-1-carboxylate (0.082 g, 0.17 mmol) in methylene chloride (2 mL) was added 4.0 M hydrochloric acid in 1,4-dioxane (1 mL). The reaction mixture was stirred at room temperature for 4 hours. The reaction was concentrated to dryness. Acetic acid (1.0 mL, 18 mmol), tetrahydrofuran (1 mL), water (0.50 mL) were added and the resulting mixture was heated at 60° C. for 3 h. The reaction mixture was concentrated to dryness and co-evaporated with toluene. The crude compound was purified on a BioCAC 700E HPLC instrument using a Waters Symmetry (21 mm×300 mm) column to afford the title compound (22 mg, 43%). ¹H NMR (300 MHz, DMSO) δ 8.38 (s, 1H), 8.07 (d, J=7.8 Hz, 1H), 7.67 (d, J=8.3 Hz, 2H), 7.34 (d, J=8.2 Hz, 2H), 4.97 (dd, J=14.4, 7.1 Hz, 1H), 2.97 (d, J=13.1 Hz, 2H), 2.66 (dd, J=20.6, 10.7 Hz, 2H), 2.08 (s, 2H), 1.52-1.39 (m, 2H), 1.36 (d, J=7.1 Hz, 3H), 1.12 (s, 3H). LC-MS: (FA) ES+ 306.

Example 215

(R)-methyl 4-(1-aminoethyl)benzoate

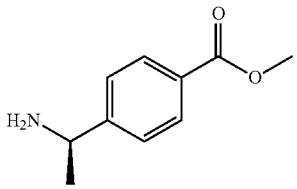

To a solution of (R)-4-(1-amino-ethyl)-benzoic acid hydrochloride (0.20 g, 0.99 mmol) in methanol (3.2 mL) was added sulfuric acid (5.29 µL, 0.0992 mmol). The resulting solution was heated at reflux overnight. The methanol was removed under reduced pressure leaving a light brown oil which was partitioned between half-saturated sodium bicarbonate solution (50 mL) and ethyl acetate (75 mL). The aqueous phase was extracted with additional ethyl acetate (50 mL). The extracts were combined, washed with saturated aqueous sodium bicarbonate and brine, dried over sodium sulfate, filtered and concentrated under reduced pressure. Purification via silica chromatography (0-50% EtOAc/hexane) afforded product as a white solid (0.124 g, 70%). LC-MS: (FA) ES+ 180.

Example 216

(R)-methyl 4-(1-((1-methylcyclohexyl)methylamino)ethyl)benzoate

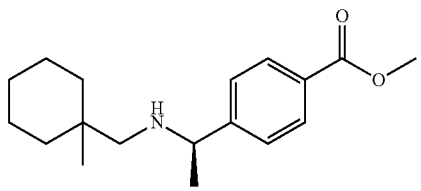 [SMILES: COC(=O)c1ccc([C@@H](C)NCC2(C)CCCCC2)cc1]

To a solution of (R)-methyl 4-(1-aminoethyl)benzoate (0.12 g, 0.67 mmol) in methanol (2.97 mL, 73.33 mmol) was added 1-methylcyclohexane-1-carboxaldehyde (0.093 g, 0.74 mmol) and acetic acid (0.152 mL, 2.67 mmol). The reaction was stirred for 1 hour at room temperature whereupon sodium cyanoborohydride (63.1 mg, 1.00 mmol) was added and the mixture further stirred at room temperature overnight. The solvent was evaporated and the residual sodium cyanoborohydride quenched with saturated aqueous NaHCO$_3$. The mixture was extracted into ethyl acetate, the organic layer washed with brine and the solvent evaporated to dryness. The residue obtained was purified via silica chromatography (0-5% MeOH/DCM) to afford the title compound as a colorless oil (123.0 mg, 63%). LC-MS: (FA) ES+ 290.

Example 217

N-hydroxy-4-((1R)-1-{[(1-methylcyclohexyl)methyl]amino}ethyl)benzamide Compound I-489

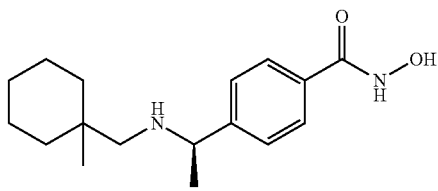 [SMILES: C[C@@H](NCC1(C)CCCCC1)c1ccc(C(=O)NO)cc1]

To a solution of methyl 4-((1R)-1-{[(1-methylcyclohexyl)methyl]amino}ethyl)benzoate (0.12 g, 0.415 mmol) in methanol (1 mL) was added 1.7 M of hydroxylamine potassium salt in methanol (2.46 mL, 4.19 mmol—prepared as described in *J. Med. Chem.* 2009, 52(21):6757-6767). The reaction mixture was stirred at room temperature for 1 hour. The reaction was neutralized with the addition of acetic acid (0.24 mL, 4.15 mmol) and was concentrated to dryness. The residue was co-evaporated with toluene (2×). The crude product was purified on a BioCAD 700E HPLC instrument using a Phenomenex (C18) Luna (21.2 mm×250 mm) column to afford product (85 mg, 70%). $^1$H NMR (400 MHz, DMSO) δ 11.13 (s, 1H), 8.17 (s, 1H), 7.67 (d, J=8.2 Hz, 2H), 7.39 (d, J=8.2 Hz, 2H), 3.69 (q, J=6.5 Hz, 1H), 2.19 (d, J=11.5 Hz, 1H), 2.03 (d, J=11.5 Hz, 1H), 1.41-1.09 (m, 13H), 0.83 (s, 3H). LC-MS: (FA) ES+ 291

Example 218

The following compounds were prepared in an analogous fashion to that described in Example 211 starting from appropriate chiral benzyl amine starting material.

| Compound No | LC-MS (FA) |
|---|---|
| I-520 | ES+ 325 |
| I-523 | ES+ 376 |
| I-527 | ES+ 350 |
| I-528 | ES+ 342 |
| I-513 | ES+ 328 |
| I-518 | ES+ 336 |
| I-517 | ES+ 328 |
| I-512 | ES+ 356 |
| I-525 | ES+ 353 |
| I-515 | ES+ 404 |
| I-524 | ES+ 378 |
| I-526 | ES+ 370 |
| I-516 | ES+ 356 |
| I-521 | ES+ 364 |
| I-514 | ES+ 356 |
| I-522 | ES+ 356 |

Example 219

4-((R)-1-amino-2-methylpropyl)-N-(tetrahydro-2H-pyran-2-yloxy)benzamide

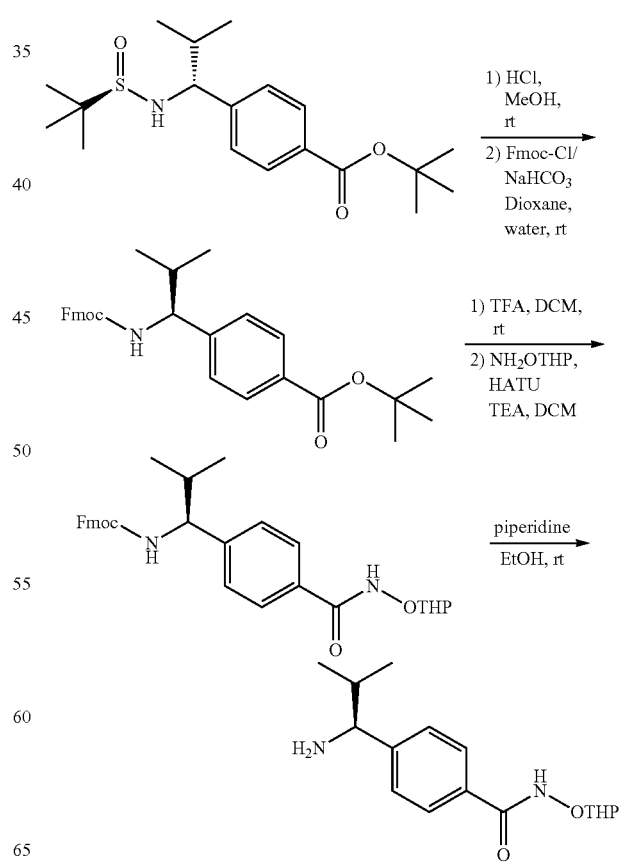

Step 1: (S)-tert-butyl 4-(1-(((9-fluoren-9-yl)methoxy)carbonylamino)-2-methylpropyl)benzoate To a 2-L round-bottom flask charged with tert-butyl 4-((R)-1-((R)-1,1-dimethylethylsulfinamido)-2-methylpropyl)benzoate (13.0 g, 0.0368 mol) was added MeOH (650 mL) and hydrochloric acid (650 mL, 4.0 M in 1,4-dioxane). The mixture was stirred at rt for 2 h. The solvent was then evaporated to give a slightly yellow solid. To the solid was added 1,4-dioxane (650 mL). sat. NaHCO₃ solution (650 mL), followed by (9H-fluoren-9-yl)methyl carbonochloridate (10.4 g, 0.0405 mol). The mixture was stirred at rt for 2 h. The reaction was quenched with EtOAc (800 mL) and water (200 mL). After separation, the aqueous phase was extracted with EtOAc (2×600 mL). Combined organic phases were washed with brine, dried (Na₂SO₄), and concentrated. Flash column chromatography gave (S)-tert-butyl 4-(1-(((9-fluoren-9-yl)methoxy)carbonylamino)-2-methylpropyl)benzoate (6.5 g, 38%).

Step 2: (9H-fluoren-9-yl)methyl (1R)-2-methyl-1-(4-(tetrahydro-2H-pyran-2-yloxycarbamoyl)phenyl)propylcarbamate To a 1-L round-bottom flask was added (S)-tert-butyl 4-(1-(((9-fluoren-9-yl)methoxy)carbonylamino)-2-methylpropyl)benzoate (6.0 g, 12.7 mmol), DCM (260 mL), and trifluoroacetic acid (28.9 g, 254 mmol). The solution was stirred at rt for 16 h. The solvent were evaporated to give an oil. To this oil in a 500-mL round-bottom flask was added diisopropylethyl amine (20.0 g, 155 mmol), DCM (100 mL), O-(tetrahydro-2H-pyran-2-yl)hydroxylamine (1.78 g, 15.24 mmol), and HBTU (5.79 g, 15.2 mmol). The mixture was stirred at rt for 4 h, then diluted with DCM (500 mL), and washed with water (2×100 mL), dried (Na₂SO₄), and concentrated. Flash column chromatography gave (9H-fluoren-9-yl) methyl (1R)-2-methyl-1-(4-(tetrahydro-2H-pyran-2-yloxycarbamoyl)phenyl)propylcarbamate (4.0 g, 62%).

Step 3: 4-((R)-1-amino-2-methylpropyl)-N-(tetrahydro-2H-pyran-2-yloxy)benzamide To a 1-L round-bottom flask was added (9H-fluoren-9-yl) methyl (1R)-2-methyl-1-(4-(tetrahydro-2H-pyran-2-yloxycarbamoyl)phenyl)propylcarbamate (10.0 g, 0.0195 mol), ethanol (588 mL), and piperidine (51.7 mL). The solution was stirred at rt for 16 h, then concentrated to give a solid. Flash column chromatography gave 4-((R)-1-amino-2-methylpropyl)-N-(tetrahydro-2H-pyran-2-yloxy)benzamide (2.3 g, 41%). ¹H NMR (CDCl₃, 400 MHz) δ7.59 (d, J=8.0 Hz, 2H), 7.23 (d, J=8.0 Hz, 2H), 5.00 (m, 1H), 3.95 (m, 1H), 3.59 (m, 2H), 1.83 (m, 4H), 1.57 (m, 3H), 1.20 (m, 1H), J=6.8 Hz, 3H), 0.67 (t, J=6.8 Hz, 3H).

Example 220

(R)—N-hydroxy-4-(2-methyl-1-(4-(3-phenylisoxazol-5-yl)thiazol-2-ylamino)propyl)benzamide Compound I-519

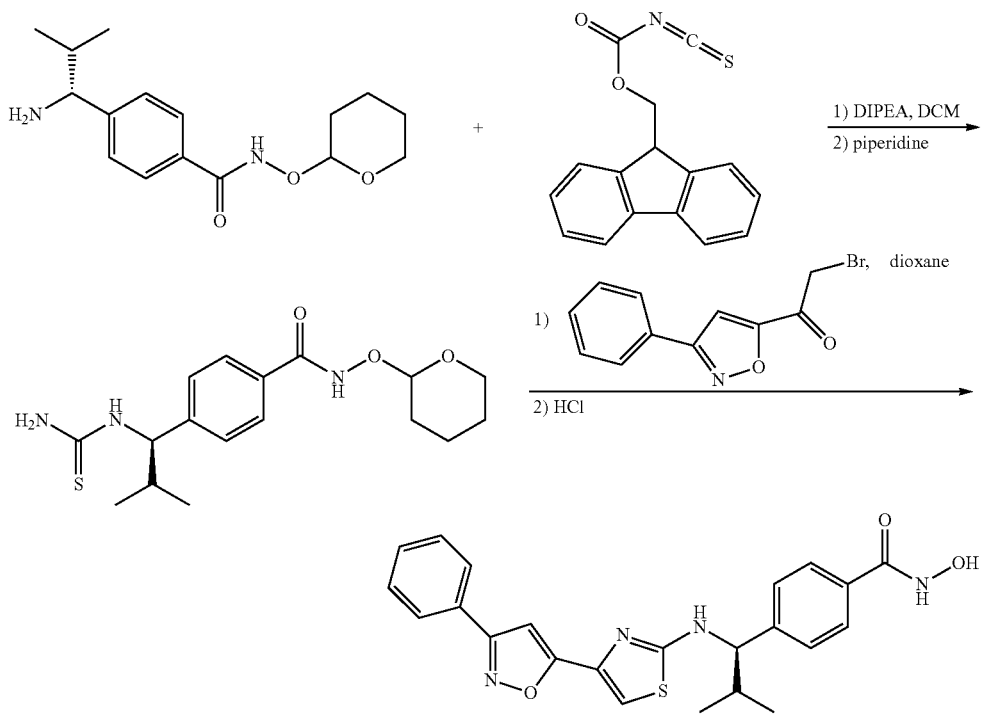

Step 1: 4-((R)-2-methyl-1-thioureidopropyl)-N-(tetrahydro-2H-pyran-2-yloxy)benzamide A solution of 4-((R)-1-amino-2-methylpropyl)-N-(tetrahydro-2H-pyran-2-yloxy)benzamide (0.1643 g, 0.562 mmol) and N,N-diisopropylethylamine (0.1 mL, 0.6 mmol) in DCM (2.5 mL) was cooled in an ice bath and added to a solution of Fmoc-isothiocyanate (0.173 g, 0.616 mmol) in DCM (2.5 mL, 38 mmol) cooled at 0° C. in an ice bath. The reaction solution was stirred at rt for 1 h. Piperidine (1.0 mL, 2.0 mmol, 2.0 M in MeOH) was then added and the reaction stirred at rt for an additional 2 h. The reaction was concentrated and the residue was purified by flash chromatography (EtOAc:hex, 7:3 to 1:0) to afford 4-((R)-2-methyl-1-thioureidopropyl)-N-(tetrahydro-2H-pyran-2-yloxy)benzamide as a white solid. LC-MS: (FA) ES+ 352.

Step 2: (R)—N-hydroxy-4-(2-methyl-1-(4-(3-phenylisoxazol-5-yl)thiazol-2-ylamino)propyl)benzamide A mixture of 4-((R)-2-methyl-1-thioureidopropyl)-N-(tetrahydro-2H-pyran-2-yloxy)benzamide (0.0252 g, 0.0717 mmol) and 5-(bromoacetyl)-3-phenylisoxazole (0.0191 g, 0.0717 mmol) in 1,4-dioxane (0.50 mL) was heated at 40° C. for 1 h. The solution was diluted with DCM (0.50 mL) and hydrochloric acid (0.20 mL, 0.80 mmol, 4.00 M of in 1,4-dioxane) was added. The reaction was stirred at rt for 3 h. The mixture was evaporated to dryness, the residue dissolved in DMSO and the solution purified on prep-HPLC to give (R)—N-hydroxy-4-(2-methyl-1-(4-(3-phenylisoxazol-5-yl)thiazol-2-ylamino)propyl)benzamide as a white solid (0.0173 g, 56%). LC-MS: (FA) ES+ 435. $^1$H NMR (dmso-d$_6$, 400 MHz) δ11.13 (s, 1H), 9.00 (s, 1H), 8.52 (d, J=8.6 Hz, 1H), 7.90 (m, 2H), 7.70 (d, J=8.3 Hz, 2H), 7.51 (dd, J=5.1, 1.9 Hz, 3H), 7.44 (d, J=8.3 Hz, 2H), 7.26 (s, 1H), 7.09 (s, 1H), 4.48 (t, J=8.1 Hz, 1H), 2.10 (m, 1H), 1.00 (d, J=6.6 Hz, 3H), 0.78 (d, J=6.7 Hz, 3H).

Example 221

(R)—N-hydroxy-4-(2-methyl-1-(4-(trifluoromethyl)thiazol-2-ylamino)propyl)benzamide Compound I-529

The title compound was prepared in an analogous fashion to that described in Example 3 starting from appropriate starting materials. LC-MS: (FA) ES+ 360. $^1$H NMR (dmso-d$_6$, 400 MHz) δ11.13 (s, 1H), 9.03 (s, 1H), 8.64 (d, J=8.5 Hz, 1H), 7.69 (d, J=8.3 Hz, 2H), 7.39 (d, J=8.3 Hz, 2H), 7.27 (d, J=0.9 Hz, 1H), 4.39 (t, J=8.0 Hz, 1H), 2.00 (m, 1H), 0.95 (d, J=6.7 Hz, 3H), 0.76 (d, J=6.7 Hz, 3H).

II. Biological Data

Example 222

HDAC6 Enzyme Assay

To measure the inhibition of HDAC6 activity, purified human HDAC6 (BPS Bioscience; Cat. No. 5006) is incubated with substrate Ac-Arg-Gly-Lys(Ac)-AMC peptide (Bachem Biosciences; Cat. No. 1-1925) for 1 hour at 30° C. in the presence of test compounds or vehicle DMSO control. The reaction is stopped with the HDAC inhibitor trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition (IC$_{50}$) values are determined from those curves.

Example 223

Nuclear Extract HDAC Assay

As a screen against Class I HDAC enzymes, HeLa nuclear extract (BIOMOL; Cat. No. KI-140) is incubated with Ac-Arg-Gly-Lys(Ac)-AMC peptide (Bachem Biosciences; Cat. No. 1-1925) in the presence of test compounds or vehicle DMSO control. The Hela nuclear extract is enriched for Class I enzymes HDAC1, -2 and -3. The reaction is stopped with the HDAC inhibitor Trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition (IC$_{50}$) values are determined from those curves.

Example 224

Western Blot and Immunofluorescence Assays

Cellular potency and selectivity of compounds are determined using a published assay (Haggarty et al., *Proc. Natl. Acad. Sci. USA* 2003, 100 (8): 4389-4394) using Hela cells (ATCC cat#CCL-2™) which are maintained in MEM medium (Invitrogen) supplemented with 10% FBS; or multiple myeloma cells RPMI-8226 (ATCC cat#CCL-155™) which are maintained in RPMI 1640 medium (Invitrogen) supplemented with 10% FBS. Briefly, cells are treated with inhibitors for 6 or 24 h and either lysed for Western blotting, or fixed for immunofluorescence analyses. HDAC6 potency is determined by measuring K40 hyperacetylation of alpha-tubulin with an acetylation selective monoclonal antibody (Sigma cat#T7451) in IC$_{50}$ experiments. Selectivity against Class I HDAC activity is determined similarly using an antibody that recognizes hyperacetylation of histone H4 (Upstate cat#06-866) in the Western blotting assay or nuclear acetylation (Abcam cat#ab21623) in the immunofluorescence assay.

Example 225

In Vivo Tumor Efficacy Model

Female NCr-Nude mice (age 6-8 weeks, Charles River Labs) are aseptically injected into the subcutaneous space in the right dorsal flank with 1.0–5.0×10$^6$ cells (SKOV-3, HCT-116, BxPC3) in 100 µL of a 1:1 ratio of serum-free culture media (Sigma Aldrich) and BD Matrigel™ (BD Biosciences) using a 1 mL 26⅜ gauge needle (Becton Dickinson Ref#309625). Alternatively, some xenograft models require the use of more immunocompromised strains of mice such as CB-17 SCID (Charles River Labs) or NOD-SCID (Jackson Laboratory). Furthermore, some xenograft models require serial passaging of tumor fragments in which small fragments of tumor tissue (approximately 1 mm$^3$) are implanted subcutaneously in the right dorsal flank of anesthetized (3-5% isoflourane/oxygen mixture) NCr-Nude, CB-17 SCID or NOD-SCID mice (age 5-8 weeks, Charles River Labs or Jackson Laboratory) via a 13-ga trocar needle (Popper & Sons 7927). Tumor volume is monitored twice weekly with Vernier calipers. The mean tumor volume is calculated using the formula V=W$^2$×L/2. When the mean tumor volume is approximately 200 mm$^3$, the animals are randomized into treatment groups of ten animals each. Drug treatment typically includes the test compound as a single agent, and may include combinations of the test compound and other anticancer agents. Dosing and schedules are determined for each experiment based on previous results obtained from pharmacokinetic/pharmacodynamic and maximum tolerated dose studies. The control group will receive vehicle without any drug. Typically, test compound (100-200 μL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 mm³, and/or if tumor volume exceeds 10% of the animal body weight or if the body weight loss exceeds 20%.

The differences in tumor growth trends over time between pairs of treatment groups are assessed using linear mixed effects regression models. These models account for the fact that each animal is measured at multiple time points. A separate model is fit for each comparison, and the areas under the curve (AUC) for each treatment group are calculated using the predicted values from the model. The percent decrease in AUC (dAUC) relative to the reference group is then calculated. A statistically significant P value suggests that the trends over time for the two treatment groups are different.

The tumor measurements observed on a date pre-specified by the researcher (typically the last day of treatment) are analyzed to assess tumor growth inhibition. For this analysis, a T/C ratio is calculated for each animal by dividing the tumor measurement for the given animal by the mean tumor measurement across all control animals. The T/C ratios across a treatment group are compared to the T/C ratios of the control group using a two-tailed Welch's t-test. To adjust for multiplicity, a False Discovery Rate (FDR) is calculated for each comparison using the approach described by Benjamini and Hochberg, *J.R. Stat. Soc. B* 1995, 57:289-300.

As detailed above, compounds of the invention inhibit HDAC6. In certain embodiments, compounds of the invention inhibit HDAC6 with an IC50 value of less than 100 nM including compounds: I-3, I-4, I-5, I-6, I-7, I-8, I-11, I-12, I-15, I-18, I-19, I-22, I-25, I-26, I-30, I-31, I-32, I-35, I-37, I-38, I-44, I-45, I-53, I-55, I-58, I-59, I-62, I-63, I-65, I-68, I-69, I-71, I-73, I-74, I-79, I-85, I-88, I-89, I-92, I-94, I-96, I-98, I-99, I-102, I-103, I-106, I-107, I-109, I-110, I-112, I-115, I-116, I-120, I-122, I-124, I-125, I-127, I-128, I-129, I-130, I-132, I-134, I-135, I-136, I-138, I-140, I-141, I-143, I-145, I-146, I-147, I-148, I-150, I-154, I-160, I-163, I-164, I-172, I-175, I-184, I-185, I-186, I-187, I-190, I-191, I-194, I-207, I-208, I-209, I-210, I-213, I-214, I-222, I-223, I-224, I-225, I-228, I-229, I-230, I-233, I-236, I-237, I-242, I-243, I-245, I-247, I-253, I-261, I-264, I-269, I-274, I-275, I-278, I-281, I-282, I-286, I-287, I-288, I-293, I-295, I-296, I-297, I-299, I-304, I-306, I-307, I-308, I-317, I-319, I-321, I-327, I-328, I-329, I-332, I-334, I-341, I-346, I-348, I-349, I-350, I-354, I-356, I-357, I-358, I-359, I-360, I-365, I-367, I-371, I-374, I-375, I-378, I-381, I-383, I-384, I-385, I-387, I-389, I-397, I-399, I-400, I-512, I-513, I-514, I-515, I-516, I-518, I-519, I-521, I-522, I-523, I-524, I-525, I-526, I-527, I-528, I-529.

In certain embodiments, compounds of the invention inhibit HDAC6 with an IC50 value of greater than 100 nM and less than 500 nM including compounds: I-1, I-2, I-10, I-16, I-17, I-20, I-21, I-23, I-40, I-42, I-43, I-46, I-47, I-48, I-66, I-67, I-76, I-77, I-78, I-84, I-86, I-87, I-97, I-105, I-113, I-114, I-117, I-121, I-123, I-126, I-133, I-142, I-156, I-158, I-173, I-174, I-176, I-178, I-182, I-192, I-193, I-196, I-201, I-202, I-203, I-206, I-215, I-219, I-220, I-226, I-227, I-232, I-239, I-240, I-249, I-252, I-255, I-258, I-260, I-262, I-266, I-267, I-270, I-277, I-279, I-290, I-291, I-294, I-298, I-300, I-301, I-302, I-305, I-310, I-315, I-316, I-318, I-330, I-331, I-336, I-338, I-342, I-344, I-352, I-353, I-355, I-363, I-364, I-368, I-369, I-372, I-376, I-377, I-380, I-382, I-388, I-395, I-401, I-480, I-485, I-487, I-489, I-488, I-517.

In certain embodiments, compounds of the invention inhibit HDAC6 with an IC$_{50}$ value of greater than 500 nM and less than 1 μM including compounds: I-9, I-13, I-28, I-29, I-41, I-52, I-75, I-81, I-91, I-101, I-108, I-137, I-139, I-151, I-179, I-181, I-183, I-195, I-199, I-204, I-216, I-246, I-251, I-259, I-268, I-271, I-272, I-273, I-303, I-309, I-339, I-351, I-393, I-536.

In certain embodiments, compounds of the invention inhibit HDAC6 with an IC$_{50}$ value of greater than 1 μM including compounds: I-24, I-34, I-36, I-39, I-56, I-57, I-70, I-72, I-80, I-83, I-93, I-100, I-104, I-111, I-144, I-149, I-155, I-157, I-159, I-162, I-165, I-167, I-169, I-171, I-177, I-180, I-189, I-200, I-211, I-212, I-217, I-218, I-231, I-234, I-238, I-241, I-244, I-248, I-250, I-257, I-263, I-265, I-280, I-283, I-285, I-289, I-292, I-311, I-312, I-313, I-314, I-320, I-322, I-323, I-324, I-326, I-333, I-337, I-343, I-345, I-362, I-366, I-370, I-373, I-379, I-386, I-390, I-392, I-396, I-402, I-403, I-481, I-483, I-484, I-486, I-488, I-491, I-490.

As detailed above, compounds of the invention are selective for HDAC6 over other Class I HDAC enzymes. In certain embodiments, the ratio of HDAC IC50 (as obtained in the nuclear extract assay described above) to HDAC6 IC50 is less than 5 (HDAC IC50/HDAC6 IC50). In certain embodiments, the ratio of HDAC IC50 to HDAC6 IC50 is between 5 and 10. In certain embodiments, the ratio of HDAC IC50 to HDAC6 IC50 is between 10 and 100.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of examples.

What is claimed is:
1. A compound of formula (I):

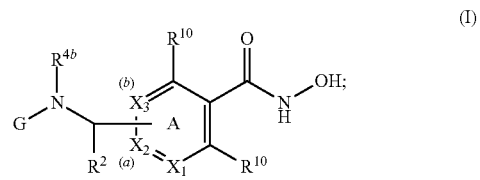

or a pharmaceutically acceptable salt thereof; wherein:
ring A is an aromatic 6-membered ring connected through one of positions (a) or (b);
  $X_1$ is $CR^1$;
  (i) when ring A is connected through position (a), $X_2$ is C; and $X_3$ is $CR^1$; or
  (ii) when ring A is connected through position (b), $X_3$ is C; and $X_2$ is $CR^1$;
each occurrence of $R^1$ is hydrogen;
each occurrence of $R^{10}$ is hydrogen;
$R^2$ is methyl, ethyl, isopropyl, n-propyl, trifluoromethyl, tert-butyl, cyclopropyl, or phenyl;
$R^{4b}$ is hydrogen;
G is —$V_1$—$R^3$;
$V_1$ is —C(O)—, —C(O)—N($R^{4a}$)—, or —S(O)$_2$—;

R³ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; and each occurrence of $R^{4a}$ is independently hydrogen, or unsubstituted or substituted $C_{1-4}$ aliphatic.

2. The compound of claim 1, wherein the compound of formula (I) is represented by:

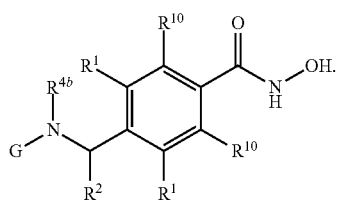

(I-i)

3. The compound of claim 1, wherein the compound of formula (I) is represented by:

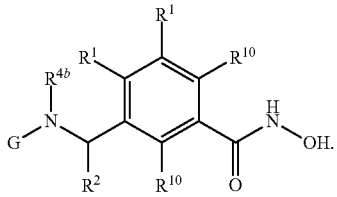

(I-v)

4. The compound of claim 1, represented by formula (II-a):

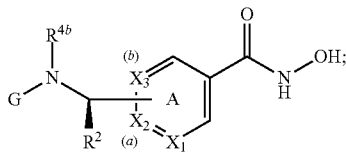

(II-a)

wherein
ring A is an aromatic 6-membered ring connected through one of positions (a) or (b);
$X_1$ is $CR^1$;
  (i) when ring A is connected through position (a), $X_2$ is C; and $X_3$ is $CR^1$; or
  (ii) when ring A is connected through position (b), $X_3$ is C; and $X_2$ is $CR^1$;
each occurrence of $R^1$ is hydrogen;
each occurrence of $R^{10}$ is hydrogen;
$R^2$ is methyl, ethyl, isopropyl, n-propyl, trifluoromethyl, tert-butyl, cyclopropyl, or phenyl;
$R^{4b}$ is hydrogen;
G is —$V_1$—$R^3$;
$V_1$ is —C(O)—, —C(O)—N($R^{4a}$)—, or —S(O)₂—;
R³ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; and each occurrence of $R^{4a}$ is independently hydrogen, or unsubstituted or substituted $C_{1-4}$ aliphatic.

5. The compound of claim 4, wherein the compound of formula (II-a) is represented by:

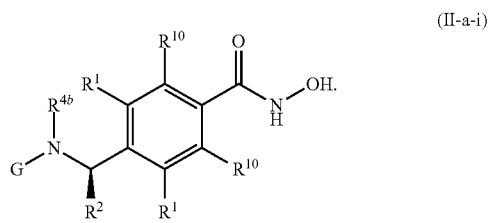

(II-a-i)

6. The compound of claim 4, wherein the compound of formula (II-a) is represented:

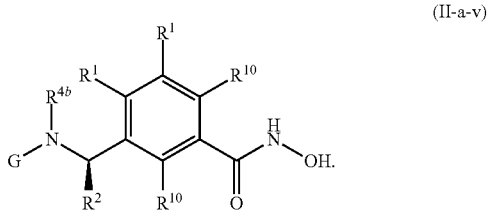

(II-a-v)

7. The compound of claim 4, wherein:
each substitutable carbon chain atom in R³ is unsubstituted or substituted with 1-2 occurrences of —$R^{5dd}$;
each substitutable saturated ring carbon atom in R³ is unsubstituted or substituted with =O, =S, =C($R^5$)₂, =N—N($R^4$)₂, =N—O$R^5$, =N—NHC(O)$R^5$, N—NHCO₂$R^6$, =N—NHSO₂$R^6$, =N—$R^5$ or —$R^{5a}$;
each substitutable unsaturated ring carbon atom in R³ is unsubstituted or is substituted with —$R^{5a}$;
each substitutable ring nitrogen atom in R³ is unsubstituted or substituted with —$R^{9b}$;
each $R^{5a}$ is independently halogen, —NO₂, —CN, —C($R^5$)=C($R^5$)₂, —C($R^5$)=C($R^5$)($R^{10}$), —C≡C—$R^5$, —O$R^5$, —S$R^6$, —S(O)$R^6$, —SO₂$R^6$, —SO₂N($R^4$)₂, —N($R^4$)₂, —$NR^4$C(O)$R^5$, —$NR^4$C(O)N($R^4$)₂, —$NR^4$CO₂$R^6$, —OC(O)N($R^4$)₂, —C(O)—C(O)$R^5$, —C(O)$R^5$, —C(O)N($R^4$)₂, —C(=$NR^4$)—N($R^4$)₂, —C(=$NR^4$)—O$R^5$, —N($R^4$)—N($R^4$)₂, —N($R^4$)C(=$NR^4$)—N($R^4$)₂, —N($R^4$)SO₂$R^6$, —N($R^4$)SO₂N($R^4$)₂, —P(O)($R^5$)₂, —P(O)(O$R^5$)₂, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{5a}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur;

each occurrence of $R^{5dd}$ is independently halogen, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl);

each $R^4$ is independently hydrogen, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur;

each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each $R^6$ is independently unsubstituted or substituted $C_{1-6}$ aliphatic, or unsubstituted or substituted 6-10-membered aryl;

each $R^7$ is independently unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each $R^{9b}$ is independently —C(O)$R^5$, —C(O)N($R^4$)$_2$, —CO$_2$$R^6$, —SO$_2$$R^6$, —SO$_2$N($R^4$)$_2$, unsubstituted $C_{1-4}$ aliphatic, or $C_{1-4}$ aliphatic substituted with 1-2 occurrences of $R^7$ or $R^8$; and each $R^8$ is independently halogen, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl).

8. The compound of claim 7, wherein:
each substitutable saturated ring carbon atom in $R^3$ is unsubstituted or substituted with —$R^{5a}$;
the total number of $R^{5a}$ substituents is p;
p is 1-2;
each $R^{5a}$ is independently halogen, —CN, —OH, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —NHC(O)NHC$_{1-3}$ alkyl, —NHS(O)$_2$$C_{1-3}$ alkyl, —NHC$_{1-3}$ alkyl, —N($C_{1-3}$alkyl)$_2$, 3-10-membered cycloaliphatic substituted with 0-2 occurrences of —$R^{7a}$, 4-10-membered heterocyclyl having 1-5 heteroatoms independently selected from nitrogen, oxygen, and sulfur substituted with 0-2 occurrences of —$R^{7a}$, 6-10-membered aryl substituted with 0-2 occurrences of $R^{7a}$, or 5-10-membered heteroaryl having 1-5 heteroatoms independently selected from nitrogen, oxygen, and sulfur substituted with 0-2 occurrences of —$R^{7a}$; and each occurrence of $R^{7a}$ is independently halogen, $C_{1-3}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, or —NHS(O)$_2$$C_{1-3}$ alkyl.

9. The compound of claim 7, represented by formula (III-a-i):

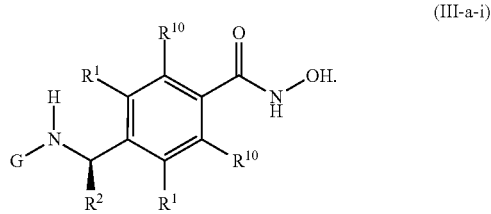

(III-a-i)

10. The compound of claim 9, wherein $R^2$ is methyl, ethyl, isopropyl, or n-propyl.

11. The compound of claim 9, wherein:
each substitutable saturated ring carbon atom in $R^3$ is unsubstituted or substituted with —$R^{5a}$;
the total number of $R^{5a}$ substituents is p;
p is 1-2;
each $R^{5a}$ is independently halogen, —CN, —OH, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, —NHS(O)$_2$$C_{1-3}$ alkyl, 3-10-membered cycloaliphatic substituted with 0-2 occurrences of —$R^{7a}$, 4-10-membered heterocyclyl having 1-5 heteroatoms independently selected from nitrogen, oxygen, and sulfur substituted with 0-2 occurrences of —$R^{7a}$, 6-10-membered aryl substituted with 0-2 occurrences of —$R^{7a}$, or 5-10-membered heteroaryl having 1-5 heteroatoms independently selected from nitrogen, oxygen, and sulfur substituted with 0-2 occurrences of —$R^{7a}$; and each occurrence of $R^{2a}$ is independently halogen, $C_{1-3}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, or —NHS(O)$_2$$C_{1-3}$ alkyl.

12. The compound of claim 7, represented by formula (III-a-v):

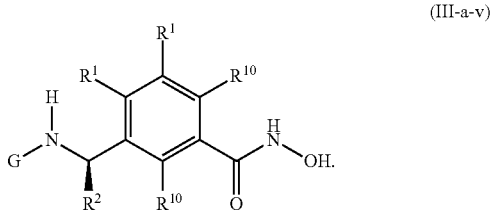

(III-a-v)

13. The compound of claim 12, wherein $R^2$ is methyl, ethyl, isopropyl, or n-propyl.

14. The compound of claim 12, wherein:
each substitutable saturated ring carbon atom in $R^3$ is unsubstituted or substituted with —$R^{5a}$;
the total number of lea substituents is p;
p is 1-2;
each $R^{5a}$ is independently halogen, —CN, —OH, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NHC$_{1-3}$ alkyl, —NHC(O)NHC$_{1-3}$ alkyl, —NHS(O)$_2$C$_{1-3}$ alkyl, 3-10-membered cycloaliphatic substituted with 0-2 occurrences of —R$^{7a}$, 4-10-membered heterocyclyl having 1-5 heteroatoms independently selected from nitrogen, oxygen, and sulfur substituted with 0-2 occurrences of —R$^{7a}$, 6-10-membered aryl substituted with 0-2 occurrences of —R$^{7a}$, or 5-10-membered heteroaryl having 1-5 heteroatoms independently selected from nitrogen, oxygen, and sulfur substituted with 0-2 occurrences of —R$^{7a}$; and each occurrence of R$^{7a}$ is independently halogen, C$_{1-3}$ alkyl, C$_{1-3}$ fluoroalkyl, —O—C$_{1-3}$ alkyl, —O—C$_{1-3}$ fluoroalkyl, —NHC(O)C$_{1-3}$ alkyl, —C(O)NHC$_{1-3}$ alkyl, —NHC(O)NHC$_{1-3}$ alkyl, or —NHS(O)$_2$C$_{1-3}$ alkyl.

15. A pharmaceutical composition comprising a compound of claim 1 and a pharmaceutically acceptable carrier.

16. A compound, where in the compound is:

| | |
|---|---|
| I-1 | 4-{1-[(ethylsulfonyl)amino]ethyl}-N-hydroxybenzamide; |
| I-2 | 4-(1-{[(4-fluorophenyl)sulfonyl]amino}ethyl)-N-hydroxybenzamide; |
| I-3 | N-(1-{4-[(hydroxyamino)carbonyl]phenyl}ethyl)adamantane-1-carboxamide; |
| I-4 | N-(1-{4-[(hydroxyamino)carbonyl]phenyl}-2,2-dimethylpropyl)-1-benzofuran-2-carboxamide; |
| I-5 | N-((1R)-1-{4-[(hydroxyamino)carbonyl]phenyl}ethyl)-4-methyl-2-phenyl-4H-furo[3,2-b]pyrrole-5-carboxamide; |
| I-6 | N-hydroxy-4-(1-{[(1-naphthylamino)carbonyl]amino}ethyl)benzamide; |
| I-7 | N-(1-{4-[(hydroxyamino)carbonyl]phenyl}ethyl)-3-methyl-1-benzofuran-2-carboxamide; |
| I-8 | 2-fluoro-N-(1-{4-[(hydroxyamino)carbonyl]phenyl}ethyl)-5-methylbenzamide; |
| I-9 | N-(1-{4-[(hydroxyamino)carbonyl]phenyl}-2,2-dimethylpropyl)-2,5-dimethyl-3-furamide; |
| I-10 | N-(1-{3-[(hydroxyamino)carbonyl]phenyl}ethyl)-1H-indole-3-carboxamide; |
| I-11 | N-(1-{4-[(hydroxyamino)carbonyl]phenyl}-2-methylpropyl)biphenyl-4-carboxamide; |
| I-12 | N-((1R)-1-{4-[(hydroxyamino)carbonyl]phenyl}ethyl)-3-methyl-1-benzothiophene-2-carboxamide; |
| I-13 | 3-(1-{[(5-chloro-1-benzothien-3-yl)acetyl]amino}ethyl)-N-hydroxybenzamide; |
| I-14 | 4-((1R)-1-{[(tert-butylamino)carbonyl]amino}ethyl)-N-hydroxybenzamide; |
| I-15 | N-((1R)-1-{4-[(hydroxyamino)carbonyl]phenyl}butyl)adamantane-1-carboxamide; |
| I-16 | N-((1R)-1-{3-[(hydroxyamino)carbonyl]phenyl}ethyl)-4-methyl-2-phenyl-4H-furo[3,2-b]pyrrole-5-carboxamide; |
| I-17 | N-(1-{4-[(hydroxyamino)carbonyl]phenyl}-2-methylpropyl)-4-methyl-2-phenylpyrimidine-5-carboxamide; |
| I-18 | 4-[(1R)-1-(1{[1-adamantylamino]carbonyl}amino)butyl]-N-hydroxybenzamide; |
| I-19 | N-((1R)-1-{4-[(hydroxyamino)carbonyl]phenyl}-2-methylpropyl)-4-methoxybenzamide; |
| I-20 | N-hydroxy-4-[-({[(4-phenoxyphenyl)amino]carbonyl}amino)ethyl]benzamide; |
| I-21 | 4-{1-[(cyclobutylcarbony)amino]ethyl}-N-hydroxybenzamide; |
| I-22 | N-((1R)-1-{4-[(hydroxyamino)carbonyl]phenyl}-2-methylpropyl)-1-benzofuran-2-carboxamide; |
| I-23 | N-hydroxy-4-(1-{[(3-methoxyphenyl)sulfonyl]amino}ethyl)benzamide; |
| I-24 | 4-(1-{[(2-chloro-6-fluorophenyl)acetyl]amino}ethyl)-N-hydroxybenzamide; |
| I-25 | N-((1S)-1-{4-[(hydroxyamino)carbonyl]phenyl}ethyl)-1-methyl-1H-pyrrole-2-carboxamide; |
| I-26 | N-hydroxy-4((1R)-1-{[(1-methylcyclohexyl)carbonyl]amino}ethyl)benzamide; |
| I-27 | 4-[1-({[(3-fluorophenyl)amino]carbonyl}amino)ethyl]-N-hydroxybenzamide; |
| I-28 | N-hydroxy-4-{1-[(mesitylacetyl)amino]-2-methylpropyl}benzamide; |
| I-29 | N-(1-{3-[(hydroxyamino)carbonyl]phenyl}ethyl)-2-methyl-1,3-thiazole-4-carboxamide; |
| I-30 | N-(1-{4-[(hydroxyamino)carbonyl]phenyl}-2-methylpropyl)-1-methyl-1H-pyrrole-2-carboxamide; |
| I-31 | N-hydroxy-4-[1-({[(2-phenoxyphenyl)amino]carbonyl}amino)ethyl]benzamide; |
| I-32 | N-(1-{4-[(hydroxyamino)carbonyl]phenyl}-2-methylpropyl)-1-benzofuran-2-carboxamide; |
| I-33 | N-hydroxy-4-{1-[(propylsulfonyl)amino]ethyl}benzamide; |
| I-34 | N-hydroxy-4-(1-{[(2-methoxyphenyl)acetyl]amino}ethyl)benzamide; |
| I-35 | 6-chloro-N-(1-{4-[(hydroxyamino)carbonyl]phenyl}ethyl)imidazo[1,2-a]pyridine-2-carboxamide; |
| I-36 | N-hydroxy-4-[1-(isobutyrylamino)ethyl]benzamide; |
| I-37 | 4-[1-({[(4-fluorophenyl)amino]carbonyl}amino)ethyl]-N-hydroxybenzamide; |
| I-38 | N-(1-{4-[(hydroxyamino)carbonyl]phenyl}ethyl)-4-isopropoxybenzamide; |
| I-39 | 4,5-dichloro-N-(1-{3-[(hydroxyamino)carbonyl]phenyl}ethyl)-1-methyl-1H-pyrrole-2-carboxamide; |
| I-40 | 4-fluoro-N-(1-{4-[(hydroxyamino)carbonyl]phenyl}-2-methylpropyl)benzamide; |
| I-41 | 4-[1-({[1-(4-chlorophenyl)cyclopropyl]carbonyl}amino)-2,2-dimethylpropyl]-N-hydroxybenzamide; |
| I-42 | N-(1-{4-[(hydroxyamino)carbonyl]phenyl}-2,2-dimethylpropyl)-2-methyl-1,3-thiazole-4-carboxamide; |
| I-43 | N-(1-{4-[(hydroxyamino)carbonyl]phenyl}-2-methylpropyl)-1,3-benzothiazole-6-carboxamide; |
| I-44 | 4-[1-({[(2,4-dimethoxyphenyl)amino]carbonyl}amino)ethyl]-N-hydroxybenzamide; |
| I-45 | N-hydroxy-4-{1-[(3-phenylpropanoyl)amino]ethyl}benzamide; |
| I-46 | N-((R)-cyclopropyl{4-[(hydroxyamino)carbonyl]phenyl}methyl)adamantane-1-carboxamide; |
| I-47 | N-hydroxy-4-(1-{[(4-methoxyphenyl)sulfonyl]amino}ethyl)benzamide; |
| I-48 | N-hydroxy-4-(2-methyl-1-{[(5-methyl-2-phenyl-1,3-oxazol-4-yl)acetyl]amino}propyl)benzamide; |
| I-49 | N-hydroxy-4-(1-{[(2-oxo-2H-chromen-6-yl)sulfonyl]amino}ethyl)benzamide; |
| I-50 | 4-{(1R)-1-[(2,2-dimethylpropanoyl)amino]-2,2,2-trifluoroethyl}-N-hydroxybenzamide; | or a pharmaceutically acceptable salt thereof.

17. A compound, where in the compound is:

| | |
|---|---|
| I-51 | 4-(1-{[(2,5-dimethylphenyl)sulfonyl]amino}ethyl)-N-hydroxybenzamide; |
| I-52 | N-(1-{4-[(hydroxyamino)carbonyl]phenyl}-2,2-dimethylpropyl)-3,5-bis(trifluoromethyl)benzamide; |
| I-53 | N-((1S)-1-{4-[(hydroxyamino)carbonyl]phenyl}ethyl)-1-benzothiophene-2-carboxamide; |
| I-54 | 4-(1-{[(1,2-dimethyl-1H-imidazol-4-yl)sulfonyl]amino}ethyl)-N-hydroxybenzamide; |
| I-55 | 4-[1-({[(3,4-dimethylphenyl)amino]carbonyl}amino)ethyl]-N-hydroxybenzamide; |
| I-56 | N-(1-{4-[(hydroxyamino)carbonyl]phenyl}ethyl)cinnoline-4-carboxamide; |
| I-57 | N-(1-{3-[(hydroxyamino)carbonyl]phenyl}ethyl)-2-(trifluoromethyl)benzamide; |
| I-58 | N-(1-{4-[(hydroxyamino)carbonyl]phenyl}-2-methylpropyl)adamantane-1-carboxamide; |
| I-59 | 4-{1-[(2,2-dimethylpropanoyl)amino]ethyl}-N-hydroxybenzamide; |
| I-60 | N-hydroxy-4-(1-{[(1,3,5-trimethyl-1H-pyrazol-4-yl)sulfonyl]amino}ethyl)benzamide; |
| I-61 | 4-(1-{[(4-fluoro-2-methylphenyl)sulfonyl]amino}ethyl)-N-hydroxybenzamide; |
| I-62 | N-((1R)-1-{4-[(hydroxyamino)carbonyl]phenyl}butyl)-3-methyl-1-benzothiophene-2-carboxamide; |
| I-63 | N-(1-{4-[(hydroxyamino)carbonyl]phenyl}ethyl)-4-(1H-pyrrol-1-yl)benzamide; |
| I-64 | 4-(1-{[(4-chlorobenzyl)sulfonyl]amino}ethyl)-N-hydroxybenzamide; |
| I-65 | N-((1R)-1-{4-[(hydroxyamino)carbonyl]phenyl}-2-methylpropyl)-1-methyl-1H-pyrrole-2-carboxamide; |
| I-66 | N-(1-{4-[(hydroxyamino)carbonyl]phenyl}-2,2-dimethylpropyl)-1-methyl-1H-pyrazole-3-carboxamide; |
| I-67 | N-((1S)-1-{4-[(hydroxyamino)carbonyl]phenyl}-2-methylpropyl)-1-benzothiophene-2-carboxamide; |
| I-68 | N-((1R)-1-{4-[(hydroxyamino)carbonyl]phenyl}-2-methylpropyl)-1H-indole-2-carboxamide; |
| I-69 | N-(1-{4-[(hydroxyamino)carbonyl]phenyl}-2-methylpropyl)-5-methyl-1H-indole-2-carboxamide; |
| I-70 | N-hydroxy-4-(1-{[4-(4-methoxyphenyl)butanoyl]amino}ethyl)benzamide; |
| I-71 | 4-(1-{[(1,3-benzodioxol-5-ylamino)carbonyl]amino}ethyl)-N-hydroxybenzamide; |
| I-72 | N-(1-{3-[(hydroxyamino)carbonyl]phenyl}ethyl)-4-methyl-2-[4-(trifluoromethyl)phenyl]-4H-furo[3,2-b]pyrrole-5-carboxamide; |
| I-73 | 4-{(1R)-1-[(2,2-dimethylpropanoyl)amino]ethyl}-N-hydroxybenzamide; |
| I-74 | 4-[1-({[(2-fluorophenyl)amino]carbonyl}amino)ethyl]-N-hydroxybenzamide; |
| I-75 | N-(1-{4-[(hydroxyamino)carbonyl]phenyl}-2,2-dimethylpropyl)-3-(methylsulfonyl)benzamide; |
| I-76 | N-hydroxy-4-[1-({[(2-methylbenzyl)amino]carbonyl}amino)ethyl]benzamide; |
| I-77 | 1-benzyl-3-tert-butyl-N-(1-{4-[(hydroxyamino)carbonyl]phenyl}-2-methylpropyl)-1H-pyrazole-5-carboxamide; |
| I-78 | 4-(1-{[(2,4-dimethylphenyl)sulfonyl]amino}ethyl)-N-hydroxybenzamide; |
| I-79 | N-((1R)-1-{4-[(hydroxyamino)carbonyl]phenyl}butyl)-1-benzofuran-2-carboxamide; |
| I-80 | 4-(2,2-dimethyl-1-{[(5-methyl-2-phenyl-1,3-oxazol-4-yl)acetyl]amino}propyl)-N-hydroxybenzamide; |
| I-81 | N-(1-{3-[(hydroxyamino)carbonyl]phenyl}ethyl)-1-methyl-1H-pyrazole-3-carboxamide; |
| I-82 | 4-{1-[(2,3-dihydro-1,4-benzodioxin-6-ylsulfonyl)amino]ethyl}-N-hydroxybenzamide; |
| I-83 | N-(1-{3-[(hydroxyamino)carbonyl]phenyl}ethyl)adamantane-1-carboxamide; |
| I-84 | N-(1-{3-[(hydroxyamino)carbonyl]phenyl}ethyl)-1,5-dimethyl-1H-pyrazole-3-carboxamide; |
| I-85 | N-hydroxy-4-[1-({[(3-methylphenyl)amino]carbonyl}amino)ethyl]benzamide; |
| I-86 | N-(1-{4-[(hydroxyamino)carbonyl]phenyl}-2,2-dimethylpropyl)-1,3-dimethyl-1H-pyrazole-4-carboxamide; |
| I-87 | N-(1-{4-[(hydroxyamino)carbonyl]phenyl}-2,2-dimethylpropyl)pyrazine-2-carboxamide; |
| I-88 | 4-{1-[(cyclopentylcarbonyl)amino]ethyl}-N-hydroxybenzamide; |
| I-89 | 4-[1-({[(2,5-dichlorophenyl)amino]carbonyl}amino)ethyl]-N-hydroxybenzamide; |
| I-90 | 4-(1-{[(3,4-difluorophenyl)sulfonyl]amino}ethyl)-N-hydroxybenzamide; |
| I-91 | N-(1-{3-[(hydroxyamino)carbonyl]phenyl}ethyl)-3,5-dimethyl-1H-pyrrole-2-carboxamide; |
| I-92 | N-((1R)-1-{4-[(hydroxyamino)carbonyl]phenyl}ethyl)biphenyl-4-carboxamide; |
| I-93 | N-(1-{3-[(hydroxyamino)carbonyl]phenyl}-2-methylpropyl)-3-methyl-1-benzofuran-2-carboxamide; |
| I-94 | N-(1-{4-[(hydroxyamino)carbonyl]phenyl}-2-methylpropyl)-1-benzothiophene-2-carboxamide; |
| I-95 | N-hydroxy-4-{1-[(1-naphthylsulfonyl)amino]ethyl}benzamide; |
| I-96 | 4,5-dichloro-N-((1R)-1-{4-[(hydroxyamino)carbonyl]phenyl}-2-methylpropyl)-1-methyl-1H-pyrrole-2-carboxamide; |
| I-97 | N-(1-{3-[(hydroxyamino)carbonyl]phenyl}ethyl)-1-benzothiophene-2-carboxamide; |
| I-98 | N-(1-{4-[(hydroxyamino)carbonyl]phenyl}ethyl)-1-methyl-1H-indole-2-carboxamide; |
| I-99 | N-[(R)-{4-[(hydroxyamino)carbonyl]phenyl}(phenyl)methyl]-1-benzothiophene-2-carboxamide; |
| I-100 | N-(1-{3-[(hydroxyamino)carbonyl]phenyl}ethyl)-1-methyl-1H-benzimidazole-2-carboxamide; | or a pharmaceutically acceptable salt thereof.

18. A compound, where in the compound is:

| | |
|---|---|
| I-101 | N-(1-{3-[(hydroxyamino)carbonyl]phenyl}ethyl)-2-methyl-4,5,6,7-tetrahydro-2H-indazole-3-carboxamide; |
| I-102 | N-((1R)-1-{4-[(hydroxyamino)carbonyl]phenyl}ethyl)-1-methyl-1H-pyrrole-2-carboxamide; |
| I-103 | 4-[1-({[(3-chloro-4-methylphenyl)amino]carbonyl}amino)ethyl]-N-hydroxybenzamide; |
| I-104 | N-(1-{3-[(hydroxyamino)carbonyl]phenyl}ethyl)-2,5-dimethyl-3-furamide; |
| I-105 | 4-((1R)-1-{[(1-adamantylamino)carbonyl]amino}-2,2,2-trifluoroethyl)-N-hydroxybenzamide; |
| I-106 | N-((1R)-1-{4-[(hydroxyamino)carbonyl]phenyl}butyl)-1-methyl-1H-indole-2-carboxamide; |
| I-107 | N-(1-{4-[(hydroxyamino)carbonyl]phenyl}-2,2-dimethylpropyl)-1-methyl-1H-indole-3-carboxamide; |
| I-108 | 4,5-dichloro-1-methyl-N-((1S)-2,2,2-trifluoro-1-{4-[(hydroxyamino)carbonyl]phenyl}ethyl)-1H-pyrrole-2-carboxamide; |
| I-109 | N-(1-{4-[(hydroxyamino)carbonyl]phenyl}ethyl)-3-phenyl-1H-pyrazole-5-carboxamide; |
| I-110 | 4-[1-({[1-(4-chlorophenyl)cyclobutyl]carbonyl}amino)ethyl]-N-hydroxybenzamide; |
| I-111 | N-hydroxy-4-{1-[(3-methylbutanoyl)amino]ethyl}benzamide; |
| I-112 | N-(1-{4-[(hydroxyamino)carbonyl]phenyl}-2-methylpropyl)thiophene-2-carboxamide; |
| I-113 | N-((1R)-1-{3-[(hydroxyamino)carbonyl]phenyl}ethyl)-3-methyl-1-benzothiophene-2-carboxamide; |
| I-114 | N-(1-{4-[(hydroxyamino)carbonyl]phenyl}ethyl)-2-methyl-4,5,6,7-tetrahydro-2H-indazole-3-carboxamide; |
| I-115 | N-((1R)-1-{4-[(hydroxyamino)carbonyl]phenyl}ethyl)-1-methyl-1H-indole-2-carboxamide; |
| I-116 | 2,4,5-trifluoro-N-(1-{4-[(hydroxyamino)carbonyl]phenyl}-2-methylpropyl)benzamide; |
| I-117 | N-(1-{3-[(hydroxyamino)carbonyl]phenyl}ethyl)-1-benzothiophene-3-carboxamide; |
| I-118 | 4-(1-{[(3-chloro-4-methylphenyl)sulfonyl]amino}ethyl)-N-hydroxybenzamide; |
| I-119 | 1-methyl-N-((1R)-2,2,2-trifluoro-1-{4-[(hydroxyamino)carbonyl]phenyl}ethyl)-1H-pyrrole-2-carboxamide; |
| I-120 | 4-[1-({[(3-fluoro-4-methylphenyl)amino]carbonyl}amino)ethyl]-N-hydroxybenzamide; |
| I-121 | N-((1R)-1-{3-[(hydroxyamino)carbonyl]phenyl}ethyl)biphenyl-4-carboxamide; |
| I-122 | 4-methoxy-N-((1S)-2,2,2-trifluoro-1-{4-[(hydroxyamino)carbonyl]phenyl}ethyl)benzamide; |
| I-123 | N-(1-{4-[(hydroxyamino)carbonyl]phenyl}-2,2-dimethylpropyl)-1,3-thiazole-4-carboxamide; |
| I-124 | N-[(S)-{4-[(hydroxyamino)carbonyl]phenyl}(phenyl)methyl]-1-benzothiophene-2-carboxamide; |
| I-125 | N-(1-{4-[(hydroxyamino)carbonyl]phenyl}ethyl)imidazo[1,2-a]pyridine-2-carboxamide; |
| I-126 | N-hydroxy-4-((1R)-2-methyl-1-{[(1-methylcyclohexyl)carbonyl]amino}propyl)benzamide; |

-continued

I-127 N-(1-{4-[(hydroxyamino)carbonyl]phenyl}-2,2-dimethylpropyl)-1H-indole-2-carboxamide;
I-128 N-(1-{4-[(hydroxyamino)carbonyl]phenyl}ethyl)quinoline-2-carboxamide;
I-129 N-(1-{4-[(hydroxyamino)carbonyl]phenyl}-2,2-dimethylpropyl)-5-methyl-1H-indole-2-carboxamide;
I-130 5-chloro-N-(1-{4-[(hydroxyamino)carbonyl]phenyl}-2-methylpropyl)-1-benzofuran-2-carboxamide;
I-131 4-(1-{[(4-tert-butylphenyl)sulfonyl]amino}ethyl)-N-hydroxybenzamide;
I-132 N-hydroxy-4-(1-{[(1-methylcyclohexyl)carbonyl]amino}ethyl)benzamide;
I-133 N-(1-{4-[(hydroxyamino)carbonyl]phenyl}-2,2-dimethylpropyl)-1-methyl-1H-pyrrole-2-carboxamide;
I-134 N-(1-{4-[(hydroxyamino)carbonyl]phenyl}ethyl)-2,3-dihydro-1-benzofuran-7-carboxamide;
I-135 N-(1-{4-[(hydroxyamino)carbonyl]phenyl}-2-methylpropyl)-2,1,3-benzothiadiazole-5-carboxamide;
I-136 4-chloro-N-(1-{4-[(hydroxyamino)carbonyl]phenyl}ethyl)benzamide;
I-137 3,5-difluoro-N-(1-{3-[(hydroxyamino)carbonyl]phenyl}ethyl)benzamide;
I-138 N-(1-{4-[(hydroxyamino)carbonyl]phenyl}ethyl)-4-(1,3-oxazol-5-yl)benzamide;
I-139 N-(1-{4-[(hydroxyamino)carbonyl]phenyl}-2-methylpropyl)-2-methyl-4-(trifluoromethyl)-1,3-thiazole-5-carboxamide;
I-140 4-[1-({[(4-tert-butylphenyl)amino]carbonyl}amino)ethyl]-N-hydroxybenzamide;
I-141 N-hydroxy-4-{1-[({[4-(trifluoromethoxy)phenyl]amino}carbonyl)amino]ethyl}benzamide;
I-142 N-(1-{3-[(hydroxyamino)carbonyl]phenyl}ethyl)biphenyl-4-carboxamide;
I-143 4'-fluoro-N-(1-{4-[(hydroxyamino)carbonyl]phenyl}-2-methylpropyl)biphenyl-4-carboxamide;
I-144 4-{1-[(3,3-dimethylbutanoyl)amino]ethyl}-N-hydroxybenzamide;
I-145 N-(1-{4-[(hydroxyamino)carbonyl]phenyl}-2,2-dimethylpropyl)-1-methyl-1H-indole-5-carboxamide;
I-146 N-((1R)-1-{4-[(hydroxyamino)carbonyl]phenyl}butyl)-4-methoxybenzamide;
I-147 N-(1-{4-[(hydroxyamino)carbonyl]phenyl}ethyl)-5-methylthiophene-2-carboxamide;
I-148 4-(1-{[(2,3-dihydro-1-benzofuran-5-ylamino)carbonyl]amino}ethyl)-N-hydroxybenzamide;
I-149 3-{1-[(cyclohexylcarbonyl)amino]ethyl}-N-hydroxybenzamide;
I-150 4-{1-[({[4-(difluoromethoxy)phenyl]amino}carbonyl)amino]ethyl}-N-hydroxybenzamide;

or a pharmaceutically acceptable salt thereof.
19. A compound, where in the compound is:

I-151 N-hydroxy-3-(1-{[4-(trifluoromethyl)benzoyl]amino}ethyl)benzamide;
I-152 4-(1-{[(2,5-difluorophenyl)sulfonyl]amino}ethyl)-N-hydroxybenzamide;
I-153 4-(1-{[(3-fluoro-4-methoxyphenyl)sulfonyl]amino}ethyl)-N-hydroxybenzamide;
I-154 N-hydroxy-4-(1-{[(1-methylcyclopropyl)carbonyl]amino}ethyl)benzamide;
I-155 N-(1-{4-[(hydroxyamino)carbonyl]phenyl}-2-methylpropyl)-2,5-bis(trifluoromethyl)benzamide;
I-156 4-[1-({[(2,6-dimethylphenyl)amino]carbonyl}amino)ethyl]-N-hydroxybenzamide;
I-157 N-((1S)-1-{4-[(hydroxyamino)carbonyl]phenyl}-2-methylpropyl)adamantane-1-carboxamide;
I-158 N-(1-{4-[(hydroxyamino)carbonyl]phenyl}-2,2-dimethylpropyl)-1-benzothiophene-3-carboxamide;
I-159 N-hydroxy-4-(1-{[(4-methoxyphenyl)acetyl]amino}ethyl)benzamide;
I-160 N-(1-{4-[(hydroxyamino)carbonyl]phenyl}ethyl)-5,7-dimethylpyrazolo[1,5-a]pyrimidine-2-carboxamide;
I-161 4-{1-[(2,1,3-benzoxadiazol-4-ylsulfonyl)amino]ethyl}-N-hydroxybenzamide;
I-162 N-(1-{4-[(hydroxyamino)carbonyl]phenyl}-2,2-dimethylpropyl)adamantane-1-carboxamide;
I-163 4-{1-[({[2-chloro-4-(trifluoromethyl)phenyl]amino}carbonyl)amino]ethyl}-N-hydroxybenzamide;
I-164 4-fluoro-N-(1-{4-[(hydroxyamino)carbonyl]phenyl}ethyl)-3-methoxybenzamide;
I-165 N-(1-{3-[(hydroxyamino)carbonyl]phenyl}ethyl)pyrazine-2-carboxamide;
I-166 N-hydroxy-4-[1-({[3-(trifluoromethyl)phenyl]sulfonyl}amino)ethyl]benzamide;
I-167 N-(1-{3-[(hydroxyamino)carbonyl]phenyl}ethyl)-1,3-dimethyl-1H-pyrazole-4-carboxamide;
I-168 N-hydroxy-4-[1-({[(3-methyl-5-phenylisoxazol-4-yl)amino]carbonyl}amino)ethyl]benzamide;
I-169 N-((1R)-1-{3-[(hydroxyamino)carbonyl]phenyl}ethyl)-3-methyl-1-benzofuran-2-carboxamide;
I-170 N-hydroxy-4-{1-[(isoquinolin-5-ylsulfonyl)amino]ethyl}benzamide;
I-171 N-hydroxy-4-[(1R)-1-({[4-(trifluoromethyl)phenyl]sulfonyl}amino)butyl]benzamide;
I-172 N-(1-{4-[(hydroxyamino)carbonyl]phenyl}-2-methylpropyl)-2-phenyl-1,3-thiazole-4-carboxamide;
I-173 N-(1-{4-[(hydroxyamino)carbonyl]phenyl}-2-methylpropyl)-3,5-bis(trifluoromethyl)benzamide;
I-174 N-hydroxy-4-(2-methyl-1-{[(2-methyl-1H-indol-3-yl)acetyl]amino}propyl)benzamide;
I-175 4-[1-({[(2,3-dimethylphenyl)amino]carbonyl}amino)ethyl]-N-hydroxybenzamide;
I-176 N-hydroxy-4-{1-[(mesitylsulfonyl)amino]ethyl}benzamide;
I-177 3-{(1R)-1-[(2,2-dimethylpropanoyl)amino]ethyl}-N-hydroxybenzamide;
I-178 N-hydroxy-4-[1-({[4-(1,3-oxazol-5-yl)phenyl]sulfonyl}amino)ethyl]benzamide;
I-179 N-(1-{3-[(hydroxyamino)carbonyl]phenyl}ethyl)-1,3-thiazole-4-carboxamide;
I-180 N-(1-{3-[(hydroxyamino)carbonyl]phenyl}ethyl)-4-methyl-2-phenyl-4H-furo[3,2-b]pyrrole-5-carboxamide;
I-181 N-(1-{3-[(hydroxyamino)carbonyl]phenyl}ethyl)-2,5-dimethyl-1H-pyrrole-3-carboxamide;
I-182 N-(1-{4-[(hydroxyamino)carbonyl]phenyl}-2,2-dimethylpropyl)-5-methyl-1-phenyl-1H-pyrazole-4-carboxamide;
I-183 3-[1-({[1-(4-chlorophenyl)cyclopropyl]carbonyl}amino)ethyl]-N-hydroxybenzamide;
I-184 N-((1R)-1-{4-[(hydroxyamino)carbonyl]phenyl}ethyl)-1-benzothiophene-2-carboxamide;
I-185 N-(1-{4-[(hydroxyamino)carbonyl]phenyl}ethyl)-4(1H-pyrazol-1-yl)benzamide;
I-186 N-(1-{4-[(hydroxyamino)carbonyl]phenyl}ethyl)-3-isopropyl-1-methyl-1H-pyrazole-5-carboxamide;
I-187 N-((1R)-1-{4-[(hydroxyamino)carbonyl]phenyl}-2-methylpropyl)-3-methyl-1-benzofuran-2-carboxamide;
I-188 4-{1-[{(2-chloro-6-methylphenyl)sulfonyl]amino}ethyl)-N-hydroxybenzamide;
I-189 N-hydroxy-4-[(1R)-2-methyl-1-({[4-(trifluoromethyl)phenyl]sulfonyl}amino)propyl]benzamide;
I-190 N-(1-{4-[(hydroxyamino)carbonyl]phenyl}-2-methylpropyl)quinoxaline-2-carboxamide;
I-191 N-(1-{4-[(hydroxyamino)carbonyl]phenyl}-2-methylpropyl)-1,3-benzothiazole-2-carboxamide;
I-192 4-tert-butyl-N-(1-{4-[(hydroxyamino)carbonyl]phenyl}-2-methylpropyl)benzamide;
I-193 N-hydroxy-3-{(1R)-1-[(4-methoxybenzoyl)amino]ethyl}benzamide;
I-194 N-(1-{4-[(hydroxyamino)carbonyl]phenyl}-2-methylpropyl)-1-benzofuran-5-carboxamide;
I-195 N-hydroxy-4-[2-methyl-1-({[3-(trifluoromethyl)phenyl]acetyl}amino)propyl]benzamide;
I-196 N-hydroxy-4-[1-({[(1-phenylethyl)amino]carbonyl}amino)ethyl]benzamide;
I-197 4-(1-{[(3-chlorophenyl)sulfonyl]amino}ethyl)-N-hydroxybenzamide;
I-198 4-(1-{[(4-fluorobenzyl)sulfonyl]amino}ethyl)-N-hydroxybenzamide;
I-199 N-(1-{3-[(hydroxyamino)carbonyl]phenyl}ethyl)-3-(methylsulfonyl)benzamide;
I-200 N-(1-{4-[(hydroxyamino)carbonyl]phenyl}-2,2-dimethylpropyl)-3,5-dimethylisoxazole-4-carboxamide;

or a pharmaceutically acceptable salt thereof.

20. A compound, where in the compound is:

| | |
|---|---|
| I-201 | N-((1R)-1-{3-[(hydroxyamino)carbonyl]phenyl}ethyl)-1-benzofuran-2-carboxamide; |
| I-202 | N-hydroxy-3-{1-[(4-methoxybenzoyl)amino]ethyl}benzamide; |
| I-203 | N-(1-{4-[(hydroxyamino)carbonyl]phenyl}-2-methylpropyl)pyrazine-2-carboxamide; |
| I-204 | 4-{1-[(diphenylacetyl)amino]-2-methylpropyl}-N-hydroxybenzamide; |
| I-205 | 4-(1-{[(5-fluoro-2-methylphenyl)sulfonyl]amino}ethyl)-N-hydroxybenzamide; |
| I-206 | 4-(1-{[(5-chloro-1-benzothien-3-yl)acetyl]amino}-2-methylpropyl)-N-hydroxybenzamide; |
| I-207 | N-(1-{4-[(hydroxyamino)carbonyl]phenyl}ethyl)-1-benzofuran-2-carboxamide; |
| I-208 | 4-{1-[(cyclohexylcarbonyl)amino]ethyl}-N-hydroxybenzamide; |
| I-209 | N-((1R)-1-{4-[(hydroxyamino)carbonyl]phenyl}ethyl)adamantane-1-carboxamide; |
| I-210 | N-hydroxy-4-[1-({[(2-phenylethyl)amino]carbonyl}amino)ethyl]benzamide; |
| I-211 | N-(1-{4-[(hydroxyamino)carbonyl]phenyl}-2,2-dimethylpropyl)-2-methyl-4,5,6,7-tetrahydro-2H-indazole-3-carboxamide; |
| I-212 | 4-(1-{[(1-adamantylacetyl]amino}ethyl)-N-hydroxybenzamide; |
| I-213 | N-(1-{4-[(hydroxyamino)carbonyl]phenyl}ethyl)cycloheptanecarboxamide; |
| I-214 | N-((1R)-1-{4-[(hydroxyamino)carbonyl]phenyl}-2-methylpropyl)-1-benzothiophene-2-carboxamide; |
| I-215 | N-(1-{4-[(hydroxyamino)carbonyl]phenyl}-2,2-dimethylpropyl)thiophene-2-carboxamide; |
| I-216 | 3-ethyl-N-(1-{3-[(hydroxyamino)carbonyl]phenyl}ethyl)-1-methyl-1H-pyrazole-5-carboxamide; |
| I-217 | 4-(1-{[(2,5-dimethyl-1,3-thiazol-4-yl)acetyl]amino}ethyl)-N-hydroxybenzamide; |
| I-218 | N-(1-{3-[(hydroxyamino)carbonyl]phenyl}ethyl)-3,5-dimethylisoxazole-4-carboxamide; |
| I-219 | N-(1-{3-[(hydroxyamino)carbonyl]phenyl}ethyl)-1-methyl-1H-indole-2-carboxamide; |
| I-220 | N-hydroxy-4-(2-methyl-1-{[(2,4,7-trimethyl-1H-indol-3-yl)acetyl]amino}propyl)benzamide; |
| I-221 | N-hydroxy-4-(1-{[(4-isopropylphenyl)sulfonyl]amino}ethyl)benzamide; |
| I-222 | N-((1R)-1-{4-[(hydroxyamino)carbonyl]phenyl}butyl)-4-methyl-2-phenyl-4H-furo[3,2-b]pyrrole-5-carboxamide; |
| I-223 | 3-hydroxy-N-((1R)-1-{4-[(hydroxyamino)carbonyl]phenyl}-2-methylpropyl)adamantane-1-carboxamide; |
| I-224 | N-(1-{4-[(hydroxyamino)carbonyl]phenyl}ethyl)-2H-chromene-3-carboxamide; |
| I-225 | N-(1-{4-[(hydroxyamino)carbonyl]phenyl}ethyl)-3-methoxybenzamide; |
| I-226 | 5-chloro-N-(1-{3-[(hydroxyamino)carbonyl]phenyl}ethyl)-1-benzofuran-2-carboxamide; |
| I-227 | N-(1-{3-[(hydroxyamino)carbonyl]phenyl}ethyl)-1H-indole-2-carboxamide; |
| I-228 | N-(1-{4-[(hydroxyamino)carbonyl]phenyl}ethyl)-3-(1H-pyrrol-1-yl)thiophene-2-carboxamide; |
| I-229 | N-((R)-cyclopropyl{4-[(hydroxyamino)carbonyl]phenyl}methyl)-1-benzothiophene-2-carboxamide; |
| I-230 | N-(1-{4-[(hydroxyamino)carbonyl]phenyl}ethyl)-2-methyl-1,3-benzothiazole-5-carboxamide; |
| I-231 | 4-methyl-2-phenyl-N-((1S)-2,2,2-trifluoro-1-{4-[(hydroxyamino)carbonyl]phenyl}ethyl)-4H-furo[3,2-b]pyrrole-5-carboxamide; |
| I-232 | N-hydroxy-4-(1-{[(2-methylphenyl)sulfonyl]amino}ethyl)benzamide; |
| I-233 | N-(1-{4-[(hydroxyamino)carbonyl]phenyl}ethyl)-2,1,3-benzothiadiazole-5-carboxamide; |
| I-234 | N-hydroxy-3-(1-{[(5-methyl-2-phenyl-1,3-oxazol-4-yl)acetyl]amino}ethyl)benzamide; |
| I-235 | 4-(1-{[(2-chloro-4-fluorophenyl)sulfonyl]amino}ethyl)-N-hydroxybenzamide; |
| I-236 | 4-[1-({[(4-cyanophenyl)amino]carbonyl}amino)ethyl]-N-hydroxybenzamide; |
| I-237 | N-((1R)-1-{4-[(hydroxyamino)carbonyl]phenyl}ethyl)-3-methyl-1-benzofuran-2-carboxamide; |
| I-238 | N-(1-{4-[(hydroxyamino)carbonyl]phenyl}-2-methylpropyl)-3,5-dimethylisoxazole-4-carboxamide; |
| I-239 | 4-{1-[(cyclopropylcarbonyl)amino]ethyl}-N-hydroxybenzamide; |
| I-240 | N-((1S)-1-{3-[(hydroxyamino)carbonyl]phenyl}ethyl)-1-benzothiophene-2-carboxamide; |
| I-241 | N-(1-{4-[(hydroxyamino)carbonyl]phenyl}ethyl)-1,5-dimethyl-1H-pyrazole-3-carboxamide; |
| I-242 | N-((1R)-1-{4-[(hydroxyamino)carbonyl]phenyl}-2-methylpropyl)-1-methyl-1H-indole-2-carboxamide; |
| I-243 | 4-[1-(butyrylamino)ethyl]-N-hydroxybenzamide; |
| I-244 | N-(1-{4-[(hydroxyamino)carbonyl]phenyl}ethyl)-1-benzothiophene-3-carboxamide; |
| I-245 | 4,5-dichloro-N-((1R)-1-{4-[(hydroxyamino)carbonyl]phenyl}butyl)-1-methyl-1H-pyrrole-2-carboxamide; |
| I-246 | N-(1-{4-[(hydroxyamino)carbonyl]phenyl}-2-methylpropyl)quinoline-4-carboxamide; |
| I-247 | 5-chloro-N-(1-{4-[(hydroxyamino)carbonyl]phenyl}-2-methylpropyl)-1H-indole-2-carboxamide; |
| I-248 | N-(1-{4-[(hydroxyamino)carbonyl]phenyl}-2,2-dimethylpropyl)-4-methyl-2-[4-(trifluoromethyl)phenyl]-4H-furo[3,2-b]pyrrole-5-carboxamide; |
| I-249 | N-((S)-cyclopropyl{4-[(hydroxyamino)carbonyl]phenyl}methyl)-1-benzothiophene-2-carboxamide; |
| I-250 | 4-[1-({[3,5-bis(trifluoromethyl)phenyl]acetyl}amino-2-methylpropyl]-N-hydroxybenzamide; | or a pharmaceutically acceptable salt thereof.

21. A compound, where in the compound is:

| | |
|---|---|
| I-251 | 3,5-difluoro-N-(1-{4-[(hydroxyamino)carbonyl]phenyl}-2,2-dimethylpropyl)benzamide; |
| I-252 | N-(1-{4-[(hydroxyamino)carbonyl]phenyl}-2-methylpropyl)-2,5-dimethyl-3-furamide; |
| I-253 | N-hydroxy-4-[1-({[(2-methoxy-5-methylphenyl)amino]carbonyl}amino)ethyl]benzamide; |
| I-254 | 4-(1-{[(2-chloro-4-cyanophenyl)sulfonyl]amino}ethyl)-N-hydroxybenzamide; |
| I-255 | 4-{1-[(cyclopentylcarbonyl)amino]-2-methylpropyl}-N-hydroxybenzamide; |
| I-256 | 4-(1-{[(2,5-dimethyl-3-thienyl)sulfonyl]amino}ethyl)-N-hydroxybenzamide; |
| I-257 | N-(1-{3-[(hydroxyamino)carbonyl]phenyl}ethyl)-5-methyl-1-phenyl-1H-pyrazole-4-carboxamide; |
| I-258 | N-hydroxy-4-(2-methyl-1-{[(1-phenylcyclopentyl)carbonyl]amino}propyl)benzamide; |
| I-259 | N-[(S)-{4-[(hydroxyamino)carbonyl]phenyl}(phenyl)methyl]adamantane-1-carboxamide; |
| I-260 | N-(1-{4-[(hydroxyamino)carbonyl]phenyl}-2,2-dimethylpropyl)-1,5-dimethyl-1H-pyrazole-3-carboxamide; |
| I-261 | 4-[1-({[(2,6-difluorophenyl)amino]carbonyl}amino)ethyl]-N-hydroxybenzamide; |
| I-262 | N-(1-{4-[(hydroxyamino)carbonyl]phenyl}-2,2-dimethylpropyl)-3,5-dimethyl-1H-pyrrole-2-carboxamide; |
| I-263 | N-(1-{3-[(hydroxyamino)carbonyl]phenyl}ethyl)-1-methyl-1H-pyrrole-2-carboxamide; |
| I-264 | N-hydroxy-4-[1-({[1-(4-methylphenyl)cyclopropyl]carbonyl}amino)ethyl]benzamide; |
| I-265 | 4-{1-[(cyclohexylcarbonyl)amino]-2,2-dimethylpropyl}-N-hydroxybenzamide; |
| I-266 | N-hydroxy-4-(1-{[(4-methylphenyl)sulfonyl]amino}ethyl)benzamide; |
| I-267 | N-(1-{3-[(hydroxyamino)carbonyl]phenyl}ethyl)thiophene-2-carboxamide; |
| I-268 | 3-{1-[(4-tert-butylbenzoyl)amino]ethyl}-N-hydroxybenzamide; |
| I-269 | 2-chloro-N-(1-{4-[(hydroxyamino)carbonyl]phenyl}ethyl)benzamide; |
| I-270 | 5-chloro-N-(1-{4-[(hydroxyamino)carbonyl]phenyl}-2,2-dimethylpropyl)-1-benzofuran-2-carboxamide; |
| I-271 | N-((1R)-1-{3-[(hydroxyamino)carbonyl]phenyl}ethyl)-1-methyl-1H-pyrrole-2-carboxamide; |
| I-272 | 4-{1-[(2,1,3-benzothiadiazol-5-ylsulfonyl)amino]ethyl}-N-hydroxybenzamide; |
| I-273 | N-hydroxy-4-((1S)-1-{[(1-methylcyclohexyl)carbonyl]amino}ethyl)benzamide; |
| I-274 | N-((1R)-1-{4-[(hydroxyamino)carbonyl]phenyl}butyl)biphenyl-4-carboxamide; |
| I-275 | 4-[1-({[(3,4-difluorophenyl)amino]carbonyl}amino)ethyl]-N-hydroxybenzamide; |
| I-276 | 1-methyl-N-((1R)-2,2,2-trifluoro-1-{4-[(hydroxyamino)carbonyl]phenyl}ethyl)-1H-indole-2-carboxamide; |

-continued

I-277 N-hydroxy-4-[1-(([[(4-methylbenzyl)amino]carbonyl}amino)ethyl]benzamide;
I-278 N-(1-{4-[(hydroxyamino)carbonyl]phenyl}ethyl)-2-methyl-1,3-thiazole-4-carboxamide;
I-279 N-((1S)-1-{4-[(hydroxyamino)carbonyl]phenyl}-2-methylpropyl)-1H-indole-2-carboxamide;
I-280 4-{1-[(1,3-benzodioxol-5-ylacetyl)amino]ethyl}-N-hydroxybenzamide;
I-281 N-((1R)-1-{4-[(hydroxyamino)carbonyl]phenyl}butyl)-1-methyl-1H-pyrrole-2-carboxamide;
I-282 3,5-bis(acetylamino)-N-(1-{4-[(hydroxyamino)carbonyl]phenyl}-2-methylpropyl)benzamide;
I-283 N-hydroxy-3-((1R)-1-{[(1-methylcyclohexyl)carbonyl]amino}ethyl)benzamide;
I-284 N-hydroxy-4-(1-{[(2,3,4-trifluorophenyl)sulfonyl]amino}ethyl)benzamide;
I-285 N-hydroxy-4-(1-{[(4-isopropylphenyl)acetyl]amino}ethyl)benzamide;
I-286 N-(1-{4-[(hydroxyamino)carbonyl]phenyl}ethyl)-5-isobutylisoxazole-3-carboxamide;
I-287 4-{(1R)-1-[(2,2-dimethylpropanoyl)amino]-2-methylpropyl}-N-hydroxybenzamide;
I-288 N-(1-{4-[(hydroxyamino)carbonyl]phenyl}ethyl)-1,3-dimethyl-1H-pyrazole-5-carboxamide;
I-289 N-hydroxy-4-{2-methyl-1-[(3-methyl-2-phenylbutanoyl)amino]propyl}benzamide;
I-290 4-((1R)-1-{[(tert-butylamino)carbonyl]amino}-2,2,2-trifluoroethyl)-N-hydroxybenzamide;
I-291 3-tert-butyl-N-(1-{4-[(hydroxyamino)carbonyl]phenyl}-2,2-dimethylpropyl)-1-methyl-1H-pyrazole-5-carboxamide;
I-292 4-(1-{[(2-chlorophenyl)acetyl]amino}ethyl)-N-hydroxybenzamide;
I-293 4-(1-{[(2,1,3-benzothiadiazol-4-ylamino)carbonyl]amino}ethyl)-N-hydroxybenzamide;
I-294 N-((1S)-1-{3-(hydroxyamino)carbonyl]phenyl}ethyl)-1-methyl-1H-indole-2-carboxamide;
I-295 N-(1-{4-[(hydroxyamino)carbonyl]phenyl}ethyl)-3-methylbenzamide;
I-296 N-((1S)-2,2,2-trifluoro-1-{4-[(hydroxyamino)carbonyl]phenyl}ethyl)biphenyl-4-carboxamide;
I-297 N-(1-{4-[(hydroxyamino)carbonyl]phenyl}ethyl)-1,3-benzodioxole-5-carboxamide;
I-298 N-hydroxy-4-(1-{[(1-phenylcyclopentyl)carbonyl]amino}ethyl)benzamide;
I-299 N-((1R)-1-{4-[(hydroxyamino)carbonyl]phenyl}butyl)-1-benzothiophene-2-carboxamide;
I-300 4-[1-({[1-(4-chlorophenyl)cyclopropyl]carbonyl}amino)-2-methylpropyl]-N-hydroxybenzamide;

or a pharmaceutically acceptable salt thereof.

22. A compound, where in the compound is:

I-301 4,5-dichloro-N-((1R)-1-{3-[hydroxyamino)carbonyl]phenyl}ethyl)-1-methyl-1H-pyrrole-2-carboxamide;
I-302 4-(1-{[(4-chlorophenyl)sulfonyl]amino}ethyl)-N-hydroxybenzamide;
I-303 4-(2,2-dimethyl-1-{[4-(trifluoromethyl)benzoyl]amino}propyl)-N-hydroxybenzamide;
I-304 3-methyl-N-((1S)-2,2,2-trifluoro-1-{4-[(hydroxyamino)carbonyl]phenyl}ethyl)-1-benzofuran-2-carboxamide;
I-305 N-hydroxy-4-[1-({[(5-methyl-3-phenylisoxazol-4-yl)amino]carbonyl}amino)ethyl]benzamide;
I-306 N-(1-{4-[(hydroxyamino)carbonyl]phenyl}-2-methylpropyl)-7-methoxy-1-benzofuran-2-carboxamide;
I-307 N-((1R)-1-{4-[(hydroxyamino)carbonyl]phenyl}-2-methylpropyl)-3-methyl-1-benzothiophene-2-carboxamide;
I-308 N-(1-{4-[(hydroxyamino)carbonyl]phenyl}-2,2-dimethylpropyl)-1-benzothiophene-2-carboxamide;
I-309 3-tert-butyl-N-(1-{3-[(hydroxyamino)carbonyl]phenyl}ethyl)-1-methyl-1H-pyrazole-5-carboxamide;
I-310 N-(1-{4-[(hydroxyamino)carbonyl]phenyl}-2,2-dimethylpropyl)-2,5-dimethyl-1H-pyrrole-3-carboxamide;
I-311 3-{1-[(cyclopentylcarbonyl)amino]ethyl}-N-hydroxybenzamide;
I-312 N-((1R)-1-{3-[(hydroxyamino)carbonyl]phenyl}ethyl)adamantane-1-carboxamide;
I-313 N-hydroxy-4-{1-[(tetrahydro-2H-pyran-4-ylacetyl)amino]ethyl}benzamide;
I-314 N-hydroxy-3-[1-({[3-(trifluoromethyl)phenyl]acetyl}amino)ethyl]benzamide;
I-315 N-hydroxy-4-{1-[(phenylsulfonyl)amino]ethyl}benzamide;
I-316 N-hydroxy-4-[1-({[(3-methylbenzyl)amino]carbonyl}amino)ethyl]benzamide;
I-317 N-((1R)-1-{4-[(hydroxyamino)carbonyl]phenyl}ethyl)-1-benzofuran-2-carboxamide;
I-318 3-ethyl-N-(1-{4-[(hydroxyamino)carbonyl]phenyl}-2,2-dimethylpropyl)-1-methyl-1H-pyrazole-5-carboxamide;
I-319 N-(1-{4-[(hydroxyamino)carbonyl]phenyl}-2,2-dimethylpropyl)-1H-indole-3-carboxamide;
I-320 3-((1R)-1-{[(tert-butylamino)carbonyl]amino}ethyl)-N-hydroxybenzamide;
I-321 N-((1R)-1-{3-[(hydroxyamino)carbonyl]phenyl}ethyl)-1-benzothiophene-2-carboxamide;
I-322 N-((S)-cyclopropyl{4-[(hydroxyamino)carbonyl]phenyl}methyl)adamantane-1-carboxamide;
I-323 N-(1-{3-[(hydroxyamino)carbonyl]phenyl}-2-methylpropyl)biphenyl-4-carboxamide;
I-324 2-(4-tert-butylphenyl)-N-(1-{3-[(hydroxyamino)carbonyl]phenyl}ethyl)-4-methyl-4H-furo[3,2-b]pyrrole-5-carboxamide;
I-325 4-{1-[({[4-chloro-3-(trifluoromethyl)phenyl]amino}carbonyl)amino]ethyl}-N-hydroxybenzamide;
I-326 N-(1-{4-[(hydroxyamino)carbonyl]phenyl}ethyl)-3,5-dimethylisoxazole-4-carboxamide;
I-327 N-(1-{4-[(hydroxyamino)carbonyl]phenyl}ethyl)-2-naphthamide;
I-328 N-((1R)-1-{4-[(hydroxyamino)carbonyl]phenyl}-2-methylpropyl)adamantane-1-carboxamide;
I-329 N-(1-{4-[(hydroxyamino)carbonyl]phenyl}-2,2-dimethylpropyl)-3,5-dimethyl-1H-indole-2-carboxamide;
I-330 N-((1R)-1-{3-[(hydroxyamino)carbonyl]phenyl}ethyl)-1-methyl-1H-indole-2-carboxamide;
I-331 N-(1-{4-[(hydroxyamino)carbonyl]phenyl}-2-methylpropyl)-1-naphthamide;
I-332 N-((1R)-1-{4-[(hydroxyamino)carbonyl]phenyl}-2-methylpropyl)-4-methyl-2-phenyl-4H-furo[3,2-b]pyrrole-5-carboxamide;
I-333 3-{1-[(3,3-dimethylbutanoyl)amino]ethyl}-N-hydroxybenzamide;
I-334 4-{1-[({[2-fluoro-5-(trifluoromethyl)phenyl]amino}carbonyl)amino]ethyl}-N-hydroxybenzamide;
I-335 N-hydroxy-4-(1-{[(1-methyl-1H-imidazol-4-yl)sulfonyl]amino}ethyl)benzamide;
I-336 N-[(R)-{4-[(hydroxyamino)carbonyl]phenyl}(phenyl)methyl]adamantane-1-carboxamide;
I-337 2-(4-tert-butylphenyl)-N-(1-{4-[(hydroxyamino)carbonyl]phenyl}-2,2-dimethylpropyl)-4-methyl-4H-furo[3,2-b]pyrrole-5-carboxamide;
I-338 4-{1-[(benzylsulfonyl)amino]ethyl}-N-hydroxybenzamide;
I-339 4-(1-{[(tert-butylamino)carbonyl]amino}ethyl)-N-hydroxybenzamide;
I-340 4-(1-{[(2-cyanophenyl)sulfonyl]amino}ethyl)-N-hydroxybenzamide;
I-341 N-((1R)-1-{4-[(hydroxyamino)carbonyl]phenyl}-2-methylpropyl)biphenyl-4-carboxamide;
I-342 N-(1-{3-[(hydroxyamino)carbonyl]phenyl}ethyl)-5-methyl-1H-indole-2-carboxamide;
I-343 3-[(1R)-1-({[1-adamantylamino]carbonyl}amino)ethyl]-N-hydroxybenzamide;
I-344 4-{1-[(cyclohexylcarbonyl)amino]-2-methylpropyl}-N-hydroxybenzamide;
I-345 4-(1-{[(5-chloro-1-benzothien-3-yl)acetyl]amino}-2,2-dimethylpropyl)-N-hydroxybenzamide;
I-346 N-(1-{4-[(hydroxyamino)carbonyl]phenyl}-2-methylpropyl)-4-methoxybenzamide;
I-347 4-(1-{[(5-chloro-2-methoxyphenyl)sulfonyl]amino}ethyl)-N-hydroxybenzamide;
I-348 4-{1-[(cyclohex-3-en-1-ylcarbonyl)amino]ethyl}-N-hydroxybenzamide;

-continued

I-349 N-(1-{4-[(hydroxyamino)carbonyl]phenyl}ethyl)-1-benzofuran-5-carboxamide;
I-350 4-tert-butyl-N-(1-{4-[(hydroxyamino)carbonyl]phenyl}ethyl)benzamide;

or a pharmaceutically acceptable salt thereof.

23. A compound, where in the compound is:

I-351 N-hydroxy-4-[(1R)-1-({[4-(trifluoromethyl)phenyl]sulfonyl}amino)ethyl]benzamide;
I-352 N-(1-{4-[(hydroxyamino)carbonyl]phenyl}-2,2-dimethylpropyl)-4-methoxybenzamide;
I-353 N-(1-{3-[(hydroxyamino)carbonyl]phenyl}ethyl)-1-methyl-1H-indole-3-carboxamide;
I-354 4-[(1R)-1-({[1-adamantylamino]carbonyl}amino)-2-methylpropyl]-N-hydroxybenzamide;
I-355 N-(1-{4-[(hydroxyamino)carbonyl]phenyl}-2,2-dimethylpropyl)biphenyl-4-carboxamide;
I-356 N-(1-{4-[(hydroxyamino)carbonyl]phenyl}ethyl)-1-methyl-1H-pyrrole-2-carboxamide;
I-357 4-{1-[(2,3-dihydro-1H-inden-2-ylacetyl)amino]ethyl}-N-hydroxybenzamide;
I-358 4-[1-({[(3-acetylphenyl)amino]carbonyl}amino)ethyl]-N-hydroxybenzamide;
I-359 4,5-dichloro-N-((1R)-1-{4-[(hydroxyamino)carbonyl]phenyl}ethyl)-1-methyl-1H-pyrrole-2-carboxamide;
I-360 N-(1-{4-[(hydroxyamino)carbonyl]phenyl}ethyl)-1,3-benzothiazole-6-carboxamide;
I-361 4-(1-{[(2-chlorophenyl)sulfonyl]amino}ethyl)-N-hydroxybenzamide;
I-362 3-[1-({[3,5-bis(trifluoromethyl)phenyl]acetyl}amino)ethyl]-N-hydroxybenzamide;
I-363 N-hydroxy-4-{1-[(quinolin-8-ylsulfonyl)amino]ethyl}benzamide;
I-364 N-(1-{4-[(hydroxyamino)carbonyl]phenyl}-2,2-dimethylpropyl)-1-methyl-1H-indole-2-carboxamide;
I-365 4-{(1R)-1-[(2,2-dimethylpropanoyl)amino]butyl}-N-hydroxybenzamide;
I-366 2,6-dichloro-N-(1-{3-[(hydroxyamino)carbonyl]phenyl}ethyl)benzamide;
I-367 N-((1R)-1-{4-[(hydroxyamino)carbonyl]phenyl}butyl)-3-methyl-1-benzofuran-2-carboxamide;
I-368 4-((1R)-1-{[(tert-butylamino)carbonyl]amino}-2-methylpropyl)-N-hydroxybenzamide;
I-369 4-{1-[(1-benzothien-2-ylsulfonyl)amino]ethyl}-N-hydroxybenzamide;
I-370 4-{1-[(cyclopentylacetyl)amino]ethyl}-N-hydroxybenzamide;
I-371 N-hydroxy-4-{1-[({[3-(trifluoromethyl)phenyl]amino}carbonyl)amino]ethyl}benzamide;
I-372 N-hydroxy-4-(1-{[(2,2,3,3-tetramethylcyclopropyl)carbonyl]amino}ethyl)benzamide;
I-373 4-{1-[(cyclopentylcarbonyl)amino]-2,2-dimethylpropyl}-N-hydroxybenzamide;
I-374 4-[(1R)-1-({[1-adamantylamino]carbonyl}amino)ethyl]-N-hydroxybenzamide;
I-375 N-(1-{4-[(hydroxyamino)carbonyl]phenyl}-2-methylpropyl)-2-oxo-6-phenyl-1,2-dihydropyridine-3-carboxamide;
I-376 N-(1-{3-[(hydroxyamino)carbonyl]phenyl}ethyl)-3,5-dimethyl-1H-indole-2-carboxamide;
I-377 4-tert-butyl-N-(1-{4-[(hydroxyamino)carbonyl]phenyl}-2,2-dimethylpropyl)benzamide;
I-378 4-(1-{[2-(4-chlorophenyl)-2-methylpropanoyl]amino}ethyl)-N-hydroxybenzamide;
I-379 4-{1-[(cyclopropylacetyl)amino]ethyl}-N-hydroxybenzamide;
I-380 4-((1R)-1-{[(tert-butylamino)carbonyl]amino}butyl)-N-hydroxybenzamide;
I-381 4-[1-({[(4-ethylphenyl)amino]carbonyl}amino)ethyl]-N-hydroxybenzamide;
I-382 N-(1-{4-[(hydroxyamino)carbonyl]phenyl}-2-methylpropyl)cycloheptanecarboxamide;
I-383 4-[1-({[(2,4-dimethylphenyl)amino]carbonyl}amino)ethyl]-N-hydroxybenzamide;
I-384 4-(1-{[(biphenyl-2-ylamino)carbonyl]amino}ethyl)-N-hydroxybenzamide;
I-385 4-[1-(benzoylamino)ethyl]-N-hydroxybenzamide;
I-386 4,5-dichloro-N-(1-{4-[(hydroxyamino)carbonyl]phenyl}-2,2-dimethylpropyl)-1-methyl-1H-pyrrole-2-carboxamide;
I-387 N-hydroxy-4-((1R)-1-{[(1-methylcyclohexyl)carbonyl]amino}butyl)benzamide;
I-388 4-[1-({[(3,5-dichlorophenyl)amino]carbonyl}amino)ethyl]-N-hydroxybenzamide;
I-389 N-(1-{4-[(hydroxyamino)carbonyl]phenyl}-2-methylpropyl)-1-methyl-1H-pyrazole-3-carboxamide;
I-390 N-(1-{3-[(hydroxyamino)carbonyl]phenyl}-2-methylpropyl)-1-benzothiophene-2-carboxamide;
I-391 N-hydroxy-4-[1-({[2-(trifluoromethyl)phenyl]sulfonyl}amino)ethyl]benzamide;
I-392 N-(1-{4-[(hydroxyamino)carbonyl]phenyl}-2,2-dimethylpropyl)-4-methyl-2-phenyl-4H-furo[3,2-b]pyrrole-5-carboxamide;
I-393 N-((1S)-1-{3-[(hydroxyamino)carbonyl]phenyl}ethyl)biphenyl-4-carboxamide;
I-394 N-hydroxy-4-[1-({[(2-methylphenyl)amino]carbonyl}amino)ethyl]benzamide;
I-395 4-(1-{[(cyclohexylamino)carbonyl]amino}ethyl)-N-hydroxybenzamide;
I-396 4-{1-[(3,3-dimethylbutanoyl)amino]-2,2-dimethylpropyl}-N-hydroxybenzamide;
I-397 4-[1-({[(3,5-dimethylphenyl)amino]carbonyl}amino)ethyl]-N-hydroxybenzamide;
I-398 4-[1-({[(4-acetylphenyl)amino]carbonyl}amino)ethyl]-N-hydroxybenzamide;
I-399 N-hydroxy-4-{1-[({[4-(trifluoromethyl)phenyl]amino}carbonyl)amino]ethyl}benzamide;
I-400 N-((1S)-2,2,2-trifluoro-1-{4-[(hydroxyamino)carbonyl]phenyl}ethyl)-1-benzofuran-2-carboxamide;
I-401 N-(1-{3-[(hydroxyamino)carbonyl]phenyl}ethyl)-1-benzofuran-2-carboxamide;
I-402 4-(1-{[(2,4-difluorophenyl)acetyl]amino}ethyl)-N-hydroxybenzamide;
I-403 N-hydroxy-3-[(1R)-1-({[4-(trifluoromethyl)phenyl]sulfonyl}amino)ethyl]benzamide;

or a pharmaceutically acceptable salt thereof.

24. A compound, where in the compound is:

I-408 N-((1S)-1-}4-(hydroxyamino)carbonyl]phenyl}propyl)-1-methylpiperidine-4-carboxamide;
I-409 N-((1S)-1-{4-[(hydroxyamino)carbonyl]phenyl}propyl)-1-methyl-1H-indole-2-carboxamide;
I-414 N-((1S)-1-{4-[(hydroxyamino)carbonyl]phenyl}-2,2-dimethylpropyl)-1-benzothiophene-2-carboxamide;
I-418 4-{(1S)-1-[(2,2-dimethylpropanoyl)amino]-2,2-dimethylpropyl}-N-hydroxybenzamide;
I-422 4-{(1S)-1-[(cyclopentylacetyl)amino]propyl}-N-hydroxybenzamide;
I-437 N-((1S)-1-{4-[(hydroxyamino)carbonyl]phenyl}-2,2-dimethylpropyl)-1-methylpiperidine-4-carboxamide;
I-441 N-((1S)-1-{4-[(hydroxyamino)carbonyl]phenyl}propyl)-1-benzothiophene-2-carboxamide;
I-452 N-((1S)-1-{4-[(hydroxyamino)carbonyl]phenyl}-2,2-dimethylpropyl)-1-methyl-1H-indole-2-carboxamide;
I-459 4-{(1S)-1-[(cyclopentylacetyl)amino]-2,2-dimethylpropyl}-N-hydroxybenzamide;
I-460 N-((1S)-1-{4-(hydroxyamino)carbonyl]phenyl}propyl)-1-methyl-1H-pyrrole-2-carboxamide;
I-462 N-((1S)-1-{4-(hydroxyamino)carbonyl]phenyl}-2,2-dimethylpropyl)-1-methyl-1H-pyrrole-2-carboxamide;
I-470 4-((1S)-1-{[(dimethylamino)acetyl]amino}propyl)-N-hydroxybenzamide;
I-471 N-((1S)-1-{4-(hydroxyamino)carbonyl]phenyl}-2,2-dimethylpropyl)biphenyl-4-carboxamide;
I-474 N-((1S)-1-{4-(hydroxyamino)carbonyl]phenyl}propyl)biphenyl-4-carboxamide;
I-475 4-{(1S)-1-[(2,2-dimethylpropanoyl)amino]propyl}-N-hydroxybenzamide;
I-478 4-((1S)-1-{[(dimethylamino)acetyl]amino}-2,2-dimethylpropyl)-N-hydroxybenzamide;
I-482 4-((1R)-1-{[(benzylamino)carbonyl]amino}ethyl)-N-hydroxybenzamide;
I-487 N-((1R)-1-{4-[(hydroxyamino)carbonyl]phenyl}ethyl)-4-methylpiperidine-4-carboxamide;
I-488 N-hydroxy-4-[1-({[4-(trifluoromethyl)phenyl]sulfonyl}amino)ethyl]benzamide;

| | |
|---|---|
| I-489 | N-hydroxy-4-((1R)-1-{[(1-methylcyclohexyl)methyl]amino}ethyl)benzamide; |
| I-492 | N-hydroxy-4-[(1R)-2-methyl-1-({[(5-phenyl-2-thienyl)amino]carbonyl}amino)propyl]benzamide; |
| I-493 | 4-((1R)-1-{[(biphenyl-2-ylamino)carbonyl]amino}-2-methylpropyl)-N-hydroxybenzamide; |
| I-494 | 4-((1R)-1-{[(biphenyl-2-ylamino)carbonyl]amino}ethyl)-N-hydroxybenzamide; |
| I-495 | N-hydroxy-4-{(1R)-2-methyl-1-[({[(1S)-1-phenylethyl]amino}carbonyl)amino]propyl}benzamide; |
| I-496 | 4-((1R)-1-{[(2,3-dihydro-1-benzofuran-5-ylamino)carbonyl]amino}ethyl)-N-hydroxybenzamide; |
| I-497 | 4-[(1R)-1-({[(3,4-dimethylphenyl)amino]carbonyl}amino)-2-methylpropyl]-N-hydroxybenzamide; |
| I-498 | 4-[(1R)-1-({[(4-cyanophenyl)amino]carbonyl}amino)-2-methylpropyl]-N-hydroxybenzamide; |
| I-499 | N-hydroxy-4-{(1R)-1-[({[(1S)-1-phenylethyl]amino}carbonyl)amino]ethyl}benzamide; |
| I-500 | 4-[(1R)-1-({[(3,4-dimethylphenyl)amino]carbonyl}amino)ethyl]-N-hydroxybenzamide; |
| I-501 | N-hydroxy-4-[(1R)-2-methyl-1-({[(2-phenylethyl)amino]carbonyl}amino)propyl]benzamide; |
| I-502 | N-hydroxy-4-{(1R)-1-[({[(1R)-1-phenylethyl]amino}carbonyl)amino]ethyl}benzamide; |
| I-503 | N-hydroxy-4-((1R)-1-{[(1-naphthylamino)carbonyl]amino}ethyl)benzamide; |
| I-504 | 4-[(1R)-1-({[(4-cyanophenyl)amino]carbonyl}amino)ethyl]-N-hydroxybenzamide; |
| I-505 | 4-[(1R)-1-({[(2,6-difluorophenyl)amino]carbonyl}amino)-2-methylpropyl]-N-hydroxybenzamide; |
| I-506 | N-hydroxy-4-[(1R)-1-({[(2-phenylethyl)amino]carbonyl}amino)ethyl]benzamide; |
| I-507 | N-hydroxy-4-{(1R)-2-methyl-1-[({[(1R)-1-phenylethyl]amino}carbonyl)amino]propyl}benzamide; |
| I-508 | 4-[(1R)-1-({[(2,6-difluorophenyl)amino]carbonyl}amino)ethyl]-N-hydroxybenzamide; |
| I-509 | 4-((1R)-1-{[(2,3-dihydro-1-benzofuran-5-ylamino)carbonyl]amino}-2-methylpropyl)-N-hydroxybenzamide; |
| I-510 | N-hydroxy-4-((1R)-2-methyl-1-{[(1-naphthylamino)carbonyl]amino}propyl)benzamide; |
| I-511 | N-hydroxy-4-[(1R)-1-({[(5-phenyl-2-thienyl)amino]carbonyl}amino)ethyl]benzamide; |
| I-512 | 4-[(1R)-1-({[(3,4-dimethylphenyl)amino]carbonyl}amino)-2-methylpropyl]-N-hydroxybenzamide; |
| I-513 | N-hydroxy-4-[(1R)-1-({[(1S)-1-phenylethyl]carbamoyl}amino)ethyl]benzamide; |
| I-514 | N-hydroxy-4-[(1R)-2-methyl-1-({[(1R)-1-phenylethyl]carbamoyl}amino)propyl]benzamide; |
| I-515 | 4-((1R)-1-{[(biphenyl-2-ylamino)carbonyl]amino}-2-methylpropyl)-N-hydroxybenzamide; |
| I-516 | N-hydroxy-4-{(1R)-2-methyl-1-[({[(1S)-1-phenylethyl]amino}carbonyl)amino]propyl}benzamide; |
| I-517 | N-hydroxy-4-[(1R)-1-({[(1R)-1-phenylethyl]carbamoyl}amino)ethyl]benzamide; |
| I-518 | 4-[(1R)-1-({[(2,6-difluorophenyl)amino]carbonyl}amino)ethyl]-N-hydroxybenzamide; |
| I-519 | N-hydroxy-4-((1R)-2-methyl-1-{[4-(3-phenylisoxazol-5-yl)-1,3-thiazol-2-yl]amino}propyl)benzamide; |
| I-520 | 4-[(1R)-1-({[(4-cyanophenyl)amino]carbonyl}amino)ethyl]-N-hydroxybenzamide; |
| I-521 | 4-[(1R)-1-({[(2,6-difluorophenyl)amino]carbonyl}amino)-2-methylpropyl]-N-hydroxybenzamide; |
| I-522 | N-hydroxy-4-[(1R)-2-methyl-1-({[(2-phenylethyl)amino]carbonyl}amino)propyl]benzamide; |
| I-523 | 4-((1R)-1-{[(biphenyl-2-ylamino)carbonyl]amino}ethyl)-N-hydroxybenzamide; |
| I-524 | N-hydroxy-4-((1R)-2-methyl-1-{[(1-naphthylamino)carbonyl]amino}propyl)benzamide; |
| I-525 | 4-[(1R)-1-({[(4-cyanophenyl)amino]carbonyl}amino)-2-methylpropyl]-N-hydroxybenzamide; |
| I-526 | 4-((1R)-1-{[(2,3-dihydro-1-benzofuran-5-ylamino)carbonyl]amino}-2-methylpropyl)-N-hydroxybenzamide; |
| I-527 | N-hydroxy-4-((1R)-1-{[(1-naphthylamino)carbonyl]amino}ethyl)benzamide; |
| I-528 | 4-((1R)-1-{[(2,3-dihydro-1-benzofuran-5-ylamino)carbonyl]amino}ethyl)-N-hydroxybenzamide; |
| I-529 | N-hydroxy-4-((1R)-2-methyl-1-{[4-(trifluoromethyl)-1,3-thiazol-2-yl]amino}propyl)benzamide; |
| I-530 | N-hydroxy-4-((1R)-1-{[(1-isopropylpiperidin-4-yl)methyl]amino}butyl)benzamide; |
| I-531 | 3-{[((1R)-1-{4-[(hydroxyamino)carbonyl]phenyl}butyl)amino]methyl}-N-pyrrolidin-3-ylbenzamide; |
| I-532 | N-(4-{[((1R)-1-{4-[(hydroxyamino)carbonyl]phenyl}-2-methylpropyl)amino]methyl}pyridin-2-yl)-4-methylpiperidine-4-carboxamide; |
| I-533 | N-(4-{[((1R)-1-{4-[(hydroxyamino)carbonyl]phenyl}-2-methylpropyl)amino]methyl}phenyl)-1-methylpiperidine-4-carboxamide; |
| I-534 | 4-((1R)-1-{[(1-ethylpiperidin-4-yl)methyl]amino}ethyl)-N-hydroxybenzamide; |
| I-535 | N-(1-{4-[(hydroxyamino)carbonyl]phenyl}-2,2-dimethylpropyl)-2-(trifluoromethyl)benzamide; |
| I-536 | 4-{(1S)-1-[(2,2-dimethylpropanoyl)amino]butyl}-N-hydroxybenzamide; | or a pharmaceutically acceptable salt thereof.

* * * * *